United States Patent
De Angelis et al.

(10) Patent No.: US 9,175,071 B2
(45) Date of Patent: *Nov. 3, 2015

(54) ANTI-SERUM ALBUMIN BINDING VARIANTS

(75) Inventors: Elena De Angelis, Cambridge (GB); Carolyn Enever, Cambridge (GB); Haiqun Liu, Cambridge (GB); Oliver Schon, Cambridge (GB)

(73) Assignee: GLAXO GROUP LIMITED (GB)

( * ) Notice: Subject to any disclaimer, the term of this patent is extended or adjusted under 35 U.S.C. 154(b) by 667 days.

This patent is subject to a terminal disclaimer.

(21) Appl. No.: 13/202,355

(22) PCT Filed: Feb. 17, 2010

(86) PCT No.: PCT/EP2010/052007
§ 371 (c)(1),
(2), (4) Date: Aug. 19, 2011

(87) PCT Pub. No.: WO2010/094722
PCT Pub. Date: Aug. 26, 2010

(65) Prior Publication Data
US 2011/0300158 A1   Dec. 8, 2011

Related U.S. Application Data

(60) Provisional application No. 61/153,746, filed on Feb. 19, 2009, provisional application No. 61/163,990, filed on Mar. 27, 2009.

(51) Int. Cl.
| | | |
|---|---|---|
| *A61K 39/395* | (2006.01) | |
| *C07K 16/28* | (2006.01) | |
| *C07K 16/18* | (2006.01) | |
| *C07K 14/56* | (2006.01) | |
| *C07K 14/575* | (2006.01) | |

(52) U.S. Cl.
CPC ............... *C07K 16/18* (2013.01); *C07K 14/56* (2013.01); *C07K 14/57563* (2013.01); *C07K 16/2878* (2013.01); *C07K 2317/31* (2013.01); *C07K 2317/34* (2013.01); *C07K 2317/565* (2013.01); *C07K 2317/569* (2013.01); *C07K 2317/92* (2013.01); *C07K 2319/00* (2013.01); *C07K 2319/31* (2013.01)

(58) Field of Classification Search
None
See application file for complete search history.

(56) References Cited

FOREIGN PATENT DOCUMENTS

| WO | WO 2008/096158 | * | 8/2008 | ............. C07K 16/00 |
|---|---|---|---|---|
| WO | WO 2008/096158 A2 | | 8/2008 | |

OTHER PUBLICATIONS

Xu et al. (Immunity, 13: 37-45, 2000).*
Mulydermans (Reviews in Molecular Biotechnology, 74: 277-302, 2001).*
McCarthy and Hill (J. Immunol. Methods, 251(1-2): 137-149, 2001).*
Barbas, C. F., et al., Gene, vol. 137, No. 1, pp. 57-62, Dec. 27, 1993.
MacCallum, R. M., et al., Journal of Mol. Biology, vol. 262, No. 5, pp. 732-745, Jan. 1, 1996.
Rudikoff, S., et al., PNAS, vol. 79, pp. 1979-1983, Mar. 1, 1982.
Vajdos, F. F., et al., Journal of Mol. Biology, vol. 320, No. 2, pp. 415-428, Jul. 5, 2002.
Wu Herren, et al., Journal of Mol. Biology, vol. 294, No. 1, pp. 151-162, Nov. 19, 1999.
Barkhordarian, et al., Isolating recombinant antibodies against specific protein morphologies using atomic force microscopy and phage display technologies. Protein Engineering, Design & Selection, vol. 19, No. 11, pp. 497-502, 2006.
Stamatopolous, et al., Immunoglobulin light chain repertoire in chronic lymphocytic leukemia. Blood, 2005 106:3575-3583.

* cited by examiner

*Primary Examiner* — Brad Duffy
*Assistant Examiner* — Nelson B Moseley, II
(74) *Attorney, Agent, or Firm* — Jason C. Fedon; William T. Han

(57) ABSTRACT

The invention relates to improved variants of the anti-serum albumin immunoglobulin single variable domain DOM7h-14, as well as ligands and drug conjugates comprising such variants, compositions, nucleic acids, vectors and hosts.

28 Claims, 6 Drawing Sheets

| Kabat Residue | | | | | 5 | | | | | 10 | | | | | 15 | | | | | 20 |
|---|---|---|---|---|---|---|---|---|---|---|---|---|---|---|---|---|---|---|---|---|
| (SEQ ID NO:422) DOM7h-14 | D | I | Q | M | T | Q | S | P | S | S | L | S | A | S | V | G | D | R | V | T |
| (SEQ ID NO:1) DOM7h-14-10 | . | . | . | . | . | . | . | . | . | . | . | . | . | . | . | . | . | . | . | . |
| (SEQ ID NO:2) DOM7h-14-18 | . | . | . | . | . | . | . | . | . | . | . | . | . | . | . | . | . | . | . | . |
| (SEQ ID NO:3) DOM7h-14-19 | . | . | . | . | . | . | . | . | . | . | . | . | . | . | . | . | . | . | . | . |
| (SEQ ID NO:4) DOM7h-14-28 | . | . | . | . | . | . | . | . | . | . | . | . | . | . | . | . | . | . | . | . |
| (SEQ ID NO:5) DOM7h-14-36 | . | . | . | . | . | . | . | . | . | . | . | . | . | . | . | . | . | . | . | . |

| Kabat Residue | | | | | 25 | | | | | 30 | | | | | 35 | | | | | 40 |
|---|---|---|---|---|---|---|---|---|---|---|---|---|---|---|---|---|---|---|---|---|
| (SEQ ID NO:422) DOM7h-14 | I | C | R | A | S | Q | S | I | W | Q | H | G | S | Q | L | S | W | Y | Q | P |
| (SEQ ID NO:1) DOM7h-14-10 | . | . | R | A | . | . | . | . | . | . | . | G | S | Q | L | S | . | . | . | . |
| (SEQ ID NO:2) DOM7h-14-18 | . | . | R | A | . | . | . | . | . | . | . | G | S | Q | L | S | . | . | . | . |
| (SEQ ID NO:3) DOM7h-14-19 | . | . | R | A | . | . | . | . | . | . | . | G | S | Q | L | S | . | . | . | . |
| (SEQ ID NO:4) DOM7h-14-28 | . | . | R | A | . | . | . | . | . | . | . | G | S | Q | L | S | . | . | . | . |
| (SEQ ID NO:5) DOM7h-14-36 | . | S | R | A | . | . | . | . | . | . | . | G | S | Q | L | S | . | . | . | . |

| Kabat Residue | | | | | 45 | | | | | 50 | | | | | 55 | | | | | 60 |
|---|---|---|---|---|---|---|---|---|---|---|---|---|---|---|---|---|---|---|---|---|
| (SEQ ID NO:422) DOM7h-14 | G | K | A | P | K | L | L | I | M | W | R | S | S | L | Q | S | G | V | P | S |
| (SEQ ID NO:1) DOM7h-14-10 | . | . | . | . | . | . | . | . | . | W | R | S | S | L | Q | S | . | . | . | . |
| (SEQ ID NO:2) DOM7h-14-18 | . | . | . | . | . | . | . | . | . | W | R | S | S | L | Q | S | . | . | . | . |
| (SEQ ID NO:3) DOM7h-14-19 | . | . | . | . | . | . | . | . | . | W | R | S | S | L | Q | S | . | . | . | . |
| (SEQ ID NO:4) DOM7h-14-28 | . | . | . | . | . | . | . | . | . | W | R | S | S | L | Q | S | . | . | . | . |
| (SEQ ID NO:5) DOM7h-14-36 | . | E | . | . | . | . | . | . | . | W | R | S | S | L | Q | S | . | . | . | . |

| Kabat Residue | | | | | 65 | | | | | 70 | | | | | 75 | | | | | 80 |
|---|---|---|---|---|---|---|---|---|---|---|---|---|---|---|---|---|---|---|---|---|
| (SEQ ID NO:422) DOM7h-14 | R | F | S | G | S | G | S | G | T | D | F | T | L | T | I | S | S | L | Q | P |
| (SEQ ID NO:1) DOM7h-14-10 | . | . | . | . | . | . | . | . | . | . | . | . | . | . | . | . | . | . | . | . |

Figure 1A

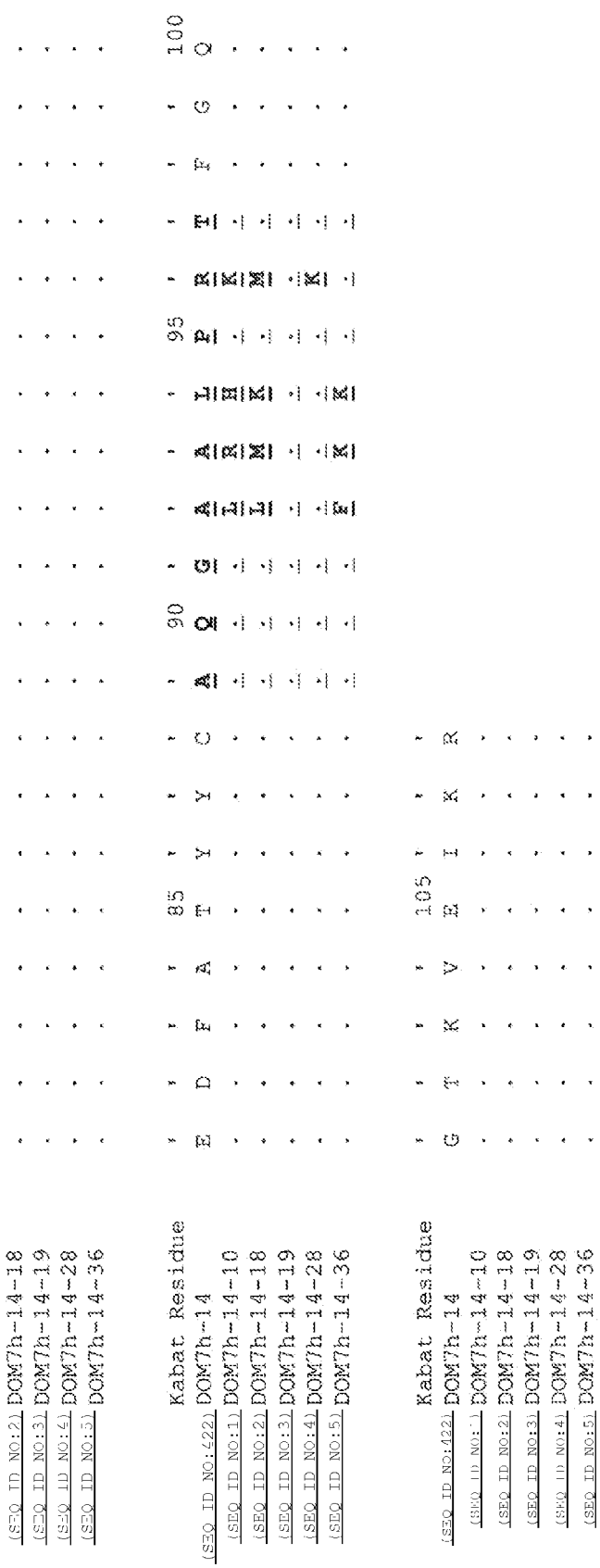

| human | kinetics based on DOM7h-14 and DOM7h-11 lineage (ranges supported by data) | | | |
|---|---|---|---|---|
| | | overall range | | |
| | | KD: 1 to 10000 | | |
| | | Kd:1.5e-4 to 0.1 ; Ka:2e6 to 1e4 | | |
| therapeutic ranges | chronic | intermediate | | acute |
| | high affinity | medium affinity | | low affinity |
| | KD: 0.1-400 | KD: 400-2000 | | KD: 2000-10000 |
| | Kd:1.5e-4 to 8e-3 ; Ka:1e6 to 5e4 | Kd: 8e-3 to 0.08 ; Ka: 2e4 to 5e4 | | Kd:0.08 to 0.1 ; Ka: 5e4 to 1e4 |
| optional ranges | KD: 1-200 | KD: 400-1500 | | KD: 2000-6000 |
| | Kd:3e-4 to 2e-3; Ka: 1e6 to 5e4 | Kd:8e-3 to 0.08; Ka: 2e4 to 6e4 | | Kd:0.08 to 0.1 ; Ka: 5e4 to 2e4 |
| Examples | DOM7h-11-15, DOM7h-14, DOM7h-14-10, DOM7h-14-18, DOM7h-14-19, DOM7h-11-18, DOM7h-11-19 DMS7321, DMS7322; DMS7324, DMS7327 | DMS7325, DMS7326; DMS7323 | | DOM7h-11 |

Figure 2A

| Cyno | overall range | | |
|---|---|---|---|
| | KD: 1 to 10000 | | |
| | Kd:1.5e-4 to 0.1 ; Ka:2e6 to 1e4 | | |
| therapeutic ranges | chronic | intermediate | acute |
| | high affinity | medium affinity | low affinity |
| | KD: 0.1-400 | KD: 400-2000 | KD: 2000-10000 |
| | Kd:1.5e-4 to 8e-3 ; Ka:2e6 to 2e4 | Kd: 8e-3 to 0.08 ; Ka: 2e4 to 5e4 | Kd:0.08 to 0.1 ; Ka: 5e4 to 1e4 |
| optional ranges | KD: 1-200 | KD: 400-1500 | KD: 2000-6000 |
| | Kd:3e-4 to 2e-3; Ka: 1e6 to 1e4 | Kd:2e-3 to 0.05; Ka: 2e4 to 1e4 | Kd:0.08 to 0.1 ; Ka: 5e4 to 2e4 |
| Examples | DMS7327; DOM7h-11-15; DOM7h-14; DOM7h-14-10; DOM7h-14-18; DOM7h-14-19, DOM7h-14-28, DOM7h-14-36 DMS7321; DMS7322 | DOM7h-11; DMS7326; DMS7324; | DOM7h11-12, DOM7h-11-18 DMS7325 |

Figure 2B

| Rat | | | | | |
|---|---|---|---|---|---|
| | | overall range | | | |
| | | KD: 1 to 10000 | | | |
| | | Kd: 2e-3 to 0.15 ; Ka: 2e6 to 1e4 | | | |
| therapeutic ranges | chronic | | intermediate | | acute |
| | high affinity | | medium affinity | | low affinity |
| | KD: 1-300 | | KD: 300-2000 | | KD: 2000-10000 |
| | Kd:2e-3 to 5e-2 ; Ka:2e6 to 2e5 | | Kd:5e-2 to 0.09 ; Ka:2e5 to 4.5e4 | | Kd:0.09 to 0.15 ; Ka: 4.5e4 to 1.5e4 |
| optional ranges | KD: 20-200 | | KD: 400-1800 | | KD: 2000-6000 |
| | Kd:9e-3 to 2e-2 ; Ka: 1e6 to 1e5 | | Kd: 4e-2 to 0.09; Ka:1e5 to 5e4 | | Kd: 0.1 to 0.14 ; Ka: 5e4 to 3e4 |
| Examples | DOM7h-11-15; DOM7h-11-12; DOM7h-11-18, DOM7h-11-19, DOM7h-14-28, DOM7h-14-36, DOM7h-14 DMS7327; DMS7322 | | DOM7h-14-18; DOM7h-14-19; DMS7321; DMS7323, DMS7324, DMS7326;, | | DMS7325; DOM7h-11; |

Figure 2C

| Mouse | | | | |
|---|---|---|---|---|
| | | overall range | | |
| | | KD: 1 to 10000 | | |
| | | Kd: 2e-3 to 0.15 ; Ka: 2e6 to 1e4 | | |
| therapeutic ranges | chronic | intermediate | | acute |
| | high affinity | medium affinity | | low affinity |
| | KD: 1-100 | KD: 100-2000 | | KD: 2000-10000 |
| | Kd:2e-3 to 1e-2 ; Ka:2e6 to 1e5 | Kd:1e-2 to 0.07 ; Ka: 1e5 to 3e4 | | Kd: 0.08 to 0.15; Ka: 4e4 to 1.5e4 |
| optional ranges | KD: 1 to 80 | KD: 120-2000 | | KD: 4000-10000 |
| | Kd:2e-3 to 1e-2 ; Ka: 2e6 to 1.5e5 | Kd: 9e-3 to 0.07 ; Ka: 1.3e5 to 3e4 | | Kd:0.1 to 0.15 ; Ka: 2.5e4 to 1.5e4 |
| Examples | DOM7h-11-15;; DOM7h-14; DOM7h-14-10, DOM7h-14-18, DOM7h-14-19, DOM7h-11-18, DOM7h-11-19, DOM7h-14-28, DOM7h-14-36 DMS7322, DMS7327 | DMS7321; DMS7323; DMS7324; DOM7h-11-12; DMS7326 | | DMS7325; DOM7h-11 |

Figure 2D

SEQUENCE LISTING

```
<160> NUMBER OF SEQ ID NOS: 422

<210> SEQ ID NO 1
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
                20                  25                  30

Leu Ser Trp Tyr Gln Gln Lys Pro Gly Lys Ala Pro Lys Leu Leu Ile
            35                  40                  45

Met Trp Arg Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
    65                  70                  75                  80

Glu Asp Phe Ala Thr Tyr Tyr Cys Ala Gln Gly Leu Arg His Pro Lys
                    85                  90                  95

Thr Phe Gly Gln Gly Thr Lys Val Glu Ile Lys Arg
                100                 105

<210> SEQ ID NO 2
<211> LENGTH: 108
<212> TYPE: PRT
<213> ORGANISM: Artificial Sequence
<220> FEATURE:
<223> OTHER INFORMATION: Derived from a Human Germline sequence.
```

-continued

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Met Lys Pro Met
                85                  90                  95

Thr Phe Gly Gln Gly Thr Lys Val Glu Ile Lys Arg
            100                 105

<210> SEQ ID NO 3
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 3

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Trp Ile Gly Ser Gln
            20                  25                  30

Leu Ser Trp Tyr Gln Gln Lys Pro Gly Glu Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95

Thr Phe Gly Gln Gly Thr Lys Val Glu Ile Lys Arg
            100                 105

<210> SEQ ID NO 4
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Lys
            85                  90                  95
Thr Phe Gly Gln Gly Thr Lys Val Glu Ile Lys Arg
            100                 105

<210> SEQ ID NO 5
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 5

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Trp Ile Gly Ser Gln
            20                  25                  30
Leu Ser Trp Tyr Gln Gln Lys Pro Gly Lys Ala Pro Lys Leu Leu Ile
            35                  40                  45
Met Trp Arg Ser Ser Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Ala Gln Gly Phe Lys Lys Pro Arg
            85                  90                  95
Thr Phe Gly Gln Gly Thr Lys Val Glu Ile Lys Arg
            100                 105

<210> SEQ ID NO 6
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 6
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat tcactctcac catcagcagt ctgcaacct   240 gaagattttg ctacgtacta ctgtgctcag ggtttgaggc atcctaagac gttcggccaa   300
gggaccaagg tggaaatcaa acgg                                          324

<210> SEQ ID NO 7
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 7
gacatccaga tgacccagtc tccatcctcc ctgtctgcat ctgtaggaga ccgtgtcacc    60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat tcactctcac catcagcagt ctgcaacct   240 gaagattttg ctacgtacta ctgtgctcag ggtcttatga agcctatgac gttcggccaa   300

```
gggaccaagg tggaaatcaa acgg                                            324
```

<210> SEQ ID NO 8
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 8

```
gacatccaga tgacccagtc tccatcctcc ctgtctgcat ctgtaggaga ccgtgtcacc     60
atctcttgcc gggcaagtca gtggattggg tctcagttat cttggtacca gcagaaacca   120
ggggaagccc ctaagctcct gatcatgtgg cgttcctcgt tgcaaagtgg ggtcccatca   180
cgtttcagtg gcagtggatc tgggacagat tcactctca ccatcagcag tctgcaacct    240
gaagattttg ctacgtacta ctgtgctcag ggtgcggcgt tgcctaggac gttcggccaa   300
gggaccaagg tggaaatcaa acgg                                           324
```

<210> SEQ ID NO 9
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 9

```
gacatccaga tgacccagtc tccatcctcc ctgtctgcat ctgtaggaga ccgtgtcacc     60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat tcactctca ccatcagcag tctgcaacct    240
gaagattttg ctacatacta ctgtgctcag ggtgcggcgt tgcctaagac gttcggccaa   300
gggaccaagg tggaaatcaa acgg                                           324
```

<210> SEQ ID NO 10
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 10

```
gacatccaga tgacccagtc tccatcctcc ctgtctgcat ctgtaggaga ccgtgtcacc     60
atcacttgcc gggcaagtca gtggattggg tctcagttat cttggtacca gcagaaacca   120
gggaaagccc ctaagctcct gatcatgtgg cgttcctcgt tgcaaagtgg ggtcccatca   180
cgtttcagtg gcagtggatc tgggacagat tcactctca ccatcagcag tctgcaacct    240
gaagattttg ctacgtacta ctgtgctcag ggttttaaga agcctcggac gttcggccaa   300
gggaccaagg tggaaatcaa acgg                                           324
```

<210> SEQ ID NO 11
<211> LENGTH: 120
<212> TYPE: PRT
<213> ORGANISM: Artificial Sequence
<220> FEATURE:
<223> OTHER INFORMATION: Derived from a Human Germline sequence.

<400> SEQUENCE: 11

Glu Val Gln Leu Leu Glu Ser Gly Gly Gly Leu Val Gln Pro Gly Gly

```
            1               5                   10                  15
Ser Leu Arg Leu Ser Cys Ala Ala Ser Gly Phe Thr Phe Ser Gln Tyr
                20                  25                  30

Arg Met His Trp Val Arg Gln Ala Pro Gly Lys Ser Leu Glu Trp Val
            35                  40                  45

Ser Ser Ile Asp Thr Arg Gly Ser Ser Thr Tyr Tyr Ala Asp Pro Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Ala Val Thr Met Phe Ser Pro Phe Phe Asp Tyr Trp Gly Gln
                100                 105                 110

Gly Thr Leu Val Thr Val Ser Ser
            115                 120

<210> SEQ ID NO 12
<211> LENGTH: 123
<212> TYPE: PRT
<213> ORGANISM: Artificial Sequence
<220> FEATURE:
<223> OTHER INFORMATION: Derived from a Human Germline sequence.

<400> SEQUENCE: 12

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Asp Tyr
                20                  25                  30

Gly Met Arg Trp Val Arg Gln Ala Pro Gly Lys Gly Leu Glu Trp Val
            35                  40                  45

Ser Ser Ile Thr Arg Thr Gly Arg Val Thr Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Trp Arg Asn Arg His Gly Glu Tyr Leu Ala Asp Phe Asp Tyr
                100                 105                 110

Trp Gly Gln Gly Thr Leu Val Thr Val Ser Ser
            115                 120

<210> SEQ ID NO 13
<211> LENGTH: 120
<212> TYPE: PRT
<213> ORGANISM: Artificial Sequence
<220> FEATURE:
<223> OTHER INFORMATION: Derived from a Human Germline sequence.

<400> SEQUENCE: 13

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Met Arg Tyr
                20                  25                  30

Arg Met His Trp Val Arg Gln Ala Pro Gly Lys Gly Leu Glu Trp Val
            35                  40                  45

Ser Ser Ile Asp Ser Asn Gly Ser Ser Thr Tyr Tyr Ala Asp Ser Val
        50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Thr Glu Arg Ser Pro Val Phe Asp Tyr Trp Gly Gln
            100                 105                 110

Gly Thr Leu Val Thr Val Ser Ser
            115                 120

<210> SEQ ID NO 14
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 14

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Asp Tyr
                 20                  25                  30

Glu Met His Trp Val Arg Gln Ala Pro Gly Lys Gly Leu Glu Trp Val
             35                  40                  45

Ser Ser Ile Ser Glu Ser Gly Thr Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Arg Phe Ser Ala Ser Thr Phe Asp Tyr Trp Gly Gln Gly
            100                 105                 110

Thr Leu Val Thr Val Ser Ser
            115

<210> SEQ ID NO 15
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 15

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Leu Glu Trp Val
             35                  40                  45

Ser Gln Ile Ser Asn Thr Gly Gly His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly His Trp Glu Pro Phe Asp Tyr Trp Gly Gln Gly
            100                 105                 110

Thr Leu Val Thr Val Ser Ser
            115
```

```
<210> SEQ ID NO 16
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 16
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Tyr Asp Tyr Trp Gly Gln Gly
            100                 105                 110

Thr Leu Val Thr Val Ser Ser
        115

```
<210> SEQ ID NO 17
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 17
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Phe Asp Tyr Trp Gly Gln Gly
            100                 105                 110

Thr Leu Val Thr Val Ser Ser
        115

```
<210> SEQ ID NO 18
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 18
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 19
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 20
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Met Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110

Thr Leu Val Thr Val Ser Ser
        115

<210> SEQ ID NO 21
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 21

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Lys Tyr
                20                  25                  30

Ser Met Gly Trp Val Arg Gln Ala Pro Gly Lys Asp Leu Glu Trp Val
            35                  40                  45

Ser Gln Ile Ser Asn Thr Gly Gly His Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110

Thr Leu Val Thr Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 22

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
            35                  40                  45

Ser Gln Ile Ser Asn Thr Gly Gly His Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Arg Trp Glu Pro Phe Asp His Trp Gly Gln Gly
                100                 105                 110

Thr Leu Val Thr Val Ser Ser
```

```
<210> SEQ ID NO 23
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 23

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Arg Trp Glu Pro Phe Asp Tyr Trp Gly Gln Gly
            100                 105                 110

Thr Leu Val Thr Val Ser Ser
            115

<210> SEQ ID NO 24
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 24

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Thr Gly Arg Trp Glu Pro Phe Asp Tyr Trp Gly Gln Gly
            100                 105                 110

Thr Leu Val Thr Val Ser Ser
            115

<210> SEQ ID NO 25
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 25
```

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
             35                  40                  45

Ser Gln Ile Ser Asn Thr Gly Asp Arg Thr Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
             100                 105                 110

Thr Leu Val Thr Val Ser Ser
             115

<210> SEQ ID NO 26
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 26

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
             35                  40                  45

Ser Gln Ile Ser Asn Thr Gly Asp His Thr Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
             100                 105                 110

Thr Leu Val Thr Val Ser Ser
             115

<210> SEQ ID NO 27
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 27

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Pro Glu Trp Val
             35                  40                  45

Ser Gln Ile Ser Asn Thr Gly Asp Arg Thr Tyr Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 28
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 28

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Pro Glu Trp Val
             35                  40                  45

Ser Gln Ile Ser Asn Thr Gly Asp His Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110

Thr Leu Val Thr Val Ser Ser
            115

<210> SEQ ID NO 29
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 29

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Lys Tyr
                 20                  25                  30

Ser Met Gly Trp Val Arg Gln Ala Pro Gly Lys Asp Leu Glu Trp Val
             35                  40                  45

Ser Gln Ile Ser Asn Thr Gly Asp Arg Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
                100                 105                 110
```

-continued

Thr Leu Val Thr Val Ser Ser
        115

<210> SEQ ID NO 30
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 30

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Asp Leu Glu Trp Val
        35                  40                  45

Ser Gln Ile Ser Asn Thr Gly Asp His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 31
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 31

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Derived from a Human Germline sequence.

-continued

```
<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Lys Pro Phe Glu Tyr Trp Gly Gln Gly
            100                 105                 110

Thr Leu Val Thr Val Ser Ser
        115

<210> SEQ ID NO 34
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45
```

```
Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
                100                 105                 110

Thr Leu Val Thr Val Ser Ser
            115
```

```
<210> SEQ ID NO 35
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 35

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Arg Pro Phe Glu Tyr Trp Gly Gln Gly
                100                 105                 110

Thr Leu Val Thr Val Ser Ser
            115
```

```
<210> SEQ ID NO 36
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 36

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ala Tyr Tyr Cys
                 85                  90                  95

Ala Ile Tyr Thr Gly Arg Trp Glu Pro Phe Asp Tyr Trp Gly Gln Gly
                100                 105                 110
```

```
Thr Leu Val Thr Val Ser Ser
        115

<210> SEQ ID NO 37
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 37

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asn Tyr Trp Gly Gln Gly
            100                 105                 110

Thr Leu Val Thr Val Ser Ser
        115

<210> SEQ ID NO 38
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 38

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 39
<211> LENGTH: 119
<212> TYPE: PRT
<213> ORGANISM: Artificial Sequence
<220> FEATURE:
<223> OTHER INFORMATION: Derived from a Human Germline sequence.
```

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Asp Asn Trp Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Thr Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Gln Tyr Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Ser Met Gly Trp Val Arg Gln Ala Pro Gly Lys Gly Leu Glu Trp Val
        35                  40                  45

```
Ser Gln Ile Ser Asn Thr Gly Asp Arg Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115
```

<210> SEQ ID NO 42
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 42

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
                 20                  25                  30

Ser Met Gly Trp Val Arg Gln Ala Pro Gly Lys Gly Leu Glu Trp Val
             35                  40                  45

Ser Gln Ile Ser Asn Thr Gly Asp Arg Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
            100                 105                 110

Thr Leu Val Thr Val Ser Ser
            115
```

<210> SEQ ID NO 43
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 43

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Leu Glu Trp Val
             35                  40                  45

Ser Gln Ile Ser Asp Thr Gly Asp Arg Arg Tyr Tyr Asp Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Asp Tyr Trp Gly Gln Gly
```

Thr Leu Val Thr Val Ser Ser
        115

<210> SEQ ID NO 44
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 45
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Lys Tyr Trp Gly Gln Gly
            100                 105                 110

Thr Leu Val Thr Val Ser Ser
        115

<210> SEQ ID NO 46
<211> LENGTH: 119
<212> TYPE: PRT
<213> ORGANISM: Artificial Sequence
<220> FEATURE:

<223> OTHER INFORMATION: Derived from a Human Germline sequence.

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Glu Arg Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Glu Tyr Trp Gly Gln Gly
            100                 105                 110

Thr Leu Val Thr Val Ser Ser
            115

<210> SEQ ID NO 47
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Asn Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Tyr Glu Tyr Trp Gly Gln Gly
            100                 105                 110

Thr Leu Val Thr Val Thr Ser
            115

<210> SEQ ID NO 48
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val

```
                35                  40                  45

Ser Gln Ile Ala Asn Thr Gly Asp Arg Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110

Thr Leu Val Thr Val Ser Ser
            115

<210> SEQ ID NO 49
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 49

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Leu Glu Trp Val
                 35                  40                  45

Ser Gln Ile Ala Asn Thr Gly Asp Arg Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Lys Pro Phe Glu Tyr Trp Gly Gln Gly
                100                 105                 110

Thr Leu Val Thr Val Ser Ser
            115

<210> SEQ ID NO 50
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 50

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Leu Glu Trp Val
                 35                  40                  45

Ser Gln Ile Ala Asn Thr Gly Asp Arg Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 53
<211> LENGTH: 119
<212> TYPE: PRT
<213> ORGANISM: Artificial Sequence -continued

```
<220> FEATURE:
<223> OTHER INFORMATION: Derived from a Human Germline sequence.

<400> SEQUENCE: 53

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Tyr Thr Gly Arg Trp Glu Pro Phe Val Tyr Trp Gly Gln Gly
            100                 105                 110

Thr Leu Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 54

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Lys Pro Phe Glu Tyr Trp Gly Gln Gly
            100                 105                 110

Thr Leu Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 55

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30
```

```
Ser Met Gly Trp Val Arg Gln Ala Pro Gly Lys Gly Leu Glu Trp Val
            35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115
```

<210> SEQ ID NO 56
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 56

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115
```

<210> SEQ ID NO 57
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 57

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 58
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 58

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 59
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 59

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Lys Pro Phe Glu Tyr Trp Gly Gln Gly
            100                 105                 110

Thr Leu Val Thr Val Ser Ser
        115

<210> SEQ ID NO 60
<211> LENGTH: 119
<212> TYPE: PRT
```

<213> ORGANISM: Artificial Sequence
<220> FEATURE:
<223> OTHER INFORMATION: Derived from a Human Germline sequence.

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 61
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115

<210> SEQ ID NO 62
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
         35                  40                  45

Ser Gln Ile Ser Asp Thr Gly Asp Arg Arg Tyr Tyr Asp Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ile Tyr Thr Gly Arg Trp Ala Pro Phe Glu Tyr Trp Gly Gln Gly
             100                 105                 110

Thr Leu Val Thr Val Ser Ser
            115

<210> SEQ ID NO 63
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 63

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Arg Tyr Tyr Ala Asp Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Ile Tyr Thr Gly Arg Trp Glu Pro Phe Val Tyr Trp Gly Gln Gly
             100                 105                 110

Thr Leu Val Thr Val Ser Ser
            115

<210> SEQ ID NO 64
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 64

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Gly Asp Arg Arg Tyr Tyr Ala Asp Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys 85                  90                  95
Ala Ile Tyr Thr Gly Arg Trp Lys Pro Phe Glu Tyr Trp Gly Gln Gly
            100                 105                 110

Thr Leu Val Thr Val Ser Ser
        115

<210> SEQ ID NO 65
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 65

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 66

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115

<210> SEQ ID NO 67
<211> LENGTH: 119

```
<212> TYPE: PRT
<213> ORGANISM: Artificial Sequence
<220> FEATURE:
<223> OTHER INFORMATION: Derived from a Human Germline sequence.

<400> SEQUENCE: 67

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 68
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 68

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Phe
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 69
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 69

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Tyr
```

```
                    20                  25                  30
Ser Met Gly Trp Val Arg Gln Ala Pro Gly Lys Gly Leu Glu Trp Val
                35                  40                  45
Ser Gln Ile Ser Asn Thr Ala Asp Arg Thr Tyr Tyr Ala His Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Ala Pro Phe Glu Tyr Trp Gly Gln Gly
            100                 105                 110
Thr Leu Val Thr Val Ser Ser
        115
```

<210> SEQ ID NO 70
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 70

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Phe Lys Tyr
            20                  25                  30
Ser Met Gly Trp Val Arg Gln Ala Pro Gly Lys Gly Leu Glu Trp Val
                35                  40                  45
Ser Gln Ile Ser Asp Thr Gly Asp Arg Arg Tyr Tyr Asp Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ile Tyr Thr Gly Arg Trp Glu Pro Phe Val Tyr Trp Gly Gln Gly
            100                 105                 110
Thr Leu Val Thr Val Ser Ser
        115
```

<210> SEQ ID NO 71
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 71

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Leu Lys Tyr
            20                  25                  30
Ser Met Gly Trp Val Arg Gln Ala Pro Gly Lys Gly Leu Glu Trp Val
                35                  40                  45
Ser Gln Ile Ser Asp Thr Gly Asp Arg Arg Tyr Tyr Asp Asp Ser Val
            50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 72

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ala Asn Thr Gly Asp Arg Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ala Tyr Tyr Cys
                 85                  90                  95

Ala Ile Tyr Thr Gly Arg Trp Pro Asp Phe Asp Tyr Trp Gly Gln Gly
            100                 105                 110

Thr Leu Val Thr Val Ser Ser
        115

<210> SEQ ID NO 73
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 73

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ala Asn Thr Gly Asp Arg Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ala Tyr Tyr Cys
                 85                  90                  95

Ala Ile Tyr Thr Gly Arg Trp Pro Asp Phe Glu Tyr Trp Gly Gln Gly
            100                 105                 110

Thr Leu Val Thr Val Ser Ser
        115

<210> SEQ ID NO 74
```

```
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 74

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Asp Phe Asp Tyr Trp Gly Gln Gly
            100                 105                 110

Thr Leu Val Thr Val Ser Ser
        115

<210> SEQ ID NO 75
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 75

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Asp Phe Glu Tyr Trp Gly Gln Gly
            100                 105                 110

Thr Leu Val Thr Val Ser Ser
        115

<210> SEQ ID NO 76
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 76

Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Asp Phe Asp Tyr Trp Gly Gln Gly
            100                 105                 110

Thr Leu Val Thr Val Ser Ser
            115

<210> SEQ ID NO 77
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Pro Asp Phe Glu Tyr Trp Gly Gln Gly
            100                 105                 110

Thr Leu Val Thr Val Ser Ser
            115

<210> SEQ ID NO 78
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Ala Trp Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 79
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 79

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asp Gly Gly Gln Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 80
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 80

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asp Ser Gly Tyr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115
```

<210> SEQ ID NO 81
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 81

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asp Gly Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115
```

<210> SEQ ID NO 82
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 82

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
        35                  40                  45

Ser Gln Ile Ser Asp Lys Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115
```

<210> SEQ ID NO 83
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 83

```
Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
            35                  40                  45

Ser Gln Ile Ser Glu Thr Gly Arg Arg Thr Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 84
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
            35                  40                  45

Ser Gln Ile Asn Asn Thr Gly Ser Thr Thr Tyr Tyr Ala Asp Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Asp Tyr Trp Gly Gln Gly
            100                 105                 110

Thr Leu Val Thr Val Ser Ser
        115

<210> SEQ ID NO 85
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Pro Glu Trp Val
            35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                    85                  90                  95

Ala Ile Tyr Thr Gly Arg Trp Val Pro Phe Glu Tyr Trp Gly Gln Gly
                100                 105                 110

Thr Leu Val Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Pro Glu Trp Val
            35                  40                  45

Ser Gln Ile Ser Asn Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Ala Pro Phe Glu Tyr Trp Gly Gln Gly
                100                 105                 110

Thr Leu Val Thr Val Ser Ser
        115

<210> SEQ ID NO 87
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Ala His Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Val Pro Phe Glu Tyr Trp Gly Gln Gly
                100                 105                 110

Thr Leu Val Thr Val Ser Ser
        115
```

```
<210> SEQ ID NO 88
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 88
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Val | Lys | Tyr |
|---|---|---|---|---|---|---|---|---|---|---|---|---|---|---|---|
| | | | 20 | | | | | 25 | | | | | 30 | | |

| Ser | Met | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gln | Ile | Ser | Asp | Thr | Ala | Asp | Arg | Thr | Tyr | Tyr | Ala | His | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ile | Tyr | Thr | Gly | Arg | Trp | Ala | Pro | Phe | Glu | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ser |
|---|---|---|---|---|---|---|
| | | | 115 | | | |

```
<210> SEQ ID NO 89
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 89
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Val | Lys | Tyr |
|---|---|---|---|---|---|---|---|---|---|---|---|---|---|---|---|
| | | | 20 | | | | | 25 | | | | | 30 | | |

| Ser | Met | Gly | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gln | Ile | Ser | Asp | Thr | Ala | Asp | Arg | Thr | Tyr | Tyr | Asp | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ile | Tyr | Thr | Gly | Arg | Trp | Arg | Pro | Phe | Glu | Tyr | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ser |
|---|---|---|---|---|---|---|
| | | | 115 | | | |

```
<210> SEQ ID NO 90
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 90
```

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|

```
                1               5                   10                  15
Glu Val Gln Leu Leu Glu Ser Gly Gly Gly Leu Val Gln Pro Gly Gly
Ser Leu Arg Leu Ser Cys Ala Ala Ser Gly Phe Thr Phe Val Lys Tyr
        20                      25                      30
Ser Met Gly Trp Val Arg Gln Ala Pro Gly Lys Gly Leu Glu Trp Val
        35                      40                      45
Ser Gln Ile Ser Asp Thr Ala Asp Arg Thr Tyr Tyr Thr His Ser Val
        50                      55                      60
Lys Gly Arg Phe Thr Ile Ser Arg Asp Asn Ser Lys Asn Thr Leu Tyr
65                      70                      75                      80
Leu Gln Met Asn Ser Leu Arg Ala Glu Asp Thr Ala Val Tyr Tyr Cys
                85                      90                      95
Ala Ile Tyr Thr Gly Arg Trp Ala Pro Phe Glu Tyr Trp Gly Gln Gly
                100                     105                     110
Thr Leu Val Thr Val Ser Ser
                115
```

<210> SEQ ID NO 91
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 91

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Val Lys Tyr
        20                      25                      30
Ser Met Gly Trp Val Arg Gln Ala Pro Gly Lys Gly Leu Glu Trp Val
        35                      40                      45
Ser Gln Ile Ser Asn Thr Ala Asp Arg Arg Tyr Tyr Ala His Ser Val
        50                      55                      60
Lys Gly Arg Phe Thr Ile Ser Arg Asp Asn Ser Lys Asn Thr Leu Tyr
65                      70                      75                      80
Leu Gln Met Asn Ser Leu Arg Ala Glu Asp Thr Ala Val Tyr Tyr Cys
                85                      90                      95
Ala Ile Tyr Thr Gly Arg Trp Ala Pro Phe Glu Tyr Trp Gly Gln Gly
                100                     105                     110
Thr Leu Val Thr Val Ser Ser
                115
```

<210> SEQ ID NO 92
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 92

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Val Lys Tyr
        20                      25                      30
Ser Met Gly Trp Val Arg Gln Ala Pro Gly Lys Gly Leu Glu Trp Val
        35                      40                      45
Ser Gln Ile Leu Asn Thr Ala Asp Arg Thr Tyr Tyr Asp His Ser Val
        50                      55                      60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115
```

<210> SEQ ID NO 93
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 93

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Asp His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115
```

<210> SEQ ID NO 94
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 94

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Arg Tyr Tyr Ala His Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115
```

<210> SEQ ID NO 95
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 95

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 96
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 96

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Tyr Thr Gly Arg Trp Val Ser Phe Glu Tyr Trp Gly Gln Gly
            100                 105                 110

Thr Leu Val Thr Val Ser Ser
        115
```

<210> SEQ ID NO 97
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 97

-continued

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Leu Tyr Thr Gly Arg Trp Val Ser Phe Glu Tyr Trp Gly Gln Gly
             100                 105                 110

Thr Leu Val Thr Val Ser Ser
             115
```

<210> SEQ ID NO 98
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 98

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Val Tyr Thr Gly Arg Trp Val Pro Phe Glu Tyr Trp Gly Gln Gly
             100                 105                 110

Thr Leu Val Thr Val Ser Ser
             115
```

<210> SEQ ID NO 99
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 99

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asn Thr Ala Asp Arg Thr Tyr Tyr Ala His Ser Val
     50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Tyr Thr Gly Arg Trp Val Pro Phe Glu Tyr Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Ala Asp Arg Arg Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 101
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
```

<210> SEQ ID NO 102
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 103
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Ala Asp Arg Arg Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 104
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Gly Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 105
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 105

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Ala Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 106
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asn Thr Ala Asp Arg Arg Tyr Tyr Ala His Ala Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110

Thr Leu Val Thr Val Ser Ser
            115

<210> SEQ ID NO 107
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 107

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Leu Glu Trp Val
             35                  40                  45

Ser Gln Ile Val Asn Thr Gly Asp Arg Arg Tyr Tyr Ala Asp Ala Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110

Thr Leu Val Thr Val Ser Ser
            115

<210> SEQ ID NO 108
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 108

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
                 20                  25                  30

Ser Met Gly Trp Val Arg Gln Ala Pro Gly Lys Gly Leu Glu Trp Val
             35                  40                  45

Ser Gln Ile Ala Asn Thr Gly Asp Arg Arg Tyr Tyr Ala Asp Ala Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110
```

-continued

Thr Leu Val Thr Val Ser Ser
        115

<210> SEQ ID NO 109
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 109

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 110

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Artificial Sequence
<220> FEATURE:
<223> OTHER INFORMATION: Derived from a Human Germline sequence.

-continued

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 112
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ser His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 113
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 113

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

```
Ser Gln Ile Ser Asp Thr Ala Asp Arg Thr Tyr Tyr Thr His Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
                100                 105                 110

Thr Leu Val Thr Val Ser Ser
            115
```

<210> SEQ ID NO 114
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 114

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr Asp Ala Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
                100                 105                 110

Thr Leu Val Thr Val Ser Ser
            115
```

<210> SEQ ID NO 115
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 115

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
                100                 105                 110
```

```
Thr Leu Val Thr Val Ser Ser
        115

<210> SEQ ID NO 116
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 116

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 117
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 117

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
             20                  25                  30

Ser Met Gly Trp Val Arg Gln Ala Pro Gly Lys Gly Leu Glu Trp Val
         35                  40                  45

Ser Gln Ile Ala Asp Thr Gly Asp Arg Arg Tyr Tyr Asp Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 118
<211> LENGTH: 119
<212> TYPE: PRT
<213> ORGANISM: Artificial Sequence
<220> FEATURE:
<223> OTHER INFORMATION: Derived from a Human Germline sequence.
```

<400> SEQUENCE: 118

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115
```

<210> SEQ ID NO 119
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 119

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp His Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115
```

<210> SEQ ID NO 120
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 120

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45
```

```
Ser Gln Ile Ser Asp Thr Gly Asp Arg Arg Tyr Tyr Asp Asp Ala Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
                100                 105                 110

Thr Leu Val Thr Val Ser Ser
            115
```

<210> SEQ ID NO 121
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 121

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
                20                  25                  30

Ser Met Gly Trp Val Arg Gln Ala Pro Gly Lys Gly Leu Glu Trp Val
                35                  40                  45

Ser Gln Ile Ala Asp Thr Ala Asp Arg Arg Tyr Tyr Asp Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
                100                 105                 110

Thr Leu Val Thr Val Ser Ser
            115
```

<210> SEQ ID NO 122
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 122

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
                20                  25                  30

Ser Met Gly Trp Val Arg Gln Ala Pro Gly Lys Gly Leu Glu Trp Val
                35                  40                  45

Ser Gln Ile Ala Asp Thr Gly Asp Arg Arg Tyr Tyr Asp His Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
```

-continued

```
                100                 105                 110
Thr Leu Val Thr Val Ser Ser
        115

<210> SEQ ID NO 123
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 123

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Gly Asp Arg Arg Tyr Tyr Asp Asp Ala Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 124
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 124

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Gly Pro Phe Val Tyr Trp Gly Gln Gly
            100                 105                 110

Thr Leu Val Thr Val Ser Ser
        115

<210> SEQ ID NO 125
<211> LENGTH: 119
<212> TYPE: PRT
<213> ORGANISM: Artificial Sequence
<220> FEATURE:
```

<223> OTHER INFORMATION: Derived from a Human Germline sequence.

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Ala Tyr Trp Gly Gln Gly
            100                 105                 110

Thr Leu Val Thr Val Ser Ser
        115

<210> SEQ ID NO 126
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Gly Pro Phe Gln Tyr Trp Gly Gln Gly
            100                 105                 110

Thr Leu Val Thr Val Ser Ser
        115

<210> SEQ ID NO 127
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val

```
                35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Gln Tyr Trp Gly Gln Gly
            100                 105                 110

Thr Leu Val Thr Val Ser Ser
        115

<210> SEQ ID NO 128
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 128

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 129
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 129

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Ile Tyr Thr Gly Arg Trp Ala Pro Phe Gln Tyr Trp Gly Gln Gly
            100                 105                 110

Thr Leu Val Thr Val Ser Ser
        115

<210> SEQ ID NO 130
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 130

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Gln Tyr Trp Gly Gln Gly
            100                 105                 110

Thr Leu Val Thr Val Ser Ser
        115

<210> SEQ ID NO 131
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 131

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Gly Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 132
<211> LENGTH: 119
<212> TYPE: PRT
<213> ORGANISM: Artificial Sequence

```
<220> FEATURE:
<223> OTHER INFORMATION: Derived from a Human Germline sequence.

<400> SEQUENCE: 132

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 133
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 133

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 134
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 134

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Tyr
            20                  25                  30
```

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
            115

<210> SEQ ID NO 135
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Arg Pro Phe Glu Tyr Trp Gly Gln Gly
            100                 105                 110

Thr Leu Val Thr Val Ser Ser
            115

<210> SEQ ID NO 136
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
            35                  40                  45

Ser Gln Ile Ser Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 137
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 137

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Asp His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Glu Pro Phe Val Tyr Trp Gly Gln Gly
            100                 105                 110

Thr Leu Val Thr Val Ser Ser
        115

<210> SEQ ID NO 138
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 138

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Ala Asp Arg Thr Tyr Tyr Ser His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 139
<211> LENGTH: 119
<212> TYPE: PRT
```

<213> ORGANISM: Artificial Sequence
<220> FEATURE:
<223> OTHER INFORMATION: Derived from a Human Germline sequence.

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ser His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 140
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 141
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 141

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Lys Tyr
            20                  25                  30

```
Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Thr His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
            100                 105                 110

Thr Leu Val Thr Val Ser Ser
        115
```

<210> SEQ ID NO 142
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 142

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115
```

<210> SEQ ID NO 143
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 143

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                 85                  90                  95

Ala Ile Tyr Thr Gly Arg Trp Ala Pro Phe Glu Tyr Trp Gly Gln Gly
                100                 105                 110

Thr Leu Val Thr Val Ser Ser
        115

<210> SEQ ID NO 144
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 144

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Gly Asp Arg Arg Tyr Tyr Asp His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Ala Pro Phe Glu Tyr Trp Gly Gln Gly
                100                 105                 110

Thr Leu Val Thr Val Ser Ser
        115

<210> SEQ ID NO 145
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 145

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Lys Tyr
             20                  25                  30

Ser Met Gly Trp Val Arg Gln Ala Pro Gly Lys Gly Leu Glu Trp Val
         35                  40                  45

Ser Gln Ile Ala Asp Thr Ala Asp Arg Thr Tyr Tyr Ala His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Tyr Thr Gly Arg Trp Val Pro Phe Glu Tyr Trp Gly Gln Gly
                100                 105                 110

Thr Leu Val Thr Val Ser Ser
        115

<210> SEQ ID NO 146
<211> LENGTH: 119
```

```
<212> TYPE: PRT
<213> ORGANISM: Artificial Sequence
<220> FEATURE:
<223> OTHER INFORMATION: Derived from a Human Germline sequence.

<400> SEQUENCE: 146

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 147
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 147

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Thr Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 148
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 148

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
```

-continued

```
                    20                  25                  30
Ser Met Gly Trp Val Arg Gln Ala Pro Gly Lys Gly Leu Glu Trp Val
                35                  40                  45

Ser Gln Ile Ala Asp Thr Ala Asp Arg Thr Tyr Tyr Asp His Ala Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
        115

<210> SEQ ID NO 149
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
                35                  40                  45

Ser Gln Ile Ala Asp Thr Ala Asp Arg Arg Tyr Tyr Ala His Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 150
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
                20                  25                  30

Ser Met Gly Trp Val Arg Gln Ala Pro Gly Lys Gly Leu Glu Trp Val
                35                  40                  45

Ser Gln Ile Ser Asp Thr Ala Asp Arg Arg Tyr Tyr Ala His Ala Val
            50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 151
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 151

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 152
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 152

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 153
```

```
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 153

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Asp His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 154
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 154

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ala Asp Thr Ala Asp Arg Arg Tyr Tyr Asp His Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Ala Pro Phe Glu Tyr Trp Gly Gln Gly
            100                 105                 110

Thr Leu Val Thr Val Ser Ser
        115

<210> SEQ ID NO 155
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 155

Glu Val Gln Leu Leu Glu Ser Gly Gly Gly Leu Val Gln Pro Gly Gly
 1               5                  10                  15
```

Ser Leu Arg Leu Ser Cys Ala Ala Ser Gly Phe Thr Phe Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Arg Tyr Tyr Asp Asp Ala Val
    50                  55                  60

Lys Gly Arg Phe Thr Ile Thr Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Glu Pro Phe Val Tyr Trp Gly Gln Gly
            100                 105                 110

Thr Leu Val Thr Val Ser Ser
            115

<210> SEQ ID NO 156
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asp Thr Ala Asp Arg Thr Tyr Tyr Ala His Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Tyr Thr Gly Arg Trp Val Pro Phe Glu Tyr Trp Gly Gln Gly
            100                 105                 110

Thr Leu Val Thr Val Ser Ser
            115

<210> SEQ ID NO 157
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 157

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Tyr Thr Gly Arg Trp Glu Pro Phe Glu Tyr Trp Gly Gln Gly
            100                 105                 110

Thr Leu Val Thr Val Ser Ser
            115

<210> SEQ ID NO 158
<211> LENGTH: 119
<212> TYPE: PRT
<213> ORGANISM: Artificial Sequence
<220> FEATURE:
<223> OTHER INFORMATION: Derived from a Human Germline sequence.

<400> SEQUENCE: 158

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Phe Lys Tyr
             20                  25                  30

Ser Met Gly Trp Val Arg Gln Ala Pro Gly Lys Gly Leu Glu Trp Val
         35                  40                  45

Ser Gln Ile Ser Asp Thr Gly Asp Arg Arg Tyr Tyr Asp His Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Ile Tyr Thr Gly Arg Trp Ala Pro Phe Glu Tyr Trp Gly Gln Gly
            100                 105                 110

Thr Leu Val Thr Val Ser Ser
            115

<210> SEQ ID NO 159
<211> LENGTH: 360
<212> TYPE: DNA
<213> ORGANISM: Artificial Sequence
<220> FEATURE:
<223> OTHER INFORMATION: Derived from a Human Germline sequence.

<400> SEQUENCE: 159
gaggtgcagc tgttggagtc tgggggaggc ttggtacagc ctggggggtc cctgcgtctc      60
tcctgtgcag cctccggatt cacctttatg aggtatagga tgcattgggt ccgccaggct     120
ccagggaagg gtctagagtg ggtctcatcg attgattcta atggttctag tacatactac     180
gcagactccg tgaagggccg gttcaccatc tcccgcgaca attccaagaa cacgctgtat     240
ctgcaaatga acagcctgcg tgccgaggac accgcggtat attactgtgc gaaagatcgt     300
acggagcgtt cgccggtttt tgactactgg ggtcaggaaa ccctggtcac cgtctcgagc     360

<210> SEQ ID NO 160
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 160
gaggtgcagc tgttggagtc tgggggaggc ttggtgcagc ctggggggtc cctgcgtctc      60
tcctgtgcag cctccggatt cacctttgtt gattatgaga tgcattgggt ccgccaggct     120

```
ccagggaagg gtctagagtg ggtctcatct attagtgaga gtggtacgac gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacgtcgt    300
ttttctgctt ctacgtttga ctactgggt cagggaaccc tggtcaccgt ctcgagc       357
```

<210> SEQ ID NO 161
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 161

```
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg gtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcattggg agccttttga ctactggggt cagggaaccc tggtcaccgt ctcgagc      357
```

<210> SEQ ID NO 162
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 162

```
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg gtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttatga ctactggggt cagggaaccc tggtcaccgt ctcgagc      357
```

<210> SEQ ID NO 163
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 163

```
gaggtgcagc tgttggagtc tgggggaggc ttggtacagc ctgggggtc cctgcgtctc     60 tcctgtgcag cctccggatt caccttttgtt aagtattcga tggggtgggt ccgccaggct   120
ccagggaagg gtctagagtg gtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttttga ctactggggt cagggaaccc tggtcaccgt ctcgagc      357
```

<210> SEQ ID NO 164
<211> LENGTH: 357
<212> TYPE: DNA

<213> ORGANISM: Artificial Sequence
<220> FEATURE:
<223> OTHER INFORMATION: Derived from a Human Germline sequence.

<400> SEQUENCE: 164

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttttga gtactggggt cagggaaccc tggtcaccgt ctcgagc       357
```

<210> SEQ ID NO 165
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 165

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag atttcgata ctgctgatcg tacatactac     180
gcacacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 166
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 166

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 167
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 167

```
gaggtgcagc tgttggagtc tgggggaggc ttggtacagc ctgggggtc cctgcgtctc      60
tcctgtgcag cctccggatt cacctttgtt aagtattcga tgggatgggt ccgccaggct    120
ccagggaaag gtccagagtg gtctcacag atttcgaata cgggtggtca tacatactac    180
gcagactccg tgaagggccg gttcaccatc tcccgcgaca attccaagaa cacgctgtat    240
```

```
ctgcaaatga acagcctgcg tgccgaggac accgcggtat attactgtgc gatatatacg    300
ggtcgttggg agccttttga ctactggggt cagggaaccc tggtcacagt ctcgagc       357
```

<210> SEQ ID NO 168
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 168

```
gaggtgcagc tgttggagtc tggggggaggc ttggtacagc ctggggggtc cctgcgtctc    60
tcctgtgcag cctccggatt cacctttgtt aagtattcga tggggtgggt ccgccaggct    120
ccagggaagg gtctagagtg gtctcacag atttcgaata cgggtggtca tacatactac     180
gcagactccg tgaagggccg gttcaccata tcccgcgaca attccaagaa cacgctgtat    240
atgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 169
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 169

```
gaggtgcagc tgttggagtc tggggggaggc ttggtacagc ctggggggtc cctgcgtctc    60
tcctgtgcag cctccggatt caccttggt aagtattcga tggggtgggt ccgccaggct     120
ccagggaagg atctagagtg gtctcacag atttcgaata cgggtggtca tacatactac     180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 170
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 170

```
gaggtgcagc tgttggagtc aggggggaggc ttggtacagc ctggggggtc cctgcgtctc    60
tcctgtgcag cctccggatt cacctttgtt aagtattcga tggggtgggt ccgccaggct    120
ccagggaagg gtctagagtg gtctcacag atttcgaata cgggtggtca tacatactac     180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttttga ccactggggt caggggaccc tggtcaccgt ctcgagc       357
```

<210> SEQ ID NO 171
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 171

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg gtctcacag atttcgaata cggtgatca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaatatacg   300
ggtcgttggg agccttttga ctactggggt cagggaaccc tggtcaccgt ctcgagc      357
```

<210> SEQ ID NO 172
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 172

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg gtctcacag atttcgaata cggtgatcg tacatactac   180
gcagactccg tgaagggccg gttcaccatc tcccgcgaca attccaagaa cacgctgtat   240
ctgcaaatga acagcctgcg tgccgaggac accgcggtat attactgtgc gaaatatacg   300
ggtcgttggg agccttttga ctactggggt cagggaaccc tggtcaccgt ctcgagc      357
```

<210> SEQ ID NO 173
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 173

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg gtctcacag atttcgaata cggtgatcg tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc      357
```

<210> SEQ ID NO 174
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 174

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg gtctcacag atttcgaata cggtgatca tacatactac   180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc      357
```

<210> SEQ ID NO 175
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 175

```
gaggtgcagc tgttggagtc tgggggaggc ttggtacagc ctgggggtc cctgcgtctc      60
tcctgtgcag cctccggatt cacctttgtt aagtattcga tgggatgggt ccgccaggct    120
ccagggaaag gtccagagtg gtctcacag atttcgaata cgggtgatcg tacatactac     180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcacagt ctcgagc       357
```

<210> SEQ ID NO 176
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 176

```
gaggtgcagc tgttggagtc tgggggaggc ttggtacagc ctgggggtc cctgcgtctc      60
tcctgtgcag cctccggatt cacctttgtt aagtattcga tgggatgggt ccgccaggct    120
ccagggaaag gtccagagtg gtctcacag atttcgaata cgggtgatca tacatactac     180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcacagt ctcgagc       357
```

<210> SEQ ID NO 177
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 177

```
gaggtgcagc tgttggagtc tgggggaggc ttggtacagc ctgggggtc cctgcgtctc      60
tcctgtgcag cctccggatt cacctttggt aagtattcga tggggtgggt ccgccaggct   120
ccagggaagg atctagagtg gtctcacag atttcgaata cgggtgatcg tacatactac    180
gcagactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttga ctactggggt cagggaaccc tggtcaccgt ctcgagc      357
```

<210> SEQ ID NO 178
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 178

```
gaggtgcagc tgttggagtc tgggggaggc ttggtacagc ctgggggtc cctgcgtctc      60
```

| tcctgtgcag cctccggatt cacctttggt aagtattcga tggggtgggt ccgccaggct | 120 |
| ccagggaagg atctagagtg ggtctcacag atttcgaata cgggtgatca tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agccttttga ctactggggt cagggaaccc tggtcaccgt ctcgagc | 357 |

<210> SEQ ID NO 179
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 179

| gaggtgcagc tgttggagtc tgggggaggc ttggtacagc ctggggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcgaata cgggtgatcg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agccttttgt ctactggggt cagggaaccc tggtcaccgt ctcgagc | 357 |

<210> SEQ ID NO 180
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 180

| gaggtgcagc tgttggagtc tgggggaggc ttggtacagc ctggggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcgaata cgggtgatcg tacatactac | 180 |
| gcagactccg tgaagggccg gttcaccatc tcccgcgaca attccaagaa cacgctgtat | 240 |
| ctgcaaatga acagcctgcg tgctgaggac accgcggtat attactgtgc gatatatacg | 300 |
| ggtcgttggg agccttttga gtactggggt cagggaaccc tggtcaccgt ctcgagc | 357 |

<210> SEQ ID NO 181
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 181

| gaggtgcagc tgttggagtc tgggggaggc ttggtacagc ctggggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcgaata cgggtgatcg tacatactac | 180 |
| gcggactccg tgaagggccg gttcaccatc tcccgcgaca attccaagaa cacgctgtat | 240 |
| ctgcaaatga acagcctgcg tgctgaggac accgcggtat attactgtgc gatatatacg | 300 |
| ggtcgttgga agccttttga gtactggggt cagggaaccc tggtcaccgt ctcgagc | 357 |

<210> SEQ ID NO 182
<211> LENGTH: 357

```
<212> TYPE: DNA
<213> ORGANISM: Artificial Sequence
<220> FEATURE:
<223> OTHER INFORMATION: Derived from a Human Germline sequence.

<400> SEQUENCE: 182
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg gtctcacag atttcgaata cgggtgatcg tacatactac     180
gcagactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357

<210> SEQ ID NO 183
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 183
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg gtctcacag atttcgaata cgggtgatcg tacatactac     180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc       357

<210> SEQ ID NO 184
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 184
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg gtctcacag attgcgaata cgggtgatcg tagatactac     180
gcagactctg tgaagggccg gttcaccatc tcccgcgaca attccaagaa cacgctgtat    240
ctgcaaatga acagcctgcg tgccgaggac accgcggcat attactgtgc gatatatacg    300
ggtcgttggg agccttttga ctactggggt cagggaaccc tggtcaccgt ctcgagc       357

<210> SEQ ID NO 185
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 185
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg gtctcacag atttcgaata ctgctgatcg tacatactac     180
```

| | |
|---|---|
| gcacactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agccttttaa ctactgggt cagggaaccc tggtcaccgt ctcgagc | 357 |

<210> SEQ ID NO 186
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 186

| | |
|---|---|
| gaggtgcagc tgttggagtc tgggggaggc ttggtacagc ctggggggtc cctgcgtctc | 60 |
| tcctgtgcag cctccggatt cacctttgtt aagtattcga tggggtgggt ccgccaggct | 120 |
| ccagggaagg gtctagagtg gtctcacag atttcgaata cgggtgatcg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcggtggg cgccttttga gtactgggt cagggaaccc tggtcaccgt ctcgagc | 357 |

<210> SEQ ID NO 187
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 187

| | |
|---|---|
| gaggtgcagc tgttggagtc tgggggaggc ttggtacagc ctggggggtc cctgcgtctc | 60 |
| tcctgtgcag cctccggatt cacctttgtt aagtattcga tggggtgggt ccgccaggct | 120 |
| ccagggaagg gtctagagtg gtctcacag atttcgaata cgggtgatcg tacatactac | 180 |
| gcagactccg tgaagggccg gttcaccatc tcccgcgaca attccaagaa ctcgctgtat | 240 |
| ctgcaaatga acagcctgcg tgccgaggac accgcggtat attactgtgc gatatatacg | 300 |
| ggtcgttggg tgccttttga caactgggt cagggaaccc tggtcaccgt ctcgagc | 357 |

<210> SEQ ID NO 188
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 188

| | |
|---|---|
| gaggtgcagc tgttggagtc tgggggaggc ttggtacagc ctggggggtc cctgcgtctc | 60 |
| tcctgtgcag cctccggatt cacctttatt acgtattcga tggggtgggt ccgccaggct | 120 |
| ccagggaagg gtctagagtg gtctcacag atttcgaata cgggtgatcg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcgttggg agccttttca gtactgggt cagggaaccc tggtcaccgt ctcgagc | 357 |

<210> SEQ ID NO 189
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 189

```
gaggtgcagc tgttggagtc tgggggaggc ttggtacagc ctggggggtc cctgcgtctc        60
tcctgtgcag cctccggatt cacctttggt aagtattcga tggggtgggt ccgccaggct       120
ccagggaagg gtctagagtg ggtctcacag atttcgaata cgggtgatcg tacatactac       180
gcggactccg tgaagggccg gttcaccatc tcccgcgaca attccaagaa cacgctgtat       240
ctgcaaatga acagcctgcg tgccgaggac accgcggtat attactgtgc gatatatacg       300
ggtcgttggg agccttttga ctactggggt cagggaaccc tggtcaccgt ctcgagc          357
```

<210> SEQ ID NO 190
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 190

```
gaggtgcagc tgttggagtc tgggggaggc ttggtacagc ctggggggtc cctgcgtctc        60
tcctgtgcag cctccggatt cacctttttt aagtattcga tggggtgggt ccgccaggct       120
ccagggaagg gtctagagtg ggtctcacag atttcgaata cgggtgatcg tacatactac       180
gcagactccg tgaagggccg gttcaccatc tcccgcgaca attccaagaa cacgctgtat       240
ctgcaaatga acagcctgcg tgccgaagac accgcggtat attactgtgc gatatatacg       300
ggtcgttggg agccttttga ctactggggt cagggaaccc tggtcaccgt ctcgagc          357
```

<210> SEQ ID NO 191
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 191

```
gaggtgcagc tgttggagtc tgggggaggc ttggtacagc ctggggggtc cctgcgtctc        60
tcctgtgcag cctccggatt cacctttgtt aagtattcga tggggtgggt ccgccaggct       120
ccagggaagg gtctagagtg ggtctcacag atttcggata cgggtgatcg tagatactac       180
gatgactctg tgaagggccg gttcaccatc tcccgcgaca attccaagaa cacgctgtat       240
ctgcaaatga acagcctgcg tgccgaggac accgcggtat attactgtgc gatatatacg       300
ggtcgttggg agccttttga ctactggggt cagggaaccc tggtcaccgt ctcgagc          357
```

<210> SEQ ID NO 192
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 192

```
gaggtgcagc tgttggagtc tgggggaggc ttggtacagc ctggggggtc cctgcgtctc        60
tcctgtgcag cctccggatt cacctttgtt aagtattcga tggggtgggt ccgccaggct       120
ccagggaagg gtctagagtg ggtctcacag atttcgaata cgggtgatcg tagatactac       180
gcagacgcgg tgaaggggcg gttcaccatc tcccgcgaca attccaagaa cacgctgtat       240
ctgcaaatga acagcctgcg tgccgaggac accgcggtat attactgtgc gatatatacg       300
```

```
ggtcgttggg agccttttga ctactgggvt cagggaaccc tggtcaccgt ctcgagc      357
```

<210> SEQ ID NO 193
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 193

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata cgggtgatcg tacatactac     180
gcagactccg tgaagggccg gttcaccatc tcccgcgaca attccaagaa cacgctgtat     240
ctgcaaatga acagcctgcg tgctgaggac accgcggtat attactgtgc gatatatacg     300
ggtcgttggg agccttttaa gtactggggt cagggaaccc tggtcaccgt ctcgagc      357
```

<210> SEQ ID NO 194
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 194

```
gaggtgcagc tgttggagtc tgggggaggc ttggtacagc ctggggggtc cctgcgtctc      60
tcctgtgcag cctccggatt cacctttagt aagtattcga tggggtgggt ccgccaggct     120
ccagggaagg gtctagagtg ggtctcacag atttcgaata cgggtgagcg tagatactac     180
gcagactcag tgaagggccg gttcaccatc tcccgcgaca atcccaagaa cacgctgtat     240
ctgcaaatga acagcctgcg tgccgaggac accgcggtat attactgtgc gatatatacg     300
ggtcggtggg agccttttga atactggggt cagggaaccc tggtcaccgt ctcgagc      357
```

<210> SEQ ID NO 195
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 195

```
gaggtgcagc tgttggagtc tgggggaggc ttggtacagc ctggggggtc cctgcgtctc      60
tcctgtgcag cctccggatt cacctttgtt aactattcga tggggtgggt ccgccaggct     120
ccagggaagg gtctagagtg ggtctcacag atttcgaata cgggtgatcg tacatactac     180
gcggactccg tgaagggccg gttcaccatc tcccgcgaca attccaagaa cacgctgtat     240
ctgcaaatga acagcctgcg tgccgaggac accgcggtat attactgtgc gatatatacg     300
ggtcgttggg agccttatga gtactggggt cagggaaccc tggtcaccgt cacgagc      357
```

<210> SEQ ID NO 196
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 196

```
gaggtgcagc tgttggagtc tgggggaggc ttggtacagc ctggggggtc cctgcgtctc      60
```

```
tcctgtgcag cctccggatt cacctttgtt aagtattcga tggggtgggt ccgccaggct    120
ccagggaagg gtctagagtg ggtctcacag attgcgaata cgggtgatcg tagatactac    180
gcagactctg tgaagggccg gttcaccatc tcccgcgata attccaagaa cacactgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 197
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 197

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag attgcgaata cgggtgatcg tagatactac    180
gcagactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga agccttttga gtactggggt cagggaaccc tggtcaccgt ctcgagc       357
```

<210> SEQ ID NO 198
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 198

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag attgcgaata cgggtgatcg tagatactac    180
gcagactctg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 199
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 199

```
gaggtgcagc tgttggagtc tgggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag attgcgaata cgggtgatcg tagatactac    180
gcagactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc       357
```

<210> SEQ ID NO 200

<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 200

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg ggtctcacag attgcgaata cgggtgatcg tagatactac   180
gcagactctg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 201
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 201

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc ggtatatacg   300
ggtcgttggg agccttttgt ctactggggt cagggaaccc tggtcaccgt ctcgagc      357
```

<210> SEQ ID NO 202
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 202

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
gcacactccg tgaagggccg gttcaccatc tcccgcgaca attccaagaa cacgctgtat   240
ctgcaaatga acagcctgcg tgctgaggac accgcggtat attactgtgc gatatatacg   300
ggtcgttgga agccttttga gtactggggt cagggaaccc tggtcaccgt ctcgagc      357
```

<210> SEQ ID NO 203
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 203

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
```

```
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 204
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 204

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc      357
```

<210> SEQ ID NO 205
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 205

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 206
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 206

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcggata cggtgatcg tagatactac   180 gatgactctg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 207
<211> LENGTH: 357
<212> TYPE: DNA
<213> ORGANISM: Artificial Sequence
<220> FEATURE:

<223> OTHER INFORMATION: Derived from a Human Germline sequence.

<400> SEQUENCE: 207

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggcc    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgctgaggac accgcggtat attactgtgc gatatatacg    300
ggtcgttgga agccttttga gtactggggt cagggaaccc tggtcaccgt ctcgagc       357
```

<210> SEQ ID NO 208
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 208

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatact    300
gggcgttggg tgccttttga gtactggggt cagggaaccc tggtcaccgt ctcgagc       357
```

<210> SEQ ID NO 209
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 209

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc       357
```

<210> SEQ ID NO 210
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 210

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
```

```
ggtcggtggg cgccttttga gtactggggt cagggaaccc tggtcaccgt ctcgagc       357
```

<210> SEQ ID NO 211
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 211

```
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg ggtctcacag atttcgaata cgggtgatcg tagatactac   180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc     357
```

<210> SEQ ID NO 212
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 212

```
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg ggtctcacag atttcgaata cgggtgatcg tagatactac   180
gcagacgcgg tgaaggggcg gttcaccatc tcccgcgaca attccaagaa cacgctgtat   240
ctgcaaatga acagcctgcg tgctgaggac accgcggtat attactgtgc gatatatacg   300
ggtcgttgga agccttttga gtactggggt cagggaaccc tggtcaccgt ctcgagc     357
```

<210> SEQ ID NO 213
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 213

```
gaggtgcagc tgttggagtc tgggggaggc ttggtacagc ctgggggtc cctgcgtctc     60
tcctgtgcag cctccggatt cacctttgtt aagtattcga tggggtgggt ccgccaggcc   120
ccagggaagg gtctagagtg ggtctcacag atttcgaata cgggtgatcg tagatactac   180
gcagacgcgg tgaaggggcg gttcaccatc tcccgcgaca attccaagaa cacgctgtat   240
ctgcaaatga acagcctgcg tgccgaagac accgcggtat attactgtgc gatatatact   300
gggcgttggg tgccttttga gtactggggt cagggaaccc tggtcaccgt ctcgagc     357
```

<210> SEQ ID NO 214
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 214

```
gaggtgcagc tgttggagtc tggggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata cgggtgatcg tagatactac   180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc     357
```

<210> SEQ ID NO 215
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 215

```
gaggtgcagc tgttggagtc tggggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcgaata cgggtgatcg tagatactac   180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc     357
```

<210> SEQ ID NO 216
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 216

```
gaggtgcagc tgttggagtc tggggggaggc ttggtacagc ctggggggtc cctgcgtctc    60
tcctgtgcag cctccggatt cacctttttg aagttttcga tggggtgggt ccgccaggct   120
ccagggaagg gtctagagtg ggtctcacag attgcgaata cgggtgatcg tagatactac   180
gcagactctg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc     357
```

<210> SEQ ID NO 217
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 217

```
gaggtgcagc tgttggagtc tggggggaggc ttggtacagc ctggggggtc cctgcgtctc    60
tcctgtgcag cctccggatt cacctttttg aagtattcga tggggtgggt ccgccaggct   120
ccagggaagg gtctagagtg ggtctcacag atttcgaata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc     357
```

-continued

```
<210> SEQ ID NO 218
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 218
gaggtgcagc tgttggagtc tgggggaggc ttggtacagc ctggggggtc cctgcgtctc      60
tcctgtgcag cctccggatt cacctttttc aagtattcga tggggtgggt ccgccaggct     120
ccagggaagg gtctagagtg ggtctcacag atttcggata cgggtgatcg tagatactac     180
gatgactctg tgaagggccg gttcaccatc tcccgcgaca attccaagaa cacgctgtat     240
ctgcaaatga acagcctgcg tgccgaggac accgcggtat attactgtgc gatatatacg     300
ggtcgttggg agccttttgt ctactggggt caggggaaccc tggtcaccgt ctcgagc      357

<210> SEQ ID NO 219
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 219
gaggtgcagc tgttggagtc tgggggaggc ttggtacagc ctggggggtc cctgcgtctc      60
tcctgtgcag cctccggatt cacctttttg aagtattcga tggggtgggt ccgccaggct     120
ccagggaagg gtctagagtg ggtctcacag atttcggata cgggtgatcg tagatactac     180
gatgactctg tgaagggccg gttcaccatc tcccgcgaca attccaagaa cacgctgtat     240
ctgcaaatga acagcctgcg tgccgaggac accgcggtat attactgtgc gatatatacg     300
ggtcgttggg agccttttgt ctactggggt cagggaaccc tggtcaccgt ctcgagc       357

<210> SEQ ID NO 220
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 220
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag attgcgaata cgggtgatcg tagatactac     180
gcagactctg tgaagggccg gttcaccatc tcccgcgaca attccaagaa cacgctgtat     240
ctgcaaatga acagcctgcg tgccgaggac accgcggcat attactgtgc gatatatacg     300
ggtcggtggc ccgactttga ctactggggt cagggaaccc tggtcaccgt ctcgagc       357

<210> SEQ ID NO 221
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 221
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
```

| | |
|---|---|
| ccagggaagg gtctagagtg ggtctcacag attgcgaata cgggtgatcg tagatactac | 180 |
| gcagactctg tgaagggccg gttcaccatc tcccgcgaca attccaagaa cacgctgtat | 240 |
| ctgcaaatga acagcctgcg tgccgaggac accgcggcat attactgtgc gatatatacg | 300 |
| ggtcggtggc ccgactttga gtactggggt cagggaaccc tggtcaccgt ctcgagc | 357 |

<210> SEQ ID NO 222
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 222

| | |
|---|---|
| gaggtgcagc tgttggagtc tgggggaggc ttggtacagc ctgggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcgaata ctgctgatcg tacatactac | 180 |
| gcacactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcggtggc ccgactttga ctactggggt cagggaaccc tggtcaccgt ctcgagc | 357 |

<210> SEQ ID NO 223
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 223

| | |
|---|---|
| gaggtgcagc tgttggagtc tgggggaggc ttggtacagc ctgggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcgaata ctgctgatcg tacatactac | 180 |
| gcacactccg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcggtggc ccgactttga gtactggggt cagggaaccc tggtcaccgt ctcgagc | 357 |

<210> SEQ ID NO 224
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 224

| | |
|---|---|
| gaggtgcagc tgttggagtc tgggggaggc ttggtacagc ctgggggtc cctgcgtctc | 60 |
| tcctgtgcag cctccggatt cacctttgtt aagtattcga tggggtgggt ccgccaggct | 120 |
| ccagggaagg gtctagagtg ggtctcacag atttcggata cgggtgatcg tagatactac | 180 |
| gatgactctg tgaagggccg gttcaccatc tcccgcgaca attccaagaa cacgctgtat | 240 |
| ctgcaaatga acagcctgcg tgccgaggac accgcggtat attactgtgc gatatatacg | 300 |
| ggtcggtggc ccgactttga ctactggggt cagggaaccc tggtcaccgt ctcgagc | 357 |

<210> SEQ ID NO 225
<211> LENGTH: 357
<212> TYPE: DNA
<213> ORGANISM: Artificial Sequence

```
<220> FEATURE:
<223> OTHER INFORMATION: Derived from a Human Germline sequence.

<400> SEQUENCE: 225
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag atttcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcggtggc ccgactttga gtactggggt cagggaaccc tggtcaccgt ctcgagc       357

<210> SEQ ID NO 226
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 226
gaggtgcagc tgttggagtc tgggggaggc ttggtacagc ctgggggtc cctgcgtctc      60 tcctgtgcag cctccggatt cacctttgtt aagtattcga tgggatgggt ccgccaggct    120
ccagggaaag gtccagagtg ggtctcacag atttcggcct gggtgacag gacatactac    180 gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357

<210> SEQ ID NO 227
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 227
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaaag gtccagagtg ggtctcacag atttcggacg gcggtcagag gacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357

<210> SEQ ID NO 228
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 228
gaggtgcagc tgttggagtc tgggggaggc ttggtacagc ctgggggtc cctgcgtctc      60 tcctgtgcag cctccggatt cacctttgtt aagtattcga tgggatgggt ccgccaggct    120
ccagggaaag gtccagagtg ggtctcacag atttcggact ccggttaccg cacatactac    180
gcagactccg tgaagggccg gttcaccatc tcccgcgaca attccaagaa cacgctgtat    240
```

-continued

```
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 229
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 229

```
gaggtgcagc tgttggagtc tgggggaggc ttggtacagc ctgggggtc cctgcgtctc     60 tcctgtgcag cctccggatt cacctttgtt aagtattcga tgggtgggt ccgccaggct    120 ccagggaagg gtccagagtg ggtctcacag atttcggacg ggggtacgcg gacatactac   180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 230
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 230

```
gaggtgcagc tgttggagtc tgggggaggc ttggtacagc ctgggggtc cctgcgtctc     60 tcctgtgcag cctccggatt cacctttgtt aagtattcga tgggatgggt ccgccaggct   120
ccagggaaag gtccagagtg ggtctcacag atttcggaca agggtacgcg cacatactac   180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 231
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 231

```
gaggtgcagc tgttggagtc tgggggaggc ttggtacagc ctgggggtc cctgcgtctc     60 tcctgtgcag cctccggatt cacctttgtt aagtattcga tgggatgggt ccgccaggct   120
ccagggaaag gtccagagtg ggtctcacag atttcggaga ccggtcgcag gacatactac   180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactggggt cagggaaccc tggtcaccgt ctcgagc       357
```

<210> SEQ ID NO 232
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 232

```
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg ggtctcacag attaacaata cgggttcgac cacatactac    180
gcagactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttga ctactgggt cagggaaccc tggtcaccgt ctcgagc       357
```

<210> SEQ ID NO 233
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 233

```
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtccagagtg gtctcacag atttcgaata ctgctgatcg tacatactac     180
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactgggt cagggaaccc tggtcaccgt ctcgagc       357
```

<210> SEQ ID NO 234
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 234

```
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtccagagtg gtctcacag atttcgaata ctgctgatcg tacatactac     180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactgggt cagggaaccc tggtcaccgt ctcgagc       357
```

<210> SEQ ID NO 235
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 235

```
gaggtgcagc tgttggagtc tgggggaggc ttggtacagc ctgggggtc cctgcgtctc      60 tcctgtgcag cctccggatt cacctttgtt aagtattcga tggggtgggt ccgccaggct    120
ccagggaagg gtctagagtg gtctcacag atttcggata ctgctgatcg tacatactac     180
gcacactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactgggt cagggaaccc tggtcaccgt ctcgagc       357
```

<210> SEQ ID NO 236
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 236

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 237
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 237

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tacatactac   180
gatgactctg tgaagggccg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc      357
```

<210> SEQ ID NO 238
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 238

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
ccagggaagg gtctagagtg ggtctcacag atttcggata ctgctgatcg tacatactac   180
acacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 239
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 239

```
gaggtgcagc tgttggagtc tggggggaggc ttggtacagc ctgggggggtc cctgcgtctc    60
tcctgtgcag cctccggatt cacctttgtt aagtattcga tggggtgggt ccgccaggct   120
```

```
ccagggaagg gtctagagtg ggtctcacag atttcgaata ctgctgatcg cagatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 240
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 240

```
gaggtgcagc tgttggagtc tggggaggc ttggtacagc ctgggggtc cctgcgtctc      60 tcctgtgcag cctccggatt caccttgtt aagtattcga tggggtgggt ccgccaggct    120
ccagggaagg gtctagagtg ggtctcacag attttgaata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 241
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 241

```
gaggtgcagc tgttggagtc tggggaggc ttggtacagc ctgggggtc cctgcgtctc      60 tcctgtgcag cctccggatt caccttgtt aagtattcga tggggtgggt ccgccaggct    120
ccagggaagg gtctagagtg ggtctcacag atttcgaata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 242
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 242

```
gaggtgcagc tgttggagtc tggggaggc ttggtacagc ctgggggtc cctgcgtctc      60 tcctgtgcag cctccggatt caccttgtt aagtattcga tggggtgggt ccgccaggct    120
ccagggaagg gtctagagtg ggtctcacag atttcggata ctgctgatcg tagatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 243
<211> LENGTH: 357
<212> TYPE: DNA

<213> ORGANISM: Artificial Sequence
<220> FEATURE:
<223> OTHER INFORMATION: Derived from a Human Germline sequence.

<400> SEQUENCE: 243

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcggata ctgctgatcg tagatactac     180
gatcactccg tgaagggccg gttcaccatc tcccgcgaca attccaagaa cacgctgtat     240
ctgcaaatga acagcctgcg tgccgaggac accgcggtat attactgtgc gatatatacg     300
ggtcggtggg cgccttttga gtactggggt cagggaaccc tggtcaccgt ctcgagc       357
```

<210> SEQ ID NO 244
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 244

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata ctgctgatcg tacatactac     180
gcacactccg tgaagggccg gttcaccatc tcccgcgaca attccaagaa cacgctgtat     240
ctgcaaatga acagcctgcg tgccgaggac accgcggtat attactgtgc ggtatatact     300
gggcgttggg tgtcttttga gtactggggt cagggaaccc tggtcaccgt ctcgagc       357
```

<210> SEQ ID NO 245
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 245

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata ctgctgatcg tacatactac     180
gcacactccg tgaagggccg gttcaccatc tcccgcgaca attccaagaa cacgctgtat     240
ctgcaaatga acagcctgcg tgccgaggac accgcggtat attactgtgc gctatatact     300
gggcgttggg tgtcttttga gtactggggt cagggaaccc tggtcaccgt ctcgagc       357
```

<210> SEQ ID NO 246
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 246

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcgaata ctgctgatcg tacatactac     180
gcacactccg tgaagggccg gtttaccatc tcccgcgaca attccaagaa cacgctgtat     240
```

```
ctgcaaatga acagcctgcg tgccgaggac accgcggtat attactgtgc ggtatatact    300
gggcgttggg tgccttttga gtactggggt cagggaaccc tggtcaccgt ctcgagc       357
```

<210> SEQ ID NO 247
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 247

```
gaggtgcagc tgttggagtc tgggggaggc ttggtacagc ctgggggtc  cctgcgtctc    60 tcctgtgcag cctccggatt cacctttgtt aagtattcga tggggtgggt ccgccaggct    120
ccagggaagg gtctagagtg ggtctcacag atttcgaata ctgctgatcg tacatactac    180
gcacactccg tgaagggccg gttcaccatc tcccgcgaca attccaagaa cacgctgtat    240
ctgcaaatga acagcctgcg tgccgaggac accgcggtat attactgtgc gctatatact    300
gggcgttggg tgccttttga gtactggggt cagggaaccc tggtcaccgt ctcgagc       357
```

<210> SEQ ID NO 248
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 248

```
gaggtgcagc tgttggagtc tgggggaggc ttggtacagc ctgggggtc  cctgcgtctc    60 tcctgtgcag cctccggatt cacctttgtt aagtattcga tggggtgggt ccgccaggct    120
ccagggaagg gtctagagtg ggtctcacag attgcgaata ctgctgatcg tagatactac    180
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc       357
```

<210> SEQ ID NO 249
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 249

```
gaggtgcagc tgttggagtc tgggggaggc ttggtacagc ctgggggtc  cctgcgtctc    60 tcctgtgcag cctccggatt cacctttgtt aagtattcga tggggtgggt ccgccaggct    120
ccagggaagg gtctagagtg ggtctcacag atttcgaata ctgctgatcg tagatactac    180
gcagacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 250
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 250

```
gaggtgcagc tgttggagtc tgggggaggc ttggtacagc ctggggggtc cctgcgtctc    60
tcctgtgcgg cctccggatt cacctttgtt aagtattcga tggggtgggt ccgccaggct   120
ccagggaagg gtctagagtg gtctcacag atttcgaata cgggcgatcg tagatactac    180
gcacacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 251
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 251

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg gtctcacag attgcgaata ctgctgatcg tagatactac    180
gcagacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 252
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 252

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg gtctcacag attgcgaata cgggtgatcg tagatactac    180
gcacacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 253
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 253

```
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg gtctcacag atttcgaata ctgctgatcg tagatactac    180
gcacacgcgg tgaaggggcg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc      357
```

<210> SEQ ID NO 254
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 254

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag attgcgaata cggctgatcg tagatactac     180
gcacacgcgg tgaaggggcg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 255
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 255

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag attgtgaata cgggtgatcg tagatactac     180
gcagacgcgg tgaaggggcg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 256
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 256

```
gaggtgcagc tgttggagtc tgggggaggc ttggtacagc ctgggggtc cctgcgtctc      60
tcctgtgcag cctccggatt cacctttgtt aagtattcga tggggtgggt ccgccaggct    120
ccagggaagg gtctagagtg gtctcacag attgcgaata cgggtgatcg tagatactac     180
gcagacgcgg tgaaggggcg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 257
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 257

```
gaggtgcagc tgttggagtc tgggggaggc ttggtacagc ctgggggtc cctgcgtctc      60
```

```
tcctgtgcag cctccggatt cacctttgtt aagtattcga tggggtgggt ccgccaggct    120
ccagggaagg gtctagagtg ggtctcacag atttcggata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 258
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 258

```
gaggtgcagc tgttggagtc tgggggaggc ttggtacagc ctgggggggtc cctgcgtctc    60 tcctgtgcag cctccggatt cacctttgtt aagtattcga tggggtgggt ccgccaggct   120
ccagggaagg gtctagagtg ggtctcacag atttcggata ctgctgatcg tacatactac   180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttgga ggccttttga gtactggggt cagggaaccc tggtcaccgt ctcgagc     357
```

<210> SEQ ID NO 259
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 259

```
gaggtgcagc tgttggagtc tgggggaggc ttggtacagc ctgggggggtc cctgcgtctc    60 tcctgtgcag cctccggatt cacctttgtt aagtattcga tggggtgggt ccgccaggct   120
ccagggaagg gtctagagtg ggtctcacag atttcggata ctgctgatcg tacatactac   180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg agccttttgt ctactggggt cagggaaccc tggtcaccgt ctcgagc     357
```

<210> SEQ ID NO 260
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 260

```
gaggtgcagc tgttggagtc tgggggaggc ttggtacagc ctgggggggtc cctgcgtctc    60 tcctgtgcag cctccggatt cacctttgtt aagtattcga tggggtgggt ccgccaggct   120
ccagggaagg gtctagagtg ggtctcacag atttcggata ctgctgatcg tacatactac   180
tcacactccg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc     357
```

<210> SEQ ID NO 261
<211> LENGTH: 357

<212> TYPE: DNA
<213> ORGANISM: Artificial Sequence
<220> FEATURE:
<223> OTHER INFORMATION: Derived from a Human Germline sequence.

<400> SEQUENCE: 261

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcggata ctgctgatcg tacatactac     180
acacactccg tgaagggccg gttcaccatc tcccgcgaca attccaagaa cacgctgtat     240
ctgcaaatga acagcctgcg tgctgaggac accgcggtat attactgtgc gatatatact     300
gggcgttggg tgccttttga gtactggggt cagggaaccc tggtcaccgt ctcgagc        357
```

<210> SEQ ID NO 262
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 262

```
gaggtgcagc tgttggagtc tgggggaggc ttggtacagc ctggggggtc cctgcgtctc      60
tcctgtgcag cctccggatt cacctttgtt aagtattcga tggggtgggt ccgccaggct     120
ccagggaagg gtctagagtg ggtctcacag atttcggata ctgctgatcg tacatactac     180
acagacgcgg tgaaggggcg gttcaccatc tcccgcgaca attccaagaa cacgctgtat     240
ctgcaaatga acagcctgcg tgccgaggac accgcggtat attactgtgc gatatatacg     300
ggtcgttggg agccttttgt ctactggggt cagggaaccc tggtcaccgt ctcgagc        357
```

<210> SEQ ID NO 263
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 263

```
gaggtgcagc tgttggagtc tgggggaggc ttggtacagc ctggggggtc cctgcgtctc      60
tcctgtgcag cctccggatt cacctttttc aagtattcga tggggtgggt ccgccaggct     120
ccagggaagg gtctagagtg ggtctcacag atttcggata ctgctgatcg tacatactac     180
gcacactccg tgaagggccg gttcaccatc tcccgcgaca attccaagaa cacgctgtat     240
ctgcaaatga acagcctgcg tgccgaggac accgcggtat attactgtgc gatatatacg     300
ggtcggtggg cgccttttga gtactggggt cagggaaccc tggtcaccgt ctcgagc        357
```

<210> SEQ ID NO 264
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 264

```
gaggtgcagc tgttggagtc tgggggaggc ttggtacagc ctggggggtc cctgcgtctc      60
tcctgtgcag cctccggatt cacctttttg aagtattcga tggggtgggt ccgccaggct     120
ccagggaagg gtctagagtg ggtctcacag atttcggata ctgctgatcg tacatactac     180
```

```
gcacactccg tgaagggccg gttcaccatc tcccgcgaca attccaagaa cacgctgtat    240
ctgcaaatga acagcctgcg tgccgaggac accgcggtat attactgtgc gatatatacg    300
ggtcggtggg cgccttttga gtactggggt cagggaaccc tggtcaccgt ctcgagc      357
```

<210> SEQ ID NO 265
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 265

```
gaggtgcagc tgttggagtc tgggggaggc ttggtacagc ctggggggtc cctgcgtctc    60
tcctgtgcag cctccggatt caccttttc aagtattcga tggggtgggt ccgccaggct    120
ccagggaagg gtctagagtg ggtctcacag attgcggata cgggtgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc      357
```

<210> SEQ ID NO 266
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 266

```
gaggtgcagc tgttggagtc tgggggaggc ttggtacagc ctggggggtc cctgcgtctc    60
tcctgtgcag cctccggatt caccttttc aagtattcga tggggtgggt ccgccaggct    120
ccagggaagg gtctagagtg ggtctcacag atttcggata ctgctgatcg tagatactac    180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc      357
```

<210> SEQ ID NO 267
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 267

```
gaggtgcagc tgttggagtc tgggggaggc ttggtacagc ctggggggtc cctgcgcctc    60
tcctgtgcag cctccggatt caccttttc aagtattcga tggggtgggt ccgccaggct    120
ccagggaagg gtctagagtg ggtctcacag atttcggata cgggtgatcg tagatactac    180
gatcactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg aaccttttgt ctactggggt cagggaaccc tggtcaccgt ctcgagc      357
```

<210> SEQ ID NO 268
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 268

```
gaggtgcagc tgttggagtc tgggggaggc ttggtacagc ctggggggtc cctgcgtctc      60
tcctgtgcag cctccggatt caccttttc aagtattcga tggggtgggt ccgccaggct      120
ccagggaagg gtctagagtg gtctcacag atttcggata cggtgatcg tagatactac      180
gatgacgcgg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 269
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 269

```
gaggtgcagc tgttggagtc tgggggaggc ttggtacagc ctggggggtc cctgcgtctc      60
tcctgtgcag cctccggatt caccttttc aagtattcga tggggtgggt ccgccaggct      120
ccagggaagg gtctagagtg gtctcacag attgcggata ctgctgatcg tagatactac      180
gatgactctg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 270
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 270

```
gaggtgcagc tgttggagtc tgggggaggc ttggtacagc ctggggggtc cctgcgtctc      60
tcctgtgcag cctccggatt caccttttc aagtattcga tggggtgggt ccgccaggct      120
ccagggaagg gtctagagtg gtctcacag attgcggata cggtgatcg tagatactac      180
gatcactctg tgaagggccg gttcactatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc       357
```

<210> SEQ ID NO 271
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 271

```
gaggtgcagc tgttggagtc tgggggaggc ttggtacagc ctggggggtc cctgcgtctc      60
tcctgtgcag cctccggatt caccttttc aagtattcga tggggtgggt ccgccaggct      120
ccagggaagg gtctagagtg gtctcacag attgcggata cggtgatcg tagatactac      180
gatgacgcgg tgaagggccg gttcaccatc tcccgcgaca attccaagaa cacgctgtat    240
ctgcaaatga acagcctgcg tgccgaggac accgcggtat attactgtgc gatatatacg    300
```

```
<210> SEQ ID NO 272
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 272
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg ggccttttgt ctactgggggt cagggaaccc tggtcaccgt ctcgagc    357

<210> SEQ ID NO 273
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 273
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg tgccttttgc ctactgggggt cagggaaccc tggtcaccgt ctcgagc    357

<210> SEQ ID NO 274
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 274
gaggtgcagc tgttggagtc tgggggaggc ttggtacagc ctgggggtc cctgcgtctc     60
tcctgtgcag cctccggatt cacctttgtt aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg gaccttttca gtactgggggt cagggaaccc tggtcaccgt ctcgagc    357

<210> SEQ ID NO 275
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 275
gaggtgcagc tgttggagtc tgggggaggc ttggtacagc ctgggggtc cctgcgtctc     60
```

```
tcctgtgcag cctccggatt cacctttgtt aagtattcga tggggtgggt ccgccaggct      120
ccagggaagg gtctagagtg ggtctcacag atttcggata ctgctgatcg tacatactac      180
gcacactccg tgaagggccg gttcaccatc tcccgcgaca attccaagaa cacgctgtat      240
ctgcaaatga acagcctgcg tgccgaggac accgcggtat attactgtgc gatatatacg      300
ggtcgttggg agccttttca gtactggggt cagggaactc tggtcaccgt ctcgagc         357
```

<210> SEQ ID NO 276
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 276

```
gaggtgcagc tgttggagtc tgggggaggc ttggtacagc ctgggggttc cctgcgtctc      60
tcctgtgcag cctccggatt cacctttgtt aagtattcga tggggtgggt ccgccaggct      120
ccagggaagg gtctagagtg ggtctcacag atttcggata ctgctgatcg tacatactac      180
gcacactccg tgaagggccg gttcaccatc tcccgcgaca attccaagaa cacgctgtat      240
ctgcaaatga acagcctgcg tgccgaggac accgcggtat attactgtgc gatatatacg      300
ggtcgttggg cgccttttga gtactggggt cagggaaccc tggtcaccgt ctcgagc         357
```

<210> SEQ ID NO 277
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 277

```
gaggtgcagc tgttggagtc tgggggaggc ttggtacagc ctgggggttc cctgcgtctc      60
tcctgtgcag cctccggatt cacctttgtt aagtattcga tggggtgggt ccgccaggct      120
ccagggaagg gtctagagtg ggtctcacag atttcggata ctgctgatcg tacatactac      180
gcacactccg tgaagggccg gttcaccatc tcccgcgaca attccaagaa cacgctgtat      240
ctgcaaatga acagcctgcg tgccgaggac accgcggtat attactgtgc gatatatacg      300
ggtcgttggg cgccttttca gtactggggt cagggaactc tggtcaccgt ctcgagc         357
```

<210> SEQ ID NO 278
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 278

```
gaggtgcagc tgttggagtc tgggggaggc ttggtacagc ctgggggttc cctgcgtctc      60
tcctgtgcag cctccggatt cacctttgtt aagtattcga tggggtgggt ccgccaggct      120
ccagggaagg gtctagagtg ggtctcacag atttcggata ctgctgatcg tacatactac      180
gcacactccg tgaagggccg gttcaccatc tcccgcgaca attccaagaa cacgctgtat      240
ctgcaaatga acagcctgcg tgccgaggac accgcggtat attactgtgc gatatatacg      300
ggtcgttggg tgccttttca gtactggggt cagggcaccc tggtcaccgt ctcgagc         357
```

<210> SEQ ID NO 279

```
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 279
gaggtgcagc tgttggagtc tgggggaggc ttggtacagc ctggggggtc cctgcgtctc    60
tcctgtgcag cctccggatt cacctttgtt aagtattcga tggggtgggt ccgccaggct   120
ccagggaagg gtctagagtg ggtctcacag atttcggata ccggtgatcg tagatactac   180
gatcactctg tgaagggccg gttcactatc tcccgcgaca attccaagaa cacgctgtat   240
ctgcaaatga acagcctgcg tgccgaggac accgcggtat attactgtgc gatatatacg   300
ggtcggtggg cgccttttga gtactggggt caggggaccc tggtcaccgt ctcgagc      357

<210> SEQ ID NO 280
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 280
gaggtgcagc tgttggagtc tgggggaggc ttggtacagc ctggggggtc cctgcgtctc    60
tcctgtgcag cctccggatt cacctttttg aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt caggggaccc tggtcaccgt ctcgagc      357

<210> SEQ ID NO 281
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 281
gaggtgcagc tgttggagtc tgggggaggc ttggtacagc ctggggggtc cctgcgtctc    60
tcctgtgcag cctccggatt caccttttc aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt caggggaccc tggtcaccgt ctcgagc      357

<210> SEQ ID NO 282
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 282
gaggtgcagc tgttggagtc tgggggaggc ttggtacagc ctggggggtc cctgcgtctc    60
tcctgtgcag cctccggatt cacctttttg aagtattcga tggggtgggt ccgccaggct   120
ccagggaagg gtctagagtg ggtctcacag atttcggata ctgctgatcg tacatactac   180
```

```
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc      357
```

<210> SEQ ID NO 283
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 283

```
gaggtgcagc tgttggagtc tgggggaggc ttggtacagc ctgggggtc cctgcgtctc      60 tcctgtgcag cctccggatt cacctttttc aagtattcga tggggtgggt ccgccaggct    120
ccagggaagg gtctagagtg ggtctcacag atttcggata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttgga ggccttttga gtactggggt cagggaaccc tggtcaccgt ctcgagc      357
```

<210> SEQ ID NO 284
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 284

```
gaggtgcagc tgttggagtc tgggggaggc ttggtacagc ctgggggtc cctgcgtctc      60 tcctgtgcag cctccggatt cacctttttc aagtattcga tggggtgggt ccgccaggct    120
ccagggaagg gtctagagtg ggtctcacag atttcggata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc      357
```

<210> SEQ ID NO 285
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 285

```
gaggtgcagc tgttggagtc tgggggaggc ttggtacagc ctgggggtc cctgcgtctc      60 tcctgtgcag cctccggatt caccttttg aagtattcga tggggtgggt ccgccaggct    120
ccagggaagg gtctagagtg ggtctcacag atttcggata ctgctgatcg tacatactac    180
gatcactccg tgaagggccg gttcaccatc tcccgcgaca attccaagaa cacgctgtat    240
ctgcaaatga acagcctgcg tgccgaggac accgcggtat attactgtgc gatatatacg    300
ggtcgttggg agccttttgt ctactggggt cagggaaccc tggtcaccgt ctcgagc      357
```

<210> SEQ ID NO 286
<211> LENGTH: 357
<212> TYPE: DNA
<213> ORGANISM: Artificial Sequence
<220> FEATURE:

<223> OTHER INFORMATION: Derived from a Human Germline sequence.

<400> SEQUENCE: 286

| gaggtgcagc tgttggagtc tgggggaggc ttggtacagc ctggggggtc cctgcgtctc | 60 |
| tcctgtgcag cctccggatt cacctttttg aagtattcga tggggtgggt ccgccaggct | 120 |
| ccagggaagg gtctagagtg ggtctcacag atttcggata ctgctgatcg tacatactac | 180 |
| tcacactccg tgaagggccg gttcaccatc tcccgcgaca attccaagaa cacgctgtat | 240 |
| ctgcaaatga acagcctgcg tgctgaggac accgcggtat attactgtgc gatatatact | 300 |
| gggcgttggg tgccttttga gtactggggt cagggaaccc tggtcaccgt ctcgagc | 357 |

<210> SEQ ID NO 287
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 287

| gaggtgcagc tgttggagtc tgggggaggc ttggtacagc ctggggggtc cctgcgtctc | 60 |
| tcctgtgcag cctccggatt cacctttttc aagtattcga tggggtgggt ccgccaggct | 120 |
| ccagggaagg gtctagagtg ggtctcacag atttcggata ctgctgatcg tacatactac | 180 |
| tcacactccg tgaagggccg gttcaccatc tcccgcgaca attccaagaa cacgctgtat | 240 |
| ctgcaaatga acagcctgcg tgctgaggac accgcggtat attactgtgc gatatatact | 300 |
| gggcgttggg tgccttttga gtactggggt cagggaaccc tggtcaccgt ctcgagc | 357 |

<210> SEQ ID NO 288
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 288

| gaggtgcagc tgttggagtc tgggggaggc ttggtacagc ctggggggtc cctgcgtctc | 60 |
| tcctgtgcag cctccggatt cacctttttc aagtattcga tggggtgggt ccgccaggct | 120 |
| ccagggaagg gtctagagtg ggtctcacag atttcggata ctgctgatcg tacatactac | 180 |
| acacactccg tgaagggccg gttcaccatc tcccgcgaca attccaagaa cacgctgtat | 240 |
| ctgcaaatga acagcctgcg tgctgaggac accgcggtat attactgtgc gatatatact | 300 |
| gggcgttggg tgccttttga gtactggggt cagggaaccc tggtcaccgt ctcgagc | 357 |

<210> SEQ ID NO 289
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 289

| gaggtgcagc tgttggagtc tgggggaggc ttggtacagc ctggggggtc cctgcgtctc | 60 |
| tcctgtgcag cctccggatt cacctttttg aagtattcga tggggtgggt ccgccaggct | 120 |
| ccagggaagg gtctagagtg ggtctcacag atttcggata ctgctgatcg tacatactac | 180 |
| acacactccg tgaagggccg gttcaccatc tcccgcgaca attccaagaa cacgctgtat | 240 |
| ctgcaaatga acagcctgcg tgctgaggac accgcggtat attactgtgc gatatatact | 300 |

```
gggcgttggg tgccttttga gtactggggt cagggaaccc tggtcaccgt ctcgagc      357
```

<210> SEQ ID NO 290
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 290

```
gaggtgcagc tgttggagtc tgggggaggc ttggtacagc ctgggggtc cctgcgtctc     60
tcctgtgcag cctccggatt cacctttttc aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg cgccttttga gtactggggt cagggaaccc tggtcaccgt ctcgagc     357
```

<210> SEQ ID NO 291
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 291

```
gaggtgcagc tgttggagtc tgggggaggc ttggtacagc ctgggggtc cctgcgtctc     60
tcctgtgcag cctccggatt cacctttttg aagtattcga tggggtgggt ccgccaggct   120
ccagggaagg gtctagagtg ggtctcacag atttcggata ctgctgatcg tacatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcgttggg cgccttttga gtactggggt cagggaaccc tggtcaccgt ctcgagc     357
```

<210> SEQ ID NO 292
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 292

```
gaggtgcagc tgttggagtc tgggggaggc ttggtacagc ctgggggtc cctgcgtctc     60
tcctgtgcag cctccggatt cacctttttg aagtattcga tggggtgggt ccgccaggct   120
ccagggaagg gtctagagtg ggtctcacag atttcggata ccgtgatcg tagatactac    180
gatcactctg tgaagggccg gttcactatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc     357
```

<210> SEQ ID NO 293
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 293

```
gaggtgcagc tgttggagtc tggggggaggc ttggtacagc ctggggggtc cctgcgtctc      60
tcctgtgcag cctccggatt cacctttttc aagtattcga tggggtgggt ccgccaggct     120
ccagggaagg gtctagagtg ggtctcacag atttcggata ccggtgatcg tagatactac     180
gatcactctg tgaagggccg gttcactatc tcccgcgaca attccaagaa cacgctgtat     240
ctgcaaatga acagcctgcg tgccgaggac accgcggtat attactgtgc gatatatacg     300
ggtcggtggg cgccttttga gtactggggt cagggaaccc tggtcaccgt ctcgagc        357
```

<210> SEQ ID NO 294
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 294

```
gaggtgcagc tgttggagtc tggggggaggc ttggtacagc ctggggggtc cctgcgtctc     60
tcctgtgcag cctccggatt cacctttgtt aagtattcga tggggtgggt ccgccaggct    120
ccagggaagg gtctagagtg ggtctcacag attgcggata ctgctgatcg tacatactac    180
gcacactccg tgaagggccg gttcaccatc tcccgcgaca attccaagaa cacgctgtat    240
ctgcaaatga acagcctgcg tgctgaggac accgcggtat attactgcgc gatatatact    300
gggcgttggg tgccttttga gtactggggt cagggaaccc tggtcaccgt ctcgagc       357
```

<210> SEQ ID NO 295
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 295

```
gaggtgcagc tgttggagtc tggggggaggc ttggtacagc ctggggggtc cctgcgtctc     60
tcctgtgcag cctccggatt caccttttttt aagtattcga tggggtgggt ccgccaggct    120
ccagggaagg gtctagagtg ggtctcacag atttcggata ctgctgatcg tacatactac    180
gcacacgcgg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 296
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 296

```
gaggtgcagc tgttggagtc tggggggaggc ttggtgcagc ctggggggtc cctgcgtctc     60
tcctgtgcag cctccggatt cacctttgtt aagtattcga tggggtgggt ccgccaggct    120
ccagggaagg gtctagagtg ggtctcacag attgcggata ctgctgatcg tacatactac    180
gatcactccg tgaagggccg gttcaccatc tcccgcgaca attccaagaa cacgctgtat    240
ctgcaaatga acagcctgcg tgctgaggac accgcggtat attactgtgc gatatatact    300
gggcgttggg tgccttttga gtactggggt cagggaaccc tggtcaccgt ctcgagc       357
```

<210> SEQ ID NO 297
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 297

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg ggtctcacag attgcggata ctgctgatcg tacatactac   180
gatcacgcgg tgaagggccg gttcaccatc tcccgcgaca attccaagaa cacgctgtat   240
ctgcaaatga acagcctgcg tgctgaggac accgcggtat attactgtgc gatatatact   300
gggcgttggg tgccttttga gtactggggt cagggaaccc tggtcaccgt ctcgagc      357
```

<210> SEQ ID NO 298
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 298

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
ccagggaagg gtctagagtg ggtctcacag attgcggata ctgctgatcg tagatactac   180
gcacactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 299
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 299

```
gaggtgcagc tgttggagtc tgggggaggc ttggtacagc ctgggggtc cctgcgtctc    60
tcctgtgcag cctccggatt cacctttgtt aagtattcga tgggtgggt ccgccaggct    120
ccagggaagg gtctagagtg ggtctcacag atttcggata ctgctgatcg tagatactac   180
gcacacgcgg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357
```

<210> SEQ ID NO 300
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 300

```
gaggtgcagc tgttggagtc tgggggaggc ttggtacagc ctgggggtc cctgcgtctc    60
tcctgtgcag cctccggatt cacctttgtt aagtattcga tggggtgggt ccgccaggct   120
```

```
ccagggaagg gtctagagtg gtctcacag attgcggata ctgctgatcg tagatactac    180
gcacacgcgg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357

<210> SEQ ID NO 301
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 301
gaggtgcagc tgttggagtc tgggggaggc ttggtacagc ctgggggtc cctgcgtctc     60 tcctgtgcag cctccggatt cacctttgtt aagtattcga tggggtgggt ccgccaggct   120
ccagggaagg gtctagagtg gtctcacag atttcggata ctgctgatcg tagatactac    180
gatcacgcgg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357

<210> SEQ ID NO 302
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 302
gaggtgcagc tgttggagtc tgggggaggc ttggtacagc ctgggggtc cctgcgtctc     60 tcctgtgcag cctccggatt cacctttgtt aagtattcga tggggtgggt ccgccaggct   120
ccagggaagg gtctagagtg gtctcacag attgcggata ctgctgatcg tagatactac    180
gatcacgcgg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactgggt caggggaccc tggtcaccgt ctcgagc       357

<210> SEQ ID NO 303
<211> LENGTH: 357
<212> TYPE: DNA
<213> ORGANISM: Artificial Sequence
<220> FEATURE:
<223> OTHER INFORMATION: Derived from a Human Germline sequence.

<400> SEQUENCE: 303
gaggtgcagc tgttggagtc tgggggaggc ttggtacagc ctgggggtc cctgcgtctc     60 tcctgtgcag cctccggatt cacctttgtt aagtattcga tggggtgggt ccgccaggct   120
ccagggaagg gtctagagtg gtctcacag attgcggata ctgctgatcg tagatactac    180
gatcactccg tgaagggccg gttcaccatc tcccgcgaca attccaagaa cacgctgtat   240
ctgcaaatga acagcctgcg tgccgaggac accgcggtat attactgtgc gatatatacg   300
ggtcggtggg cgccttttga gtactggggt cagggaaccc tggtcaccgt ctcgagc      357

<210> SEQ ID NO 304
<211> LENGTH: 357
<212> TYPE: DNA
<213> ORGANISM: Artificial Sequence
```

<220> FEATURE:
<223> OTHER INFORMATION: Derived from a Human Germline sequence.

<400> SEQUENCE: 304

```
gaggtgcagc tgctggagtc tgggggaggc ttggtacagc ctggggggtc cctgcgtctc    60
tcctgtgcag cctccggatt cacctttttc aagtattcga tggggtgggt ccgccaggct   120
ccagggaagg gtctagagtg ggtctcacag atttcggata ctgctgatcg tagatactac   180
gatgacgcgt gaagggccg gttcaccatc acccgcgaca attccaagaa cacgctgtat   240
ctgcaaatga acagcctgcg tgccgaggac accgcggtat attactgtgc gatatatacg   300
ggtcgttggg agccttttgt ctactgggggt cagggaaccc tggtcaccgt ctcgagc     357
```

<210> SEQ ID NO 305
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 305

```
His Gly Glu Gly Thr Phe Thr Ser Asp Leu Ser Lys Gln Met Glu Glu
 1               5                  10                  15
Glu Ala Val Arg Leu Phe Ile Glu Trp Leu Lys Asn Gly Gly Pro Ser
            20                  25                  30
Ser Gly Ala Pro Pro Ser Gly Gly Gly Gly Ser Gly Gly Gly
        35                  40                  45
Gly Ser Gly Gly Gly Gly Ser Asp Ile Gln Met Thr Gln Ser Pro Ser
    50                  55                  60
Ser Leu Ser Ala Ser Val Gly Asp Arg Val Thr Ile Thr Cys Arg Ala
65                  70                  75                  80
Ser Gln Trp Ile Gly Ser Gln Leu Ser Trp Tyr Gln Gln Lys Pro Gly
                85                  90                  95
Lys Ala Pro Lys Leu Leu Ile Met Trp Arg Ser Ser Leu Gln Ser Gly
            100                 105                 110
Val Pro Ser Arg Phe Ser Gly Ser Gly Ser Gly Thr Asp Phe Thr Leu
        115                 120                 125
Thr Ile Ser Ser Leu Gln Pro Glu Asp Phe Ala Thr Tyr Tyr Cys Ala
    130                 135                 140
Gln Gly Ala Ala Leu Pro Arg Thr Phe Gly Gln Gly Thr Lys Val Glu
145                 150                 155                 160
Ile Lys Arg
```

<210> SEQ ID NO 306
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 306

```
catggtgaag gaacatttac cagtgacttg tcaaaacaga tggaagagga ggcagtgcgg    60
ttatttattg agtggcttaa gaacggagga ccaagtagcg gggcacctcc gccatcgggt   120
ggtggaggcg gttcaggcgg aggtggcagc ggcggtggcg ggtcggacat ccagatgacc   180
cagtctccat cctccctgtc tgcatctgta ggagaccgtg tcaccatcac ttgccgggca   240
agtcagtgga ttgggtctca gttatcttgg taccagcaga aaccagggaa agcccctaag   300
```

```
ctcctgatca tgtggcgttc ctcgttgcaa agtggggtcc catcacgttt cagtggcagt        360
ggatctggga cagatttcac tctcaccatc agcagtctgc aacctgaaga ttttgctacg        420
tactactgtg ctcagggtgc ggcgttgcct aggacgttcg gccaagggac caaggtggaa        480
atcaaacgg                                                                489
```

<210> SEQ ID NO 307
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 307

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Ser Gly Gly Gly
        35                  40                  45

Gly Ser Gly Gly Gly Ser Asp Ile Gln Met Thr Gln Ser Pro Ser
    50                  55                  60

Ser Leu Ser Ala Ser Val Gly Asp Arg Val Thr Ile Thr Cys Arg Ala
65                  70                  75                  80

Ser Gln Trp Ile Gly Ser Gln Leu Ser Trp Tyr Gln Gln Lys Pro Gly
                85                  90                  95

Lys Ala Pro Lys Leu Leu Ile Met Trp Arg Ser Ser Leu Gln Ser Gly
            100                 105                 110

Val Pro Ser Arg Phe Ser Gly Ser Gly Ser Gly Thr Asp Phe Thr Leu
        115                 120                 125

Thr Ile Ser Ser Leu Gln Pro Glu Asp Phe Ala Thr Tyr Tyr Cys Ala
130                 135                 140

Gln Gly Leu Arg His Pro Lys Thr Phe Gly Gln Gly Thr Lys Val Glu
145                 150                 155                 160

Ile Lys Arg
```

<210> SEQ ID NO 308
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 308

```
catggtgaag gaacatttac cagtgacttg tcaaaacaga tggaagagga ggcagtgcgg         60
ttatttattg agtggcttaa gaacggagga ccaagtagcg gggcacctcc gccatcgggt        120
ggtggaggcg gttcaggcgg aggtggcagc ggcggtggcg gtcggacat ccagatgacc         180 cagtctccat cctccctgtc tgcatctgta ggagaccgtg tcaccatcac ttgccgggca        240
agtcagtgga ttgggtctca gttatcttgg taccagcaga accagggaa agcccctaag         300 ctcctgatca tgtggcgttc ctcgttgcaa agtggggtcc catcacgttt cagtggcagt        360
ggatctggga cagatttcac tctcaccatc agcagtctgc aacctgaaga ttttgctacg        420
tactactgtg ctcagggttt gaggcatcct aagacgttcg gccaagggac caaggtggaa        480
atcaaacgg                                                                489
```

<210> SEQ ID NO 309
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 309

```
His Gly Glu Gly Thr Phe Thr Ser Asp Leu Ser Lys Gln Met Glu Glu
 1               5                  10                  15
Glu Ala Val Arg Leu Phe Ile Glu Trp Leu Lys Asn Gly Gly Pro Ser
            20                  25                  30
Ser Gly Ala Pro Pro Pro Ser Gly Gly Gly Gly Ser Gly Gly Gly Gly
        35                  40                  45
Gly Ser Gly Gly Gly Gly Ser Asp Ile Gln Met Thr Gln Ser Pro Ser
    50                  55                  60
Ser Leu Ser Ala Ser Val Gly Asp Arg Val Thr Ile Thr Cys Arg Ala
 65                 70                  75                  80
Ser Gln Trp Ile Gly Ser Gln Leu Ser Trp Tyr Gln Lys Pro Gly
                85                  90                  95
Lys Ala Pro Lys Leu Leu Ile Met Trp Arg Ser Ser Leu Gln Ser Gly
            100                 105                 110
Val Pro Ser Arg Phe Ser Gly Ser Gly Ser Gly Thr Asp Phe Thr Leu
        115                 120                 125
Thr Ile Ser Ser Leu Gln Pro Glu Asp Phe Ala Thr Tyr Tyr Cys Ala
    130                 135                 140
Gln Gly Leu Met Lys Pro Met Thr Phe Gly Gln Gly Thr Lys Val Glu
145                 150                 155                 160
Ile Lys Arg
```

<210> SEQ ID NO 310
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 310

```
catggtgaag gaacatttac cagtgacttg tcaaaacaga tggaagagga ggcagtgcgg    60
ttatttattg agtggcttaa gaacggagga ccaagtagcg gggcacctcc gccatcgggt   120
ggtggaggcg gttcaggcgg aggtggcagc ggcggtggcg gtcggacat ccagatgacc   180
cagtctccat cctccctgtc tgcatctgta ggagaccgtg tcaccatcac ttgccgggca   240
agtcagtgga ttgggtctca gttatcttgg taccagcaga accagggaa agcccctaag   300
ctcctgatca tgtggcgttc ctcgttgcaa agtggggtcc catcacgttt cagtggcagt   360
ggatctggga cagatttcac tctcaccatc agcagtctgc aacctgaaga ttttgctacg   420
tactactgtg ctcagggtct tatgaagcct atgacgttcg gccaagggac caaggtggaa   480
atcaaacgg                                                           489
```

<210> SEQ ID NO 311
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 311

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Gly Ser Gly Gly Gly
            35                  40                  45

Gly Ser Gly Gly Gly Gly Ser Asp Ile Gln Met Thr Gln Ser Pro Ser
    50                  55                  60

Ser Leu Ser Ala Ser Val Gly Asp Arg Val Thr Ile Ser Cys Arg Ala
65                  70                  75                  80

Ser Gln Trp Ile Gly Ser Gln Leu Ser Trp Tyr Gln Gln Lys Pro Gly
                85                  90                  95

Glu Ala Pro Lys Leu Leu Ile Met Trp Arg Ser Ser Leu Gln Ser Gly
                100                 105                 110

Val Pro Ser Arg Phe Ser Gly Ser Gly Ser Gly Thr Asp Phe Thr Leu
                115                 120                 125

Thr Ile Ser Ser Leu Gln Pro Glu Asp Phe Ala Thr Tyr Tyr Cys Ala
        130                 135                 140

Gln Gly Ala Ala Leu Pro Arg Thr Phe Gly Gln Gly Thr Lys Val Glu
145                 150                 155                 160

Ile Lys Arg

<210> SEQ ID NO 312
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 312
catggtgaag gaacatttac cagtgacttg tcaaaacaga tggaagagga ggcagtgcgg    60
ttatttattg agtggcttaa gaacggagga ccaagtagcg gggcaccctcc gccatcgggt   120 ggtggaggcg gttcaggcgg aggtggcagc ggcggtggcg ggtcggacat ccagatgacc   180
cagtctccat cctccctgtc tgcatctgta ggagaccgtg tcaccatctc ttgccgggca   240
agtcagtgga ttgggtctca gttatcttgg taccagcaga accaggggaa agcccctaag   300
ctcctgatca tgtggcgttc ctcgttgcaa agtggggtcc catcacgttt cagtggcagt   360
ggatctggga cagatttcac tctcaccatc agcagtctgc aacctgaaga ttttgctacg   420
tactactgtg ctcagggtgc ggcgttgcct aggacgttcg gccaagggac caaggtggaa   480
atcaaacgg                                                          489

<210> SEQ ID NO 313
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 313

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Gly Ser Gly Gly Gly
            35                  40                  45

Gly Ser Gly Gly Gly Gly Ser Asp Ile Gln Met Thr Gln Ser Pro Ser
50                  55                  60

Ser Leu Ser Ala Ser Val Gly Asp Arg Val Thr Ile Thr Cys Arg Ala
65                  70                  75                  80

Ser Arg Pro Ile Gly Thr Thr Leu Ser Trp Tyr Gln Gln Lys Pro Gly
                85                  90                  95

Lys Ala Pro Lys Leu Leu Ile Trp Phe Gly Ser Arg Leu Gln Ser Gly
                100                 105                 110

Val Pro Ser Arg Phe Ser Gly Ser Gly Ser Gly Thr Asp Phe Thr Leu
                115                 120                 125

Thr Ile Ser Ser Leu Gln Pro Glu Asp Phe Ala Thr Tyr Tyr Cys Ala
    130                 135                 140

Gln Ala Gly Thr His Pro Thr Thr Phe Gly Gln Gly Thr Lys Val Glu
145                 150                 155                 160

Ile Lys Arg

<210> SEQ ID NO 314
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 314
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcgtccga ttgggacgac gttaagttgg taccagcaga accagggaa agcccctaag     300 ctcctgatct ggtttggttc ccggttgcaa agtggggtcc catcacgttt cagtggcagt     360
ggatctggga cagatttcac tctcaccatc agcagtctgc aacctgaaga ttttgctacg     420
tactactgtg cgcaggctgg gacgcatcct acgacgttcg gccaagggac caaggtggaa     480
atcaaacgg                                                             489

<210> SEQ ID NO 315
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 315

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Gly Gly Gly Gly Ser Gly Gly Gly
            35                  40                  45

Gly Ser Gly Gly Gly Gly Ser Asp Ile Gln Met Thr Gln Ser Pro Ser
50                  55                  60

Ser Leu Ser Ala Ser Val Gly Asp Arg Val Thr Ile Thr Cys Arg Ala
65                  70                  75                  80

Ser Arg Pro Ile Gly Thr Met Leu Ser Trp Tyr Gln Gln Lys Pro Gly
                85                  90                  95

Lys Ala Pro Lys Leu Leu Ile Leu Phe Gly Ser Arg Leu Gln Ser Gly
                100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
    130                 135                 140

Gln Ala Gly Thr His Pro Thr Thr Phe Gly Gln Gly Thr Lys Val Glu
145                 150                 155                 160

Ile Lys Arg

<210> SEQ ID NO 316
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 316
catggtgaag gaacatttac cagtgacttg tcaaaacaga tggaagagga ggcagtgcgg      60
ttatttattg agtggcttaa gaacggagga ccaagtagcg gggcacctcc gccatcgggt     120
ggtggaggcg gttcaggcgg aggtggcagc ggcggtggcg ggtcggacat ccagatgacc     180
cagtctccat cctccctgtc tgcatctgta ggagaccgtg tcaccatcac ttgccgggca     240
agtcgtccga ttgggacgat gttaagttgg taccagcaga aaccagggaa agcccctaag     300
ctcctgatct gtttggttc ccggttgcaa agtggggtcc catcacgttt cagtggcagt     360
ggatctggga cagatttcac tctcaccatc agcagtctgc aacctgaaga ttttgctacg     420
tactactgtg cgcaggctgg gacgcatcct acgacgttcg gccaagggac caaggtggaa     480
atcaaacgg                                                             489

<210> SEQ ID NO 317
<211> LENGTH: 163
<212> TYPE: PRT
<213> ORGANISM: Artificial Sequence
<220> FEATURE:
<223> OTHER INFORMATION: Derived from a Human Germline sequence.

<400> SEQUENCE: 317

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Gly Ser Gly Gly Gly
        35                  40                  45

Gly Ser Gly Gly Gly Gly Ser Asp Ile Gln Met Thr Gln Ser Pro Ser
50                  55                  60

Ser Leu Ser Ala Ser Val Gly Asp Arg Val Thr Ile Thr Cys Arg Ala
65                  70                  75                  80

Ser Arg Pro Ile Gly Thr Met Leu Ser Trp Tyr Gln Gln Lys Pro Gly
                85                  90                  95

Lys Ala Pro Lys Leu Leu Ile Leu Ala Phe Ser Arg Leu Gln Ser Gly
                100                 105                 110

Val Pro Ser Arg Phe Ser Gly Ser Gly Ser Gly Thr Asp Phe Thr Leu
            115                 120                 125

Thr Ile Ser Ser Leu Gln Pro Glu Asp Phe Ala Thr Tyr Tyr Cys Ala
    130                 135                 140

Gln Ala Gly Thr His Pro Thr Thr Phe Gly Gln Gly Thr Lys Val Glu
145                 150                 155                 160

Ile Lys Arg

<210> SEQ ID NO 318
<211> LENGTH: 489
<212> TYPE: DNA
<213> ORGANISM: Artificial Sequence
<220> FEATURE:
<223> OTHER INFORMATION: Derived from a Human Germline sequence.

<400> SEQUENCE: 318

| | |
|---|---|
| catggtgaag gaacatttac cagtgacttg tcaaaacaga tggaagagga ggcagtgcgg | 60 |
| ttatttattg agtggcttaa aacggagga ccaagtagcg gggcacctcc gccatcgggt | 120 |
| ggtggaggcg gttcaggcgg aggtggcagc ggcggtggcg ggtcggacat ccagatgacc | 180 |
| cagtctccat cctccctgtc tgcatctgta ggagaccgtg tcaccatcac ttgccgggca | 240 |
| agtcgtccga ttgggacgat gttaagttgg taccagcaga accagggaa agcccctaag | 300 |
| ctcctgatcc ttgcttttc ccgtttgcaa agtggggtcc catcacgttt cagtggcagt | 360 |
| ggatctggga cagatttcac tctcaccatc agcagtctgc aacctgaaga ttttgctacg | 420 |
| tactactgcg cgcaggctgg gacgcatcct acgacgttcg gccaagggac caaggtggaa | 480 |
| atcaaacgg | 489 |

<210> SEQ ID NO 319
<211> LENGTH: 114
<212> TYPE: PRT
<213> ORGANISM: Artificial Sequence
<220> FEATURE:
<223> OTHER INFORMATION: Derived from a Human Germline sequence.

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Leu Arg His Pro Lys
                85                  90                  95

Thr Phe Gly Gln Gly Thr Lys Val Glu Ile Lys Arg Gly Gly Gly Gly
            100                 105                 110

Ser Cys

<210> SEQ ID NO 320
<211> LENGTH: 345
<212> TYPE: DNA
<213> ORGANISM: Artificial Sequence
<220> FEATURE:
<223> OTHER INFORMATION: Derived from a Human Germline sequence.

<400> SEQUENCE: 320

| | |
|---|---|
| gacatccaga tgacccagtc tccatcctcc ctgtctgcat ctgtaggaga ccgtgtcacc | 60 |
| atcacttgcc gggcaagtca gtggattggg tctcagttat cttggtacca gcagaaacca | 120 |

```
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa acggggtggc ggagggggtt cctgt                     345
```

<210> SEQ ID NO 321
<211> LENGTH: 115
<212> TYPE: PRT
<213> ORGANISM: Artificial Sequence
<220> FEATURE:
<223> OTHER INFORMATION: Derived from a Human Germline sequence.

<400> SEQUENCE: 321

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
                 20                  25                  30

Leu Ser Trp Tyr Gln Gln Lys Pro Gly Lys Ala Pro Lys Leu Leu Ile
             35                  40                  45

Met Trp Arg Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala Gln Gly Leu Arg His Pro Lys
                 85                  90                  95

Thr Phe Gly Gln Gly Thr Lys Val Glu Ile Lys Arg Thr Val Ala Ala
            100                 105                 110

Pro Ser Cys
        115
```

<210> SEQ ID NO 322
<211> LENGTH: 345
<212> TYPE: DNA
<213> ORGANISM: Artificial Sequence
<220> FEATURE:
<223> OTHER INFORMATION: Derived from a Human Germline sequence.

<400> SEQUENCE: 322

```
gacatccaga tgacccagtc tccatcctcc ctgtctgcat ctgtaggaga ccgtgtcacc    60
atcacttgcc gggcaagtca gtggattggg tctcagttat cttggtacca gcagaaacca    120
gggaaagccc ctaagctcct gatcatgtgg cgttcctcgt tgcaaagtgg ggtcccatca    180
cgtttcagtg gcagtggatc tgggacagat ttcactctca ccatcagcag tctgcaacct    240
gaagattttg ctacgtacta ctgtgctcag ggtttgaggc atcctaagac gttcggccaa    300
gggaccaagg tggaaatcaa acggaccgtc gctgctccat cttgt                    345
```

<210> SEQ ID NO 323
<211> LENGTH: 235
<212> TYPE: PRT
<213> ORGANISM: Artificial Sequence
<220> FEATURE:
<223> OTHER INFORMATION: Derived from a Human Germline sequence.

<400> SEQUENCE: 323

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Arg Tyr
```

```
                    20                  25                  30
Ser Met Gly Trp Leu Arg Gln Ala Pro Gly Lys Gly Leu Glu Trp Val
                35                  40                  45

Ser Arg Ile Asp Ser Tyr Gly Arg Gly Thr Tyr Tyr Glu Asp Pro Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
                100                 105                 110

Gly Thr Gln Val Thr Val Ser Ser Ala Ser Thr Ser Gly Pro Ser Asp
                115                 120                 125

Ile Gln Met Thr Gln Ser Pro Ser Ser Leu Ser Ala Ser Val Gly Asp
                130                 135                 140

Arg Val Thr Ile Thr Cys Arg Ala Ser Arg Pro Ile Gly Thr Thr Leu
145                 150                 155                 160

Ser Trp Tyr Gln Gln Lys Pro Gly Lys Ala Pro Lys Leu Leu Ile Trp
                165                 170                 175

Phe Gly Ser Arg Leu Gln Ser Gly Val Pro Ser Arg Phe Ser Gly Ser
                180                 185                 190

Gly Ser Gly Thr Asp Phe Thr Leu Thr Ile Ser Ser Leu Gln Pro Glu
                195                 200                 205

Asp Phe Ala Thr Tyr Tyr Cys Ala Gln Ala Gly Thr His Pro Thr Thr
                210                 215                 220

Phe Gly Gln Gly Thr Lys Val Glu Ile Lys Arg
225                 230                 235

<210> SEQ ID NO 324
<211> LENGTH: 249
<212> TYPE: PRT
<213> ORGANISM: Artificial Sequence
<220> FEATURE:
<223> OTHER INFORMATION: Derived from a Human Germline sequence.

<400> SEQUENCE: 324

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Asn Arg Tyr
                20                  25                  30

Ser Met Gly Trp Leu Arg Gln Ala Pro Gly Lys Gly Leu Glu Trp Val
                35                  40                  45

Ser Arg Ile Asp Ser Tyr Gly Arg Gly Thr Tyr Tyr Glu Asp Pro Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
                100                 105                 110

Gly Thr Gln Val Thr Val Ser Ser Ala Ser Thr Ser Gly Pro Ser Asp
                115                 120                 125

Ile Gln Met Thr Gln Ser Pro Ser Ser Leu Ser Ala Ser Val Gly Asp
                130                 135                 140

Arg Val Thr Ile Thr Cys Arg Ala Ser Arg Pro Ile Gly Thr Thr Leu
```

```
                145                 150                 155                 160
Ser Trp Tyr Gln Gln Lys Pro Gly Lys Ala Pro Lys Leu Leu Ile Trp
                165                 170                 175

Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg Ala Ala Ala Glu Gln
225                 230                 235                 240

Lys Leu Ile Ser Glu Glu Asp Leu Asn
                245

<210> SEQ ID NO 325
<211> LENGTH: 705
<212> TYPE: DNA
<213> ORGANISM: Artificial Sequence
<220> FEATURE:
<223> OTHER INFORMATION: Derived from a Human Germline sequence.

<400> SEQUENCE: 325
gaggtgcagc tgttggagtc tgggggaggc ttggtacagc ctgggggtc cctgcgtctc        60 tcctgtgcag cctccggatt caccttaat aggtatagta tggggtggct ccgccaggct       120
ccagggaagg gtctagagtg gtctcacgg attgattctt atggtcgtgg tacatactac       180
gaagaccccg tgaagggccg gttcagcatc tcccgcgaca attccaagaa cacgctgtat       240
ctgcaaatga acagcctgcg tgccgaggac accgccgtat attactgtgc gaaaatttct       300
cagtttgggt caaatgcgtt tgactactgg ggtcagggaa cccaggtcac cgtctcgagc       360
gctagcacca gtggtccatc ggacatccag atgacccagt ctccatcctc cctgtctgca       420
tctgtaggag accgtgtcac catcacttgc cgggcaagtc gtccgattgg gacgacgtta       480
agttggtacc agcagaaacc agggaaagcc cctaagctcc tgatctggtt tggttcccgg       540
ttgcaaagtg gggtcccatc acgtttcagt ggcagtggat ctgggacaga tttcactctc       600
accatcagca gtctgcaacc tgaagatttt gctacgtact actgtgcgca ggctgggacg       660
catcctacga cgttcggcca agggaccaag gtggaaatca aacgg               705

<210> SEQ ID NO 326
<211> LENGTH: 750
<212> TYPE: DNA
<213> ORGANISM: Artificial Sequence
<220> FEATURE:
<223> OTHER INFORMATION: Derived from a Human Germline sequence.

<400> SEQUENCE: 326
gaggtgcagc tgttggagtc tgggggaggc ttggtacagc ctgggggtc cctgcgtctc        60 tcctgtgcag cctccggatt caccttaat aggtatagta tggggtggct ccgccaggct       120
ccagggaagg gtctagagtg gtctcacgg attgattctt atggtcgtgg tacatactac       180
gaagaccccg tgaagggccg gttcagcatc tcccgcgaca attccaagaa cacgctgtat       240
ctgcaaatga acagcctgcg tgccgaggac accgccgtat attactgtgc gaaaatttct       300
cagtttgggt caaatgcgtt tgactactgg ggtcagggaa cccaggtcac cgtctcgagc       360
gctagcacca gtggtccatc ggacatccag atgacccagt ctccatcctc cctgtctgca       420
tctgtaggag accgtgtcac catcacttgc cgggcaagtc gtccgattgg gacgacgtta       480
```

```
agttggtacc agcagaaacc agggaaagcc cctaagctcc tgatctggtt tggttcccgg    540
ttgcaaagtg gggtcccatc acgtttcagt ggcagtggat ctgggacaga tttcactctc    600
accatcagca gtctgcaacc tgaagatttt gctacgtact actgtgcgca ggctgggacg    660
catcctacga cgttcggcca agggaccaag gtggaaatca acgggcggc cgcagaacaa     720 aaactcatct cagaagagga tctgaattaa                                     750
```

```
<210> SEQ ID NO 327
<211> LENGTH: 235
<212> TYPE: PRT
<213> ORGANISM: Artificial Sequence
<220> FEATURE:
<223> OTHER INFORMATION: Derived from a Human Germline sequence.

<400> SEQUENCE: 327
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175

Phe Gly Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg
225                 230                 235

```
<210> SEQ ID NO 328
<211> LENGTH: 249
<212> TYPE: PRT
<213> ORGANISM: Artificial Sequence
<220> FEATURE:
<223> OTHER INFORMATION: Derived from a Human Germline sequence.

<400> SEQUENCE: 328
```

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Asn Arg Tyr
         20                  25                  30
Ser Met Gly Trp Leu Arg Gln Ala Pro Gly Lys Gly Leu Glu Trp Val
         35                  40                  45
Ser Arg Ile Asp Ser Tyr Gly Arg Gly Thr Tyr Tyr Glu Asp Pro Val
         50                  55                  60
Lys Gly Arg Phe Ser Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Ile Ser Gln Phe Gly Ser Asn Ala Phe Asp Tyr Trp Gly Gln
            100                 105                 110
Gly Thr Gln Val Thr Val Ser Ser Ala Ser Thr Ser Gly Pro Ser Asp
            115                 120                 125
Ile Gln Met Thr Gln Ser Pro Ser Ser Leu Ser Ala Ser Val Gly Asp
            130                 135                 140
Arg Val Thr Ile Thr Cys Arg Ala Ser Arg Pro Ile Gly Thr Met Leu
145                 150                 155                 160
Ser Trp Tyr Gln Gln Lys Pro Gly Lys Ala Pro Lys Leu Leu Ile Leu
                165                 170                 175
Phe Gly Ser Arg Leu Gln Ser Gly Val Pro Ser Arg Phe Ser Gly Ser
            180                 185                 190
Gly Ser Gly Thr Asp Phe Thr Leu Thr Ile Ser Ser Leu Gln Pro Glu
            195                 200                 205
Asp Phe Ala Thr Tyr Tyr Cys Ala Gln Ala Gly Thr His Pro Thr Thr
            210                 215                 220
Phe Gly Gln Gly Thr Lys Val Glu Ile Lys Arg Ala Ala Ala Glu Gln
225                 230                 235                 240
Lys Leu Ile Ser Glu Glu Asp Leu Asn
                245

<210> SEQ ID NO 329
<211> LENGTH: 705
<212> TYPE: DNA
<213> ORGANISM: Artificial Sequence
<220> FEATURE:
<223> OTHER INFORMATION: Derived from a Human Germline sequence.

<400> SEQUENCE: 329
gaggtgcagc tgttggagtc tgggggaggc ttggtacagc ctgggggtc cctgcgtctc     60 tcctgtgcag cctccggatt cacctttaat aggtatagta tggggtggct ccgccaggct    120
ccagggaagg gtctagagtg ggtctcacgg attgattctt atggtcgtgg tacatactac    180
gaagaccccg tgaagggccg gttcagcatc tcccgcgaca attccaagaa cacgctgtat    240
ctgcaaatga acagcctgcg tgccgaggac accgccgtat attactgtgc gaaaatttct    300
cagtttgggt caaatgcgtt tgactactgg ggtcagggaa cccaggtcac cgtctcgagc    360
gctagcacca gtggtccatc ggacatccag atgacccagt ctccatcctc cctgtctgca    420
tctgtaggag accgtgtcac catcacttgc cgggcaagtc gtccgattgg gacgatgtta    480
agttggtacc agcagaaacc aggaaaagcc cctaagctcc tgatcttgtt tggttcccgg    540
ttgcaaagtg gggtcccatc acgtttcagt ggcagtggat ctgggacaga tttcactctc    600
accatcagca gtctgcaacc tgaagatttt gctacgtact actgtgcgca ggctgggacg    660
catcctacga cgttcggcca aggaccaag gtggaaatca aacgg              705
```

<210> SEQ ID NO 330
<211> LENGTH: 750
<212> TYPE: DNA
<213> ORGANISM: Artificial Sequence
<220> FEATURE:
<223> OTHER INFORMATION: Derived from a Human Germline sequence.

<400> SEQUENCE: 330

```
gaggtgcagc tgttggagtc tgggggaggc ttggtacagc ctgggggtc cctgcgtctc      60 tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcaggga cccaggtcac cgtctcgagc      360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc cctaagctcc tgatcttgtt tggttcccgg     540
ttgcaaagtg gggtcccatc acgtttcagt ggcagtggat ctgggacaga tttcactctc     600
accatcagca gtctgcaacc tgaagatttt gctacgtact actgtgcgca ggctgggacg     660
catcctacga cgttcggcca agggaccaag gtggaaatca aacgggcggc cgcagaacaa     720
aaactcatct cagaagagga tctgaattaa                                      750
```

<210> SEQ ID NO 331
<211> LENGTH: 235
<212> TYPE: PRT
<213> ORGANISM: Artificial Sequence
<220> FEATURE:
<223> OTHER INFORMATION: Derived from a Human Germline sequence.

<400> SEQUENCE: 331

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Arg Tyr
             20                  25                  30

Ser Met Gly Trp Leu Arg Gln Ala Pro Gly Lys Gly Leu Glu Trp Val
         35                  40                  45

Ser Arg Ile Asp Ser Tyr Gly Arg Gly Thr Tyr Tyr Glu Asp Pro Val
     50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175
```

-continued

```
Ala Phe Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg
225                 230                 235

<210> SEQ ID NO 332
<211> LENGTH: 249
<212> TYPE: PRT
<213> ORGANISM: Artificial Sequence
<220> FEATURE:
<223> OTHER INFORMATION: Derived from a Human Germline sequence.

<400> SEQUENCE: 332

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Ala Ser Thr Ser Gly Pro Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Arg Pro Ile Gly Thr Met Leu
145                 150                 155                 160

Ser Trp Tyr Gln Gln Lys Pro Gly Lys Ala Pro Lys Leu Leu Ile Leu
                165                 170                 175

Ala Phe Ser Arg Leu Gln Ser Gly Val Pro Ser Arg Phe Ser Gly Ser
            180                 185                 190

Gly Ser Gly Thr Asp Phe Thr Leu Thr Ile Ser Ser Leu Gln Pro Glu
        195                 200                 205

Asp Phe Ala Thr Tyr Tyr Cys Ala Gln Ala Gly Thr His Pro Thr Thr
    210                 215                 220

Phe Gly Gln Gly Thr Lys Val Glu Ile Lys Arg Ala Ala Ala Glu Gln
225                 230                 235                 240

Lys Leu Ile Ser Glu Glu Asp Leu Asn
                245

<210> SEQ ID NO 333
<211> LENGTH: 705
<212> TYPE: DNA
<213> ORGANISM: Artificial Sequence
<220> FEATURE:
<223> OTHER INFORMATION: Derived from a Human Germline sequence.

<400> SEQUENCE: 333
```

```
gaggtgcagc tgttggagtc tgggggaggc ttggtacagc ctggggggtc cctgcgtctc      60
tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcagggaa cccaggtcac cgtctcgagc     360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc cctaagctcc tgatccttgc ttttttcccgt     540 ttgcaaagtg gggtcccatc acgtttcagt ggcagtggat ctgggacaga tttcactctc     600
accatcagca gtctgcaacc tgaagatttt gctacgtact actgcgcgca ggctgggacg     660
catcctacga cgttcggcca agggaccaag gtggaaatca aacgg                     705
```

<210> SEQ ID NO 334
<211> LENGTH: 750
<212> TYPE: DNA
<213> ORGANISM: Artificial Sequence
<220> FEATURE:
<223> OTHER INFORMATION: Derived from a Human Germline sequence.

<400> SEQUENCE: 334

```
gaggtgcagc tgttggagtc tgggggaggc ttggtacagc ctggggggtc cctgcgtctc      60
tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
ctgcaaatga acagcctgcg tgccgaggac accgccgtat attactgtgc gaaaatttct     300
cagtttgggt caaatgcgtt tgactactgg ggtcagggaa cccaggtcac cgtctcgagc     360
gctagcacca gtggtccatc ggacatccag atgacccagt ctccatcctc cctgtctgca     420
tctgtaggag accgtgtcac catcacttgc cgggcaagtc gtccgattgg gacgatgtta     480
agttggtacc agcagaaacc agggaaagcc cctaagctcc tgatccttgc ttttttcccgt     540 ttgcaaagtg gggtcccatc acgtttcagt ggcagtggat ctgggacaga tttcactctc     600
accatcagca gtctgcaacc tgaagatttt gctacgtact actgcgcgca ggctgggacg     660
catcctacga cgttcggcca agggaccaag gtggaaatca aacgggcggc cgcagaacaa     720
aaactcatct cagaagagga tctgaattaa                                      750
```

<210> SEQ ID NO 335
<211> LENGTH: 9
<212> TYPE: PRT
<213> ORGANISM: Homo Sapiens

<400> SEQUENCE: 335

Ser Gln Ser Ile Ser Ser Tyr Leu Asn
 1               5

<210> SEQ ID NO 336
<211> LENGTH: 8
<212> TYPE: PRT
<213> ORGANISM: Homo Sapiens

<400> SEQUENCE: 336

Tyr Ala Ala Ser Ser Leu Gln Ser
1               5

<210> SEQ ID NO 337
<211> LENGTH: 9
<212> TYPE: PRT
<213> ORGANISM: Homo Sapiens

<400> SEQUENCE: 337

Gln Gln Ser Tyr Ser Thr Pro Asn Thr
1               5

<210> SEQ ID NO 338
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 338

Ser Arg Pro Ile Gly Thr Thr Leu Ser
1               5

<210> SEQ ID NO 339
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 339

Trp Phe Gly Ser Arg Leu Gln Ser
1               5

<210> SEQ ID NO 340
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 340

Ala Gln Ala Gly Thr His Pro Thr Thr
1               5

<210> SEQ ID NO 341
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 341

Ser Arg Pro Ile Gly Thr Met Leu Ser
1               5

<210> SEQ ID NO 342
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 342

Leu Phe Gly Ser Arg Leu Gln Ser
1               5

<210> SEQ ID NO 343
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 343

Ala Gln Ala Gly Thr His Pro Thr Thr
1               5

<210> SEQ ID NO 344
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 344

Ser Arg Pro Ile Gly Thr Met Leu Ser
1               5

<210> SEQ ID NO 345
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 345

Leu Ala Phe Ser Arg Leu Gln Ser
1               5

<210> SEQ ID NO 346
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 346

Ala Gln Ala Gly Thr His Pro Thr Thr
1               5

<210> SEQ ID NO 347
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 347

Ser Arg Pro Ile Gly Thr Met Leu Ser
1               5

<210> SEQ ID NO 348
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 348

Trp Phe Gly Ser Arg Leu Gln Ser
1               5

<210> SEQ ID NO 349
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 349

Ala Gln Ala Gly Thr His Pro Thr Thr
1               5

<210> SEQ ID NO 350
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 350

Ser Arg Pro Ile Gly Thr Met Leu Ser
1               5

<210> SEQ ID NO 351
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 351

Leu Phe Gly Ser Arg Leu Gln Ser
1               5

<210> SEQ ID NO 352
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 352

Ala Gln Thr Gly Thr His Pro Thr Thr
1               5

<210> SEQ ID NO 353
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 353

Ser Arg Pro Ile Gly Thr Thr Leu Ser
1               5

<210> SEQ ID NO 354
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 354

Leu Trp Phe Ser Arg Leu Gln Ser
1               5

```
<210> SEQ ID NO 355
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 355

Ala Gln Ala Gly Thr His Pro Thr Thr
 1               5

<210> SEQ ID NO 356
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 356

Ser Gln Trp Ile Gly Ser Gln Leu Ser
 1               5

<210> SEQ ID NO 357
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 357

Met Trp Arg Ser Ser Leu Gln Ser
 1               5

<210> SEQ ID NO 358
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 358

Ala Gln Gly Ala Ala Leu Pro Arg Thr
 1               5

<210> SEQ ID NO 359
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 359

Ser Gln Trp Ile Gly Ser Gln Leu Ser
 1               5

<210> SEQ ID NO 360
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 360

Met Trp Arg Ser Ser Leu Gln Ser
 1               5

<210> SEQ ID NO 361
```

```
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 361

Ala Gln Gly Leu Arg His Pro Lys Thr
 1               5

<210> SEQ ID NO 362
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 362

Ser Gln Trp Ile Gly Ser Gln Leu Ser
 1               5

<210> SEQ ID NO 363
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 363

Met Trp Arg Ser Ser Leu Gln Ser
 1               5

<210> SEQ ID NO 364
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 364

Ala Gln Gly Leu Met Lys Pro Met Thr
 1               5

<210> SEQ ID NO 365
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 365

Ser Gln Trp Ile Gly Ser Gln Leu Ser
 1               5

<210> SEQ ID NO 366
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 366

Met Trp Arg Ser Ser Leu Gln Ser
 1               5

<210> SEQ ID NO 367
<211> LENGTH: 9
```

```
<210> SEQ ID NO 367
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 367

Ala Gln Gly Ala Ala Leu Pro Arg Thr
1               5

<210> SEQ ID NO 368
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 368

Ser Gln Trp Ile Gly Ser Gln Leu Ser
1               5

<210> SEQ ID NO 369
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 369

Met Trp Arg Ser Ser Leu Gln Ser
1               5

<210> SEQ ID NO 370
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 370

Ala Gln Gly Ala Ala Leu Pro Lys Thr
1               5

<210> SEQ ID NO 371
<211> LENGTH: 9
<212> TYPE: PRT
<213> ORGANISM: Artificial Sequence
<220> FEATURE:
<223> OTHER INFORMATION: Derived from a Human Germline sequence.

<400> SEQUENCE: 371

Ser Gln Trp Ile Gly Ser Gln Leu Ser
1               5

<210> SEQ ID NO 372
<211> LENGTH: 8
<212> TYPE: PRT
<213> ORGANISM: Artificial Sequence
<220> FEATURE:
<223> OTHER INFORMATION: Derived from a Human Germline sequence.

<400> SEQUENCE: 372

Met Trp Arg Ser Ser Leu Gln Ser
1               5

<210> SEQ ID NO 373
<211> LENGTH: 9
<212> TYPE: PRT
```

<213> ORGANISM: Artificial Sequence
<220> FEATURE:
<223> OTHER INFORMATION: Derived from a Human Germline sequence.

<400> SEQUENCE: 373

Ala Gln Gly Phe Lys Lys Pro Arg Thr
1               5

<210> SEQ ID NO 374
<211> LENGTH: 165
<212> TYPE: PRT
<213> ORGANISM: Homo Sapiens

<400> SEQUENCE: 374

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 375
<211> LENGTH: 495
<212> TYPE: DNA
<213> ORGANISM: Homo Sapiens

<400> SEQUENCE: 375
tgtgatctgc ctcaaaccca cagcctgggt agcaggagga ccttgatgct cctggcacag      60
atgaggagaa tctctctttt ctcctgcttg aaggacagac atgactttgg atttccccag     120
gaggagtttg gcaaccagtt ccaaaaggct gaaaccatcc ctgtcctcca tgagatgatc     180
cagcagatct tcaatctctt cagcacaaag gactcatctg ctgcttggga tgagaccctc     240
ctagacaaat tctacactga actctaccag cagctgaatg acctggaagc tgtgtgata     300 caggggtgg gggtgacaga gactcccctg atgaaggagg actccattct ggctgtgagg     360
aaatacttcc aaagaatcac tctctatctg aaagagaaga atacagccc ttgtgcctgg     420 gaggttgtca gagcagaaat catgagatct ttttctttgt caacaaactt gcaagaaagt     480
ttaagaagta aggaa                                                      495

<210> SEQ ID NO 376
<211> LENGTH: 25

```
<212> TYPE: DNA
<213> ORGANISM: Artificial Sequence
<220> FEATURE:
<223> OTHER INFORMATION: Derived from a Human Germline sequence.

<400> SEQUENCE: 376
gcccggatcc accggctgtg atctg                                          25

<210> SEQ ID NO 377
<211> LENGTH: 30
<212> TYPE: DNA
<213> ORGANISM: Artificial Sequence
<220> FEATURE:
<223> OTHER INFORMATION: Derived from a Human Germline sequence.

<400> SEQUENCE: 377
ggaggatgga gactgggtca tctggatgtc                                     30

<210> SEQ ID NO 378
<211> LENGTH: 30
<212> TYPE: DNA
<213> ORGANISM: Artificial Sequence
<220> FEATURE:
<223> OTHER INFORMATION: Derived from a Human Germline sequence.

<400> SEQUENCE: 378
gacatccaga tgacccagtc tccatcctcc                                     30

<210> SEQ ID NO 379
<211> LENGTH: 82
<212> TYPE: DNA
<213> ORGANISM: Artificial Sequence
<220> FEATURE:
<223> OTHER INFORMATION: Derived from a Human Germline sequence.

<400> SEQUENCE: 379
gcgcaagctt ttattaattc agatcctctt ctgagatgag ttttttgttct gcggccgccc   60 gtttgatttc caccttggtc cc                                             82

<210> SEQ ID NO 380
<211> LENGTH: 56
<212> TYPE: DNA
<213> ORGANISM: Artificial Sequence
<220> FEATURE:
<223> OTHER INFORMATION: Derived from a Human Germline sequence.

<400> SEQUENCE: 380
gcccggatcc accggctgtg atctggcgca agcttttatt aattcagatc ctcttc        56

<210> SEQ ID NO 381
<211> LENGTH: 51
<212> TYPE: DNA
<213> ORGANISM: Artificial Sequence
<220> FEATURE:
<223> OTHER INFORMATION: Derived from a Human Germline sequence.

<400> SEQUENCE: 381
tgagatgagt ttttgttctg cggccgcccg tttgatttcc accttggtcc c              51

<210> SEQ ID NO 382
<211> LENGTH: 1
<212> TYPE: PRT
<213> ORGANISM: Murine

<400> SEQUENCE: 382
```

Gly
 1

<210> SEQ ID NO 383
<211> LENGTH: 61
<212> TYPE: DNA
<213> ORGANISM: Murine

<400> SEQUENCE: 383
atggagaccg acaccctgct gctgtgggtg ctgctgctgt gggtgcccgg atccaccggg    60
c    61

<210> SEQ ID NO 384
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 384

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
        195                 200                 205

Gln Lys Pro Gly Lys Ala Pro Lys Leu Leu Ile Met Trp Arg Ser Ser
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Ala Ala Leu Pro Arg Thr Phe Gly Gln Gly
            260                 265                 270

Thr Lys Val Glu Ile Lys Arg Ala Ala Ala Glu Gln Lys Leu Ile Ser
        275                 280                 285

Glu Glu Asp Leu Asn
      290

<210> SEQ ID NO 385
<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 385

```
tgcgacttgc cacagacaca tagtttggga tcaagaagaa cattgatgtt attagcacaa      60
atgcgtagaa tttctttgtt ctcttgtcta aggaccgtc acgacttcgg attccctcag      120
gaagagtttg gaaaccaatt ccaaaaagca gaaactattc ctgtcttgca cgaaatgatc      180
cagcaaatat tcaatttgtt ttctacaaag gactcatcag ccgcttggga tgaaactctg      240
ttagataaat tctacactga actatatcaa caactgaacg atctagaggc ttgcgttatt      300
cagggtgtag gagttactga aactccccta atgaaagaag attcaattct agccgttaga      360
aaatactttc agcgtatcac attgtattta aaggaaaaga atactcccc atgtgcatgg      420
gaggtggtta gagcagaaat tatgaggtcc ttctctcttt ctacgaattt gcaagaatct      480
ttgagatcta aggaaaccgt cgctgctcca tctgacatcc agatgaccca gtctccatcc      540
tccctgtctg catctgtagg agaccgtgtc accatcactt gccgggcaag tcagtggatt      600
gggtctcagt tatcttggta ccagcagaaa ccagggaaag cccctaagct cctgatcatg      660
tggcgttcct cgttgcaaag tggggtccca tcacgtttca gtggcagtgg atctgggaca      720
gatttcactc tcaccatcag cagtctgcaa cctgaagatt ttgctacgta ctactgtgct      780
cagggtgcgg cgttgcctag gacgttcggc caagggacca aggtggaaat caaacgggcg      840
gccgcagaac aaaaactcat ctcagaagag gatctgaatt aa                         882
```

<210> SEQ ID NO 386
<211> LENGTH: 279
<212> TYPE: PRT
<213> ORGANISM: Artificial Sequence
<220> FEATURE:
<223> OTHER INFORMATION: Derived from a Human Germline sequence.

<400> SEQUENCE: 386

Cys Asp Leu Pro Gln Thr His Ser Leu Gly Ser Arg Arg Thr Leu Met
  1               5                   10                  15

Leu Leu Ala Gln Met Arg Arg Ile Ser Leu Phe Ser Cys Leu Lys Asp
              20                  25                  30

Arg His Asp Phe Gly Phe Pro Gln Glu Glu Phe Gly Asn Gln Phe Gln
          35                  40                  45

Lys Ala Glu Thr Ile Pro Val Leu His Glu Met Ile Gln Gln Ile Phe
      50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                  85                  90                  95

Ala Cys Val Ile Gln Gly Val Gly Val Thr Glu Thr Pro Leu Met Lys
             100                 105                 110

Glu Asp Ser Ile Leu Ala Val Arg Lys Tyr Phe Gln Arg Ile Thr Leu
         115                 120                 125

Tyr Leu Lys Glu Lys Lys Tyr Ser Pro Cys Ala Trp Glu Val Val Arg
     130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
            165                 170                 175

Gln Ser Pro Ser Ser Leu Ser Ala Ser Val Gly Asp Arg Val Thr Ile
        180                 185                 190

Thr Cys Arg Ala Ser Gln Trp Ile Gly Ser Gln Leu Ser Trp Tyr Gln
    195                 200                 205

Gln Lys Pro Gly Lys Ala Pro Lys Leu Leu Ile Met Trp Arg Ser Ser
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Ala Ala Leu Pro Arg Thr Phe Gly Gln Gly
            260                 265                 270

Thr Lys Val Glu Ile Lys Arg
        275

<210> SEQ ID NO 387
<211> LENGTH: 837
<212> TYPE: DNA
<213> ORGANISM: Artificial Sequence
<220> FEATURE:
<223> OTHER INFORMATION: Derived from a Human Germline sequence.

<400> SEQUENCE: 387
tgcgacttgc cacagacaca tagtttggga tcaagaagaa cattgatgtt attagcacaa      60
atgcgtagaa tttctttgtt ctcttgtcta aaggaccgtc acgacttcgg attccctcag    120
gaagagtttg aaaccaatt ccaaaaagca gaaactattc ctgtcttgca cgaaatgatc     180
cagcaaatat tcaatttgtt ttctacaaag gactcatcag ccgcttggga tgaaactctg    240
ttagataaat tctacactga actatatcaa caactgaacg atctagaggc ttgcgttatt    300
cagggtgtag gagttactga aactccccta atgaaagaag attcaattct agccgttaga    360
aaatactttc agcgtatcac attgtattta aaggaaaaga atactcccc atgtgcatgg     420
gaggtggtta gagcagaaat tatgaggtcc ttctctcttt ctacgaattt gcaagaatct    480
ttgagatcta aggaaaccgt cgctgctcca tctgacatcc agatgaccca gtctccatcc    540
tccctgtctg catctgtagg agaccgtgtc accatcactt gccgggcaag tcagtggatt    600
gggtctcagt tatcttggta ccagcagaaa ccagggaaag cccctaagct cctgatcatg    660
tggcgttcct cgttgcaaag tggggtccca tcacgtttca gtggcagtgg atctgggaca    720
gatttcactc tcaccatcag cagtctgcaa cctgaagatt ttgctacgta ctactgtgct    780
cagggtgcgg cgttgcctag gacgttcggc caagggacca aggtggaaat caaacgg       837

<210> SEQ ID NO 388
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 388

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
           20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
            195                 200                 205

Gln Lys Pro Gly Lys Ala Pro Lys Leu Leu Ile Met Trp Arg Ser Ser
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Leu Arg His Pro Lys Thr Phe Gly Gln Gly
            260                 265                 270

Thr Lys Val Glu Ile Lys Arg Ala Ala Ala Glu Gln Lys Leu Ile Ser
            275                 280                 285

Glu Glu Asp Leu Asn
    290

<210> SEQ ID NO 389
<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 389
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactcccta atgaagaag attcaattct agccgttaga     360
aaatactttc agcgtatcac attgtattta aggaaaaga aatactcccc atgtgcatgg     420
gaggtggtta gagcagaaat tatgaggtcc ttctctcttt ctacgaattt gcaagaatct     480

```
ttgagatcta aggaaaccgt cgctgctcca tctgacatcc agatgaccca gtctccatcc      540
tccctgtctg catctgtagg agaccgtgtc accatcactt gccgggcaag tcagtggatt      600
gggtctcagt tatcttggta ccagcagaaa ccagggaaag cccctaagct cctgatcatg      660
tggcgttcct cgttgcaaag tggggtccca tcacgtttca gtggcagtgg atctgggaca      720
gatttcactc tcaccatcag cagtctgcaa cctgaagatt ttgctacgta ctactgtgct      780
cagggtttga ggcatcctaa gacgttcggc caagggacca aggtggaaat caaacgggcg      840
gccgcagaac aaaaactcat ctcagaagag gatctgaatt aa                        882
```

<210> SEQ ID NO 390
<211> LENGTH: 279
<212> TYPE: PRT
<213> ORGANISM: Artificial Sequence
<220> FEATURE:
<223> OTHER INFORMATION: Derived from a Human Germline sequence.

<400> SEQUENCE: 390

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
        195                 200                 205

Gln Lys Pro Gly Lys Ala Pro Lys Leu Leu Ile Met Trp Arg Ser Ser
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Leu Arg His Pro Lys Thr Phe Gly Gln Gly
            260                 265                 270

Thr Lys Val Glu Ile Lys Arg
        275
```

<210> SEQ ID NO 391
<211> LENGTH: 837
<212> TYPE: DNA
<213> ORGANISM: Artificial Sequence
<220> FEATURE:
<223> OTHER INFORMATION: Derived from a Human Germline sequence.

<400> SEQUENCE: 391

```
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg aaaccaatt ccaaaaagca gaaactattc ctgtcttgca cgaaatgatc      180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aggaaaaga aatactcccc atgtgcatgg      420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcagtggatt     600
gggtctcagt tatcttggta ccagcagaaa ccagggaaag cccctaagct cctgatcatg     660
tggcgttcct cgttgcaaag tggggtccca tcacgtttca gtggcagtgg atctgggaca     720
gatttcactc tcaccatcag cagtctgcaa cctgaagatt ttgctacgta ctactgtgct     780
cagggtttga ggcatcctaa gacgttcggc caagggacca aggtggaaat caaacgg       837
```

<210> SEQ ID NO 392
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 392

```
Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
           100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
```

```
                165                 170                 175
Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
            195                 200                 205

Gln Lys Pro Gly Lys Ala Pro Lys Leu Leu Ile Met Trp Arg Ser Ser
            210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Leu Met Lys Pro Met Thr Phe Gly Gln Gly
            260                 265                 270

Thr Lys Val Glu Ile Lys Arg Ala Ala Ala Glu Gln Lys Leu Ile Ser
            275                 280                 285

Glu Glu Asp Leu Asn
    290
```

<210> SEQ ID NO 393
<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 393

```
tgcgacttgc cacagacaca tagtttggga tcaagaagaa cattgatgtt attagcacaa        60
atgcgtagaa tttctttgtt ctcttgtcta aaggaccgtc acgacttcgg attccctcag       120
gaagagtttg gaaaccaatt ccaaaaagca gaaactattc ctgtcttgca cgaaatgatc       180
cagcaaatat tcaatttgtt ttctacaaag gactcatcag ccgcttggga tgaaactctg       240
ttagataaat tctacactga actatatcaa caactgaacg atctagaggc ttgcgttatt       300
cagggtgtag gagttactga aactccccta atgaaagaag attcaattct agccgttaga       360
aaatactttc agcgtatcac attgtattta aaggaaaaga aatactcccc atgtgcatgg       420
gaggtggtta gagcagaaat tatgaggtcc ttctctcttt ctacgaattt gcaagaatct       480
ttgagatcta aggaaaccgt cgctgctcca tctgacatcc agatgaccca gtctccatcc       540
tccctgtctg catctgtagg agaccgtgtc accatcactt gccgggcaag tcagtggatt       600
gggtctcagt tatcttggta ccagcagaaa ccagggaaag cccctaagct cctgatcatg       660
tggcgttcct cgttgcaaag tggggtccca tcacgtttca gtggcagtgg atctgggaca       720
gatttcactc tcaccatcag cagtctgcaa cctgaagatt ttgctacgta ctactgtgct       780
cagggtctta tgaagcctat gacgttcggc caagggacca aggtggaaat caaacgggcg       840
gccgcagaac aaaaactcat ctcagaagag gatctgaatt aa                          882
```

<210> SEQ ID NO 394
<211> LENGTH: 279
<212> TYPE: PRT
<213> ORGANISM: Artificial Sequence
<220> FEATURE:
<223> OTHER INFORMATION: Derived from a Human Germline sequence.

<400> SEQUENCE: 394

```
Cys Asp Leu Pro Gln Thr His Ser Leu Gly Ser Arg Arg Thr Leu Met
1               5                   10                  15
```

| | | | | | | | | | | | |
|---|---|---|---|---|---|---|---|---|---|---|---|
| Leu | Leu | Ala | Gln | Met | Arg | Arg | Ile | Ser | Leu | Phe | Ser | Cys | Lys | Asp |
| | | | 20 | | | | 25 | | | | 30 |

Arg His Asp Phe Gly Phe Pro Gln Glu Glu Phe Gly Asn Gln Phe Gln
        35                40                  45

Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Gln Trp Ile Gly Ser Gln Leu Ser Trp Tyr Gln
        195                 200                 205

Gln Lys Pro Gly Lys Ala Pro Lys Leu Leu Ile Met Trp Arg Ser Ser
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Leu Met Lys Pro Met Thr Phe Gly Gln Gly
            260                 265                 270

Thr Lys Val Glu Ile Lys Arg
        275

<210> SEQ ID NO 395
<211> LENGTH: 837
<212> TYPE: DNA
<213> ORGANISM: Artificial Sequence
<220> FEATURE:
<223> OTHER INFORMATION: Derived from a Human Germline sequence.

<400> SEQUENCE: 395
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aaggaaaaga atactcccc atgtgcatgg     420 gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540

-continued

```
tccctgtctg catctgtagg agaccgtgtc accatcactt gccgggcaag tcagtggatt      600
gggtctcagt tatcttggta ccagcagaaa ccagggaaag cccctaagct cctgatcatg      660
tggcgttcct cgttgcaaag tggggtccca tcacgtttca gtggcagtgg atctgggaca      720
gatttcactc tcaccatcag cagtctgcaa cctgaagatt ttgctacgta ctactgtgct      780
cagggtctta tgaagcctat gacgttcggc caagggacca aggtggaaat caaacgg        837
```

<210> SEQ ID NO 396
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 396

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Ser Cys Arg Ala Ser Gln Trp Ile Gly Ser Gln Leu Ser Trp Tyr Gln
        195                 200                 205

Gln Lys Pro Gly Glu Ala Pro Lys Leu Leu Ile Met Trp Arg Ser Ser
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Ala Ala Leu Pro Arg Thr Phe Gly Gln Gly
            260                 265                 270

Thr Lys Val Glu Ile Lys Arg Ala Ala Ala Glu Gln Lys Leu Ile Ser
        275                 280                 285

Glu Glu Asp Leu Asn
    290
```

<210> SEQ ID NO 397

<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 397

```
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaccaatt  ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag agttactga  aactccccta atgaaagaag attcaattct agccgttaga     360
aaatactttc agcgtatcac attgtattta aaggaaaaga atactcccc  atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatctctt gccgggcaag tcagtggatt     600
gggtctcagt tatcttggta ccagcagaaa ccaggggaag cccctaagct cctgatcatg     660
tggcgttcct cgttgcaaag tggggtccca tcacgtttca gtggcagtgg atctgggaca     720
gatttcactc tcaccatcag cagtctgcaa cctgaagatt ttgctacgta ctactgtgct     780
cagggtgcgg cgttgcctag gacgttcggc caagggacca aggtggaaat caaacgggcg     840
gccgcagaac aaaaactcat ctcagaagag gatctgaatt aa                        882
```

<210> SEQ ID NO 398
<211> LENGTH: 279
<212> TYPE: PRT
<213> ORGANISM: Artificial Sequence
<220> FEATURE:
<223> OTHER INFORMATION: Derived from a Human Germline sequence.

<400> SEQUENCE: 398

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
```

165                 170                 175
Gln Ser Pro Ser Ser Leu Ser Ala Ser Val Gly Asp Arg Val Thr Ile
            180                 185                 190

Ser Cys Arg Ala Ser Gln Trp Ile Gly Ser Gln Leu Ser Trp Tyr Gln
            195                 200                 205

Gln Lys Pro Gly Glu Ala Pro Lys Leu Leu Ile Met Trp Arg Ser Ser
            210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Gly Ala Ala Leu Pro Arg Thr Phe Gly Gln Gly
            260                 265                 270

Thr Lys Val Glu Ile Lys Arg
            275

<210> SEQ ID NO 399
<211> LENGTH: 837
<212> TYPE: DNA
<213> ORGANISM: Artificial Sequence
<220> FEATURE:
<223> OTHER INFORMATION: Derived from a Human Germline sequence.

<400> SEQUENCE: 399
tgcgacttgc cacagacaca tagtttggga tcaagaagaa cattgatgtt attagcacaa     60
atgcgtagaa tttctttgtt ctcttgtcta aaggaccgtc acgacttcgg attccctcag    120
gaagagtttg gaaccaatt ccaaaaagca gaaactattc ctgtcttgca cgaaatgatc    180
cagcaaatat tcaatttgtt ttctacaaag gactcatcag ccgcttggga tgaaactctg    240
ttagataaat tctacactga actatatcaa caactgaacg atctagaggc ttgcgttatt    300
cagggtgtag gagttactga aactccccta atgaaagaag attcaattct agccgttaga    360
aaatactttc agcgtatcac attgtattta aaggaaaaga aatactcccc atgtgcatgg    420
gaggtggtta gagcagaaat tatgaggtcc ttctctcttt ctacgaattt gcaagaatct    480
ttgagatcta aggaaaccgt cgctgctcca tctgacatcc agatgaccca gtctccatcc    540
tccctgtctg catctgtagg agaccgtgtc accatctctt gccgggcaag tcagtggatt    600
gggtctcagt tatcttggta ccagcagaaa ccaggggaag cccctaagct cctgatcatg    660
tggcgttcct cgttgcaaag tggggtccca tcacgtttca gtggcagtgg atctgggaca    720
gatttcactc tcaccatcag cagtctgcaa cctgaagatt ttgctacgta ctactgtgct    780
cagggtgcgg cgttgcctag gacgttcggc caagggacca aggtggaaat caaacgg      837

<210> SEQ ID NO 400
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 400

Cys Asp Leu Pro Gln Thr His Ser Leu Gly Ser Arg Arg Thr Leu Met
1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

```
Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
                180                 185                 190

Thr Cys Arg Ala Ser Arg Pro Ile Gly Thr Thr Leu Ser Trp Tyr Gln
            195                 200                 205

Gln Lys Pro Gly Lys Ala Pro Lys Leu Leu Ile Trp Phe Gly Ser Arg
            210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg Ala Ala Ala Glu Gln Lys Leu Ile Ser
            275                 280                 285

Glu Glu Asp Leu Asn
            290

<210> SEQ ID NO 401
<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 401
tgcgacttgc cacagacaca tagtttggga tcaagaagaa cattgatgtt attagcacaa      60
atgcgtagaa tttctttgtt ctcttgtcta aggaccgtc acgacttcgg attccctcag     120
gaagagtttg gaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aggaaaaga atactcccc atgtgcatgg      420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
```

```
gggacgacgt taagttggta ccagcagaaa ccagggaaag cccctaagct cctgatctgg      660
tttggttccc ggttgcaaag tggggtccca tcacgtttca gtggcagtgg atctgggaca      720
gatttcactc tcaccatcag cagtctgcaa cctgaagatt ttgctacgta ctactgtgcg      780
caggctggga cgcatcctac gacgttcggc caagggacca aggtggaaat caaacgggcg      840
gccgcagaac aaaaactcat ctcagaagag gatctgaatt aa                        882
```

<210> SEQ ID NO 402  
<211> LENGTH: 279  
<212> TYPE: PRT  
<213> ORGANISM: Artificial Sequence  
<220> FEATURE:  
<223> OTHER INFORMATION: Derived from a Human Germline sequence.

<400> SEQUENCE: 402

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Arg Pro Ile Gly Thr Thr Leu Ser Trp Tyr Gln
        195                 200                 205

Gln Lys Pro Gly Lys Ala Pro Lys Leu Leu Ile Trp Phe Gly Ser Arg
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg
        275
```

<210> SEQ ID NO 403  
<211> LENGTH: 837  
<212> TYPE: DNA  
<213> ORGANISM: Artificial Sequence

```
<220> FEATURE:
<223> OTHER INFORMATION: Derived from a Human Germline sequence.

<400> SEQUENCE: 403
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg aaaccaatt ccaaaaagca gaaactattc ctgtcttgca cgaaatgatc      180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aaggaaaaga atactcccc atgtgcatgg      420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
gggacgacgt taagttggta ccagcagaaa ccagggaaag cccctaagct cctgatctgg     660
tttggttccc ggttgcaaag tggggtccca tcacgtttca gtggcagtgg atctgggaca     720
gatttcactc tcaccatcag cagtctgcaa cctgaagatt ttgctacgta ctactgtgcg     780
caggctggga cgcatcctac gacgttcggc caagggacca aggtggaaat caaacgg       837

<210> SEQ ID NO 404
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 404

Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190
```

Thr Cys Arg Ala Ser Arg Pro Ile Gly Thr Met Leu Ser Trp Tyr Gln
            195                 200                 205

Gln Lys Pro Gly Lys Ala Pro Lys Leu Leu Ile Leu Phe Gly Ser Arg
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg Ala Ala Ala Glu Gln Lys Leu Ile Ser
            275                 280                 285

Glu Glu Asp Leu Asn
    290

<210> SEQ ID NO 405
<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 405
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aggaaaaga aatactcccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
gggacgatgt taagttggta ccagcagaaa ccagggaaag cccctaagct cctgatcttg     660
tttggttccc ggttgcaaag tggggtccca tcacgtttca gtggcagtgg atctgggaca     720
gatttcactc tcaccatcag cagtctgcaa cctgaagatt ttgctacgta ctactgtgcg     780
caggctggga cgcatcctac gacgttcggc caagggacca aggtggaaat caaacgggcg     840
gccgcagaac aaaaactcat ctcagaagag gatctgaatt aa                        882

<210> SEQ ID NO 406
<211> LENGTH: 279
<212> TYPE: PRT
<213> ORGANISM: Artificial Sequence
<220> FEATURE:
<223> OTHER INFORMATION: Derived from a Human Germline sequence.

<400> SEQUENCE: 406

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

```
Lys Ala Glu Thr Ile Pro Val Leu His Glu Met Ile Gln Gln Ile Phe
 50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Arg Pro Ile Gly Thr Met Leu Ser Trp Tyr Gln
        195                 200                 205

Gln Lys Pro Gly Lys Ala Pro Lys Leu Leu Ile Leu Phe Gly Ser Arg
210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg
        275

<210> SEQ ID NO 407
<211> LENGTH: 837
<212> TYPE: DNA
<213> ORGANISM: Artificial Sequence
<220> FEATURE:
<223> OTHER INFORMATION: Derived from a Human Germline sequence.

<400> SEQUENCE: 407
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaagaag attcaattct agccgttaga     360
aaatactttc agcgtatcac attgtattta aaggaaaaga aatactcccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
gggacgatgt taagttggta ccagcagaaa ccagggaaag cccctaagct cctgatcttg     660
tttggttccc ggttgcaaag tggggtccca tcacgtttca gtggcagtgg atctgggaca     720
```

```
gatttcactc tcaccatcag cagtctgcaa cctgaagatt ttgctacgta ctactgtgcg      780
caggctggga cgcatcctac gacgttcggc caagggacca ggtggaaat caaacgg          837
```

<210> SEQ ID NO 408
<211> LENGTH: 293
<212> TYPE: PRT
<213> ORGANISM: Artificial Sequence
<220> FEATURE:
<223> OTHER INFORMATION: Derived from a Human Germline sequence.

<400> SEQUENCE: 408

```
Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu Thr Val Ala Ala Pro Ser Asp Ile Gln Met Thr
                165                 170                 175

Gln Ser Pro Ser Ser Leu Ser Ala Ser Val Gly Asp Arg Val Thr Ile
            180                 185                 190

Thr Cys Arg Ala Ser Arg Pro Ile Gly Thr Met Leu Ser Trp Tyr Gln
        195                 200                 205

Gln Lys Pro Gly Lys Ala Pro Lys Leu Leu Ile Leu Ala Phe Ser Arg
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
            260                 265                 270

Thr Lys Val Glu Ile Lys Arg Ala Ala Ala Gln Lys Leu Ile Ser
        275                 280                 285

Glu Glu Asp Leu Asn
    290
```

<210> SEQ ID NO 409
<211> LENGTH: 882
<212> TYPE: DNA
<213> ORGANISM: Artificial Sequence
<220> FEATURE:
<223> OTHER INFORMATION: Derived from a Human Germline sequence.

<400> SEQUENCE: 409

```
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactcccta atgaaagaag attcaattct agccgttaga     360
aaatactttc agcgtatcac attgtattta aggaaaaga atactcccc atgtgcatgg       420
gaggtggtta gagcagaaat tatgaggtcc ttctctcttt ctacgaattt gcaagaatct    480
ttgagatcta aggaaaccgt cgctgctcca tctgacatcc agatgaccca gtctccatcc    540
tccctgtctg catctgtagg agaccgtgtc accatcactt gccgggcaag tcgtccgatt    600
gggacgatgt taagttggta ccagcagaaa ccagggaaag cccctaagct cctgatcctt    660
gcttttcccc gtttgcaaag tggggtccca tcacgtttca gtggcagtgg atctgggaca    720
gatttcactc tcaccatcag cagtctgcaa cctgaagatt ttgctacgta ctactgcgcg    780
caggctggga cgcatcctac gacgttcggc caagggacca aggtggaaat caaacgggcg    840
gccgcagaac aaaaactcat ctcagaagag gatctgaatt aa                        882
```

<210> SEQ ID NO 410
<211> LENGTH: 279
<212> TYPE: PRT
<213> ORGANISM: Artificial Sequence
<220> FEATURE:
<223> OTHER INFORMATION: Derived from a Human Germline sequence.

<400> SEQUENCE: 410

```
Cys Asp Leu Pro Gln Thr His Ser Leu Gly Ser Arg Arg Thr Leu Met
  1               5                  10                  15
Leu Leu Ala Gln Met Arg Arg Ile Ser Leu Phe Ser Cys Leu Lys Asp
             20                  25                  30
Arg His Asp Phe Gly Phe Pro Gln Glu Glu Phe Gly Asn Gln Phe Gln
         35                  40                  45
Lys Ala Glu Thr Ile Pro Val Leu His Glu Met Ile Gln Gln Ile Phe
     50                  55                  60
Asn Leu Phe Ser Thr Lys Asp Ser Ser Ala Ala Trp Asp Glu Thr Leu
 65                  70                  75                  80
Leu Asp Lys Phe Tyr Thr Glu Leu Tyr Gln Gln Leu Asn Asp Leu Glu
                 85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Glu Ser
145                 150                 155                 160
Leu Arg Ser Lys Glu Thr Val Ala Ala Pro Ser Asp Ile Gln Met Thr
                165                 170                 175
Gln Ser Pro Ser Ser Leu Ser Ala Ser Val Gly Asp Arg Val Thr Ile
            180                 185                 190
```

```
Thr Cys Arg Ala Ser Arg Pro Ile Gly Thr Met Leu Ser Trp Tyr Gln
            195                 200                 205

Gln Lys Pro Gly Lys Ala Pro Lys Leu Leu Ile Leu Ala Phe Ser Arg
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Ala Gln Ala Gly Thr His Pro Thr Thr Phe Gly Gln Gly
                260                 265                 270

Thr Lys Val Glu Ile Lys Arg
            275
```

<210> SEQ ID NO 411
<211> LENGTH: 837
<212> TYPE: DNA
<213> ORGANISM: Artificial Sequence
<220> FEATURE:
<223> OTHER INFORMATION: Derived from a Human Germline sequence.

<400> SEQUENCE: 411

```
tgcgacttgc cacagacaca tagtttggga tcaagaagaa cattgatgtt attagcacaa      60
atgcgtagaa tttctttgtt ctcttgtcta aaggaccgtc acgacttcgg attccctcag     120
gaagagtttg gaaaccaatt ccaaaaagca gaaactattc ctgtcttgca cgaaatgatc     180
cagcaaatat tcaatttgtt ttctacaaag gactcatcag ccgcttggga tgaaactctg     240
ttagataaat tctacactga actatatcaa caactgaacg atctagaggc ttgcgttatt     300
cagggtgtag gagttactga aactccccta atgaaagaag attcaattct agccgttaga     360
aaatactttc agcgtatcac attgtattta aggaaaagaa atactccccc atgtgcatgg     420
gaggtggtta gagcagaaat tatgaggtcc ttctctcttt ctacgaattt gcaagaatct     480
ttgagatcta aggaaaccgt cgctgctcca tctgacatcc agatgaccca gtctccatcc     540
tccctgtctg catctgtagg agaccgtgtc accatcactt gccgggcaag tcgtccgatt     600
gggacgatgt taagttggta ccagcagaaa ccagggaaag cccctaagct cctgatcctt     660
gcttttcc gtttgcaaag tggggtccca tcacgtttca gtggcagtgg atctgggaca     720
gatttcactc tcaccatcag cagtctgcaa cctgaagatt ttgctacgta ctactgcgcg     780
caggctggga cgcatcctac gacgttcggc caagggacca aggtggaaat caaacgg      837
```

<210> SEQ ID NO 412
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 412

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Ser Gln
            20                  25                  30

Leu Ser Trp Tyr Gln Gln Lys Pro Gly Lys Ala Pro Lys Leu Leu Ile
        35                  40                  45

Met Trp Arg Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Ala Gln Gly Leu Arg His Pro Lys
                    85                  90                  95

Thr Phe Gly Gln Gly Thr Lys Val Glu Ile Lys Cys
                100                 105

<210> SEQ ID NO 413
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 413
gacatccaga tgacccagtc tccatcctcc ctgtctgcat ctgtaggaga ccgtgtcacc      60
atcacttgcc gggcaagtca gtggattggg tctcagttat cttggtacca gcagaaacca     120
gggaaagccc ctaagctcct gatcatgtgg cgttcctcgt tgcaaagtgg ggtcccatca     180
cgtttcagtg gcagtggatc tgggacagat ttcactctca ccatcagcag tctgcaacct     240
gaagattttg ctacgtacta ctgtgctcag ggtttgaggc atcctaagac gttcggccaa     300
gggaccaagg tggaaatcaa atgc                                            324

<210> SEQ ID NO 414
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 414

Asp Ile Gln Met Thr Gln Ser Pro Ser Ser Leu Pro Ala Ser Val Gly
 1               5                  10                  15

Asp Arg Val Thr Ile Thr Cys Arg Ala Ser Arg Pro Ile Gly Thr Met
                20                  25                  30

Leu Ser Trp Tyr Gln Gln Lys Pro Gly Lys Ala Pro Lys Leu Leu Ile
            35                  40                  45

Leu Ala Phe Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Ala Gly Thr His Pro Thr
                    85                  90                  95

Thr Phe Gly Gln Gly Thr Lys Val Glu Ile Lys Arg
                100                 105

<210> SEQ ID NO 415
<211> LENGTH: 324
<212> TYPE: DNA
<213> ORGANISM: Artificial Sequence
<220> FEATURE:
<223> OTHER INFORMATION: Derived from a Human Germline sequence.

<400> SEQUENCE: 415
gacatccaga tgacccagtc tccatcctcc ctgcctgcat ctgtaggaga ccgtgtcacc      60
atcacttgcc gggcaagtcg tccgattggg acgatgttaa gttggtacca gcagaaacca     120
gggaaagccc ctaagctcct gatccttgct ttttcccgtt tgcaaagtgg ggtcccatca     180
cgtttcagtg gcagtggatc tgggacagat ttcactctca ccatcagcag tctgcaacct     240
```

```
gaagattttg ctacgtacta ctgcgcgcag gctgggacgc atcctacgac gttcggccaa    300
gggaccaagg tggaaatcaa acgg                                           324
```

<210> SEQ ID NO 416
<211> LENGTH: 62
<212> TYPE: DNA
<213> ORGANISM: Artificial Sequence
<220> FEATURE:
<223> OTHER INFORMATION: Derived from a Human Germline sequence.

<400> SEQUENCE: 416

```
gcaacagcgt cgacggacat ccagatgacc cagtctccat cctccctgcc tgcatctgta    60
gg                                                                   62
```

<210> SEQ ID NO 417
<211> LENGTH: 360
<212> TYPE: DNA
<213> ORGANISM: Artificial Sequence
<220> FEATURE:
<223> OTHER INFORMATION: Derived from a Human Germline sequence.

<400> SEQUENCE: 417

```
gaggtgcagc tgttggagtc tgggggaggc ttggtacagc ctggggggtc cctgcgtctc    60
tcctgtgcag cctccggatt cacctttagt cagtatagga tgcattgggt ccgccaggct    120
ccagggaaga gtctagagtg ggtctcaagt attgatacta ggggttcgtc tacatactac    180
gcagaccccg tgaagggccg gttcaccatc tcccgcgaca attccaagaa cacgctgtat    240
ctgcaaatga acagcctgcg tgccgaggac accgcggtat attactgtgc gaaagctgtg    300
acgatgtttt ctccttttttt tgactactgg ggtcagggaa ccctggtcac cgtctcgagc   360
```

<210> SEQ ID NO 418
<211> LENGTH: 369
<212> TYPE: DNA
<213> ORGANISM: Artificial Sequence
<220> FEATURE:
<223> OTHER INFORMATION: Derived from a Human Germline sequence.

<400> SEQUENCE: 418

```
gaggtgcagc tgttggagtc tgggggaggc ttggtacagc ctggggggtc cctgcgtctc    60
tcctgtgcag cctccggatt cacctttgct gattatggga tgcgttgggt ccgccaggct    120
ccagggaagg gtctagagtg ggtctcatct attacgcgga ctggtcgtgt tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatggcgg    300
aatcggcatg gtgagtatct tgctgatttt gactactggg gtcagggaac cctggtcacc   360
gtctcgagc                                                            369
```

<210> SEQ ID NO 419
<211> LENGTH: 7
<212> TYPE: PRT
<213> ORGANISM: Artificial Sequence
<220> FEATURE:
<223> OTHER INFORMATION: Derived from a Human Germline sequence.

<400> SEQUENCE: 419

Thr Val Ala Ala Pro Ser Cys
 1               5

<210> SEQ ID NO 420

```
<211> LENGTH: 6
<212> TYPE: PRT
<213> ORGANISM: Artificial Sequence
<220> FEATURE:
<223> OTHER INFORMATION: Synthetic Linker Sequence

<400> SEQUENCE: 420

Gly Gly Gly Gly Ser Cys
 1               5

<210> SEQ ID NO 421
<211> LENGTH: 6
<212> TYPE: PRT
<213> ORGANISM: Artificial Sequence
<220> FEATURE:
<223> OTHER INFORMATION: Derived from a Human Germline sequence.

<400> SEQUENCE: 421

Thr Val Ala Ala Pro Ser
 1               5

<210> SEQ ID NO 422
<211> LENGTH: 108
<212> TYPE: PRT
<213> ORGANISM: Artificial Sequence
<220> FEATURE:
<223> OTHER INFORMATION: Derived from a Human Germline sequence.

<400> SEQUENCE: 422

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Trp Ile Gly Ser Gln
                20                  25                  30

Leu Ser Trp Tyr Gln Gln Lys Pro Gly Lys Ala Pro Lys Leu Leu Ile
            35                  40                  45

Met Trp Arg Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Gln Gly Ala Ala Leu Pro Arg
                85                  90                  95

Thr Phe Gly Gln Gly Thr Lys Val Glu Ile Lys Arg
            100                 105
```

ANTI-SERUM ALBUMIN BINDING VARIANTS

This application is a 371 of International Application No. PCT/EP2010/052007, filed 17 Feb. 2010, which claims the benefit of U.S. Provisional Application Nos. 61/153,746, filed 19 Feb. 2009, and 61/163,990, filed 27 Mar. 2009, which are incorporated herein in their entirety.

The invention relates to improved variants of the anti-serum albumin immunoglobulin single variable domain DOM7h-14, as well as ligands and drug conjugates comprising such variants, compositions, nucleic acids, vectors and hosts.

BACKGROUND OF THE INVENTION

WO04003019 and WO2008/096158 disclose anti-serum albumin (SA) binding moieties, such as anti-SA immunoglobulin single variable domains (dAbs), which have therapeutically-useful half-lives. These documents disclose monomer anti-SA dAbs as well as multi-specific ligands comprising such dAbs, eg, ligands comprising an anti-SA dAb and a dAb that specifically binds a target antigen, such as TNFR1. Binding moieties are disclosed that specifically bind serum albumins from more than one species, eg human/mouse cross-reactive anti-SA dAbs.

WO05118642 and WO2006/059106 disclose the concept of conjugating or associating an anti-SA binding moiety, such as an anti-SA immunoglobulin single variable domain, to a drug, in order to increase the half-life of the drug. Protein, peptide and NCE (new chemical entity) drugs are disclosed and exemplified. WO2006/059106 discloses the use of this concept to increase the half-life of insulintropic agents, eg, incretin hormones such as glucagon-like peptide (GLP)-1.

Reference is also made to Holt et al, "Anti-Serum albumin domain antibodies for extending the half-lives of short lived drugs", Protein Engineering, Design & Selection, vol 21, no 5, pp 283-288, 2008.

WO2008/096158 discloses DOM7h-14, which is a good anti-SA dAb. It would be desirable to provide improved dAbs that are variants of DOM7h-14 and that specifically bind serum albumin, preferably albumins from human and non-human species, which would provide utility in animal models of disease as well as for human therapy and/or diagnosis. It would also be desirable to provide for the choice between relatively modest- and high-affinity anti-SA binding moieties (dAbs). Such moieties could be linked to drugs, the anti-SA binding moiety being chosen according to the contemplated end-application. This would allow the drug to be better tailored to treating and/or preventing chronic or acute indications, depending upon the choice of anti-SA binding moiety. It would also be desirable to provide anti-dAbs, that are monomeric or substantially so in solution. This would especially be advantageous when the anti-SA dAb is linked to a binding moiety, eg, a dAb, that specifically binds a cell-surface receptor, such as TNFR1, with the aim of antagonizing the receptor. The monomeric state of the anti-SA dAb is useful in reducing the chance of receptor cross-linking, since multimers are less likely to form which could bind and cross-link receptors (eg, TNFR1) on the cell surface, thus increasing the likelihood of receptor agonism and detrimental receptor signaling.

SUMMARY OF THE INVENTION

Aspects of the present invention solve these problems.

To this end, the present inventors surprisingly found that beneficial mutations can be targeted to the CDR3 region 92 to 96 (position numbering according to Kabat) compared of DOM7h-14.

In one aspect the invention, therefore, provides an anti-serum albumin (SA) immunoglobulin single variable domain variant of DOM7h-14, wherein the variant comprises at least one mutation in CDR3 region 92 to 96 (position numbering according to Kabat) compared to DOM7h-14, and wherein the variant has from 1 to 8 changes compared to the amino acid sequence of DOM7h-14. There is also provided an anti-serum albumin (SA) binding moiety comprising CDR3 of a variant of this aspect of the invention.

Another aspect of the invention provides an anti-serum albumin (SA) immunoglobulin single variable domain variant of DOM7h-14, wherein the variant comprises a Ser at position 22 and a Glu at position 42 (numbering according to Kabat) compared to DOM7h-14, and wherein the variant has from 0 to 4 further changes compared to the amino acid sequence of DOM7h-14.

Embodiments of any aspect of the invention provide DOM7h-14 variants of good anti-serum albumin affinities. The choice of variant can allow for tailoring of half-life according to the desired therapeutic and/or prophylactic setting. For example, in one embodiment, the affinity of the variant for serum albumin is relatively high, such that the variant would be useful for inclusion in products that find utility in treating and/or preventing chronic or persistent diseases, conditions, toxicity or other chronic indications. In one embodiment, the affinity of the variant for serum albumin is relatively modest, such that the variant would be useful for inclusion in products that find utility in treating and/or preventing acute diseases, conditions, toxicity or other acute indications. In one embodiment, the affinity of the variant for serum albumin is intermediate, such that the variant would be useful for inclusion in products that find utility in treating and/or preventing acute or chronic diseases, conditions, toxicity or other acute or chronic indications.

It is conceivable that a molecule with an appropriately high affinity and specificity for serum albumin would stay in circulation long enough to have the desired therapeutic effect. (Tomlinson, Nature Biotechnology 22, 521-522 (2004)). Here, a high affinity anti-SA variant would stay in serum circulation matching that of the species' serum albumin (WO2008096158). Once in circulation, any fused therapeutic agent to the AlbudAb™ variant (an AlbudAb is an anti-serum albumin dAb or immunoglobulin single variable domain), be it NCE, peptide or protein, consequently would be able to act longer on its target and exhibit a longer lasting therapeutic effect. This would allow for targeting chronic or persistent diseases without the need of frequent dosing.

A variant with moderate affinity (but specificity to SA) would only stay in serum circulation for a short time (eg, for a few hours or a few days) allowing for the specific targeting of therapeutic targets involved in acute diseases by the fused therapeutic agent.

This way it is possible to tailor the anti-SA-containing product to the therapeutic disease area by choosing an anti-SA variant with the appropriate albumin binding affinity and/or serum half-life.

An aspect of the invention provides a multispecific ligand comprising any anti-SA variant as described above and a binding moiety that specifically binds a target antigen other than SA.

An aspect of the invention provides a fusion product, eg, a fusion protein or fusion with a peptide or NCE (new chemical entity) drug, comprising a polypeptide, protein, peptide or NCE drug fused or conjugated (for an NCE) to any variant as described above, wherein the variant is DOM7h-14-10 (or a variant having an amino acid that is at least 95, 96, 97, 98 or 99% identical to the amino acid sequence of DOM7h-14-10). DOM7h-14-10 gives only a modest drop in affinity when fused or conjugated to partner, making it useful in fusion products.

An aspect of the invention provides a composition comprising a variant, fusion protein or ligand of any preceding aspect and a pharmaceutically acceptable diluent, carrier, excipient or vehicle.

An aspect of the invention provides a method of treating or preventing a disease or disorder in a patient, comprising administering at least one dose of a variant according to any aspect or embodiment of the invention to said patient.

An aspect of the invention provides a polypeptide fusion or conjugate comprising an anti-serum albumin dAb as disclosed herein (eg, DOM7h-14-10) and an incretin or insulinotropic agent, eg, exendin-4, GLP-1(7-37), GLP-1(6-36) or any incretin or insulinotropic agent disclosed in WO06/059106, these agents being explicitly incorporated herein by reference as though written herein for inclusion in the present invention and claims below.

BRIEF DESCRIPTION OF THE DRAWINGS

FIG. 1: Amino-acid sequence alignment for DOM7h-14 variant dAbs. A "." at a particular position indicates the same amino as found in DOM7h-14 at that position. The CDRs are indicated by underlining and bold text (the first underlined sequence is CDR1, the second underlined sequence is CDR2 and the third underlined sequence is CDR3).

FIG. 2: Kinetic parameters of DOM7h-14 variants. KD units=nM; Kd units=sec$^{-1}$; Ka units=M$^{-1}$ sec$^{-1}$. The notation A e-B means A×10$^{-B}$ and C e D means C×10$^{D}$. The overall kinetic ranges in various species, as supported by the examples below, are indicated. Optional ranges are also provided for use in particular therapeutic settings (acute or chronic indications, conditions or diseases and "intermediate" for use in both chronic and acute settings). High affinity dAbs and products comprising these are useful for chronic settings. Medium affinity dAbs and products comprising these are useful for intermediate settings. Low affinity dAbs and products comprising these are useful for acute settings. The affinity in this respect is the affinity for serum albumin. Various example anti-serum dAbs and fusion proteins are listed, and these support the ranges disclosed. Many of the examples have favourable kinetics in human and one or more non-human animals (eg, in human and *Cynomolgus* monkey and/or mouse). Choice of dAb or product comprising this can be tailored, according to the invention, depending on the setting (eg, chronic or acute) to be treated therapeutically.

DETAILED DESCRIPTION OF THE INVENTION

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

As used herein, the term "antagonist of Tumor Necrosis Factor Receptor 1 (TNFR1)" or "anti-TNFR1 antagonist" or the like refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1.

A "patient" is any animal, eg, a mammal, eg, a non-human primate (such as a baboon, rhesus monkey or *Cynomolgus* monkey), mouse, human, rabbit, rat, dog, cat or pig. In one embodiment, the patient is a human.

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein an antibody refers to IgG, IgM, IgA, IgD or IgE or a fragment (such as a Fab, F(ab')$_2$, Fv, disulfide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of different V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

In the instant application, the term "prevention" and "preventing" involves administration of the protective composition prior to the induction of the disease or condition. "Treatment" and "treating" involves administration of the protective composition after disease or condition symptoms become manifest. "Suppression" or "suppressing" refers to administration of the composition after an inductive event, but prior to the clinical appearance of the disease or condition.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds target antigen) administered to a subject over the course of one day (24 hours) (daily dose), two days, one week, two weeks, three weeks or one or more months (e.g., by a single administration, or by two or more administrations). The interval between doses can be any desired amount of time. The term "pharmaceutically effective" when referring to a dose means sufficient amount of the ligand, domain or pharmaceutically active agent to provide the desired effect. The amount that is "effective" will vary from subject to subject, depending on the age and general condition of the individual, the particular drug or pharmaceutically active agent and the like. Thus, it is not always possible to specify an exact "effective" amount applicable for all patients. However, an appropriate "effective" dose in any individual case may be determined by one of ordinary skill in the art using routine experimentation.

Methods for pharmacokinetic analysis and determination of ligand (eg, single variable domain, fusion protein or multispecific ligand) half-life will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC). Optionally, all pharmacokinetic parameters and values quoted herein are to be read as being values in a human. Optionally, all pharmacokinetic parameters and values quoted herein are to be read as being values in a mouse or rat or *Cynomolgus* monkey.

Half lives (t½ alpha and t½ beta) and AUC can be determined from a curve of serum concentration of ligand against time. The WinNonlin analysis package, eg version 5.1 (available from Pharsight Corp., Mountain View, Calif. 94040, USA) can be used, for example, to model the curve. When two-compartment modeling is used, in a first phase (the alpha phase) the ligand is undergoing mainly distribution in the patient, with some elimination. A second phase (beta phase) is the phase when the ligand has been distributed and the serum concentration is decreasing as the ligand is cleared from the patient. The t alpha half life is the half life of the first phase and the t beta half life is the half life of the second phase. Thus, in one embodiment, in the context of the present invention, the variable domain, fusion protein or ligand has a tα half-life in the range of (or of about) 15 minutes or more. In one embodiment, the lower end of the range is (or is about) 30 minutes, 45 minutes, 1 hour, 2 hours, 3 hours, 4 hours, 5 hours, 6 hours, 7 hours, 10 hours, 11 hours or 12 hours. In addition, or alternatively, the variable domain, fusion protein or ligand according to the invention will have a tα half life in the range of up to and including 12 hours (or about 12 hours). In one embodiment, the upper end of the range is (or is about) 11, 10, 9, 8, 7, 6 or 5 hours. An example of a suitable range is (or is about) 1 to 6 hours, 2 to 5 hours or 3 to 4 hours.

In one embodiment, the present invention provides the variable domain, fusion protein or ligand according to the invention has a tβ half-life in the range of (or of about) 2.5 hours or more. In one embodiment, the lower end of the range is (or is about) 3 hours, 4 hours, 5 hours, 6 hours, 7 hours, 10 hours, 11 hours, or 12 hours. In addition, or alternatively, the tβ half-life is (or is about) up to and including 21 or 25 days. In one embodiment, the upper end of the range is (or is about) 12 hours, 24 hours, 2 days, 3 days, 5 days, 10 days, 15 days, 19 days, 20 days, 21 days or 22 days. For example, the variable domain, fusion protein or ligand according to the invention will have a tβ half life in the range 12 to 60 hours (or about 12 to 60 hours). In a further embodiment, it will be in the range 12 to 48 hours (or about 12 to 48 hours). In a further embodiment still, it will be in the range 12 to 26 hours (or about 12 to 26 hours).

As an alternative to using two-compartment modeling, the skilled person will be familiar with the use of non-compartmental modeling, which can be used to determine terminal half-lives (in this respect, the term "terminal half-life" as used herein means a terminal half-life determined using non-compartmental modeling). The WinNonlin analysis package, eg version 5.1 (available from Pharsight Corp., Mountain View, Calif. 94040, USA) can be used, for example, to model the curve in this way. In this instance, in one embodiment the single variable domain, fusion protein or ligand has a terminal half life of at least (or at least about) 8 hours, 10 hours, 12 hours, 15 hours, 28 hours, 20 hours, 1 day, 2 days, 3 days, 7 days, 14 days, 15 days, 16 days, 17 days, 18 days, 19 days, 20 days, 21 days, 22 days, 23 days, 24 days or 25 days. In one embodiment, the upper end of this range is (or is about) 24 hours, 48 hours, 60 hours or 72 hours or 120 hours. For example, the terminal half-life is (or is about) from 8 hours to 60 hours, or 8 hours to 48 hours or 12 to 120 hours, eg, in man.

In addition, or alternatively to the above criteria, the variable domain, fusion protein or ligand according to the invention has an AUC value (area under the curve) in the range of (or of about) 1 mg·min/ml or more. In one embodiment, the lower end of the range is (or is about) 5, 10, 15, 20, 30, 100, 200 or 300 mg·min/ml. In addition, or alternatively, the variable domain, fusion protein or ligand according to the invention has an AUC in the range of (or of about) up to 600 mg·min/ml. In one embodiment, the upper end of the range is (or is about) 500, 400, 300, 200, 150, 100, 75 or 50 mg·min/ml. Advantageously the variable domain, fusion protein or ligand will have an AUC in (or about in) the range selected from the group consisting of the following: 15 to 150 mg·min/ml, 15 to 100 mg·min/ml, 15 to 75 mg·min/ml, and 15 to 50 mg·min/ml.

"Surface Plasmon Resonance": Competition assays can be used to determine if a specific antigen or epitope, such as human serum albumin, competes with another antigen or epitope, such as *cynomolgus* serum albumin, for binding to a serum albumin binding ligand described herein, such as a specific dAb. Similarly competition assays can be used to determine if a first ligand such as dAb, competes with a second ligand such as a dAb for binding to a target antigen or epitope. The term "competes" as used herein refers to substance, such as a molecule, compound, preferably a protein, which is able to interfere to any extent with the specific binding interaction between two or more molecules. The phrase "does not competitively inhibit" means that substance, such as a molecule, compound, preferably a protein, does not interfere to any measurable or significant extent with the specific binding interaction between two or more molecules. The specific binding interaction between two or more molecules preferably includes the specific binding interaction between a single variable domain and its cognate partner or target. The interfering or competing molecule can be another single variable domain or it can be a molecule that is structurally and/or functionally similar to a cognate partner or target.

The term "binding moiety" refers to a domain that specifically binds an antigen or epitope independently of a different epitope or antigen binding domain. A binding moiety may be a domain antibody (dAb) or may be a domain which is a derivative of a non-immunoglobulin protein scaffold, eg, a scaffold selected from the group consisting of CTLA-4, lipocalin, SpA, an affibody, an avimer, GroEl, transferrin, GroES and fibronectin, which binds to a ligand other than the natural ligand (in the case of the present invention, the moiety binds serum albumin). See WO2008/096158, which discloses examples of protein scaffolds and methods for selecting antigen or epitope-specific binding domains from repertoires (see Examples 17 to 25). These specific disclosures of WO2008/096158 are expressly incorporated herein by reference as though explicitly written herein and for use with the present invention, and it is contemplated that any part of such disclosure can be incorporated into one or more claims herein).

In a first aspect, the invention provides an anti-serum albumin (SA) immunoglobulin single variable domain variant of DOM7h-14, wherein the variant comprises at least one mutation in CDR3 region 92 to 96 (position numbering according to Kabat) compared to DOM7h-14, and wherein the variant has from 1 to 8 changes compared to the amino acid sequence of DOM7h-14.

Optionally, the variant comprises a AQG(X1)(X2)(X3)P(X4)T motif, wherein A is at position 89 (according to Kabat), and at least one of (X1) to (X4) represents an amino acid change compared to the sequence of DOM7h-14.
In one embodiment, position 95 (according to Kabat) is Pro. Additionally or alternatively, in one embodiment position 89 (according to Kabat) is Ala. Additionally or alternatively, in one embodiment position 90 (according to Kabat) is Gln. Additionally or alternatively, in one embodiment position 91 (according to Kabat) is Gly. Additionally or alternatively, in one embodiment position 97 (according to Kabat) is Thr.

In an embodiment, the variant comprises a mutation at each of positions 92, 93 and 94 and optionally position 96 (numbering according to Kabat) compared to DOM7h-14.
Optionally, the variant comprises one or more amino acid residues selected from
Position 92=L or F,
Position 93=R, M or K,
Position 94=H or K, and
Position 96=K or M (numbering according to Kabat).
In one embodiment, the variant comprises a Lys or Met at position 96 (numbering according to Kabat) compared to DOM7h-14. In this embodiment, optionally the variant comprises one or more amino acid residues selected from
Position 92=L or F,
Position 93=R, M or K, and
Position 94=H or K (numbering according to Kabat).

In one embodiment, the variant comprises an amino acid sequence that is identical to the amino acid sequence of a single variable domain selected from DOM7h-14-10, DOM7h-14-18, DOM7h-14-28 and DOM7h-14-36 or has up to 4 changes compared to the selected amino acid sequence, wherein the variant comprises at least one mutation in CDR3 region 92 to 96 (position numbering according to Kabat) compared to DOM7h-14.

An aspect of the invention provides an anti-serum albumin (SA) binding moiety comprising CDR3 of a variant according to the first aspect of the invention. In one embodiment, the SA-binding moiety comprises CDR1 of the selected variant or an amino acid sequence that is at least 50% identical to CDR1 of the selected variant. Additionally or alternatively, in an embodiment the SA-binding moiety comprises CDR2 of the selected variant or an amino acid sequence that is at least 50% identical to CDR2 of the selected variant.

In a further aspect of the invention, there is provided an anti-serum albumin (SA) immunoglobulin single variable domain variant of DOM7h-14, wherein the variant comprises a Ser at position 22 and a Glu at position 42 (numbering according to Kabat) compared to DOM7h-14, and wherein the variant has from 0 to 4 further changes compared to the amino acid sequence of DOM7h-14. In one embodiment, the variant comprises an amino acid sequence that is identical to the amino acid sequence of DOM7h-14-19 or has up to 4 changes compared to the amino acid sequence of DOM7h-14-19, wherein the variant comprises a Ser at position 22 and a Glu at position 42 (numbering according to Kabat) compared to DOM7h-14.

In one embodiment, the variant or binding moiety according to any aspect or embodiment of the invention comprises one or more of the following kinetic characteristics:—
 (a) The variant or moiety comprises a binding site that specifically binds human SA with a dissociation constant (KD) from (or from about) 0.1 to (or to about) 10000 nM, optionally from (or from about) 1 to (or to about) 6000 nM, as determined by surface plasmon resonance;
 (b) The variant or moiety comprises a binding site that specifically binds human SA with an off-rate constant ($K_d$) from (or from about) $1.5 \times 10^{-4}$ to (or to about) 0.1 sec$^{-1}$, optionally from (or from about) $3 \times 10^{-4}$ to (or to about) 0.1 sec$^{-1}$ as determined by surface plasmon resonance;
 (c) The variant or moiety comprises a binding site that specifically binds human SA with an on-rate constant ($K_a$) from (or from about) $2 \times 10^6$ to (or to about) $1 \times 10^4 M^{-1}$ sec$^{-1}$, optionally from (or from about) $1 \times 10^6$ to (or to about) $2 \times 10^4 M^{-1}$ sec$^{-1}$ as determined by surface plasmon resonance;

(d) The variant or moiety comprises a binding site that specifically binds *Cynomolgus* monkey SA with a dissociation constant (KD) from (or from about) 0.1 to (or to about) 10000 nM, optionally from (or from abou)t 1 to (or to about) 6000 nM, as determined by surface plasmon resonance;

(e) The variant or moiety of any preceding claim, wherein the variant comprises a binding site that specifically binds *Cynomolgus* monkey SA with an off-rate constant ($K_d$) from (or from about) $1.5 \times 10^{-4}$ to (or to about) 0.1 sec$^{-1}$, optionally from (or from about) $3 \times 10^{-4}$ to (or to about) 0.1 sec$^{-1}$ as determined by surface plasmon resonance;

(f) The variant or moiety of any preceding claim, wherein the variant comprises a binding site that specifically binds *Cynomolgus* monkey SA with an on-rate constant ($K_a$) from (or from about) $2 \times 10^6$ to (or to about) $1 \times 10^4 M^{-1}$ sec$^{-1}$, optionally from (or from about) $1 \times 10^6$ to (or to about) $5 \times 10^3 M^{-1}$ sec$^{-1}$ as determined by surface plasmon resonance;

(g) The variant or moiety comprises a binding site that specifically binds rat SA with a dissociation constant (KD) from (or from about) 1 to (or to about) 10000 nM, optionally from (or from about) 20 to (or to about) 6000 nM, as determined by surface plasmon resonance;

(h) The variant or moiety comprises a binding site that specifically binds rat SA with an off-rate constant ($K_d$) from (or from about) $2 \times 10^{-3}$ to (or to about) 0.15 sec$^{-1}$, optionally from (or from about) $9 \times 10^{-3}$ to (or to about) 0.14 sec$^{-1}$ as determined by surface plasmon resonance;

(i) The variant or moiety comprises a binding site that specifically binds rat SA with an on-rate constant ($K_a$) from (or from about) $2 \times 10^6$ to (or to about) $1 \times 10^4 M^{-1}$ sec$^{-1}$, optionally from (or from about) $1 \times 10^6$ to (or to about) $3 \times 10^4 M^{-1}$ sec$^{-1}$ as determined by surface plasmon resonance;

(j) The variant or moiety comprises a binding site that specifically binds mouse SA with a dissociation constant (KD) from (or from about) 1 to (or to about) 10000 nM as determined by surface plasmon resonance;

(k) The variant or moiety comprises a binding site that specifically binds mouse SA with an off-rate constant ($K_d$) from (or from about) $2 \times 10^{-3}$ to (or to about) 0.15 sec$^{-1}$ as determined by surface plasmon resonance; and/or (l) The variant or moiety comprises a binding site that specifically binds mouse SA with an on-rate constant ($K_a$) from (or from about) $2 \times 10^6$ to (or to about) $1 \times 10^4 M^{-1}$ sec$^{-1}$, optionally from (or from about) $2 \times 10^6$ to (or to about) $1.5 \times 10^4 M^{-1}$ sec$^{-1}$ as determined by surface plasmon resonance.

Optionally, the variant or moiety has

I: a KD according to (a) and (d), a $K_d$ according to (b) and (e), and a $K_a$ according to (c) and (f); or II: a KD according to (a) and (g), a $K_d$ according to (b) and (h), and a $K_a$ according to (c) and (i); or III: a KD according to (a) and (j), a $K_d$ according to (b) and (k), and a $K_a$ according to (c) and (l); or IV: kinetics according to I and II; or V: kinetics according to I and III; or VI: kinetics according to I, II and III.

The invention also provides a ligand comprising a variant or moiety of any preceding aspect or embodiment of the invention. For example, the ligand can be a dual-specific ligand (see WO04003019 for examples of dual-specific ligands). In one aspect, the invention provides a multispecific ligand comprising an anti-SA variant or moiety of any preceding aspect or embodiment of the invention and a further binding moiety that specifically binds a target antigen other than SA. The or each binding moiety can be any binding moiety that specifically binds a target, eg, the moiety is an antibody, antibody fragment, scFv, Fab, dAb or a binding moiety comprising a non-immunoglobulin protein scaffold. Such moieties are disclosed in detail in WO2008/096158 (see examples 17 to 25, which disclosure is incorporated herein by reference). Examples of non-immunoglobulin scaffolds are CTLA-4, lipocallin, staphylococcal protein A (spA), Affibody™, Avimers™, GroEL and fibronectin.

In one embodiment, a linker is provided between the anti-target binding moiety and the anti-SA single variant or moiety, the linker comprising the amino acid sequence AST, optionally ASTSGPS, eg, where anti-SA and anti-target dAbs are used. Alternative linkers are described in WO2007085814 (incorporated herein by reference) and WO2008/096158 (see the passage at page 135, line 12 to page 140, line 14, which disclosure and all sequences of linkers are expressly incorporated herein by reference as though explicitly written herein and for use with the present invention, and it is contemplated that any part of such disclosure can be incorporated into one or more claims herein).

In one embodiment of the multispecific ligand, the target antigen may be, or be part of, polypeptides, proteins or nucleic acids, which may be naturally occurring or synthetic. In this respect, the ligand of the invention may bind the target antigen and act as an antagonist or agonist (e.g., EPO receptor agonist). One skilled in the art will appreciate that the choice is large and varied. They may be for instance, human or animal proteins, cytokines, cytokine receptors, where cytokine receptors include receptors for cytokines, enzymes, co-factors for enzymes or DNA binding proteins. Suitable cytokines and growth factors include, but are preferably not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalizing receptors that are over-expressed on certain cells, such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, α1-antitrypsin, tissue factor protease inhibitor, PDK1, GSK1, Bad, caspase-9, Forkhead, an antigen of *Helicobacter pylori*, an antigen of *Mycobacterium tuberculosis*, and an antigen of influenza virus. It will be appreciated that this list is by no means exhaustive.

In one embodiment, the multispecific ligand comprises an anti-SA dAb variant or moiety of the invention and an anti-TNFR1 binding moiety, eg, an anti-TNFR1 dAb. Optionally, the ligand has only one anti-TNFR1 binding moiety (eg, dAb) to reduce the chance of receptor cross-linking. In one embodiment, the anti-SA dAb variant is DOM7h-14-10.

In one embodiment, the anti-TNFR1 binding moiety is DOM1h-131-206 disclosed in WO2008149148 (the amino acid sequence of which and the nucleotide sequence of which, as disclosed in that PCT application, are expressly incorporated herein by reference as though explicitly written herein and for use with the present invention, and it is contemplated that any part of such disclosure can be incorporated into one or more claims herein). In one embodiment, the multispecific ligand comprises or consists of the amino acid sequence of DOM1h-131-206 and the amino acid sequence of DOM7h-14-10.

In one embodiment, the anti-TNFR1 binding moiety or dAb is any such moiety or dAb disclosed in co-pending application U.S. Ser. No. 61/153,746, the disclosure of which is incorporated herein by reference. In one embodiment, the anti-TNFR1 binding moiety comprises an amino acid sequence that is at least 95% identical to the amino acid sequence of DOM1h-574-156, DOM1h-574-72, DOM1h-574-109, DOM1h-574-138, DOM1h-574-162 or DOM1h-574-180 or the amino acid sequence of any anti-TNFR1 dAb disclosed in Table 3. In one embodiment, the multispecific ligand comprises or consists of the amino acid sequence of DOM1h-574-156 and the amino acid sequence of DOM7h-14-10.

In one embodiment, the ligand of the invention is a fusion protein comprising a variant or moiety of the invention fused directly or indirectly to one or more polypeptides. For example, the fusion protein can be a "drug fusion" as disclosed in WO2005/118642 (the disclosure of which is incorporated herein by reference), comprising a variant or moiety of the invention and a polypeptide drug as defined in that PCT application.

As used herein, "drug" refers to any compound (e.g., small organic molecule, nucleic acid, polypeptide) that can be administered to an individual to produce a beneficial, therapeutic or diagnostic effect through binding to and/or altering the function of a biological target molecule in the individual. The target molecule can be an endogenous target molecule encoded by the individual's genome (e.g. an enzyme, receptor, growth factor, cytokine encoded by the individual's genome) or an exogenous target molecule encoded by the genome of a pathogen (e. g. an enzyme encoded by the genome of a virus, bacterium, fungus, nematode or other pathogen). Suitable drugs for use in fusion proteins and conjugates comprising an anti-SA dAb variant of the invention are disclosed in WO2005/118642 and WO2006/059106 (the entire disclosures of which are incorporated herein by reference, and including the entire list of specific drugs as though this list were expressly written herein, and it is contemplated that such incorporation provides disclosure of specific drugs for inclusion in claims herein). For example, the drug can be glucagon-like peptide 1 (GLP-1) or a variant, interferon alpha 2b or a variant or exendin-4 or a variant.

In one embodiment, the invention provides a drug conjugate as defined and disclosed in WO2005/118642 and WO2006/059106, wherein the conjugate comprises a variant or moiety of the invention. In one example, the drug is covalently linked to the variant or moiety (eg, the variant or moiety and the drug are expressed as part of a single polypeptide). Alternatively, in an example, the drug is non-covalently bonded or associated with the variant or moiety. The drug can be covalently or noncovalently bonded to the variant or moiety directly or indirectly (e.g., through a suitable linker and/or noncovalent binding of complementary binding partners (e.g., biotin and avidin)). When complementary binding partners are employed, one of the binding partners can be covalently bonded to the drug directly or through a suitable linker moiety, and the complementary binding partner can be covalently bonded to the variant or moiety directly or through a suitable linker moiety. When the drug is a polypeptide or peptide, the drug composition can be a fusion protein, wherein the polypeptide or peptide, drug and the polypeptide binding moiety are discrete parts (moieties) of a continuous polypeptide chain. As described herein, the polypeptide binding moieties and polypeptide drug moieties can be directly bonded to each other through a peptide bond, or linked through a suitable amino acid, or peptide or polypeptide linker.

A ligand which contains one single variable domain (monomer) variant or moiety of the invention or more than one single variable domain or moiety (multimer, fusion protein, conjugate, and dual specific ligand as defined herein) which specifically binds to serum albumin, can further comprise one or more entities selected from, but preferably not limited to a label, a tag, an additional single variable domain, a dAb, an antibody, an antibody fragment, a marker and a drug. One or more of these entities can be located at either the COOH terminus or at the N terminus or at both the N terminus and the COOH terminus of the ligand comprising the single variable domain or moiety, (either immunoglobulin or non-immunoglobulin single variable domain). One or more of these entities can be located at either the COOH terminus, or the N terminus, or both the N terminus and the COOH terminus of the single variable domain or moiety which specifically binds serum albumin of the ligand which contains one single variable domain (monomer) or moiety or more than one single variable domains or moieties (multimer, fusion protein, conjugate, and dual specific ligand as defined herein). Non-limiting examples of tags which can be positioned at one or both of these termini include a HA, his or a myc tag. The entities, including one or more tags, labels and drugs, can be bound to the ligand which contains one single variable domain (monomer) or more than one single variable domain or moiety (multimer, fusion protein, conjugate, and dual specific ligand as defined herein), which binds serum albumin, either directly or through linkers as described above.

An aspect of the invention provides a fusion product, eg, a fusion protein or fusion with a peptide or conjugate with an NCE (new chemical entity) drug, comprising a polypeptide drug fused or conjugated (for an NCE) to any variant or moiety as described above, optionally wherein the variant or moiety is DOM7h-14-10 (or a variant having an amino acid that is at least 95, 96, 97, 98 or 99% identical to the amino acid sequence of DOM7h-14-10). DOM7h-14-10 gives only a modest drop in affinity when fused or conjugated to partner, making them useful in fusion products.

The invention provides a composition comprising a variant, fusion protein, conjugate or ligand of any aspect of the invention and a pharmaceutically acceptable diluent, carrier, excipient or vehicle.

Also encompassed herein is an isolated nucleic acid encoding any of the variants, moieties, fusion proteins, conjugates or ligands described herein, e.g., a ligand which contains one single variable domain (monomer) variant of the invention or more than one single variable domain (e.g., multimer, fusion protein, conjugate, and dual specific ligand as defined herein) variant which specifically binds to serum albumin, or which specifically binds both human serum albumin and at least one non-human serum albumin, or functionally active fragments thereof. Also encompassed herein is a vector and/or an expression vector, a host cell comprising the vector, e.g., a plant or animal cell and/or cell line transformed with a vector, a method of expressing and/or producing one or more variants, moieties, fusion proteins or ligands which contains one single variable domain (monomer) variant or moiety or more than one single variable domain variants or moieties (e.g., multimer, fusion protein, conjugate, and dual specific ligand as defined herein) which specifically binds to serum albumin, or fragment(s) thereof encoded by said vectors, including in some instances culturing the host cell so that the one or more variants, moieties, fusion proteins or ligands or fragments thereof are expressed and optionally recovering the ligand which contains one single variable domain or moiety (monomer) or more than one single variable domain or moiety (e.g., multimer, fusion protein, conjugate, and dual specific ligand as defined herein) which specifically binds to serum albumin, from the host cell culture medium. Also encompassed are methods of contacting a ligand described herein with serum albumin, including serum albumin and/or non-human serum albumin(s), and/or one or more targets other than serum albumin, where the targets include biologically active molecules, and include animal proteins, cytokines as listed above, and include methods where the contacting is in vitro as well as administering any of the variants, moieties, fusion proteins or ligands described herein to an individual host animal or cell in vivo and/or ex vivo. Preferably, administering ligands described herein which comprises a single variable domain (immunoglobulin or non-immunoglobulin) directed to serum albumin and/or non-human serum albumin(s), and one or more domains directed to one or more targets other than serum albumin, will increase the half life, including the T beta and/or terminal half life, of the anti-target ligand. Nucleic acid molecules encoding the variants, fusion proteins or single domain containing ligands or fragments thereof, including functional fragments thereof, are contemplated herein. Vectors encoding the nucleic acid molecules, including but preferably not limited to expression vectors, are contemplated herein, as are host cells from a cell line or organism containing one or more of these expression vectors. Also contemplated are methods of producing any variant, fusion protein or ligand, including, but preferably not limited to any of the aforementioned nucleic acids, vectors and host cells.

An aspect of the invention provides a nucleic acid comprising a nucleotide sequence encoding a variant according to the invention or a multispecific ligand of the invention or fusion protein of the invention.

An aspect of the invention provides a nucleic acid comprising the nucleotide sequence of a DOM7h-14 variant selected from DOM7h-14-10, DOM7h-14-18, DOM7h-14-28, DOM7h-14-36 and DOM7h-14-19 or a nucleotide sequence that is at least 70, 75, 80, 85, 90, 95, 96, 97, 98 or 99% identical to said selected sequence.

An aspect of the invention provides a vector comprising the nucleic acid of the invention. An aspect of the invention provides an isolated host cell comprising the vector.

Reference is made to WO2008/096158 for details of library vector systems, combining single variable domains, characterization of dual specific ligands, structure of dual specific ligands, scaffolds for use in constructing dual specific ligands, uses of anti-serum albumin dAbs and multispecific ligands and half-life-enhanced ligands, and compositions and formulations of comprising anti-serum albumin dAbs. These disclosures are incorporated herein by reference to provide guidance for use with the present invention, including for variants, moieties, ligands, fusion proteins, conjugates, nucleic acids, vectors, hosts and compositions of the present invention.

DOM7h-11 variant sequences, which are not according to the invention, are disclosed in a co-pending US provisional patent application entitled IMPROVED ANTI-SERUM ALBUMIN BINDING VARIANTS, filed on the same day as the present application. These sequences of DOM7h-11 variants (SEQ ID NO:s 1-10 in the co-pending application) are incorporated herein by reference as though explicitly written herein.

Sequences

TABLE 1

Amino Acid Sequences of DOM7h-14 Variant dAbs

DOM7h-14-10 (SEQ ID NO: 1)
DIQMTQSPSSLSASVGDRVTITCRASQWIGSQLSWYQQKPGKAPKLLI

MWRSSLQSGVPSRFSGSGSGTDFTLTISSLQPEDFATYYCAQGLRHPK

TFGQGTKVEIKR

DOM7h-14-18 (SEQ ID NO: 2)
DIQMTQSPSSLSASVGDRVTITCRASQWIGSQLSWYQQKPGKAPKLLIM

WRSSLQSGVPSRFSGSGSGTDFTLTISSLQPEDFATYYCAQGLMKPMT

FGQGTKVEIKR

DOM7h-14-19 (SEQ ID NO: 3)
DIQMTQSPSSLSASVGDRVTISCRASQWIGSQLSWYQQKPGEAPKLLIM

WRSSLQSGVPSRFSGSGSGTDFTLTISSLQPEDFATYYCAQGAALPRT

FGQGTKVEIKR

DOM7h-14-28 (SEQ ID NO: 4)
DIQMTQSPSSLSASVGDRVTITCRASQWIGSQLSWYQQKPGKAPKLLIM

WRSSLQSGVPSRFSGSGSGTDFTLTISSLQPEDFATYYCAQGAALPKT

FGQGTKVEIKR

DOM7h-14-36 (SEQ ID NO: 5)
DIQMTQSPSSLSASVGDRVTITCRASQWIGSQLSWYQQKPGKAPKLLIM

WRSSLQSGVPSRFSGSGSGTDFTLTISSLQPEDFATYYCAQGFKKPRT

FGQGTKVEIKR

TABLE 2

Nucleotide Sequences of DOM7h-14 Variant dAbs

DOM7h-14-10 (SEQ ID NO: 6)
GACATCCAGA TGACCCAGTC TCCATCCTCC CTGTCTGCAT

CTGTAGGAGA CCGTGT CACC ATCACTTGCC GGGCAAGTCA

GTGGATTGGG TCTCAGTTAT CTTGGTACCA GC AGAAACCA

GGGAAAGCCC CTAAGCTCCT GATCATGTGG CGTTCCTCGT

TGCAAAGT GG GGTCCCATCA CGTTTCAGTG GCAGTGGATC

TGGGACAGAT TTCACTCTCA CCAT CAGCAG TCTGCAACCT

GAAGATTTTG CTACGTACTA CTGTGCTCAG GGTTTGAGGC

ATCCTAAGAC GTTCGGCCAA GGGACCAAGG TGGAAATCAA ACGG

TABLE 2-continued

Nucleotide Sequences of DOM7h-14 Variant dAbs

DOM7h-14-18 (SEQ ID NO: 7)
GACATCCAGA TGACCCAGTC TCCATCCTCC CTGTCTGCAT
CTGTAGGAGA CCGTGT CACC ATCACTTGCC GGGCAAGTCA
GTGGATTGGG TCTCAGTTAT CTTGGTACCA GC AGAAACCA
GGGAAAGCCC CTAAGCTCCT GATCATGTGG CGTTCCTCGT
TGCAAAGT GG GGTCCCATCA CGTTTCAGTG GCAGTGGATC
TGGGACAGAT TCACTCTCA CCAT CAGCAG TCTGCAACCT
GAAGATTTTG CTACGTACTA CTGTGCTCAG GGTCTTATGA
AGCCTATGAC GTTCGGCCAA GGGACCAAGG TGGAAATCAA ACGG

DOM7h-14-19 (SEQ ID NO: 8)
GACATCCAGA TGACCCAGTC TCCATCCTCC CTGTCTGCAT
CTGTAGGAGA CCGTGT CACC ATCTCTTGCC GGGCAAGTCA
GTGGATTGGG TCTCAGTTAT CTTGGTACCA GC AGAAACCA
GGGGAAGCCC CTAAGCTCCT GATCATGTGG CGTTCCTCGT
TGCAAAGT GG GGTCCCATCA CGTTTCAGTG GCAGTGGATC
TGGGACAGAT TCACTCTCA CCAT CAGCAG TCTGCAACCT
GAAGATTTTG CTACGTACTA CTGTGCTCAG GGTGCGGCGT
TGCCTAGGAC GTTCGGCCAA GGGACCAAGG TGGAAATCAA ACGG

TABLE 2-continued

Nucleotide Sequences of DOM7h-14 Variant dAbs

DOM7h-14-28 (SEQ ID NO: 9)
GACATCCAGA TGACCCAGTC TCCATCCTCC CTGTCTGCAT
CTGTAGGAGA CCGTGT CACC ATCACTTGCC GGGCAAGTCA
GTGGATTGGG TCTCAGTTAT CTTGGTACCA GC AGAAACCA
GGGAAAGCCC CTAAGCTCCT GATCATGTGG CGTTCCTCGT
TGCAAAGT GG GGTCCCATCA CGTTTCAGTG GCAGTGGATC
TGGGACAGAT TCACTCTCA CCAT CAGCAG TCTGCAACCT
GAAGATTTTG CTACATACTA CTGTGCTCAG GGTGCGGCGT
TGCCTAAGAC GTTCGGCCAA GGGACCAAGG TGGAAATCAA ACGG

DOM7h-14-36 (SEQ ID NO: 10)
GACATCCAGA TGACCCAGTC TCCATCCTCC CTGTCTGCAT
CTGTAGGAGA CCGTGT CACC ATCACTTGCC GGGCAAGTCA
GTGGATTGGG TCTCAGTTAT CTTGGTACCA GC AGAAACCA
GGGAAAGCCC CTAAGCTCCT GATCATGTGG CGTTCCTCGT
TGCAAAGT GG GGTCCCATCA CGTTTCAGTG GCAGTGGATC
TGGGACAGAT TCACTCTCA CCAT CAGCAG TCTGCAACCT
GAAGATTTTG CTACGTACTA CTGTGCTCAG GGTTTTAAGA
AGCCTCGGAC GTTCGGCCAA GGGACCAAGG TGGAAATCAA ACGG

TABLE 3

Amino Acid Sequences of anti-TNFR1 dAbs

>DOM1h-509 (SEQ ID NO: 11)
EVQLLESGGGLVQPGGSLRLSCAASGFTFSQYRMHWVRQAPGKSLEWVSSIDTRGSST
YYADPVKGRFTISRDNSKNTLYLQMNSLRAEDTAVYYCAKAVTMFSPFFDYWGQGTLV
TVSS

>DOM1h-510 (SEQ ID NO: 12)
EVQLLESGGGLVQPGGSLRLSCAASGFTFADYGMRWVRQAPGKGLEWVSSITRTGRVT
YYADSVKGRFTISRDNSKNTLYLQMNSLRAEDTAVYYCAKWRNRHGEYLADFDYWGQG
TLVTVSS

>DOM1h-543 (SEQ ID NO: 13)
EVQLLESGGGLVQPGGSLRLSCAASGFTFMRYRMHWVRQAPGKGLEWVSSIDSNGSST
YYADSVKGRFTISRDNSKNTLYLQMNSLRAEDTAVYYCAKDRTERSPVFDYWGQGTLV
TVSS

>DOM1h-549 (SEQ ID NO: 14)
EVQLLESGGGLVQPGGSLRLSCAASGFTFVDYEMHWVRQAPGKGLEWVSSISESGTTT
YYADSVKGRFTISRDNSKNTLYLQMNSLRAEDTAVYYCAKRRFSASTFDYWGQGTLVT
VSS

>DOM1h-574 (SEQ ID NO: 15)
EVQLLESGGGLVQPGGSLRLSCAASGFTFVKYSMGWVRQAPGKGLEWVSQISNTGGHT
YYADSVKGRFTISRDNSKNTLYLQMNSLRAEDTAVYYCAKYTGHWEPFDYWGQGTLVT
VSS

TABLE 3-continued

Amino Acid Sequences of anti-TNFR1 dAbs

>DOM1h-574-1 (SEQ ID NO: 16)
EVQLLESGGGLVQPGGSLRLSCAASGFTFVKYSMGWVRQAPGKGLEWVSQISNTGGHT

YYADSVKGRFTISRDNSKNTLYLQMNSLRAEDTAVYYCAKYTGRWEPYDYWGQGTLVT

VSS

>DOM1h-574-2 (SEQ ID NO: 17)
EVQLLESGGGLVQPGGSLRLSCAASGFTFVKYSMGWVRQAPGKGLEWVSQISNTGGHT

YYADSVKGRFTISRDNSKNTLYLQMNSLRAEDTAVYYCAKYTGRWEPFDYWGQGTLVT

VSS

>DOM1h-574-7 (SEQ ID NO: 18)
EVQLLESGGGLVQPGGSLRLSCAASGFTFVKYSMGWVRQAPGKGLEWVSQISNTGGHT

YYADSVKGRFTISRDNSKNTLYLQMNSLRAEDTAVYYCAIYTGRWEPFDYWGQGTLVT

VSS

>DOM1h-574-8 (SEQ ID NO: 19)
EVQLLESGGGLVQPGGSLRLSCAASGFTFVKYSMGWVRQAPGKGPEWVSQISNTGGHT

YYADSVKGRFTISRDNSKNTLYLQMNSLRAEDTAVYYCAIYTGRWEPFDYWGQGTLVT

VSS

>DOM1h-574-9 (SEQ ID NO: 20)
EVQLLESGGGLVQPGGSLRLSCAASGFTFVKYSMGWVRQAPGKGLEWVSQISNTGGHT

YYADSVKGRFTISRDNSKNTLYMQMNSLRAEDTAVYYCAIYTGRWEPFDYWGQGTLVT

VSS

>DOM1h-574-10 (SEQ ID NO: 21)
EVQLLESGGGLVQPGGSLRLSCAASGFTFGKYSMGWVRQAPGKDLEWVSQISNTGGHT

YYADSVKGRFTISRDNSKNTLYLQMNSLRAEDTAVYYCAIYTGRWEPFDYWGQGTLVT

VSS

>DOM1h-574-11 (SEQ ID NO: 22)
EVQLLESGGGLVQPGGSLRLSCAASGFTFVKYSMGWVRQAPGKGLEWVSQISNTGGHT

YYADSVKGRFTISRDNSKNTLYLQMNSLRAEDTAVYYCAKYTGRWEPFDHWGQGTLVT

VSS

>DOM1h-574-12 (SEQ ID NO: 23)
EVQLLESGGGLVQPGGSLRLSCAASGFTFVKYSMGWVRQAPGKGLEWVSQISNTGDHT

YYADSVKGRFTISRDNSKNTLYLQMNSLRAEDTAVYYCAKYTGRWEPFDYWGQGTLVT

VSS

>DOM1h-574-13 (SEQ ID NO: 24)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAKYTGRWEPFDYWGQGTLVT

VSS

>DOM1h-574-14 (SEQ ID NO: 25)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWEPFDYWGQGTLVT

VSS

>DOM1h-574-15 (SEQ ID NO: 26)
EVQLLESGGGLVQPGGSLRLSCAASGFTFVKYSMGWVRQAPGKGLEWVSQISNTGDHT

YYADSVKGRFTISRDNSKNTLYLQMNSLRAEDTAVYYCAIYTGRWEPFDYWGQGTLVT

VSS

TABLE 3-continued

Amino Acid Sequences of anti-TNFR1 dAbs

>DOM1h-574-16 (SEQ ID NO: 27)
EVQLLESGGGLVQPGGSLRLSCAASGFTFVKYSMGWVRQAPGKGPEWVSQISNTGDRT

YYADSVKGRFTISRDNSKNTLYLQMNSLRAEDTAVYYCAIYTGRWEPFDYWGQGTLVT

VSS

>DOM1h-574-17 (SEQ ID NO: 28)
EVQLLESGGGLVQPGGSLRLSCAASGFTFVKYSMGWVRQAPGKGPEWVSQISNTGDHT

YYADSVKGRFTISRDNSKNTLYLQMNSLRAEDTAVYYCAIYTGRWEPFDYWGQGTLVT

VSS

>DOM1h-574-18 (SEQ ID NO: 29)
EVQLLESGGGLVQPGGSLRLSCAASGFTFGKYSMGWVRQAPGKDLEWVSQISNTGDRT

YYADSVKGRFTISRDNSKNTLYLQMNSLRAEDTAVYYCAIYTGRWEPFDYWGQGTLVT

VSS

>DOM1h-574-19 (SEQ ID NO: 30)
EVQLLESGGGLVQPGGSLRLSCAASGFTFGKYSMGWVRQAPGKDLEWVSQISNTGDHT

YYADSVKGRFTISRDNSKNTLYLQMNSLRAEDTAVYYCAIYTGRWEPFDYWGQGTLVT

VSS

>DOM1h-574-25 (SEQ ID NO: 31)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWEPFVYWGQGTLVT

VSS

>DOM1h-574-26 (SEQ ID NO: 32)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWEPFEYWGQGTLVT

VSS

>DOM1h-574-27 (SEQ ID NO: 33)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWKPFEYWGQGTLVT

VSS

>DOM1h-574-28 (SEQ ID NO: 34)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWVPFEYWGQGTLVT

VSS

>DOM1h-574-29 (SEQ ID NO: 35)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWRPFEYWGQGTLVT

VSS

>DOM1h-574-30 (SEQ ID NO: 36)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAAYYCAIYTGRWEPFDYWGQGTLVT

VSS

>DOM1h-574-31 (SEQ ID NO: 37)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWEPFNYWGQGTLVT

VSS

TABLE 3-continued

Amino Acid Sequences of anti-TNFR1 dAbs

>DOM1h-574-32 (SEQ ID NO: 38)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWAPFEYWGQGTLVT

VSS

>DOM1h-574-33 (SEQ ID NO: 39)
EVQLLESGGGLVQPGGSLRLSCAASGFTFVKYSMGWVRQAPGKGLEWVSQISNTGDRT

YYADSVKGRFTISRDNSKNSLYLQMNSLRAEDTAVYYCAIYTGRWVPFDNWGQGTLVT

VSS

>DOM1h-574-35 (SEQ ID NO: 40)
EVQLLESGGGLVQPGGSLRLSCAASGFTFITYSMGWVRQAPGKGLEWVSQISNTGDRT

YYADSVKGRFTISRDNSKNTLYLQMNSLRAEDTAVYYCAIYTGRWEPFQYWGQGTLVT

VSS

>DOM1h-574-36 (SEQ ID NO: 41)
EVQLLESGGGLVQPGGSLRLSCAASGFTFGKYSMGWVRQAPGKGLEWVSQISNTGDRT

YYADSVKGRFTISRDNSKNTLYLQMNSLRAEDTAVYYCAIYTGRWEPFDYWGQGTLVT

VSS

>DOM1h-574-37 (SEQ ID NO: 42)
EVQLLESGGGLVQPGGSLRLSCAASGFTFFFKYSMGWVRQAPGKGLEWVSQISNTGDRT

YYADSVKGRFTISRDNSKNTLYLQMNSLRAEDTAVYYCAIYTGRWEPFDYWGQGTLVT

VSS

>DOM1h-574-38 (SEQ ID NO: 43)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWEPFDYWGQGTLVT

VSS

>DOM1h-574-39 (SEQ ID NO: 44)
EVQLLESGGGLVQPGGSLRLSCAASGFTFVKYSMGWVRQAPGKGLEWVSQISNTGDRR

YYADAVKGRFTISRDNSKNTLYLQMNSLRAEDTAVYYCAIYTGRWEPFDYWGQGTLVT

VSS

>DOM1h-574-40 (SEQ ID NO: 45)
EVQLLESGGGLVQPGGSLRLSCAASGFTFVKYSMGWVRQAPGKGLEWVSQISNTGDRT

YYADSVKGRFTISRDNSKNTLYLQMNSLRAEDTAVYYCAIYTGRWEPFKYWGQGTLVT

VSS

>DOM1h-574-53 (SEQ ID NO: 46)
EVQLLESGGGLVQPGGSLRLSCAASGFTFSKYSMGWVRQAPGKGLEWVSQISNTGERR

YYADSVKGRFTISRDNPKNTLYLQMNSLRAEDTAVYYCAIYTGRWEPFEYWGQGTLVT

VSS

>DOM1h-574-54 (SEQ ID NO: 47)
EVQLLESGGGLVQPGGSLRLSCAASGFTFVNYSMGWVRQAPGKGLEWVSQISNTGDRT

YYADSVKGRFTISRDNSKNTLYLQMNSLRAEDTAVYYCAIYTGRWEPYEYWGQGTLVT

VTS

>DOM1h-574-65 (SEQ ID NO: 48)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAVYYCAIYTGRWEPFVYWGQGTLVT

VSS

TABLE 3-continued

Amino Acid Sequences of anti-TNFR1 dAbs

>DOM1h-574-66 (SEQ ID NO: 49)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAVYYCAIYTGRWKPFEYWGQGTLVT

VSS

>DOM1h-574-67 (SEQ ID NO: 50)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAVYYCAIYTGRWVPFEYWGQGTLVT

VSS

>DOM1h-574-68 (SEQ ID NO: 51)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAVYYCAIYTGRWRPFEYWGQGTLVT

VSS

>DOM1h-574-69 (SEQ ID NO: 52)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAVYYCAIYTGRWAPFEYWGQGTLVT

VSS

>DOM1h-574-70 (SEQ ID NO: 53)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAVYTGRWEPFVYWGQGTLVT

VSS

>DOM1h-574-71 (SEQ ID NO: 54)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWKPFEYWGQGTLVT

VSS

>DOM1h-574-72 (SEQ ID NO: 55)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWVPFEYWGQGTLVT

VSS

>DOM1h-574-73 (SEQ ID NO: 56)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWRPFEYWGQGTLVT

VSS

>DOM1h-574-74 (SEQ ID NO: 57)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWAPFEYWGQGTLVT

VSS

>DOM1h-574-75 (SEQ ID NO: 58)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWEPFVYWGQGTLVT

VSS

>DOM1h-574-76 (SEQ ID NO: 59)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWKPFEYWGQGTLVT

VSS

TABLE 3-continued

Amino Acid Sequences of anti-TNFR1 dAbs

>DOM1h-574-77 (SEQ ID NO: 60)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWVPFEYWGQGTLVT

VSS

>DOM1h-574-78 (SEQ ID NO: 61)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWRPFEYWGQGTLVT

VSS

>DOM1h-574-79 (SEQ ID NO: 62)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWAPFEYWGQGTLVT

VSS

>DOM1h-574-84 (SEQ ID NO: 63)
EVQLLESGGGLVQPGGSLRLSCAASGFTFVKYSMGWVRQAPGKGLEWVSQISNTGDRR

YYADAVKGRFTISRDNSKNTLYLQMNSLRAEDTAVYYCAIYTGRWEPFVYWGQGTLVT

VSS

>DOM1h-574-85 (SEQ ID NO: 64)
EVQLLESGGGLVQPGGSLRLSCAASGFTFVKYSMGWVRQAPGKGLEWVSQISNTGDRR

YYADAVKGRFTISRDNSKNTLYLQMNSLRAEDTAVYYCAIYTGRWKPFEYWGQGTLVT

VSS

>DOM1h-574-86 (SEQ ID NO: 65)
EVQLLESGGGLVQPGGSLRLSCAASGFTFVKYSMGWVRQAPGKGLEWVSQISNTGDRR

YYADAVKGRFTISRDNSKNTLYLQMNSLRAEDTAVYYCAIYTGRWVPFEYWGQGTLVT

VSS

>DOM1h-574-87 (SEQ ID NO: 66)
EVQLLESGGGLVQPGGSLRLSCAASGFTFVKYSMGWVRQAPGKGLEWVSQISNTGDRR

YYADAVKGRFTISRDNSKNTLYLQMNSLRAEDTAVYYCAIYTGRWRPFEYWGQGTLVT

VSS

>DOM1h-574-88 (SEQ ID NO: 67)
EVQLLESGGGLVQPGGSLRLSCAASGFTFVKYSMGWVRQAPGKGLEWVSQISNTGDRR

YYADAVKGRFTISRDNSKNTLYLQMNSLRAEDTAVYYCAIYTGRWAPFEYWGQGTLVT

VSS

>DOM1h-574-90 (SEQ ID NO: 68)
EVQLLESGGGLVQPGGSLRLSCAASGFTFLKFSMGWVRQAPGKGLEWVSQIANTGDRR

YYADSVKGRFTISRDNSKNTLYLQMNSLRAEDTAVYYCAIYTGRWAPFEYWGQGTLVT

VSS

>DOM1h-574-91 (SEQ ID NO: 69)
EVQLLESGGGLVQPGGSLRLSCAASGFTFLKYSMGWVRQAPGKGLEWVSQISNTADRT

YYAHSVKGRFTISRDNSKNTLYLQMNSLRAEDTAVYYCAIYTGRWAPFEYWGQGTLVT

VSS

>DOM1h-574-92 (SEQ ID NO: 70)
EVQLLESGGGLVQPGGSLRLSCAASGFTFFKYSMGWVRQAPGKGLEWVSQISDTGDRR

YYDDSVKGRFTISRDNSKNTLYLQMNSLRAEDTAVYYCAIYTGRWEPFVYWGQGTLVT

VSS

TABLE 3-continued

Amino Acid Sequences of anti-TNFR1 dAbs

>DOM1h-574-93 (SEQ ID NO: 71)
EVQLLESGGGLVQPGGSLRLSCAASGFTFLKYSMGWVRQAPGKGLEWVSQISDTGDRR

YYDDSVKGRFTISRDNSKNTLYLQMNSLRAEDTAVYYCAIYTGRWEPFVYWGQGTLVT

VSS

>DOM1h-574-94 (SEQ ID NO: 72)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAAYYCAIYTGRWPDFDYWGQGTLVT

VSS

>DOM1h-574-95 (SEQ ID NO: 73)
EVQLLESGGGLVQPGGSLRLSCAASGFTFVKYSMGWVRQAPGKGLEWVSQIANTGDRR

YYADSVKGRFTISRDNSKNTLYLQMNSLRAEDTAAYYCAIYTGRWPDFEYWGQGTLVT

VSS

>DOM1h-574-96 (SEQ ID NO: 74)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWPDFDYWGQGTLVT

VSS

>DOM1h-574-97 (SEQ ID NO: 75)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAIYTGRWPDFEYWGQGTLVT

VSS

>DOM1h-574-98 (SEQ ID NO: 76)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWPDFDYWGQGTLVT

VSS

>DOM1h-574-99 (SEQ ID NO: 77)
EVQLLESGGGLVQPGGSLRLSCAASGFTFVKYSMGWVRQAPGKGLEWVSQISDTGDRR

YYDDSVKGRFTISRDNSKNTLYLQMNSLRAEDTAVYYCAIYTGRWPDFEYWGQGTLVT

VSS

>DOM1h-574-100 (SEQ ID NO: 78)
EVQLLESGGGLVQPGGSLRLSCAASGFTFVKYSMGWVRQAPGKGPEWVSQISAWGDRT

YYADSVKGRFTISRDNSKNTLYLQMNSLRAEDTAVYYCAIYTGRWEPFDYWGQGTLVT

VSS

>DOM1h-574-101 (SEQ ID NO: 79)
EVQLLESGGGLVQPGGSLRLSCAASGFTFVKYSMGWVRQAPGKGPEWVSQISDGGQRT

YYADSVKGRFTISRDNSKNTLYLQMNSLRAEDTAVYYCAIYTGRWEPFDYWGQGTLVT

VSS

>DOM1h-574-102 (SEQ ID NO: 80)
EVQLLESGGGLVQPGGSLRLSCAASGFTFVKYSMGWVRQAPGKGPEWVSQISDSGYRT

YYADSVKGRFTISRDNSKNTLYLQMNSLRAEDTAVYYCAIYTGRWEPFDYWGQGTLVT

VSS

>DOM1h-574-103 (SEQ ID NO: 81)
EVQLLESGGGLVQPGGSLRLSCAASGFTFVKYSMGWVRQAPGKGPEWVSQISDGGTRT

YYADSVKGRFTISRDNSKNTLYLQMNSLRAEDTAVYYCAIYTGRWEPFDYWGQGTLVT

VSS

TABLE 3-continued

Amino Acid Sequences of anti-TNFR1 dAbs

>DOM1h-574-104 (SEQ ID NO: 82)
EVQLLESGGGLVQPGGSLRLSCAASGFTFVKYSMGWVRQAPGKGPEWVSQISDKGTRT

YYADSVKGRFTISRDNSKNTLYLQMNSLRAEDTAVYYCAIYTGRWEPFDYWGQGTLVT

VSS

>DOM1h-574-105 (SEQ ID NO: 83)
EVQLLESGGGLVQPGGSLRLSCAASGFTFVKYSMGWVRQAPGKGPEWVSQISETGRRT

YYADSVKGRFTISRDNSKNTLYLQMNSLRAEDTAVYYCAIYTGRWEPFDYWGQGTLVT

VSS

>DOM1h-574-106 (SEQ ID NO: 84)
EVQLLESGGGLVQPGGSLRLSCAASGFTFVKYSMGWVRQAPGKGLEWVSQINNTGSTT

YYADSVKGRFTISRDNSKNTLYLQMNSLRAEDTAVYYCAIYTGRWEPFDYWGQGTLVT

VSS

>DOM1h-574-107 (SEQ ID NO: 85)
EVQLLESGGGLVQPGGSLRLSCAASGFTFVKYSMGWVRQAPGKGPEWVSQISNTADRT

YYAHSVKGRFTISRDNSKNTLYLQMNSLRAEDTAVYYCAIYTGRWVPFEYWGQGTLVT

VSS

>DOM1h-574-108 (SEQ ID NO: 86)
EVQLLESGGGLVQPGGSLRLSCAASGFTFVKYSMGWVRQAPGKGPEWVSQISNTADRT

YYAHSVKGRFTISRDNSKNTLYLQMNSLRAEDTAVYYCAIYTGRWAPFEYWGQGTLVT

VSS

>DOM1h-574-109 (SEQ ID NO: 87)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWVPFEYWGQGTLVT

VSS

>DOM1h-574-110 (SEQ ID NO: 88)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-111 (SEQ ID NO: 89)
EVQLLESGGGLVQPGGSLRLSCAASGFTFVKYSMGWVRQAPGKGLEWVSQISDTADRT

YYDDSVKGRFTISRDNSKNTLYLQMNSLRAEDTAVYYCAIYTGRWRPFEYWGQGTLVT

VSS

>DOM1h-574-112 (SEQ ID NO: 90)
EVQLLESGGGLVQPGGSLRLSCAASGFTFVKYSMGWVRQAPGKGLEWVSQISDTADRT

YYTHSVKGRFTISRDNSKNTLYLQMNSLRAEDTAVYYCAIYTGRWAPFEYWGQGTLVT

VSS

>DOM1h-574-113 (SEQ ID NO: 91)
EVQLLESGGGLVQPGGSLRLSCAASGFTFVKYSMGWVRQAPGKGLEWVSQISNTADRR

YYAHSVKGRFTISRDNSKNTLYLQMNSLRAEDTAVYYCAIYTGRWAPFEYWGQGTLVT

VSS

>DOM1h-574-114 (SEQ ID NO: 92)
EVQLLESGGGLVQPGGSLRLSCAASGFTFVKYSMGWVRQAPGKGLEWVSQILNTADRT

YYDHSVKGRFTISRDNSKNTLYLQMNSLRAEDTAVYYCAIYTGRWAPFEYWGQGTLVT

VSS

TABLE 3-continued

Amino Acid Sequences of anti-TNFR1 dAbs

>DOM1h-574-115 (SEQ ID NO: 93)
EVQLLESGGGLVQPGGSLRLSCAASGFTFVKYSMGWVRQAPGKGLEWVSQISNTADRT

YYDHSVKGRFTISRDNSKNTLYLQMNSLRAEDTAVYYCAIYTGRWAPFEYWGQGTLVT

VSS

>DOM1h-574-116 (SEQ ID NO: 94)
EVQLLESGGGLVQPGGSLRLSCAASGFTFVKYSMGWVRQAPGKGLEWVSQISDTADRR

YYAHSVKGRFTISRDNSKNTLYLQMNSLRAEDTAVYYCAIYTGRWAPFEYWGQGTLVT

VSS

>DOM1h-574-117 (SEQ ID NO: 95)
EVQLLESGGGLVQPGGSLRLSCAASGFTFVKYSMGWVRQAPGKGLEWVSQISDTADRR

YYDHSVKGRFTISRDNSKNTLYLQMNSLRAEDTAVYYCAIYTGRWAPFEYWGQGTLVT

VSS

>DOM1h-574-118 (SEQ ID NO: 96)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAVYTGRWVSFEYWGQGTLVT

VSS

>DOM1h-574-119 (SEQ ID NO: 97)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCALYTGRWVSFEYWGQGTLVT

VSS

>DOM1h-574-120 (SEQ ID NO: 98)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCAVYTGRWVPFEYWGQGTLVT

VSS

>DOM1h-574-121 (SEQ ID NO: 99)
EVQLLESGGGLVQPGGSLRLSCAASGFTFVKYSMGWVRQAPGKGLEWVSQISNTADRT

YYAHSVKGRFTISRDNSKNTLYLQMNSLRAEDTAVYYCALYTGRWVPFEYWGQGTLVT

VSS

>DOM1h-574-122 (SEQ ID NO: 100)
EVQLLESGGGLVQPGGSLRLSCAASGFTFVKYSMGWVRQAPGKGLEWVSQIANTADRR

YYAHSVKGRFTISRDNSKNTLYLQMNSLRAEDTAVYYCAIYTGRWAPFEYWGQGTLVT

VSS

>DOM1h-574-123 (SEQ ID NO: 101)
EVQLLESGGGLVQPGGSLRLSCAASGFTFVKYSMGWVRQAPGKGLEWVSQISNTADRR

YYADAVKGRFTISRDNSKNTLYLQMNSLRAEDTAVYYCAIYTGRWEPFVYWGQGTLVT

VSS

>DOM1h-574-124 (SEQ ID NO: 102)
EVQLLESGGGLVQPGGSLRLSCAASGFTFVKYSMGWVRQAPGKGLEWVSQISNTGDRR

YYAHAVKGRFTISRDNSKNTLYLQMNSLRAEDTAVYYCAIYTGRWEPFVYWGQGTLVT

VSS

>DOM1h-574-125 (SEQ ID NO: 103)
EVQLLESGGGLVQPGGSLRLSCAASGFTFVKYSMGWVRQAPGKGLEWVSQIANTADRR

YYADAVKGRFTISRDNSKNTLYLQMNSLRAEDTAVYYCAIYTGRWEPFVYWGQGTLVT

VSS

TABLE 3-continued

Amino Acid Sequences of anti-TNFR1 dAbs

>DOM1h-574-126 (SEQ ID NO: 104)
EVQLLESGGGLVQPGGSLRLSCAASGFTFVKYSMGWVRQAPGKGLEWVSQIANTGDRR

YYAHAVKGRFTISRDNSKNTLYLQMNSLRAEDTAVYYCAIYTGRWEPFVYWGQGTLVT

VSS

>DOM1h-574-127 (SEQ ID NO: 105)
EVQLLESGGGLVQPGGSLRLSCAASGFTFVKYSMGWVRQAPGKGLEWVSQISNTADRR

YYAHAVKGRFTISRDNSKNTLYLQMNSLRAEDTAVYYCAIYTGRWEPFVYWGQGTLVT

VSS

>DOM1h-574-128 (SEQ ID NO: 106)
EVQLLESGGGLVQPGGSLRLSCAASGFTFVKYSMGWVRQAPGKGLEWVSQIANTADRR

YYAHAVKGRFTISRDNSKNTLYLQMNSLRAEDTAVYYCAIYTGRWEPFVYWGQGTLVT

VSS

>DOM1h-574-129 (SEQ ID NO: 107)
EVQLLESGGGLVQPGGSLRLSCAASGFTFVKYSMGWVRQAPGKGLEWVSQIVNTGDRR

YYADAVKGRFTISRDNSKNTLYLQMNSLRAEDTAVYYCAIYTGRWEPFVYWGQGTLVT

VSS

>DOM1h-574-130 (SEQ ID NO: 108)
EVQLLESGGGLVQPGGSLRLSCAASGFTFVKYSMGWVRQAPGKGLEWVSQIANTGDRR

YYADAVKGRFTISRDNSKNTLYLQMNSLRAEDTAVYYCAIYTGRWEPFVYWGQGTLVT

VSS

>DOM1h-574-131 (SEQ ID NO: 109)
EVQLLESGGGLVQPGGSLRLSCAASGFTFVKYSMGWVRQAPGKGLEWVSQISDTADRT

YYDHSVKGRFTISRDNSKNTLYLQMNSLRAEDTAVYYCAIYTGRWAPFEYWGQGTLVT

VSS

>DOM1h-574-132 (SEQ ID NO: 110)
EVQLLESGGGLVQPGGSLRLSCAASGFTFVKYSMGWVRQAPGKGLEWVSQISDTADRT

YYDHSVKGRFTISRDNSKNTLYLQMNSLRAEDTAVYYCAIYTGRWRPFEYWGQGTLVT

VSS

>DOM1h-574-133 (SEQ ID NO: 111)
EVQLLESGGGLVQPGGSLRLSCAASGFTFVKYSMGWVRQAPGKGLEWVSQISDTADRT

YYDHSVKGRFTISRDNSKNTLYLQMNSLRAEDTAVYYCAIYTGRWEPFVYWGQGTLVT

VSS

>DOM1h-574-134 (SEQ ID NO: 112)
EVQLLESGGGLVQPGGSLRLSCAASGFTFVKYSMGWVRQAPGKGLEWVSQISDTADRT

YYSHSVKGRFTISRDNSKNTLYLQMNSLRAEDTAVYYCAIYTGRWVPFEYWGQGTLVT

VSS

>DOM1h-574-135 (SEQ ID NO: 113)
EVQLLESGGGLVQPGGSLRLSCAASGFTFVKYSMGWVRQAPGKGLEWVSQISDTADRT

YYTHSVKGRFTISRDNSKNTLYLQMNSLRAEDTAVYYCAIYTGRWVPFEYWGQGTLVT

VSS

>DOM1h-574-137 (SEQ ID NO: 114)
EVQLLESGGGLVQPGGSLRLSCAASGFTFVKYSMGWVRQAPGKGLEWVSQISDTADRT

YYTDAVKGRFTISRDNSKNTLYLQMNSLRAEDTAVYYCAIYTGRWEPFVYWGQGTLVT

VSS

TABLE 3-continued

Amino Acid Sequences of anti-TNFR1 dAbs

>DOM1h-574-138 (SEQ ID NO: 115)
EVQLLESGGGLVQPGGSLRLSCAASGFTFFKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-139 (SEQ ID NO: 116)
EVQLLESGGGLVQPGGSLRLSCAASGFTFLKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-140 (SEQ ID NO: 117)
EVQLLESGGGLVQPGGSLRLSCAASGFTFFKYSMGWVRQAPGKGLEWVSQIADTGDRR

YYDDSVKGRFTISRDNSKNTLYLQMNSLRAEDTAVYYCAIYTGRWEPFVYWGQGTLVT

VSS

>DOM1h-574-141 (SEQ ID NO: 118)
EVQLLESGGGLVQPGGSLRLSCAASGFTFFKYSMGWVRQAPGKGLEWVSQISDTADRR

YYDDSVKGRFTISRDNSKNTLYLQMNSLRAEDTAVYYCAIYTGRWEPFVYWGQGTLVT

VSS

>DOM1h-574-142 (SEQ ID NO: 119)
EVQLLESGGGLVQPGGSLRLSCAASGFTFFKYSMGWVRQAPGKGLEWVSQISDTGDRR

YYDHSVKGRFTISRDNSKNTLYLQMNSLRAEDTAVYYCAIYTGRWEPFVYWGQGTLVT

VSS

>DOM1h-574-143 (SEQ ID NO: 120)
EVQLLESGGGLVQPGGSLRLSCAASGFTFFKYSMGWVRQAPGKGLEWVSQISDTGDRR

YYDDAVKGRFTISRDNSKNTLYLQMNSLRAEDTAVYYCAIYTGRWEPFVYWGQGTLVT

VSS

>DOM1h-574-144 (SEQ ID NO: 121)
EVQLLESGGGLVQPGGSLRLSCAASGFTFFKYSMGWVRQAPGKGLEWVSQIADTADRR

YYDDSVKGRFTISRDNSKNTLYLQMNSLRAEDTAVYYCAIYTGRWEPFVYWGQGTLVT

VSS

>DOM1h-574-145 (SEQ ID NO: 122)
EVQLLESGGGLVQPGGSLRLSCAASGFTFFKYSMGWVRQAPGKGLEWVSQIADTGDRR

YYDHSVKGRFTISRDNSKNTLYLQMNSLRAEDTAVYYCAIYTGRWEPFVYWGQGTLVT

VSS

>DOM1h-574-146 (SEQ ID NO: 123)
EVQLLESGGGLVQPGGSLRLSCAASGFTFFKYSMGWVRQAPGKGLEWVSQIADTGDRR

YYDDAVKGRFTISRDNSKNTLYLQMNSLRAEDTAVYYCAIYTGRWEPFVYWGQGTLVT

VSS

>DOM1h-574-147 (SEQ ID NO: 124)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWGPFVYWGQGTLVT

VSS

>DOM1h-574-148 (SEQ ID NO: 125)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWVPFAYWGQGTLVT

VSS

TABLE 3-continued

Amino Acid Sequences of anti-TNFR1 dAbs

>DOM1h-574-149 (SEQ ID NO: 126)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWGPFQYWGQGTLVT

VSS

>DOM1h-574-150 (SEQ ID NO: 127)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWEPFQYWGQGTLVT

VSS

>DOM1h-574-151 (SEQ ID NO: 128)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-152 (SEQ ID NO: 129)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWAPFQYWGQGTLVT

VSS

>DOM1h-574-153 (SEQ ID NO: 130)
EVQLLESGGGLVQPGGSLRLSCAASGFTFVKYSMGWVRQAPGKGLEWVSQISDTADRT

YYAHSVKGRFTISRDNSKNTLYLQMNSLRAEDTAVYYCAIYTGRWVPFQYWGQGTLVT

VSS

>DOM1h-574-154 (SEQ ID NO: 131)
EVQLLESGGGLVQPGGSLRLSCAASGFTFVKYSMGWVRQAPGKGLEWVSQISDTGDRR

YYDHSVKGRFTISRDNSKNTLYLQMNSLRAEDTAVYYCAIYTGRWAPFEYWGQGTLVT

VSS

>DOM1h-574-155 (SEQ ID NO: 132)
EVQLLESGGGLVQPGGSLRLSCAASGFTFLKYSMGWVRQAPGKGLEWVSQISDTADRT

YYAHSVKGRFTISRDNSKNTLYLQMNSLRAEDTAVYYCAIYTGRWVPFEYWGQGTLVT

VSS

>DOM1h-574-156 (SEQ ID NO: 133)
EVQLLESGGGLVQPGGSLRLSCAASGFTFFKYSMGWVRQAPGKGLEWVSQISDTADRT

YYAHSVKGRFTISRDNSKNTLYLQMNSLRAEDTAVYYCAIYTGRWVPFEYWGQGTLVT

VSS

>DOM1h-574-157 (SEQ ID NO: 134)
EVQLLESGGGLVQPGGSLRLSCAASGFTFLKYSMGWVRQAPGKGLEWVSQISDTADRT

YYDHSVKGRFTISRDNSKNTLYLQMNSLRAEDTAVYYCAIYTGRWRPFEYWGQGTLVT

VSS

>DOM1h-574-158 (SEQ ID NO: 135)
EVQLLESGGGLVQPGGSLRLSCAASGFTFFKYSMGWVRQAPGKGLEWVSQISDTADRT

YYDHSVKGRFTISRDNSKNTLYLQMNSLRAEDTAVYYCAIYTGRWRPFEYWGQGTLVT

VSS

>DOM1h-574-159 (SEQ ID NO: 136)
EVQLLESGGGLVQPGGSLRLSCAASGFTFFKYSMGWVRQAPGKGLEWVSQISDTADRT

YYDHSVKGRFTISRDNSKNTLYLQMNSLRAEDTAVYYCAIYTGRWEPFVYWGQGTLVT

VSS

TABLE 3-continued

Amino Acid Sequences of anti-TNFR1 dAbs

>DOM1h-574-160 (SEQ ID NO: 137)
EVQLLESGGGLVQPGGSLRLSCAASGFTFLKYSMGWVRQAPGKGLEWVSQISDTADRT

YYDHSVKGRFTISRDNSKNTLYLQMNSLRAEDTAVYYCAIYTGRWEPFVYWGQGTLVT

VSS

>DOM1h-574-161 (SEQ ID NO: 138)
EVQLLESGGGLVQPGGSLRLSCAASGFTFLKYSMGWVRQAPGKGLEWVSQISDTADRT

YYSHSVKGRFTISRDNSKNTLYLQMNSLRAEDTAVYYCAIYTGRWVPFEYWGQGTLVT

VSS

>DOM1h-574-162 (SEQ ID NO: 139)
EVQLLESGGGLVQPGGSLRLSCAASGFTFFKYSMGWVRQAPGKGLEWVSQISDTADRT

YYSHSVKGRFTISRDNSKNTLYLQMNSLRAEDTAVYYCAIYTGRWVPFEYWGQGTLVT

VSS

>DOM1h-574-163 (SEQ ID NO: 140)
EVQLLESGGGLVQPGGSLRLSCAASGFTFFKYSMGWVRQAPGKGLEWVSQISDTADRT

YYTHSVKGRFTISRDNSKNTLYLQMNSLRAEDTAVYYCAIYTGRWVPFEYWGQGTLVT

VSS

>DOM1h-574-164 (SEQ ID NO: 141)
EVQLLESGGGLVQPGGSLRLSCAASGFTFLKYSMGWVRQAPGKGLEWVSQISDTADRT

YYTHSVKGRFTISRDNSKNTLYLQMNSLRAEDTAVYYCAIYTGRWVPFEYWGQGTLVT

VSS

>DOM1h-574-165 (SEQ ID NO: 142)
EVQLLESGGGLVQPGGSLRLSCAASGFTFFKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-166 (SEQ ID NO: 143)
EVQLLESGGGLVQPGGSLRLSCAASGFTFLKYSMGWVRQAPGKGLEWVSQISDTADRT

YYAHSVKGRFTISRDNSKNTLYLQMNSLRAEDTAVYYCAIYTGRWAPFEYWGQGTLVT

VSS

>DOM1h-574-167 (SEQ ID NO: 144)
EVQLLESGGGLVQPGGSLRLSCAASGFTFLKYSMGWVRQAPGKGLEWVSQISDTGDRR

YYDHSVKGRFTISRDNSKNTLYLQMNSLRAEDTAVYYCAIYTGRWAPFEYWGQGTLVT

VSS

>DOM1h-574-169 (SEQ ID NO: 145)
EVQLLESGGGLVQPGGSLRLSCAASGFTFVKYSMGWVRQAPGKGLEWVSQIADTADRT

YYAHSVKGRFTISRDNSKNTLYLQMNSLRAEDTAVYYCAIYTGRWVPFEYWGQGTLVT

VSS

>DOM1h-574-170 (SEQ ID NO: 146)
EVQLLESGGGLVQPGGSLRLSCAASGFTFFKYSMGWVRQAPGKGLEWVSQISDTADRT

YYAHAVKGRFTISRDNSKNTLYLQMNSLRAEDTAVYYCAIYTGRWVPFEYWGQGTLVT

VSS

>DOM1h-574-171 (SEQ ID NO: 147)
EVQLLESGGGLVQPGGSLRLSCAASGFTFVKYSMGWVRQAPGKGLEWVSQIADTADRT

YYDHSVKGRFTISRDNSKNTLYLQMNSLRAEDTAVYYCAIYTGRWVPFEYWGQGTLVT

VSS

TABLE 3-continued

Amino Acid Sequences of anti-TNFR1 dAbs

>DOM1h-574-172 (SEQ ID NO: 148)
EVQLLESGGGLVQPGGSLRLSCAASGFTFVKYSMGWVRQAPGKGLEWVSQIADTADRT

YYDHAVKGRFTISRDNSKNTLYLQMNSLRAEDTAVYYCAIYTGRWVPFEYWGQGTLVT

VSS

>DOM1h-574-173 (SEQ ID NO: 149)
EVQLLESGGGLVQPGGSLRLSCAASGFTFVKYSMGWVRQAPGKGLEWVSQIADTADRR

YYAHSVKGRFTISRDNSKNTLYLQMNSLRAEDTAVYYCAIYTGRWAPFEYWGQGTLVT

VSS

>DOM1h-574-174 (SEQ ID NO: 150)
EVQLLESGGGLVQPGGSLRLSCAASGFTFVKYSMGWVRQAPGKGLEWVSQISDTADRR

YYAHAVKGRFTISRDNSKNTLYLQMNSLRAEDTAVYYCAIYTGRWAPFEYWGQGTLVT

VSS

>DOM1h-574-175 (SEQ ID NO: 151)
EVQLLESGGGLVQPGGSLRLSCAASGFTFVKYSMGWVRQAPGKGLEWVSQIADTADRR

YYAHAVKGRFTISRDNSKNTLYLQMNSLRAEDTAVYYCAIYTGRWAPFEYWGQGTLVT

VSS

>DOM1h-574-176 (SEQ ID NO: 152)
EVQLLESGGGLVQPGGSLRLSCAASGFTFVKYSMGWVRQAPGKGLEWVSQISDTADRR

YYDHAVKGRFTISRDNSKNTLYLQMNSLRAEDTAVYYCAIYTGRWAPFEYWGQGTLVT

VSS

>DOM1h-574-177 (SEQ ID NO: 153)
EVQLLESGGGLVQPGGSLRLSCAASGFTFVKYSMGWVRQAPGKGLEWVSQIADTADRR

YYDHAVKGRFTISRDNSKNTLYLQMNSLRAEDTAVYYCAIYTGRWAPFEYWGQGTLVT

VSS

>DOM1h-574-178 (SEQ ID NO: 154)
EVQLLESGGGLVQPGGSLRLSCAASGFTFVKYSMGWVRQAPGKGLEWVSQIADTADRR

YYDHSVKGRFTISRDNSKNTLYLQMNSLRAEDTAVYYCAIYTGRWAPFEYWGQGTLVT

VSS

>DOM1h-574-179 (SEQ ID NO: 155)
EVQLLESGGGLVQPGGSLRLSCAASGFTFFKYSMGWVRQAPGKGLEWVSQISDTADRR

YYDDAVKGRFTITRDNSKNTLYLQMNSLRAEDTAVYYCAIYTGRWEPFVYWGQGTLVT

VSS

>DOM1h-574-180 (SEQ ID NO: 156)
EVQLLESGGGLVQPGGSLRLSCAASGFTFVKYSMGWVRQAPGKGLEWVSQISDTADRT

YYAHAVKGRFTISRDNSKNTLYLQMNSLRAEDTAVYYCAIYTGRWVPFEYWGQGTLVT

VSS

>DOM1h-574-4 (SEQ ID NO: 157)
EVQLLESGGGLVQPGGSLRLSCAASGFTFVKYSMGWVRQAPGKGLEWVSQISNTGGHT

YYADSVKGRFTISRDNSKNTLYLQMNSLRAEDTAVYYCAKYTGRWEPFEYWGQGTLVT

VSS

>DOM1h-574-168 (SEQ ID NO: 158)
EVQLLESGGGLVQPGGSLRLSCAASGFTFFKYSMGWVRQAPGKGLEWVSQISDTGDRR

YYDHSVKGRFTISRDNSKNTLYLQMNSLRAEDTAVYYCAIYTGRWAPFEYWGQGTLVT

VSS

TABLE 4

Nucleotide sequences of anti-TNFR1 dAbs

>DOM1h-509 (SEQ ID NO: 157)
GAGGTGCAGCTGTTGGAGTCTGGGGGAGGCTTGGTACAGCCTGGGGGGTCCCTGCGTC
TCTCCTGTGCAGCCTCCGGATTCACCTTTAGTCAGTATAGGATGCATTGGGTCCGCCA
GGCTCCAGGGAAGAGTCTAGAGTGGGTCTCAAGTATTGATACTAGGGGTTCGTCTACA
TACTACGCAGACCCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAAGCTGTGACGATGTTTTCTCCTTTTTTTGACTACTGGGGTCAGGGAACCCTGGTC
ACCGTCTCGAGC

>DOM1h-510 (SEQ ID NO: 158)
GAGGTGCAGCTGTTGGAGTCTGGGGGAGGCTTGGTACAGCCTGGGGGGTCCCTGCGTC
TCTCCTGTGCAGCCTCCGGATTCACCTTTGCTGATTATGGGATGCGTTGGGTCCGCCA
GGCTCCAGGGAAGGGTCTAGAGTGGGTCTCATCTATTACGCGGACTGGTCGTGTTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATGGCGGAATCGGCATGGTGAGTATCTTGCTGATTTTGACTACTGGGGTCAGGGA
ACCCTGGTCACCGTCTCGAGC

>DOM1h-543 (SEQ ID NO: 159)
GAGGTGCAGCTGTTGGAGTCTGGGGGAGGCTTGGTACAGCCTGGGGGGTCCCTGCGTC
TCTCCTGTGCAGCCTCCGGATTCACCTTTATGAGGTATAGGATGCATTGGGTCCGCCA
GGCTCCAGGGAAGGGTCTAGAGTGGGTCTCATCGATTGATTCTAATGGTTCTAGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAAGATCGTACGGAGCGTTCGCCGGTTTTTGACTACTGGGGTCAGGGAACCCTGGTC
ACCGTCTCGAGC

>DOM1h-549 (SEQ ID NO: 160)
GAGGTGCAGCTGTTGGAGTCTGGGGGAGGCTTGGTGCAGCCTGGGGGGTCCCTGCGTC
TCTCCTGTGCAGCCTCCGGATTCACCTTTGTTGATTATGAGATGCATTGGGTCCGCCA
GGCTCCAGGGAAGGGTCTAGAGTGGGTCTCATCTATTAGTGAGAGTGGTACGACGACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAACGTCGTTTTTCTGCTTCTACGTTTGACTACTGGGGTCAGGGAACCCTGGTCACC
GTCTCGAGC

>DOM1h-574 (SEQ ID NO: 161)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCATTGGGAGCCTTTTGACTACTGGGGTCAGGGAACCCTGGTCACC
GTCTCGAGC

TABLE 4-continued

Nucleotide sequences of anti-TNFR1 dAbs

>DOM1h-574-1 (SEQ ID NO: 162)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCGTTGGGAGCCTTATGACTACTGGGGTCAGGGAACCCTGGTCACC
GTCTCGAGC

>DOM1h-574-2 (SEQ ID NO: 163)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCGTTGGGAGCCTTTTGACTACTGGGGTCAGGGAACCCTGGTCACC
GTCTCGAGC

>DOM1h-574-4 (SEQ ID NO: 164)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCGTTGGGAGCCTTTTGAGTACTGGGGTCAGGGAACCCTGGTCACC
GTCTCGAGC

>DOM1h-574-180 (SEQ ID NO: 165)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACGCGGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-7 (SEQ ID NO: 166)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

TABLE 4-continued

Nucleotide sequences of anti-TNFR1 dAbs

>DOM1h-574-8 (SEQ ID NO: 167)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACA
GTCTCGAGC

>DOM1h-574-9 (SEQ ID NO: 168)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATATCCCGCGACAATTCCAAGAACA
CGCTGTATATGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-10 (SEQ ID NO: 169)
GAGGTGCAGCTGTTGGAGTCTGGGGGAGGCTTGGTACAGCCTGGGGGGTCCCTGCGTC
TCTCCTGTGCAGCCTCCGGATTCACCTTTGGTAAGTATTCGATGGGGTGGGTCCGCCA
GGCTCCAGGGAAGGATCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-11 (SEQ ID NO: 170)
GAGGTGCAGCTGTTGGAGTCAGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGGTCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCGTTGGGAGCCTTTTGACCACTGGGGTCAGGGGACCCTGGTCACC
GTCTCGAGC

>DOM1h-574-12 (SEQ ID NO: 171)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCGTTGGGAGCCTTTTGACTACTGGGGTCAGGGAACCCTGGTCACC
GTCTCGAGC

TABLE 4-continued

Nucleotide sequences of anti-TNFR1 dAbs

>DOM1h-574-13 (SEQ ID NO: 172)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GAAATATACGGGTCGTTGGGAGCCTTTTGACTACTGGGGTCAGGGAACCCTGGTCACC
GTCTCGAGC

>DOM1h-574-14 (SEQ ID NO: 173)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-15 (SEQ ID NO: 174)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-16 (SEQ ID NO: 175)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACA
GTCTCGAGC

>DOM1h-574-17 (SEQ ID NO: 176)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGAATACGGGTGATCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACA
GTCTCGAGC

TABLE 4-continued

Nucleotide sequences of anti-TNFR1 dAbs

>DOM1h-574-18 (SEQ ID NO: 177)
GAGGTGCAGCTGTTGGAGTCTGGGGGAGGCTTGGTACAGCCTGGGGGGTCCCTGCGTC
TCTCCTGTGCAGCCTCCGGATTCACCTTTGGTAAGTATTCGATGGGGTGGGTCCGCCA
GGCTCCAGGGAAGGATCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-19 (SEQ ID NO: 178)
GAGGTGCAGCTGTTGGAGTCTGGGGGAGGCTTGGTACAGCCTGGGGGGTCCCTGCGTC
TCTCCTGTGCAGCCTCCGGATTCACCTTTGGTAAGTATTCGATGGGGTGGGTCCGCCA
GGCTCCAGGGAAGGATCTAGAGTGGGTCTCACAGATTTCGAATACGGGTGATCATACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-25 (SEQ ID NO: 179)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-26 (SEQ ID NO: 180)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACGGGTCGTTGGGAGCCTTTTGAGTACTGGGGTCAGGGAACCCTGGTCACC
GTCTCGAGC

>DOM1h-574-27 (SEQ ID NO: 181)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCGGACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACGGGTCGTTGGAAGCCTTTTGAGTACTGGGGTCAGGGAACCCTGGTCACC
GTCTCGAGC

TABLE 4-continued

Nucleotide sequences of anti-TNFR1 dAbs

>DOM1h-574-28 (SEQ ID NO: 182)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-29 (SEQ ID NO: 183)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-30 (SEQ ID NO: 184)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGCATATTACTGTGC
GATATATACGGGTCGTTGGGAGCCTTTTGACTACTGGGGTCAGGGAACCCTGGTCACC
GTCTCGAGC

>DOM1h-574-31 (SEQ ID NO: 185)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTAACTACTGGGGTCAGGGAACCCTGGTCACC
GTCTCGAGC

>DOM1h-574-32 (SEQ ID NO: 186)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-33 (SEQ ID NO: 187)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACT
CGCTGTATCTGCAAATGAACAGCCTGCGTGCCGAGGACACCGCGGTATATTACTGTGC
GATATATACGGGTCGTTGGGTGCCTTTTGACAACTGGGGTCAGGGAACCCTGGTCACC
GTCTCGAGC

>DOM1h-574-35 (SEQ ID NO: 188)
GAGGTGCAGCTGTTGGAGTCTGGGGGAGGCTTGGTACAGCCTGGGGGGTCCCTGCGTC
TCTCCTGTGCAGCCTCCGGATTCACCTTTATTACGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTCAGTACTGGGGTCAGGGAACCCTGGTCACC
GTCTCGAGC

>DOM1h-574-36 (SEQ ID NO: 189)
GAGGTGCAGCTGTTGGAGTCTGGGGGAGGCTTGGTACAGCCTGGGGGGTCCCTGCGTC
TCTCCTGTGCAGCCTCCGGATTCACCTTTGGTAAGTATTCGATGGGGTGGGTCCGCCA
GGCTCCAGGGAAGGGTCTAGAGTGGGTCTCACAGATTTCGAATACGGGTGATCGTACA
TACTACGCGGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-37 (SEQ ID NO: 190)
GAGGTGCAGCTGTTGGAGTCTGGGGGAGGCTTGGTACAGCCTGGGGGGTCCCTGCGTC
TCTCCTGTGCAGCCTCCGGATTCACCTTTTTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCCGAAGACACCGCGGTATATTACTGTGC
GATATATACGGGTCGTTGGGAGCCTTTTGACTACTGGGGTCAGGGAACCCTGGTCACC
GTCTCGAGC

>DOM1h-574-38 (SEQ ID NO: 191)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

TABLE 4-continued

Nucleotide sequences of anti-TNFR1 dAbs

>DOM1h-574-39 (SEQ ID NO: 192)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-40 (SEQ ID NO: 193)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTACA
TACTACGCAGACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACGGGTCGTTGGGAGCCTTTTAAGTACTGGGGTCAGGGAACCCTGGTCACC
GTCTCGAGC

>DOM1h-574-53 (SEQ ID NO: 194)
GAGGTGCAGCTGTTGGAGTCTGGGGGAGGCTTGGTACAGCCTGGGGGGTCCCTGCGTC
TCTCCTGTGCAGCCTCCGGATTCACCTTTAGTAAGTATTCGATGGGGTGGGTCCGCCA
GGCTCCAGGGAAGGGTCTAGAGTGGGTCTCACAGATTTCGAATACGGGTGAGCGTAGA
TACTACGCAGACTCAGTGAAGGGCCGGTTCACCATCTCCCGCGACAATCCCAAGAACA
CGCTGTATCTGCAAATGAACAGCCTGCGTGCCGAGGACACCGCGGTATATTACTGTGC
GATATATACGGGTCGGTGGGAGCCTTTTGAATACTGGGGTCAGGGAACCCTGGTCACC
GTCTCGAGC

>DOM1h-574-54 (SEQ ID NO: 195)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAACTATTCGATGGGGTGGGTCCGCCA
GGCTCCAGGGAAGGGTCTAGAGTGGGTCTCACAGATTTCGAATACGGGTGATCGTACA
TACTACGCGGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTATGAGTACTGGGGTCAGGGAACCCTGGTCACC
GTCACGAGC

>DOM1h-574-65 (SEQ ID NO: 196)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGATAATTCCAAGAACA
CACTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-66 (SEQ ID NO: 197)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAAGCCTTTTGAGTACTGGGGTCAGGGAACCCTGGTCACC
GTCTCGAGC

>DOM1h-574-67 (SEQ ID NO: 198)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-68 (SEQ ID NO: 199)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-69 (SEQ ID NO: 200)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-70 (SEQ ID NO: 201)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GGTATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-71 (SEQ ID NO: 202)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACGGGTCGTTGGAAGCCTTTTGAGTACTGGGGTCAGGGAACCCTGGTCACC
GTCTCGAGC

>DOM1h-574-72 (SEQ ID NO: 203)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACGACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-73 (SEQ ID NO: 204)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-74 (SEQ ID NO: 205)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-75 (SEQ ID NO: 206)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-76 (SEQ ID NO: 207)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCCCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACGGGTCGTTGGAAGCCTTTTGAGTACTGGGGTCAGGGAACCCTGGTCACC
GTCTCGAGC

>DOM1h-574-77 (SEQ ID NO: 208)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-78 (SEQ ID NO: 209)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-79 (SEQ ID NO: 210)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-84 (SEQ ID NO: 211)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-85 (SEQ ID NO: 212)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCTGAGGACACCGCGGTATATTACTGTGC
GATATATACGGGTCGTTGGAAGCCTTTTGAGTACTGGGGTCAGGGAACCCTGGTCACC
GTCTCGAGC

>DOM1h-574-86 (SEQ ID NO: 213)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCCCCAGGGAAGGGTCTAGAGTGGGTCTCACAGATTTCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAAGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-87 (SEQ ID NO: 214)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-88 (SEQ ID NO: 215)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-90 (SEQ ID NO: 216)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTTTTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-91 (SEQ ID NO: 217)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-92 (SEQ ID NO: 218)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-93 (SEQ ID NO: 219)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-94 (SEQ ID NO: 220)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGCATATTACTGTGC
GATATATACGGGTCGGTGGCCCGACTTTGACTACTGGGGTCAGGGAACCCTGGTCACC
GTCTCGAGC

>DOM1h-574-95 (SEQ ID NO: 221)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACTCTGTGAAGGGCCGGTTCACCATCTCCCGCGACAATTCCAAGAACA
CGCTGTATCTGCAAATGAACAGCCTGCGTGCCGAGGACACCGCGGCATATTACTGTGC
GATATATACGGGTCGGTGGCCCGACTTTGAGTACTGGGGTCAGGGAACCCTGGTCACC
GTCTCGAGC

TABLE 4-continued

Nucleotide sequences of anti-TNFR1 dAbs

>DOM1h-574-96 (SEQ ID NO: 222)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGCCCGACTTTGACTACTGGGGTCAGGGAACCCTGGTCACC
GTCTCGAGC

>DOM1h-574-97 (SEQ ID NO: 223)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGCCCGACTTTGAGTACTGGGGTCAGGGAACCCTGGTCACC
GTCTCGAGC

>DOM1h-574-98 (SEQ ID NO: 224)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGCCCGACTTTGACTACTGGGGTCAGGGAACCCTGGTCACC
GTCTCGAGC

>DOM1h-574-99 (SEQ ID NO: 225)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGCCCGACTTTGAGTACTGGGGTCAGGGAACCCTGGTCACC
GTCTCGAGC

>DOM1h-574-100 (SEQ ID NO: 226)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGGCCTGGGGTGACAGGACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

TABLE 4-continued

Nucleotide sequences of anti-TNFR1 dAbs

>DOM1h-574-101 (SEQ ID NO: 227)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAAGGTCCAGAGTGGGTCTCACAGATTTCGGACGGCGGTCAGAGGACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-102 (SEQ ID NO: 228)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGGACTCCGGTTACCGCACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-103 (SEQ ID NO: 229)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGTGGGTCCGCCA
GGCTCCAGGGAAGGGTCCAGAGTGGGTCTCACAGATTTCGGACGGGGTACGCGGACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-104 (SEQ ID NO: 230)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGGACAAGGGTACGCGCACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-105 (SEQ ID NO: 231)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGATGGGTCCGCCA
GGCTCCAGGGAAAGGTCCAGAGTGGGTCTCACAGATTTCGGAGACCGGTCGCAGGACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

TABLE 4-continued

Nucleotide sequences of anti-TNFR1 dAbs

>DOM1h-574-106 (SEQ ID NO: 232)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTAACAATACGGGTTCGACCACA
TACTACGCAGACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGACTACTGGGGTCAGGGAACCCTGGTCACC
GTCTCGAGC

>DOM1h-574-107 (SEQ ID NO: 233)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCCAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-108 (SEQ ID NO: 234)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCCAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-109 (SEQ ID NO: 235)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-110 (SEQ ID NO: 236)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-111 (SEQ ID NO: 237)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-112 (SEQ ID NO: 238)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACACACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-113 (SEQ ID NO: 239)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGCAGA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-114 (SEQ ID NO: 240)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTTGAATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-115 (SEQ ID NO: 241)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-116 (SEQ ID NO: 242)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTAGA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-117 (SEQ ID NO: 243)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTAGA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-118 (SEQ ID NO: 244)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GGTATATACTGGGCGTTGGGTGTCTTTTGAGTACTGGGGTCAGGGAACCCTGGTCACC
GTCTCGAGC

>DOM1h-574-119 (SEQ ID NO: 245)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GCTATATACTGGGCGTTGGGTGTCTTTTGAGTACTGGGGTCAGGGAACCCTGGTCACC
GTCTCGAGC

>DOM1h-574-120 (SEQ ID NO: 246)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTTACCATCTCCCGCGACAATTCCAAGAACA
CGCTGTATCTGCAAATGAACAGCCTGCGTGCCGAGGACACCGCGGTATATTACTGTGC
GGTATATACTGGGCGTTGGGTGCCTTTTGAGTACTGGGGTCAGGGAACCCTGGTCACC
GTCTCGAGC

TABLE 4-continued

Nucleotide sequences of anti-TNFR1 dAbs

>DOM1h-574-121 (SEQ ID NO: 247)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GCTATATACTGGGCGTTGGGTGCCTTTTGAGTACTGGGGTCAGGGAACCCTGGTCACC
GTCTCGAGC

>DOM1h-574-122 (SEQ ID NO: 248)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACTGCTGATCGTAGA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-123 (SEQ ID NO: 249)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-124 (SEQ ID NO: 250)
GAGGTGCAGCTGTTGGAGTCTGGGGGAGGCTTGGTACAGCCTGGGGGGTCCCTGCGTC
TCTCCTGTGCGGCCTCCGGATTCACCTTTGTTAAGTATTCGATGGGGTGGGTCCGCCA
GGCTCCAGGGAAGGGTCTAGAGTGGGTCTCACAGATTTCGAATACGGGCGATCGTAGA
TACTACGCACACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-125 (SEQ ID NO: 251)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACTGCTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-126 (SEQ ID NO: 252)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCACACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-127 (SEQ ID NO: 253)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGAATACTGCTGATCGTAGA
TACTACGCACACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-128 (SEQ ID NO: 254)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGCTGATCGTAGA
TACTACGCACACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-129 (SEQ ID NO: 255)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGTGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-130 (SEQ ID NO: 256)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGAATACGGGTGATCGTAGA
TACTACGCAGACGCGGTGAAGGGGCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-131 (SEQ ID NO: 257)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-132 (SEQ ID NO: 258)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-133 (SEQ ID NO: 259)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-134 (SEQ ID NO: 260)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACTCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-135 (SEQ ID NO: 261)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACACACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

TABLE 4-continued

Nucleotide sequences of anti-TNFR1 dAbs

>DOM1h-574-137 (SEQ ID NO: 262)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACACAGACGCGGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-138 (SEQ ID NO: 263)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-139 (SEQ ID NO: 264)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-140 (SEQ ID NO: 265)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTGCGGATACGGGTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-141 (SEQ ID NO: 266)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTAGA
TACTACGATGACTCTGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

TABLE 4-continued

Nucleotide sequences of anti-TNFR1 dAbs

>DOM1h-574-142 (SEQ ID NO: 267)
GAGGTGCAGCTGTTGGAGTCTGGGGGAGGCTTGGTACAGCCTGGGGGGTCCCTGCGCC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTTCGGATACGGGTGATCGTAGA

TACTACGATCACTCTGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGTTGGGAACCTTTTGTCTACTGGGGTCAGGGAACCCTGGTCACC

GTCTCGAGC

>DOM1h-574-143 (SEQ ID NO: 268)
GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTTCGGATACGGGTGATCGTAGA

TACTACGATGACGCGGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGTTGGGAGCCTTTTGTCTACTGGGGTCAGGGAACCCTGGTCACC

GTCTCGAGC

>DOM1h-574-144 (SEQ ID NO: 269)
GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTGCGGATACTGCTGATCGTAGA

TACTACGATGACTCTGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGTTGGGAGCCTTTTGTCTACTGGGGTCAGGGAACCCTGGTCACC

GTCTCGAGC

>DOM1h-574-145 (SEQ ID NO: 270)
GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTGCGGATACGGGTGATCGTAGA

TACTACGATCACTCTGTGAAGGGCCGGTTCACTATCTCCCGCGACAATTCCAAGAACA

CGCTGTATCTGCAAATGAACAGCCTGCGTGCCGAGGACACCGCGGTATATTACTGTGC

GATATATACGGGTCGTTGGGAGCCTTTTGTCTACTGGGGTCAGGGAACCCTGGTCACC

GTCTCGAGC

>DOM1h-574-146 (SEQ ID NO: 271)
GAGGTGCAGCTGTTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTGCGGATACGGGTGATCGTAGA

TACTACGATGACGCGGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGTTGGGAGCCTTTTGTCTACTGGGGTCAGGGAACCCTGGTCACC

GTCTCGAGC

TABLE 4-continued

Nucleotide sequences of anti-TNFR1 dAbs

>DOM1h-574-147 (SEQ ID NO: 272)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGGGCCTTTTGTCTACTGGGGTCAGGGAACCCTGGTCACC
GTCTCGAGC

>DOM1h-574-148 (SEQ ID NO: 273)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGTGCCTTTTGCCTACTGGGGTCAGGGAACCCTGGTCACC
GTCTCGAGC

>DOM1h-574-149 (SEQ ID NO: 274)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGGACCTTTTCAGTACTGGGGTCAGGGAACCCTGGTCACC
GTCTCGAGC

>DOM1h-574-150 (SEQ ID NO: 275)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTCAGTACTGGGGTCAGGGAACTCTGGTCACC
GTCTCGAGC

>DOM1h-574-151 (SEQ ID NO: 276)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-152 (SEQ ID NO: 277)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGCGCCTTTTCAGTACTGGGGTCAGGGAACTCTGGTCACC
GTCTCGAGC

>DOM1h-574-153 (SEQ ID NO: 278)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGTGCCTTTTCAGTACTGGGGTCAGGGCACCCTGGTCACC
GTCTCGAGC

>DOM1h-574-154 (SEQ ID NO: 279)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACCGGTGATCGTAGA
TACTACGATCACTCTGTGAAGGGCCGGTTCACTATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-155 (SEQ ID NO: 280)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-156 (SEQ ID NO: 281)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

TABLE 4-continued

Nucleotide sequences of anti-TNFR1 dAbs

>DOM1h-574-157 (SEQ ID NO: 282)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-158 (SEQ ID NO: 283)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGAGGCCTTTTGAGTACTGGGGTCAGGGAACCCTGGTCACC
GTCTCGAGC

>DOM1h-574-159 (SEQ ID NO: 284)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-160 (SEQ ID NO: 285)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGAGCCTTTTGTCTACTGGGGTCAGGGAACCCTGGTCACC
GTCTCGAGC

>DOM1h-574-161 (SEQ ID NO: 286)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACTCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

TABLE 4-continued

Nucleotide sequences of anti-TNFR1 dAbs

>DOM1h-574-162 (SEQ ID NO: 287)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACTCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-163 (SEQ ID NO: 288)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACACACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-164 (SEQ ID NO: 289)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACACACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-165 (SEQ ID NO: 290)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGCGCCTTTTGAGTACTGGGGTCAGGGAACCCTGGTCACC
GTCTCGAGC

>DOM1h-574-166 (SEQ ID NO: 291)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGTTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-167 (SEQ ID NO: 292)
GAGGTGCAGCTGTTGGAGTCTGGGGGAGGCTTGGTACAGCCTGGGGGGTCCCTGCGTC
TCTCCTGTGCAGCCTCCGGATTCACCTTTTTGAAGTATTCGATGGGGTGGGTCCGCCA
GGCTCCAGGGAAGGGTCTAGAGTGGGTCTCACAGATTTCGGATACCGGTGATCGTAGA
TACTACGATCACTCTGTGAAGGGCCGGTTCACTATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-168 (SEQ ID NO: 293)
GAGGTGCAGCTGTTGGAGTCTGGGGGAGGCTTGGTACAGCCTGGGGGGTCCCTGCGTC
TCTCCTGTGCAGCCTCCGGATTCACCTTTTTCAAGTATTCGATGGGGTGGGTCCGCCA
GGCTCCAGGGAAGGGTCTAGAGTGGGTCTCACAGATTTCGGATACCGGTGATCGTAGA
TACTACGATCACTCTGTGAAGGGCCGGTTCACTATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-169 (SEQ ID NO: 294)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGGATACTGCTGATCGTACA
TACTACGCACACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGCGC
GATATATACTGGGCGTTGGGTGCCTTTTGAGTACTGGGGTCAGGGAACCCTGGTCACC
GTCTCGAGC

>DOM1h-574-170 (SEQ ID NO: 295)
GAGGTGCAGCTGTTGGAGTCTGGGGGAGGCTTGGTACAGCCTGGGGGGTCCCTGCGTC
TCTCCTGTGCAGCCTCCGGATTCACCTTTTTTAAGTATTCGATGGGGTGGGTCCGCCA
GGCTCCAGGGAAGGGTCTAGAGTGGGTCTCACAGATTTCGGATACTGCTGATCGTACA
TACTACGCACACGCGGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-171 (SEQ ID NO: 296)
GAGGTGCAGCTGTTGGAGTCTGGGGGAGGCTTGGTGCAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGGATACTGCTGATCGTACA
TACTACGATCACTCCGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

TABLE 4-continued

Nucleotide sequences of anti-TNFR1 dAbs

>DOM1h-574-172 (SEQ ID NO: 297)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGGATACTGCTGATCGTACA
TACTACGATCACGCGGTGAAGGGCCGGTTCACCATCTCCCGCGACAATTCCAAGAACA
CGCTGTATCTGCAAATGAACAGCCTGCGTGCTGAGGACACCGCGGTATATTACTGTGC
GATATATACTGGGCGTTGGGTGCCTTTTGAGTACTGGGGTCAGGGAACCCTGGTCACC
GTCTCGAGC

>DOM1h-574-173 (SEQ ID NO: 298)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGGATACTGCTGATCGTAGA
TACTACGCACACTCCGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-174 (SEQ ID NO: 299)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTAGA
TACTACGCACACGCGGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-175 (SEQ ID NO: 300)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTGCGGATACTGCTGATCGTAGA
TACTACGCACACGCGGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

>DOM1h-574-176 (SEQ ID NO: 301)
GAGGTGCAGCTGTTGGAGTCTGGGGGAGGCTTGGTACAGCCTGGGGGGTCCCTGCGTC
TCTCCTGTGCAGCCTCCGGATTCACCTTTGTTAAGTATTCGATGGGGTGGGTCCGCCA
GGCTCCAGGGAAGGGTCTAGAGTGGGTCTCACAGATTTCGGATACTGCTGATCGTAGA
TACTACGATCACGCGGTGAAGGGCCGGTTCACCATCTCCCGCGACAATTCCAAGAACA
CGCTGTATCTGCAAATGAACAGCCTGCGTGCCGAGGACACCGCGGTATATTACTGTGC
GATATATACGGGTCGGTGGGCGCCTTTTGAGTACTGGGGTCAGGGAACCCTGGTCACC
GTCTCGAGC

TABLE 4-continued

Nucleotide sequences of anti-TNFR1 dAbs

>DOM1h-574-177 (SEQ ID NO: 302)
GAGGTGCAGCTGTTGGAGTCTGGGGGAGGCTTGGTACAGCCTGGGGGGTCCCTGCGTC

TCTCCTGTGCAGCCTCCGGATTCACCTTTGTTAAGTATTCGATGGGGTGGGTCCGCCA

GGCTCCAGGGAAGGGTCTAGAGTGGGTCTCACAGATTGCGGATACTGCTGATCGTAGA

TACTACGATCACGCGGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGGTGGGCGCCTTTTGAGTACTGGGGTCAGGGGACCCTGGTCACC

GTCTCGAGC

>DOM1h-574-178 (SEQ ID NO: 303)
GAGGTGCAGCTGTTGGAGTCTGGGGGAGGCTTGGTACAGCCTGGGGGGTCCCTGCGTC

TCTCCTGTGCAGCCTCCGGATTCACCTTTGTTAAGTATTCGATGGGGTGGGTCCGCCA

GGCTCCAGGGAAGGGTCTAGAGTGGGTCTCACAGATTGCGGATACTGCTGATCGTAGA

TACTACGATCACTCCGTGAAGGGCCGGTTCACCATCTCCCGCGACAATTCCAAGAACA

CGCTGTATCTGCAAATGAACAGCCTGCGTGCCGAGGACACCGCGGTATATTACTGTGC

GATATATACGGGTCGGTGGGCGCCTTTTGAGTACTGGGGTCAGGGAACCCTGGTCACC

GTCTCGAGC

>DOM1h-574-179 (SEQ ID NO: 304)
GAGGTGCAGCTGCTGGAGTCTGGGGGAGGCTTGGTACAGCCTGGGGGGTCCCTGCGTC

TCTCCTGTGCAGCCTCCGGATTCACCTTTTTCAAGTATTCGATGGGGTGGGTCCGCCA

GGCTCCAGGGAAGGGTCTAGAGTGGGTCTCACAGATTTCGGATACTGCTGATCGTAGA

TACTACGATGACGCGGTGAAGGGCCGGTTCACCATCACCCGCGACAATTCCAAGAACA

CGCTGTATCTGCAAATGAACAGCCTGCGTGCCGAGGACACCGCGGTATATTACTGTGC

GATATATACGGGTCGTTGGGAGCCTTTTGTCTACTGGGGTCAGGGAACCCTGGTCACC

GTCTCGAGC

TABLE 5

Anti-serum albumin dAb (DOM7h) fusions (used in Rat studies):-
DOM7h-14/Exendin-4 fusion DMS number 7138
Amino acid sequence (SEQ ID NO: 305)
HGEGTFTSDLSKQMEEEAVRLFIEWLKNGGPSSGAPPPSGGGGGSGGGSGGG

GSDIQMTQSPSSLSASVGDRVTITCRASQWIGSQLSWYQQKPGKAPKLLIMWRS

SLQSGVPSRFSGSGSGTDFTLTISSLQPEDFATYYCAQGAALPRTFGQGTKVEIKR

Nucleotide sequence (SEQ ID NO: 306)
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

CTGTAGGAGACCGTGTCACCATACTTGCCGGGCAAGTCAGTGGATTGGGT

CTCAGTTATCTTGGTACCAGCAGAAACCAGGGAAAGCCCCTAAGCTCCTGA

TCATGTGGCGTTCCTCGTTGCAAAGTGGGGTCCCATCACGTTTCAGTGGCAG

TGGATCTGGGACAGATTTCACTCTCACCATCAGCAGTCTGCAACCTGAAGAT

TABLE 5-continued

Anti-serum albumin dAb (DOM7h) fusions

TTTGCTACGTACTACTGTGCTCAGGGTGCGGCGTTGCCTAGGACGTTCGGCC

AAGGGACCAAGGTGGAAATCAAACGG

DOM7h-14-10/Exendin-4 fusion DMS number 7139
Amino acid sequence (SEQ ID NO: 307)
HGEGTFTSDLSKQMEEEAVRLFIEWLKNGGPSSGAPPPSGGGGGSGGGGSGGG

GSDIQMTQSPSSLSASVGDRVTITCRASQWIGSQLSWYQQKPGKAPKLLIMWRS

SLQSGVPSRFSGSGSGTDFTLTISSLQPEDFATYYCAQGLRHPKTFGQGTKVEIKR

Nucleotide sequence (SEQ ID NO: 308)
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

CTGTAGGAGACCGTGTCACCATCACTTGCCGGGCAAGTCAGTGGATTGGGT

CTCAGTTATCTTGGTACCAGCAGAAACCAGGGAAAGCCCCTAAGCTCCTGA

TCATGTGGCGTTCCTCGTTGCAAAGTGGGGTCCCATCACGTTTCAGTGGCAG

TGGATCTGGGACAGATTTCACTCTCACCATCAGCAGTCTGCAACCTGAAGAT

TTTGCTACGTACTACTGTGCTCAGGGTTTGAGGCATCCTAAGACGTTCGGCC

AAGGGACCAAGGTGGAAATCAAACGG

DOM7h-14-18/Exendin-4 fusion DMS number 7140
Amino acid sequence (SEQ ID NO: 309)
HGEGTFTSDLSKQMEEEAVRLFIEWLKNGGPSSGAPPPSGGGGGSGGGGSGGG

GSDIQMTQSPSSLSASVGDRVTITCRASQWIGSQLSWYQQKPGKAPKLLIMWRS

SLQSGVPSRFSGSGSGTDFTLTISSLQPEDFATYYCAQGLMKPMTFGQGTKVEIKR

Nucleotide sequence (SEQ ID NO: 310)
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

CTGTAGGAGACCGTGTCACCATCACTTGCCGGGCAAGTCAGTGGATTGGGT

CTCAGTTATCTTGGTACCAGCAGAAACCAGGGAAAGCCCCTAAGCTCCTGA

TCATGTGGCGTTCCTCGTTGCAAAGTGGGGTCCCATCACGTTTCAGTGGCAG

TGGATCTGGGACAGATTTCACTCTCACCATCAGCAGTCTGCAACCTGAAGAT

TTTGCTACGTACTACTGTGCTCAGGGTCTTATGAAGCCTATGACGTTCGGCC

AAGGGACCAAGGTGGAAATCAAACGG

DOM7h-14-19/Exendin-4 fusion DMS number 7141
Amino acid sequence (SEQ ID NO: 311)
HGEGTFTSDLSKQMEEEAVRLFIEWLKNGGPSSGAPPPSGGGGGSGGGGSGGG

GSDIQMTQSPSSLSASVGDRVTISCRASQWIGSQLSWYQQKPGEAPKLLIMWRS

SLQSGVPSRFSGSGSGTDFTLTISSLQPEDFATYYCAQGAALPRTFGQGTKVEIKR

Nucleotide sequence (SEQ ID NO: 312)
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

TABLE 5-continued

Anti-serum albumin dAb (DOM7h) fusions

```
CTGTAGGAGACCGTGTCACCATCTCTTGCCGGGCAAGTCAGTGGATTGGGTC

TCAGTTATCTTGGTACCAGCAGAAACCAGGGGAAGCCCCTAAGCTCCTGAT

CATGTGGCGTTCCTCGTTGCAAAGTGGGGTCCCATCACGTTTCAGTGGCAGT

GGATCTGGGACAGATTTCACTCTCACCATCAGCAGTCTGCAACCTGAAGATT

TTGCTACGTACTACTGTGCTCAGGGTGCGGCGTTGCCTAGGACGTTCGGCCA

AGGGACCAAGGTGGAAATCAAACGG
```

DOM7h-11/Exendin-4 fusion DMS number 7142
Amino acid sequence (SEQ ID NO: 313)
HGEGTFTSDLSKQMEEEAVRLFIEWLKNGGPSSGAPPPSGGGGGSGGGGSGGG

GSDIQMTQSPSSLSASVGDRVTITCRASRPIGTTLSWYQQKPGKAPKLLIWFGSR

LQSGVPSRFSGSGSGTDFTLTISSLQPEDFATYYCAQAGTHPTTFGQGTKVEIKR

Nucleotide sequence (SEQ ID NO: 314)
```
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

CTGTAGGAGACCGTGTCACCATCACTTGCCGGGCAAGTCGTCCGATTGGGA

CGACGTTAAGTTGGTACCAGCAGAAACCAGGGAAAGCCCCTAAGCTCCTGA

TCTGGTTTGGTTCCCGGTTGCAAAGTGGGGTCCCATCACGTTTCAGTGGCAG

TGGATCTGGGACAGATTTCACTCTCACCATCAGCAGTCTGCAACCTGAAGAT

TTTGCTACGTACTACTGTGCGCAGGCTGGGACGCATCCTACGACGTTCGGCC

AAGGGACCAAGGTGGAAATCAAACGG
```

DOM7h-11-12/Exendin-4 fusion DMS number 7147
Amino acid sequence (SEQ ID NO: 315)
HGEGTFTSDLSKQMEEEAVRLFIEWLKNGGPSSGAPPPSGGGGGSGGGGSGGG

GSDIQMTQSPSSLSASVGDRVTITCRASRPIGTMLSWYQQKPGKAPKLLILFGSR

LQSGVPSRFSGSGSGTDFTLTISSLQPEDFATYYCAQAGTHPTTFGQGTKVEIKR

Nucleotide sequence (SEQ ID NO: 316)
```
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

CTGTAGGAGACCGTGTCACCATCACTTGCCGGGCAAGTCGTCCGATTGGGA

CGATGTTAAGTTGGTACCAGCAGAAACCAGGGAAAGCCCCTAAGCTCCTGA

TCTTGTTTGGTTCCCGGTTGCAAAGTGGGGTCCCATCACGTTTCAGTGGCAG

TGGATCTGGGACAGATTTCACTCTCACCATCAGCAGTCTGCAACCTGAAGAT

TTTGCTACGTACTACTGTGCGCAGGCTGGGACGCATCCTACGACGTTCGGCC

AAGGGACCAAGGTGGAAATCAAACGG
```

DOM7h-11-15/Exendin-4 fusion DMS number 7143
Amino acid sequence (SEQ ID NO: 317)
HGEGTFTSDLSKQMEEEAVRLFIEWLKNGGPSSGAPPPSGGGGGSGGGGSGGG

GSDIQMTQSPSSLSASVGDRVTITCRASRPIGTMLSWYQQKPGKAPKLLILAFSR

LQSGVPSRFSGSGSGTDFTLTISSLQPEDFATYYCAQAGTHPTTFGQGTKVEIKR

TABLE 5-continued

Anti-serum albumin dAb (DOM7h) fusions

Nucleotide sequence (SEQ ID NO: 318)
CATGGTGAAGGAACATTTACCAGTGACTTGTCAAAACAGATGGAAGAGGAG

GCAGTGCGGTTATTTATTGAGTGGCTTAAGAACGGAGGACCAAGTAGCGGG

GCACCTCCGCCATCGGGTGGTGGAGGCGGTTCAGGCGGAGGTGGCAGCGGC

GGTGGCGGGTCGGACATCCAGATGACCCAGTCTCCATCCTCCCTGTCTGCAT

CTGTAGGAGACCGTGTCACCATCACTTGCCGGGCAAGTCGTCCGATTGGGA

CGATGTTAAGTTGGTACCAGCAGAAACCAGGGAAAGCCCCTAAGCTCCTGA

TCCTTGCTTTTTCCCGTTTGCAAAGTGGGGTCCCATCACGTTTCAGTGGCAGT

GGATCTGGGACAGATTTCACTCTCACCATCAGCAGTCTGCAACCTGAAGATT

TTGCTACGTACTACTGCGCGCAGGCTGGGACGCATCCTACGACGTTCGGCCA

AGGGACCAAGGTGGAAATCAAACGG

DOM7h14-10/G4SC-NCE fusion
Amino acid sequence (SEQ ID NO: 319) encoding DOM7h14-10/G4SC
DIQMTQSPSSLSASVGDRVTITCRASQWIGSQLSWYQQKPGKAPKLLIMWRSSL

QSGVPSRFSGSGSGTDFTLTISSLQPEDFATYYCAQGLRHPKTFGQGTKVEIKRG

GGGSC

The C-terminal cysteine can be linked to a new chemical entity (pharmaceutical
chemical compound, NCE), eg using maleimide linkage.
Nucleotide sequence (SEQ ID NO: 320) encoding DOM7h14-10/G4SC
GACATCCAGATGACCCAGTCTCCATCCTCCCTGTCTGCATCTGTAGGAGACC

GTGTCACCATCACTTGCCGGGCAAGTCAGTGGATTGGGTCTCAGTTATCTTG

GTACCAGCAGAAACCAGGGAAAGCCCCTAAGCTCCTGATCATGTGGCGTTC

CTCGTTGCAAAGTGGGGTCCCATCACGTTTCAGTGGCAGTGGATCTGGGAC

AGATTTCACTCTCACCATCAGCAGTCTGCAACCTGAAGATTTTGCTACGTAC

TACTGTGCTCAGGGTTTGAGGCATCCTAAGACGTTCGGCCAAGGGACCAAG

GTGGAAATCAAACGGGGTGGCGGAGGGGGTTCCTGT

DOM7h14-10/TVAAPSC fusion
Amino acid sequence (SEQ ID NO: 321)
DIQMTQSPSSLSASVGDRVTITCRASQWIGSQLSWYQQKPGKAPKLLIMWRSSL

QSGVPSRFSGSGSGTDFTLTISSLQPEDFATYYCAQGLRHPKTFGQGTKVEIKRT

VAAPSC

The C-terminal cysteine can be linked to a new chemical entity (pharmaceutical
chemical compound, NCE), eg using maleimide linkage.
Nucleotide sequence (SEQ ID NO: 322)
GACATCCAGATGACCCAGTCTCCATCCTCCCTGTCTGCATCTGTAGGAGACC

GTGTCACCATCACTTGCCGGGCAAGTCAGTGGATTGGGTCTCAGTTATCTTG

GTACCAGCAGAAACCAGGGAAAGCCCCTAAGCTCCTGATCATGTGGCGTTC

CTCGTTGCAAAGTGGGGTCCCATCACGTTTCAGTGGCAGTGGATCTGGGAC

AGATTTCACTCTCACCATCAGCAGTCTGCAACCTGAAGATTTTGCTACGTAC

TACTGTGCTCAGGGTTTGAGGCATCCTAAGACGTTCGGCCAAGGGACCAAG

GTGGAAATCAAACGGACCGTCGCTGCTCCATCTTGT (used in mouse studies):-
DOM7h-11/DOM1m-21-23 fusion DMS number 5515
Amino acid sequence (SEQ ID NO: 323)
EVQLLESGGGLVQPGGSLRLSCAASGFTFNRYSMGWLRQAPGKGLEWVSRIDS

YGRGTYYEDPVKGRFSISRDNSKNTLYLQMNSLRAEDTAVYYCAKISQFGSNA

TABLE 5-continued

Anti-serum albumin dAb (DOM7h) fusions

FDYWGQGTQVTVSSASTSGPSDIQMTQSPSSLSASVGDRVTITCRASRPIGTTLS

WYQQKPGKAPKLLIWFGSRLQSGVPSRFSGSGSGTDFTLTISSLQPEDFATYYC

AQAGTHPTTFGQGTKVEIKR

Amino acid plus nucleotide plus myc tag sequence (SEQ ID NO: 324)
EVQLLESGGGLVQPGGSLRLSCAASGFTFNRYSMGWLRQAPGKGLEWVSRIDS

YGRGTYYEDPVKGRFSISRDNSKNTLYLQMNSLRAEDTAVYYCAKISQFGSNA

FDYWGQGTQVTVSSASTSGPSDIQMTQSPSSLSASVGDRVTITCRASRPIGTTLS

WYQQKPGKAPKLLIWFGSRLQSGVPSRFSGSGSGTDFTLTISSLQPEDFATYYC

AQAGTHPTTFGQGTKVEIKRAAAEQKLISEEDLN

Nucleotide sequence (SEQ ID NO: 325)
GAGGTGCAGCTGTTGGAGTCTGGGGGAGGCTTGGTACAGCCTGGGGGGTCC

CTGCGTCTCTCCTGTGCAGCCTCCGGATTCACCTTTAATAGGTATAGTATGG

GGTGGCTCCGCCAGGCTCCAGGGAAGGGTCTAGAGTGGGTCTCACGGATTG

ATTCTTATGGTCGTGGTACATACTACGAAGACCCCGTGAAGGGCCGGTTCA

GCATCTCCCGCGACAATTCCAAGAACACGCTGTATCTGCAAATGAACAGCC

TGCGTGCCGAGGACACCGCCGTATATTACTGTGCGAAAATTTCTCAGTTTGG

GTCAAATGCGTTTGACTACTGGGGTCAGGGAACCCAGGTCACCGTCTCGAG

CGCTAGCACCAGTGGTCCATCGGACATCCAGATGACCCAGTCTCCATCCTCC

CTGTCTGCATCTGTAGGAGACCGTGTCACCATCACTTGCCGGGCAAGTCGTC

CGATTGGGACGACGTTAAGTTGGTACCAGCAGAAACCAGGGAAAGCCCCTA

AGCTCCTGATCTGGTTTGGTTCCCGGTTGCAAAGTGGGGTCCCATCACGTTT

CAGTGGCAGTGGATCTGGGACAGATTTCACTCTCACCATCAGCAGTCTGCA

ACCTGAAGATTTTGCTACGTACTACTGTGCGCAGGCTGGGACGCATCCTACG

ACGTTCGGCCAAGGGACCAAGGTGGAAATCAAACGG

Nucleotide plus myc tag sequence (SEQ ID NO: 326)
GAGGTGCAGCTGTTGGAGTCTGGGGGAGGCTTGGTACAGCCTGGGGGGTCC

CTGCGTCTCTCCTGTGCAGCCTCCGGATTCACCTTTAATAGGTATAGTATGG

GGTGGCTCCGCCAGGCTCCAGGGAAGGGTCTAGAGTGGGTCTCACGGATTG

ATTCTTATGGTCGTGGTACATACTACGAAGACCCCGTGAAGGGCCGGTTCA

GCATCTCCCGCGACAATTCCAAGAACACGCTGTATCTGCAAATGAACAGCC

TGCGTGCCGAGGACACCGCCGTATATTACTGTGCGAAAATTTCTCAGTTTGG

GTCAAATGCGTTTGACTACTGGGGTCAGGGAACCCAGGTCACCGTCTCGAG

CGCTAGCACCAGTGGTCCATCGGACATCCAGATGACCCAGTCTCCATCCTCC

CTGTCTGCATCTGTAGGAGACCGTGTCACCATCACTTGCCGGGCAAGTCGTC

CGATTGGGACGACGTTAAGTTGGTACCAGCAGAAACCAGGGAAAGCCCCTA

AGCTCCTGATCTGGTTTGGTTCCCGGTTGCAAAGTGGGGTCCCATCACGTTT

CAGTGGCAGTGGATCTGGGACAGATTTCACTCTCACCATCAGCAGTCTGCA

ACCTGAAGATTTTGCTACGTACTACTGTGCGCAGGCTGGGACGCATCCTACG

ACGTTCGGCCAAGGGACCAAGGTGGAAATCAAACGGGCGGCCGCAGAACA

AAAACTCATCTCAGAAGAGGATCTGAATTAA

TABLE 5-continued

Anti-serum albumin dAb (DOM7h) fusions

DOM7h-11-12/DOM1m-21-23 fusion DMS number 5516
Amino acid sequence (SEQ ID NO: 327)
EVQLLESGGGLVQPGGSLRLSCAASGFTFNRYSMGWLRQAPGKGLEWVSRIDS

YGRGTYYEDPVKGRFSISRDNSKNTLYLQMNSLRAEDTAVYYCAKISQFGSNA

FDYWGQGTQVTVSSASTSGPSDIQMTQSPSSLSASVGDRVTITCRASRPIGTMLS

WYQQKPGKAPKLLILFGSRLQSGVPSRFSGSGSGTDFTLTISSLQPEDFATYYCA

QAGTHPTTFGQGTKVEIKR

Amino acid plus nucleotide plus myc tag sequence (SEQ ID NO: 328)
EVQLLESGGGLVQPGGSLRLSCAASGFTFNRYSMGWLRQAPGKGLEWVSRIDS

YGRGTYYEDPVKGRFSISRDNSKNTLYLQMNSLRAEDTAVYYCAKISQFGSNA

FDYWGQGTQVTVSSASTSGPSDIQMTQSPSSLSASVGDRVTITCRASRPIGTMLS

WYQQKPGKAPKLLILFGSRLQSGVPSRFSGSGSGTDFTLTISSLQPEDFATYYCA

QAGTHPTTFGQGTKVEIKRAAAEQKLISEEDLN

Nucleotide sequence (SEQ ID NO: 329)
GAGGTGCAGCTGTTGGAGTCTGGGGGAGGCTTGGTACAGCCTGGGGGGTCC

CTGCGTCTCTCCTGTGCAGCCTCCGGATTCACCTTTAATAGGTATAGTATGG

GGTGGCTCCGCCAGGCTCCAGGGAAGGGTCTAGAGTGGGTCTCACGGATTG

ATTCTTATGGTCGTGGTACATACTACGAAGACCCCGTGAAGGGCCGGTTCA

GCATCTCCCGCGACAATTCCAAGAACACGCTGTATCTGCAAATGAACAGCC

TGCGTGCCGAGGACACCGCCGTATATTACTGTGCGAAAATTTCTCAGTTTGG

GTCAAATGCGTTTGACTACTGGGGTCAGGGAACCCAGGTCACCGTCTCGAG

CGCTAGCACCAGTGGTCCATCGGACATCCAGATGACCCAGTCTCCATCCTCC

CTGTCTGCATCTGTAGGAGACCGTGTCACCATCACTTGCCGGGCAAGTCGTC

CGATTGGGACGATGTTAAGTTGGTACCAGCAGAAACCAGGGAAAGCCCCTA

AGCTCCTGATCTTGTTTGGTTCCCGGTTGCAAAGTGGGGTCCCATCACGTTT

CAGTGGCAGTGGATCTGGGACAGATTTCACTCTCACCATCAGCAGTCTGCA

ACCTGAAGATTTTGCTACGTACTACTGTGCGCAGGCTGGGACGCATCCTACG

ACGTTCGGCCAAGGGACCAAGGTGGAAATCAAACGG

Nucleotide plus myc tag sequence (SEQ ID NO: 330)
GAGGTGCAGCTGTTGGAGTCTGGGGGAGGCTTGGTACAGCCTGGGGGGTCC

CTGCGTCTCTCCTGTGCAGCCTCCGGATTCACCTTTAATAGGTATAGTATGG

GGTGGCTCCGCCAGGCTCCAGGGAAGGGTCTAGAGTGGGTCTCACGGATTG

ATTCTTATGGTCGTGGTACATACTACGAAGACCCCGTGAAGGGCCGGTTCA

GCATCTCCCGCGACAATTCCAAGAACACGCTGTATCTGCAAATGAACAGCC

TGCGTGCCGAGGACACCGCCGTATATTACTGTGCGAAAATTTCTCAGTTTGG

GTCAAATGCGTTTGACTACTGGGGTCAGGGAACCCAGGTCACCGTCTCGAG

CGCTAGCACCAGTGGTCCATCGGACATCCAGATGACCCAGTCTCCATCCTCC

CTGTCTGCATCTGTAGGAGACCGTGTCACCATCACTTGCCGGGCAAGTCGTC

CGATTGGGACGATGTTAAGTTGGTACCAGCAGAAACCAGGGAAAGCCCCTA

AGCTCCTGATCTTGTTTGGTTCCCGGTTGCAAAGTGGGGTCCCATCACGTTT

CAGTGGCAGTGGATCTGGGACAGATTTCACTCTCACCATCAGCAGTCTGCA

ACCTGAAGATTTTGCTACGTACTACTGTGCGCAGGCTGGGACGCATCCTACG

TABLE 5-continued

Anti-serum albumin dAb (DOM7h) fusions

ACGTTCGGCCAAGGGACCAAGGTGGAAATCAAACGGGCGGCCGCAGAACA

AAAACTCATCTCAGAAGAGGATCTGAATTAA

DOM7h-11-15/DOM1m-21-23 fusion DMS number 5517
Amino acid sequence (SEQ ID NO: 331)
EVQLLESGGGLVQPGGSLRLSCAASGFTFNRYSMGWLRQAPGKGLEWVSRIDS

YGRGTYYEDPVKGRFSISRDNSKNTLYLQMNSLRAEDTAVYYCAKISQFGSNA

FDYWGQGTQVTVSSASTSGPSDIQMTQSPSSLSASVGDRVTITCRASRPIGTMLS

WYQQKPGKAPKLLILAFSRLQSGVPSRFSGSGSGTDFTLTISSLQPEDFATYYCA

QAGTHPTTFGQGTKVEIKR

Amino acid plus nucleotide plus myc tag sequence(SEQ ID NO: 332)
EVQLLESGGGLVQPGGSLRLSCAASGFTFNRYSMGWLRQAPGKGLEWVSRIDS

YGRGTYYEDPVKGRFSISRDNSKNTLYLQMNSLRAEDTAVYYCAKISQFGSNA

FDYWGQGTQVTVSSASTSGPSDIQMTQSPSSLSASVGDRVTITCRASRPIGTMLS

WYQQKPGKAPKLLILAFSRLQSGVPSRFSGSGSGTDFTLTISSLQPEDFATYYCA

QAGTHPTTFGQGTKVEIKRAAAEQKLISEEDLN

Nucleotide sequence (SEQ ID NO: 333)
GAGGTGCAGCTGTTGGAGTCTGGGGGAGGCTTGGTACAGCCTGGGGGGTCC

CTGCGTCTCTCCTGTGCAGCCTCCGGATTCACCTTTAATAGGTATAGTATGG

GGTGGCTCCGCCAGGCTCCAGGGAAGGGTCTAGAGTGGGTCTCACGGATTG

ATTCTTATGGTCGTGGTACATACTACGAAGACCCCGTGAAGGGCCGGTTCA

GCATCTCCCGCGACAATTCCAAGAACACGCTGTATCTGCAAATGAACAGCC

TGCGTGCCGAGGACACCGCCGTATATTACTGTGCGAAAATTTCTCAGTTTGG

GTCAAATGCGTTTGACTACTGGGGTCAGGGAACCCAGGTCACCGTCTCGAG

CGCTAGCACCAGTGGTCCATCGGACATCCAGATGACCCAGTCTCCATCCTCC

CTGTCTGCATCTGTAGGAGACCGTGTCACCATCACTTGCCGGGCAAGTCGTC

CGATTGGGACGATGTTAAGTTGGTACCAGCAGAAACCAGGGAAAGCCCCTA

AGCTCCTGATCCTTGCTTTTTCCCGTTTGCAAAGTGGGGTCCCATCACGTTTC

AGTGGCAGTGGATCTGGGACAGATTTCACTCTCACCATCAGCAGTCTGCAA

CCTGAAGATTTTGCTACGTACTACTGCGCGCAGGCTGGGACGCATCCTACGA

CGTTCGGCCAAGGGACCAAGGTGGAAATCAAACGG

Nucleotide plus myc tag sequence (SEQ ID NO: 334)
GAGGTGCAGCTGTTGGAGTCTGGGGGAGGCTTGGTACAGCCTGGGGGGTCC

CTGCGTCTCTCCTGTGCAGCCTCCGGATTCACCTTTAATAGGTATAGTATGG

GGTGGCTCCGCCAGGCTCCAGGGAAGGGTCTAGAGTGGGTCTCACGGATTG

ATTCTTATGGTCGTGGTACATACTACGAAGACCCCGTGAAGGGCCGGTTCA

GCATCTCCCGCGACAATTCCAAGAACACGCTGTATCTGCAAATGAACAGCC

TGCGTGCCGAGGACACCGCCGTATATTACTGTGCGAAAATTTCTCAGTTTGG

GTCAAATGCGTTTGACTACTGGGGTCAGGGAACCCAGGTCACCGTCTCGAG

CGCTAGCACCAGTGGTCCATCGGACATCCAGATGACCCAGTCTCCATCCTCC

CTGTCTGCATCTGTAGGAGACCGTGTCACCATCACTTGCCGGGCAAGTCGTC

CGATTGGGACGATGTTAAGTTGGTACCAGCAGAAACCAGGGAAAGCCCCTA

TABLE 5-continued

Anti-serum albumin dAb (DOM7h) fusions

```
AGCTCCTGATCCTTGCTTTTTCCCGTTTGCAAAGTGGGGTCCCATCACGTTTC

AGTGGCAGTGGATCTGGGACAGATTTCACTCTCACCATCAGCAGTCTGCAA

CCTGAAGATTTTGCTACGTACTACTGCGCGCAGGCTGGGACGCATCCTACGA

CGTTCGGCCAAGGGACCAAGGTGGAAATCAAACGGGCGGCCGCAGAACAA

AAACTCATCTCAGAAGAGGATCTGAATTAA
``` where a myc-tagged molecule is indicated in this table, this was the version used in PK studies in the examples. Where no myc-tagged sequences are given, the PK studies in the examples were not done with myc-tagged material, ie, the studies were done with the non-tagged constructs shown.

EXEMPLIFICATION

All numbering in the experimental section is according to Kabat (Kabat, E. A. National Institutes of Health (US) & Columbia University. Sequences of proteins of immunological interst, edn 5 (US Dept. Of Health and Human Services Public Health Service, National Institues of Health, Bethesda, Md., 1991)).

Derivation of DOM7h-11 and DOM7h-14 variants is described. DOM7h-11 variants are not according to the invention.

Example 1

Vk Affinity Maturation

Selections:

HSA (Human Serum Albumin) and RSA (Rat Serum Albumin) antigens were obtained from Sigma (essentially fatty acid free, ~99% (agarose gel electrophoresis), lyophilized powder Cat. No. A3782 and A6414 respectively)

Biotinylated products of above two antigens were made by using EZ Link Sulfo-NHS-SS-Biotin (Pierce, Cat. No. 21331). Free biotin reagent was removed by passing the samples twice through PD10 desalting column followed by overnight dialysis against 1000× excess volume of PBS at 4° C. Resulting product was tested by mass spec and 1-2 biotins per molecule were observed.

Affinity Maturation Libraries:

Both error-prone and CDR libraries were created using DOM7h-11 and DOM7h-14 parental dAbs (see WO2008/096158 for the sequences of DOM7h-11 and DOM7h-14). The CDR libraries were generated in the pDOM4 vector and the error prone libraries were generated in the pDOM33 vector (to allow for selection with or without protease treatment). Vector pDOM4, is a derivative of the Fd phage vector in which the gene III signal peptide sequence is replaced with the yeast glycolipid anchored surface protein (GAS) signal peptide. It also contains a c-myc tag between the leader sequence and gene III, which puts the gene III back in frame. This leader sequence functions well both in phage display vectors but also in other prokaryotic expression vectors and can be universally used. pDOM33 is a modified version of the pDOM4 vector where the c-myc tag has been removed which renders the dAb-phage fusion resistant to the protease trypsin. This allows the use of trypsin within the phage selection to select for dAbs that are more protease stable (see WO2008149143).

For error-prone maturation libraries, plasmid DNA encoding the dAb to be matured was amplified by PCR, using the GENEMORPH® II RANDOM MUTAGENESIS KIT (random, unique mutagenesis kit, Stratagene). The product was digested with Sal I and Not I and used in a ligation reaction with cut phage vector pDOM33.

For the CDR libraries, PCR reactions were performed using degenerate oligonucleotides containing NNK or NNS codons to diversify the required positions in the dAb to be affinity matured. Assembly PCR was then used to generate a full length diversified insert. The insert was digested with Sal I and Not I and used in a ligation reaction with pDOM4 for mutagenesis of multiple residues and pDOM5 for mutagenesis of single residues. The pDOM5 vector is a pUC119-based expression vector where protein expression is driven by the LacZ promoter. A GAS 1 leader sequence (see WO 2005/093074) ensures secretion of isolated, soluble dAbs into the periplasm and culture supernatant of $E.\ coli$. dAbs are cloned SalI/NotI in this vector, which appends a myc tag at the C-terminus of the dAb. This protocol using SalI and Not I results in inclusion of an ST amino acid sequence at the N-terminus.

The ligation produced by either method was then used to transform $E.\ coli$ strain TB1 by electroporation and the transformed cells plated on 2×TY agar containing 15 μg/ml tetracycline, yielding library sizes of $>5\times10^7$ clones.

The error-prone libraries had the following average mutation rate and size: DOM7h-11 (2.5 mutations per dAb), size: $6.1\times10^8$, DOM7h-14 (2.9 mutations per dAb), size:$5.4\times108$.

Each CDR library has four amino acid diversity. Two libraries were generated for each of CDRs 1 and 3, and one library for CDR2. The positions diversified within each library are as follows (amino acids based on VK dummy DPK9 sequence):

| | Library size | |
|---|---|---|
| | DOM7h-11 | DOM7h-14 |
| 1 - Q27, S28, S30, S31 (CDR1) | $8.8\times10^7$ | $5.8\times10^7$ |
| 2 - S30, S31, Y32, N34 (CDR1) | $4.6\times10^8$ | $4.2\times10^8$ |
| 3 - Y49, A50, A51, S53 (CDR2) | $3.9\times10^8$ | $2.4\times10^8$ |
| 4 - Q89, S91, Y92, S93 (CDR3) | $1.8\times10^8$ | $2.5\times10^8$ |
| 5 - Y92, Y93, T94, N96 (CDR3) | $4.0\times10^8$ | $3.3\times10^8$ |

Example 2

Selection Strategies

Three phage selection strategies were adopted for Vκ AlbudAb™ (anti-serum albumin dAb) affinity maturation:

1) Selections against HSA only:

Three rounds of selection against HSA were carried out. The error prone libraries and each CDR library were selected as an individual pool in all rounds. The first round of selection was performed against HSA passively coated onto an immunotube at 1 mg/ml. Round 2 was performed against 100 nM HSA and round 3 against 10 nM (CDR selections) or 20 or 100 nM (Error prone selections) HSA, both as soluble selections followed by a fourth round of selection with the error prone libraries against 1.5 nM HSA as a soluble selection. The error prone libraries were eluted with 0.1M glycine pH 2.0 before neutralisation with 1M Tris pH 8.0 and the CDR libraries were eluted with 1 mg/ml trypsin before infection into log phase TG1 cells. The third round of each selection was subcloned into pDOM5 for screening. Soluble selections used biotinylated HSA.

2) Trypsin Selections Against HSA:

In order to select dAbs with increased protease resistance compared to the parental clone and with potentially improved biophysical properties, trypsin was used in phage selections (see WO2008149143). Four rounds of selection were preformed against HSA. The first round of selection of error prone libraries was performed against passively coated HSA at 1 mg/ml without trypsin; the second round against passively coated HSA at 1 mg/ml with 20 μg/ml trypsin for 1 hour at 37° C.; the third round selection was performed by soluble selection using biotinylated HSA against 100 nM HSA with 20 μg/ml or 100 μg/ml trypsin for 1 hour at 37° C. The final round of selection was performed by soluble selection using biotinylated HSA against 100 nM HSA with 100 μg/ml trypsin overnight at 37° C.

3) Cross-over selections against HSA (round 1) and RSA (rounds 2-4):

The first round selection was carried out against 1 mg/ml passively coated HSA or 1 μM HSA (soluble selection), followed by a further three rounds of soluble selections against biotinylated RSA at concentrations of 1 μM for round 1, 100 nm for round 2 and 20 nM, 10 nM or 1 nM for round 3.

Screening Strategy and Affinity Determination:

In each case after selection a pool of phage DNA from the appropriate round of selection is prepared using a QIAfilter midiprep kit (Qiagen), the DNA is digested using the restriction enzymes Sal1 and Not1 and the enriched V genes are ligated into the corresponding sites in pDOM5 the soluble expression vector which expresses the dAb with a myc tag (see PCT/EP2008/067789). The ligated DNA is used to electro-transform E. coli HB 2151 cells which are then grown overnight on agar plates containing the antibiotic carbenicillin. The resulting colonies are individually assessed for antigen binding. In each case at least 96 clones were tested for binding to HSA, CSA (Cynomlgus monkey Serum Albumin), MSA (mouse serum albumin) and RSA by BIAcore™ (surface plasmon resonance). MSA antigen was obtained from Sigma (essentially fatty acid free, ~99% (agarose gel electrophoresis), lyophilized powder Cat. No. A3559) and CSA was purified from Cynomolgus serum albumin using prometic blue resin (Amersham). Soluble dAb fragments were produced in bacterial culture in ONEX culture media (Novagen) overnight at 37° C. in 96 well plates. The culture supernatant containing soluble dAb was centrifuged and analysed by BIAcore for binding to high density HSA, CSA, MSA and RSA CM5 chips. Clones were found to bind to all these species of serum albumin by off-rate screening. The clones were sequenced revealing unique dAb sequences.

The minimum identity to parent (at the amino acid level) of the clones selected was 97.2% (DOM7h-11-3: 97.2%, DOM7h-11-12: 98.2%, DOM7h11-15: 96.3%, DOM7h-11-18: 98.2%, DOM7h-11-19: 97.2%)

The minimum identity to parent (at the amino acid level) of the clones selected was 96.3% (DOM7h-14-10: 96.3%, DOM7h-14-18: 96.3%, DOM7h-14-19: 98.2%, DOM7h-14-28: 99.1%, DOM7h-14-36: 97.2%)

Unique dAbs were expressed as bacterial supernatants in 2.5 L shake flasks in Onex media at 30° C. for 48 hrs at 250 rpm. dAbs were purified from the culture media by absorption to protein L agarose followed by elution with 10 mM glycine pH2.0. Binding to HSA, CSA, MSA and RSA by BIAcore was confirmed using purified protein at 3 concentrations 1 μM, 500 nM and 50 nM. To determine the binding affinity ($K_D$) of the AlbudAbs to each serum albumin; purified dAbs were analysed by BIAcore over albumin concentration range from 5000 nM to 39 nM (5000 nM, 2500 nM, 1250 nM, 625 nM, 312 nM, 156 nM, 78 nM, 39 nM).

TABLE 6

| AlbudAb | Affinity ($K_D$) to SA (nM) | Kd | Ka |
|---|---|---|---|
| Rat | | | |
| DOM7h-14 | 60 | 2.095E−01 | 4.00E+06 |
| DOM7h-14-10 | 4 | 9.640E−03 | 4.57E+06 |
| DOM7h-14-18 | 410 | 2.275E−01 | 5.60E+05 |
| DOM7h-14-19 | 890 | 2.870E−01 | 3.20E+05 |
| DOM 7h-14-28 | 45 (140) | 7.0E−02 (1.141e−1) | 2.10E+06 (8.3e5) |
| DOM 7h-14-36 | 30 (6120) | 2.9E−02 (5.54e−2) | 1.55E+06 (9e3) |
| DOM 7h-11 | 2100 | 1.00E−01 | 4.80E+04 |
| DOM 7h-11-3 | 10000 (88000) | (7.18e−1) | (8.11e3) |
| DOM 7h-11-12 | 200 | 5.22E−01 | 2.76E+06 |
| DOM 7h-11-15 | 20 | 2.10E−02 | 1.10E+06 |
| DOM 7h-11-18 | 80 (29000) | 6.0E−02 (3.7e−1) | 1.64E+06 (1.3e4) |
| DOM 7h-11-19 | 28 (17000) | 9.1e−02 (1.4e−1) | 9.80E+05 (8.1e3) |
| Cyno | | | |
| DOM 7h-14 | 66 | 9.65E−02 | 1.50E+06 |
| DOM 7h-14-10 | 9 | 1.15E−02 | 1.60E+06 |
| DOM 7h-14-18 | 180 | 1.05E−01 | 6.30E+5 |
| DOM 7h-14-19 | 225 | 1.56E−01 | 7.00E+05 |
| DOM 7h-14-28 | 66 (136) | 1.3E−01 (1.34e−1) | 2.50E+06 (9.8e5) |
| DOM 7h-14-36 | 35 (7830) | 1.9E−02 (1.1e−1) | 9.80E+06 (1.43e4) |
| DOM 7h-11 | 1000 | 6.82E−01 | 8.00E+05 |
| DOM 7h-11-3 | 670 (200) | 9.6E−02 (1.5e−1) | 2.90E+05 (7.26e5) |
| DOM 7h-11-12 | ≥6000 | | |
| DOM 7h-11-15 | 3 | 5.57E−03 | 5.80E+06 |
| DOM 7h-11-18 | 10000 (65000) | 1.36 (4.8e−1) | 2.25E+05 (7.3e3) |
| DOM 7h-11-19 | ≥10000 (375000) | (6.2e−1) | (1.7e3) |
| Mouse | | | |
| DOM 7h-14 | 12 | 4.82E−02 | 4.10E+06 |
| DOM 7h-14-10 | 30 | 3.41E−02 | 1.29E+06 |
| DOM 7h-14-18 | 65 | 9.24E−02 | 2.28E+06 |
| DOM 7h-14-19 | 60 | 5.76E−02 | 1.16E+06 |
| DOM 7h-14-28 | 26 (31) | 3.4E−02 (7.15e−2) | 1.60E+06 (2.28e6) |

TABLE 6-continued

| AlbudAb | Affinity ($K_D$) to SA (nM) | Kd | Ka |
|---|---|---|---|
| DOM 7h-14-36 | 35 (33) | 2.3E-02 (7.06e-2) | 8.70E+05 (2.11e6) |
| DOM 7h-11 | 5000 | 9.00E-01 | |
| DOM 7h-11-3 | ≥10000 (36000) | (6.12e-1) | (1.67e4) |
| DOM 7h-11-12 | 130 | 1.89E-01 | 1.53E+06 |
| DOM 7h-11-15 | 10 | 9.40E-03 | 1.10E+06 |
| DOM 7h-11-18 | 150 (1600) | 2.4E-02 (6.23e-2) | 4.40E+05 (4e4) |
| DOM 7h-11-19 | 100 (18000) | 3.7E-02 (8.8e-2) | 1.40E+06 (4.9e3) |
| Human | | | |
| DOM 7h-14 | 33 | 4.17E-02 | 1.43E+06 |
| DOM 7h-14-10 | 12 | 1.39E-02 | 1.50E+06 |
| DOM 7h-14-18 | 280 | 3.39E-02 | 1.89E+05 |
| DOM 7h-14-19 | 70 | 5.25E-02 | 8.26E+05 |
| DOM 7h-14-28 | 30 (8260) | 3.3E-02 (5.6e-2) | 1.24E+06 (6.78e3) |
| DOM 7h-14-36 | 28 (1260) | 2.4E-02 (6.7e-2) | 1.23E+06 (5.4e4) |
| DOM 7h-11 | 2800 | 6.41E-01 | 7.00E+05 |
| DOM 7h-11-3 | 32 (130) | 1.6E-02 (2.35e-2) | 6.50E+05 (1.86e5) |
| DOM 7h-11-12 | 350 | 4.13E-01 | 1.26E+06 |
| DOM 7h-11-15 | 1 | 1.84E-03 | 2.00E+06 |
| DOM 7h-11-18 | 36 (32000) | 5.1E-02 (2.7e-1) | 3.40E+06 (8.39e3) |
| DOM 7h-11-19 | 65 (38000) | 1.1E-01 (2.09e-1) | 1.80E+06 (5.4e3) |

*: values in brackets were derived from a second, independent SPR experiment.

All DOM7h-14 derived variants are cross-reactive to mouse, rat, human and cyno serum albumin. DOM7h-14-10 has improved affinity to rat, cyno and human serum albumin compared to parent. DOM7h-14-28 has an improved affinity to RSA. DOM7h-14-36 has an improved affinity to RSA, CSA and MSA.

DOM7h-11-3 has improved affinity to CSA and HSA. DOM7h-11-12 has improved affinity to RSA, MSA and HSA. DOM7h-11-15 has improved affinity to RSA, MSA, CSA and HSA. DOM7h-11-18 and DOM7h-11-19 have improved affinity to RSA, MSA and HSA.

Example 3

Origins of Key DOM7h-11 Lineage Clones

DOM7h-11-3: From affinity maturation performed against HSA using the CDR2 library (Y49, A50, A51, S53), round 3 output 10 nM HSA DOM7h-11-12: From affinity maturation performed against HSA using the error prone library, round 3 outputs (100 nM, HSA) with 100 ug/ml trypsin.

DOM7h-11-15: From cross-over selections performed against HSA as round 1 followed by additional 3 rounds of selections against RSA using the CDR2 library (Y49, A50, A51, S53) at round 3 selection with 1 nM of RSA.

DOM7h-11-18 From cross-over selections performed against HSA as round 1 followed by additional 3 rounds of selections against RSA using the error prone library, round 3 output at 20 nM of RSA DOM7h-11-19 From cross-over selections performed against HSA as round 1 followed by additional 3 rounds of selections against RSA using the error prone library, round 3 output at 5 nM of RSA

TABLE 7

CDR sequences (according to Kabat; ref. as above)

| AlbudAb | CDR1 | CDR2 | CDR3 |
|---|---|---|---|
| DPK9 Vk dummy | SQSISSYLN (SEQ ID NO: 335) | YAASSLQS (SEQ ID NO: 336) | QQSYSTPNT (SEQ ID NO: 337) |
| DOM7h-11 | SRPIGTTLS (SEQ ID NO: 338) | WFGSRLQS (SEQ ID NO: 339) | AQAGTHPTT (SEQ ID NO: 340) |
| DOM7h-11-12 | SRPIGTMLS (SEQ ID NO: 341) | LFGSRLQS (SEQ ID NO: 342) | AQAGTHPTT (SEQ ID NO: 343) |
| DOM 7h-11-15 | SRPIGTMLS (SEQ ID NO: 344) | LAFSRLQS (SEQ ID NO: 345) | AQAGTHPTT (SEQ ID NO: 346) |
| DOM 7h-11-18 | SRPIGTMLS (SEQ ID NO: 347) | WFGSRLQS (SEQ ID NO: 348) | AQAGTHPTT (SEQ ID NO: 349) |
| DOM 7h-11-19 | SRPIGTMLS (SEQ ID NO: 350) | LFGSRLQS (SEQ ID NO: 351) | AQTGTHPTT (SEQ ID NO: 352) |
| DOM 7h-11-3 | SRPIGTTLS (SEQ ID NO: 353) | LWFSRLQS (SEQ ID NO: 354) | AQAGTHPTT (SEQ ID NO: 355) |

Example 4

Origins of Key DOM7h-14 Lineage Clones

DOM7h-14-19: From affinity maturation performed against HSA using the error prone library, round 3 outputs (100 nM, HSA) with 100 ug/ml trypsin.

DOM7h-14-10, DOM7h-14-18, DOM7h-14-28, DOM7h-14-36: From affinity maturation performed against HSA using CDR3 library (Y92, Y93, T94, N96), round 3 output.

TABLE 8

CDR sequences (according to Kabat; ref. as above)

| AlbudAb | CDR1 | CDR2 | CDR3 |
|---|---|---|---|
| DPK9 Vk dummy | SQSISSYLN (SEQ ID NO: 335) | YAASSLQS (SEQ ID NO: 336) | QQSYSTPNT (SEQ ID NO: 337) |
| DOM 7h-14 | SQWIGSQLS (SEQ ID NO: 356) | MWRSSLQS (SEQ ID NO: 357) | AQGAALPRT (SEQ ID NO: 358) |
| DOM 7h-14-10 | SQWIGSQLS (SEQ ID NO: 359) | MWRSSLQS (SEQ ID NO: 360) | AQGLRHPKT (SEQ ID NO: 361) |
| DOM 7h-14-18 | SQWIGSQLS (SEQ ID NO: 362) | MWRSSLQS (SEQ ID NO: 363) | AQGLMKPMT (SEQ ID NO: 364) |
| DOM 7h-14-19 | SQWIGSQLS (SEQ ID NO: 365) | MWRSSLQS (SEQ ID NO: 366) | AQGAALPRT (SEQ ID NO: 367) |
| DOM 7h-14-28 | SQWIGSQLS (SEQ ID NO: 368) | MWRSSLQS (SEQ ID NO: 369) | AQGAALPKT (SEQ ID NO: 370) |
| DOM 7h-14-36 | SQWIGSQLS (SEQ ID NO: 371) | MWRSSLQS (SEQ ID NO: 372) | AQGFKKPRT (SEQ ID NO: 373) |

Example 5

Expression and Biophysical Characterisation

The routine bacterial expression level in 2.5 L shake flasks was determined following culture in Onex media at 30° C. for 48 hrs at 250 rpm. The biophysical characteristics were determined by SEC MALLS and DSC.

SEC MALLS (size exclusion chromatography with multi-angle-LASER-light-scattering) is a non-invasive technique for the characterizing of macromolecules in solution. Briefly, proteins (at concentration of 1 mg/mL in buffer Dulbecco's PBS at 0.5 ml/min are separated according to their hydrodynamic properties by size exclusion chromatography (column: TSK3000 from TOSOH Biosciences; S200 from Pharmacia). Following separation, the propensity of the protein to scatter light is measured using a multi-angle-LASER-light-scattering (MALLS) detector. The intensity of the scattered light while protein passes through the detector is measured as a function of angle. This measurement taken together with the protein concentration determined using the refractive index (RI) detector allows calculation of the molar mass using appropriate equations (integral part of the analysis software Astra v.5.3.4.12).

DSC (Differential Scanning calorimetry): briefly, the protein is heated at a constant rate of 180° C./hrs (at 1 mg/mL in PBS) and a detectable heat change associated with thermal denaturation measured. The transition midpoint ($_{app}T_m$) is determined, which is described as the temperature where 50% of the protein is in its native conformation and the other 50% is denatured. Here, DSC determined the apparent transition midpoint (appTm) as most of the proteins examined do not fully refold. The higher the Tm, the more stable the molecule. Unfolding curves were analysed by non-2-state equations. The software package used was Origin® v7.0383.

TABLE 9

| | Biophysical parameters | |
|---|---|---|
| AlbudAb | SEC MALLS | DSC Tm (° C.) |
| DOM7h-14 | M | 60 |
| DOM 7h-14-10 | M | 59 |
| DOM 7h-14-18 | M | 58 |
| DOM 7h-14-19 | M | 59 |
| DOM 7h-14-28 | M | 58.3/60.2 |
| DOM 7h-14-36 | M | 59.2 |
| DOM 7h-11 | M | 66.9-72.2 |
| DOM 7h-11-3 | M (95%)* | 66.6/70.5 |
| DOM 7h-11-12 | M (<2% D) | 71.7 |
| DOM 7h-11-15 | M (<5% D) | 58.5-60.5 |
| DOM 7h-11-18 | M (98%) | 58.9/65.8 |
| DOM 7h-11-19 | M | 71.8/76.6 |

*in one other trial, monomer was primarily seen by SEC MALLS, although lower than 95%

We observed expression levels for all clones in Table 9 in the range from 15 to 119 mg/L in *E coli*.

For DOM7h-14 and DOM7h-11 variants, favorable biophysical parameters (monomeric in solution as determined by SEC MALLs and appTm of >55° C. as determined by DSC) and expression levels were maintained during affinity maturation. Monomeric state is advantageous because it avoids dimerisation and the risk of products that may cross-link targets such as cell-surface receptors.

Example 6

Determination of Serum Half Life in Rat, Mouse and Cynomolgus Monkey

AlbudAbs DOM7h-14-10, DOM7h-14-18, DOM7h-14-19, DOM7h-11, DOM7h11-12 and DOM7h-11-15 were cloned into the pDOM5 vector. For each AlbudAb™, 20-50 mg quantities were expressed in *E. coli* and purified from bacterial culture supernatant using protein L affinity resin and eluted with 100 mM glycine pH2. The proteins were concentred to greater than 1 mg/ml, buffer exchanged into PBS and endotoxin depleted using Q spin columns (Vivascience). For Rat pharmacokinetic (PK) analysis, AlbudAbs were dosed as single i.v injections at 2.5 mg/kg using 3 rats per compound. Serum samples were taken at 0.16, 1, 4, 12, 24, 48, 72, 120, 168 hrs. Analysis of serum levels was by anti-myc ELISA as per the method described below.

For Mouse PK, DOM7h-11, DOM7h11-12 and DOM7h-11-15 were dosed as single i.v injections at 2.5 mg/kg per dose group of 3 subjects and serum samples taken at 10 mins; 1 h; 8 h; 24 h; 48 h; 72 h; 96 h. Analysis of serum levels was by anti-myc ELISA as per the method described below.

For *Cynomolgus* monkey PK DOM7h-14-10 and DOM7h-11-15 were dosed as single i.v injections at 2.5 mg/kg into 3 female *Cynomolgus* monkeys per dose group and serum samples taken at 0.083, 0.25, 0.5, 1, 2, 4, 8, 24, 48, 96, 144, 192, 288, 336, 504 hrs. Analysis of serum levels was by anti-myc ELISA as per the method described below.

Anti-Myc ELISA Method

The AlbudAb concentration in serum was measured by anti-myc ELISA. Briefly, goat anti-myc polyclonal antibody (1:500; Abcam, catalogue number ab9132) was coated overnight onto Nunc 96-well Maxisorp plates and blocked with 5% BSA/PBS+1% tween. Serum samples were added at a range of dilutions alongside a standard at known concentrations. Bound myc-tagged AlbudAb was then detected using a rabbit polyclonal anti-Vk (1:1000; in-house reagent, bleeds were pooled and protein A purified before use) followed by an anti-rabbit IgG HRP antibody (1:10,000; Sigma, catalogue number A2074). Plates were washed between each stage of the assay with 3×PBS+0.1% Tween20 followed by 3×PBS. TMB (SureBlue TMB 1-Component Microwell Peroxidase Substrate, KPL, catalogue number 52-00-00) was added after the last wash and was allowed to develop. This was stopped with 1M HCl and the signal was then measured using absorbance at 450 nm.

From the raw ELISA data, the concentration of unknown samples was established by interpolation against the standard curve taking into account dilution factors. The mean concentration result from each time point was determined from replicate values and entered into WinNonLin analysis package (eg version 5.1 (available from Pharsight Corp., Mountain View, Calif. 94040, USA). The data was fitted using a non-compartmental model, where PK parameters were estimated by the software to give terminal half-lives. Dosing information and time points were selected to reflect the terminal phase of each PK profile.

TABLE 10

Single AlbudAb ™ PK

| Species | AlbudAb | Albumin $K_D$ (nM) | AUC h × μg/ml | CL ml/h/kg | $t_{1/2}$ h | Vz ml/kg |
|---|---|---|---|---|---|---|
| Rat | DOM7h-14* | 60 | | | | |
| | DOM7h-14-10 | 4 | 2134.6 | 1.2 | 42.1 | 71.2 |
| | DOM7h-14-18 | 410 | 617.3 | 4.1 | 38.4 | 228.1 |
| | DOM7h-14-19 | 890 | 632.6 | 4.1 | 36.3 | 213.3 |
| | DOM7h-11 | 2100 | 320.1 | 7.8 | 23.3 | 263.9 |
| | DOM7h-11-12 | 200 | 398.7 | 6.4 | 35.5 | 321.2 |
| | DOM7h-11-15 | 20 | 843.4 | 3.0 | 30.3 | 130.7 |
| mouse | DOM7h-11 | 5000 | 304.7 | 8.2 | 18.3 | 216.8 |
| | DOM7h-11-12 | 130 | 646.6 | 3.9 | 43.9 | 244.8 |
| | DOM7h-11-15 | 10 | 499.2 | 5.0 | 33.7 | 243.4 |
| Cyno | DOM7h-14* | 66 | | | 217.5 | |
| | DOM7h-14-10 | 9 | 6174.6 | 0.4 | 200.8 | 117.8 |
| | DOM7h-11* | 3300 | | | 135.1 | |
| | DOM7h-11-15 | 3 | 4195 | 0.6 | 198.1 | 170.3 |

*Historical data

Pharmacokinetic parameters derived from rat, mouse and *cynomolgus* monkey studies were fitted using a non-compartmental model. Key: AUC: Area under the curve from dosing time extrapolated to infinity; CL: clearance; $t_{1/2}$: is the time during which the blood concentration is halved; Vz: volume of distribution based on the terminal phase.

DOM7h-11 12 and DOM7h-11-15 have an improved AUC and $t_{1/2}$ in rat and mouse compared to parent. DOM7h-11-15 also has an improved AUC and $t_{1/2}$ in cyno compared to parent. This improvement in AUC/$t_{1/2}$ correlates with an improved in vitro KD to serum albumin.

Example 7

AlbudAb™ IFN Fusions

Cloning and Expression

As well as single AlbudAbs, the affinity matured Vk Albudabs were linked to Interferon alpha 2b (IFNα2b) to determine whether a useful PK of the AlbudAb was maintained as a fusion protein.

Interferon Alpha 2b Amino Acid Sequence:

(SEQ ID NO: 374)
CDLPQTHSLGSRRTLMLLAQMRRISLFSCLKDRHDFGFPQEEFGNQFQKA

ETIPVLHEMIQQIFNLFSTKDSSAAWDETLLDKFYTELYQQLNDLEACVI

QGVGVTETPLMKEDSILAVRKYFQRITLYLKEKKYSPCAWEVVRAEI

MRSFSLSTNLQESLRSKE

Interferon Alpha 2b Nucleotide Sequence:

(SEQ ID NO: 375)
TGTGATCTGCCTCAAACCCACAGCCTGGGTAGCAGGAGGACCTTGATGCT

CCTGGCACAGATGAGGAGAATCTCTCTTTTCTCCTGCTTGAAGGACAGAC

ATGACTTTGGATTTCCCCAGGAGGAGTTTGGCAACCAGTTCCAAAAGGCT

GAAACCATCCCTGTCCTCCATGAGATGATCCAGCAGATCTTCAATCTCTT

CAGCACAAAGGACTCATCTGCTGCTTGGGATGAGACCCTCCTAGACAAAT

TCTACACTGAACTCTACCAGCAGCTGAATGACCTGGAAGCCTGTGTGATA

CAGGGGGTGGGGGTGACAGAGACTCCCCTGATGAAGGAGGACTCCATTC

-continued

TGGCTGTGAGGAAATACTTCCAAAGAATCACTCTCTATCTGAAAGAGAAG

AAATACAGCCCTTGTGCCTGGGAGGTTGTCAGAGCAGAAATCATGAGAT

CTTTTTCTTTGTCAACAAACTTGCAAGAAAGTTTAAGAAGTAAGGAA

IFNa2b was linked to the AlbudAb via a TVAAPS linker region (see WO2007085814). The constructs were cloned by SOE-PCR (single overlap extension according to the method of Horton et al. Gene, 77, p 61 (1989)). PCR amplification of the AlbudAb and IFN sequences were carried out separately using primers with a ~15 base pair overlap at the TVAAPS linker region. The primers used are as follows:—

IFNα2b SOE fragment 5'
(SEQ ID NO: 376)
GCCCGGATCCACCGGCTGTGATCTG

IFNα2b SOE fragment 3'
(SEQ ID NO: 377)
GGAGGATGGAGACTGGGTCATCTGGATGTC

Vk SOE fragment 5'
(SEQ ID NO: 378)
GACATCCAGATGACCCAGTCTCCATCCTCC

Vk SOE fragment 3' to also introduce a myc tag
(SEQ ID NO: 379)
GCGCAAGCTTTTATTAATTCAGATCCTCTTCTGAGATGAGTTTTGTTC

TGCGGCCGCCCGTTTGATTTCCACCTTGGTCCC

The fragments were purified separately and subsequently assembled in a SOE (single overlap extension PCR extension) reaction using only the flanking primers.

IFNα2b SOE fragment 5'
(SEQ ID NO: 380)
GCCCGGATCCACCGGCTGTGATCTG

Vk SOE fragment 3' to also introduce a myc tag
(SEQ ID NO: 381)
GCGCAAGCTTTTATTAATTCAGATCCTCTTCTGAGATGAGTTTTGTTCT

GCGGCCGCCCGTTTGATTTCCACCTTGGTCCC

The assembled PCR product was digested using the restriction enzymes BamHI and HindIII and the gene ligated into the corresponding sites in the pDOM50, a mammalian expression vector which is a pTT5 derivative with an N-terminal V-J2-C mouse IgG secretory leader sequence to facilitate expression into the cell media.

Leader Sequence (Amino Acid):

METDTLLLWVLLLWVPGSTG    (SEQ ID NO: 382)

Leader Sequence (Nucleotide):

(SEQ ID NO: 383)
ATGGAGACCGACACCCTGCTGCTGTGGGTGCTGCTGCTGTGGGTGCCCGG

ATCCACCGGGC

Plasmid DNA was prepared using QIAfilter megaprep (Qiagen). 1 µg DNA/ml was transfected with 293-Fectin into HEK293E cells and grown in serum free media. The protein is expressed in culture for 5 days and purified from culture supernatant using protein L affinity resin and eluted with 100 mM glycine pH2. The proteins were concentred to greater than 1 mg/ml, buffer exchanged into PBS and endotoxin depleted using Q spin columns (Vivascience).

TABLE 11

Interferon alpha 2b-AlbudAb sequences with and without myc-tag (as amino acid- and nucleotide sequence)
The Interferon alpha 2b is N-terminal to the AlbudAb in the following fusions.

| | aa + myc | nt + myc | aa no tag | nt no tag |
|---|---|---|---|---|
| DMS7321 (IFNα2b-DOM7h-14) | CDLPQTHSLGSRRT LMLLAQMRRISLFS CLKDRHDFGFPQE EFGNQFQKAETIPV LHEMIQQIFNLFST KDSSAAWDETLLD KFYTELYQQLNDL EACVIQGVGVTETP LMKEDSILAVRKY FQRITLYLKEKKYS PCAWEVVRAEIMR SFSLSTNLQESLRS KETVAAPSDIQMT QSPSSLSASVGDRV TITCRASQWIGSQL SWYQQKPGKAPKL LIMWRSSLQSGVPS RFSGSGSGTDFTLT ISSLQPEDFATYYC AQGAALPRTFGQG TKVEIKR AAAEQKLISEEDL N\* (SEQ ID NO: 384) | TGCGACTTGCC ACAGACACAT AGTTTGGGATC AAGAAGAACA TTGATGTTATT AGCACAAATG CGTAGAATTTC TTTGTTCTCTT GTCTAAAGGAC CGTCACGACTT CGGATTCCCTC AGGAAGAGTTT GGAAACCAATT CCAAAAGCA GAAACTATTCC TGTCTTGCACG AAATGATCCAG CAAATATTCAA TTTGTTTTCTA CAAAGGACTC ATCAGCCGCTT GGGATGAAAC TCTGTTAGATA AATTCTACACT GAACTATATCA ACAACTGAAC GATCTAGAGGC TTGCGTTATTC AGGGTGTAGG AGTTACTGAAA | CDLPQTHSLG SRRTLMLLA QMRRISLFSC LKDRHDFGFP QEEFGNQFQ KAETIPVLHE MIQQIFNLFS TKDSSAAWD ETLLDKFYTE LYQQLNDLE ACVIQGVGV TETPLMKEDS ILAVRKYFQR ITLYLKEKKY SPCAWEVVR AEIMRSFSLS TNLQESLRSK ETVAAPSDIQ MTQSPSSLSA SVGDRVTITC RASQWIGSQL SWYQQKPGK APKLLIMWR SSLQSGVPSR FSGSGSGTDF TLTISSLQPED FATYYCAQG AALPRTFGQ GTKVEIKR (SEQ ID | TGCGACTTGCC ACAGACACAT AGTTTGGGATC AAGAAGAACA TTGATGTTATT AGCACAAATG CGTAGAATTTC TTTGTTCTCTT GTCTAAAGGA CCGTCACGACT TCGGATTCCCT CAGGAAGAGT TTGGAAACCA ATTCCAAAAA GCAGAAACTA TTCCTGTCTTG CACGAAATGA TCCAGCAAATA TTCAATTTGTT TTCTACAAAGG ACTCATCAGCC GCTTGGGATGA AACTCTGTTAG ATAAATTCTAC ACTGAACTATA TCAACAACTGA ACGATCTAGA GGCTTGCGTTA TTCAGGGTGTA GGAGTTACTGA |

TABLE 11-continued

Interferon alpha 2b-AlbudAb sequences with and without myc-tag (as amino acid- and nucleotide sequence) The Interferon alpha 2b is N-terminal to the AlbudAb in the following fusions.

| aa + myc | nt + myc | aa no tag | nt no tag |
|---|---|---|---|
| | CTCCCCTAATG<br>AAAGAAGATT<br>CAATTCTAGCC<br>GTTAGAAAATA<br>CTTTCAGCGTA<br>TCACATTGTAT<br>TTAAAGGAAA<br>AGAAATACTCC<br>CCATGTGCATG<br>GGAGGTGGTTA<br>GAGCAGAAAT<br>TATGAGGTCCT<br>TCTCTCTTTCT<br>ACGAATTTGCA<br>AGAATCTTTGA<br>GATCTAAGGA<br>AACCGTCGCTG<br>CTCCATCTGAC<br>ATCCAGATGAC<br>CCAGTCTCCAT<br>CCTCCCTGTCT<br>GCATCTGTAGG<br>AGACCGTGTCA<br>CCATCACTTGC<br>CGGGCAAGTC<br>AGTGGATTGGG<br>TCTCAGTTATC<br>TTGGTACCAGC<br>AGAAACCAGG<br>GAAAGCCCCTA<br>AGCTCCTGATC<br>ATGTGGCGTTC<br>CTCGTTGCAAA<br>GTGGGGTCCCA<br>TCACGTTTCAG<br>TGGCAGTGGAT<br>CTGGGACAGAT<br>TTCACTCTCAC<br>CATCAGCAGTC<br>TGCAACCTGAA<br>GATTTTGCTAC<br>GTACTACTGTG<br>CTCAGGGTGCG<br>GCGTTGCCTAG<br>GACGTTCGGCC<br>AAGGGACCAA<br>GGTGGAAATC<br>AAACGGGCGG<br>CCGCAGAACA<br>AAAACTCATC<br>TCAGAAGAGG<br>ATCTGAATTA<br>A (SEQ ID NO: 385) | NO: 386) | AACTCCCCTAA<br>TGAAAGAAGA<br>TTCAATTCTAG<br>CCGTTAGAAA<br>ATACTTTCAGC<br>GTATCACATTG<br>TATTTAAAGGA<br>AAAGAAATAC<br>TCCCCATGTGC<br>ATGGGAGGTG<br>GTTAGAGCAG<br>AAATTATGAG<br>GTCCTTCTCTC<br>TTTCTACGAAT<br>TTGCAAGAATC<br>TTTGAGATCTA<br>AGGAAACCGT<br>CGCTGCTCCAT<br>CTGACATCCAG<br>ATGACCCAGTC<br>TCCATCCTCCC<br>TGTCTGCATCT<br>GTAGGAGACC<br>GTGTCACCATC<br>ACTTGCCGGGC<br>AAGTCAGTGG<br>ATTGGGTCTCA<br>GTTATCTTGGT<br>ACCAGCAGAA<br>ACCAGGGAAA<br>GCCCCTAAGCT<br>CCTGATCATGT<br>GGCGTTCCTCG<br>TTGCAAAGTGG<br>GGTCCCATCAC<br>GTTTCAGTGGC<br>AGTGGATCTGG<br>GACAGATTTCA<br>CTCTCACCATC<br>AGCAGTCTGCA<br>ACCTGAAGATT<br>TTGCTACGTAC<br>TACTGTGCTCA<br>GGGTGCGGCG<br>TTGCCTAGGAC<br>GTTCGGCCAAG<br>GGACCAAGGT<br>GGAAATCAAA<br>CGG (SEQ ID NO: 387) |
| DMS732<br>(IFNα2b-<br>DOM7h-<br>14-10) | CDLPQTHSLGSRRT<br>LMLLAQMRRISLFS<br>CLKDRHDFGFPQE<br>EFGNQFQKAETIPV<br>LHEMIQQIFNLFST<br>KDSSAAWDETLLD<br>KFYTELYQQLNDL<br>EACVIQGVGVTETP<br>LMKEDSILAVRKY<br>FQRITLYLKEKKYS<br>PCAWEVVRAEIMR<br>SFSLSTNLQESLRS<br>KETVAAPSDIQMT<br>QSPSSLSASVGDRV<br>TITCRASQWIGSQL<br>SWYQQKPGKAPKL<br>LIMWRSSLQSGVPS<br>RFSGSGSGTDFTLT | TGCGACTTGCC<br>ACAGACACAT<br>AGTTTGGGATC<br>AAGAAGAACA<br>TTGATGTTATT<br>AGCACAAATG<br>CGTAGAATTTC<br>TTTGTTCTCTT<br>GTCTAAAGGAC<br>CGTCACGACTT<br>CGGATTCCCTC<br>AGGAAGAGTTT<br>GGAAACCAATT<br>CCAAAAAGCA<br>GAAACTATTCC<br>TGTCTTGCACG<br>AAATGATCCAG<br>CAAATATTCAA | CDLPQTHSLG<br>SRRTLMLLA<br>QMRRISLFSC<br>LKDRHDFGFP<br>QEEFGNQFQ<br>KAETIPVLHE<br>MIQQIFNLFS<br>TKDSSAAWD<br>ETLLDKFYTE<br>LYQQLNDLE<br>ACVIQGVGV<br>TETPLMKEDS<br>ILAVRKYFQR<br>ITLYLKEKKY<br>SPCAWEVVR<br>AEIMRSFSLS<br>TNLQESLRSK<br>ETVAAPSDIQ | TGCGACTTGCC<br>ACAGACACAT<br>AGTTTGGGATC<br>AAGAAGAACA<br>TTGATGTTATT<br>AGCACAAATG<br>CGTAGAATTTC<br>TTTGTTCTCTT<br>GTCTAAAGGA<br>CCGTCACGACT<br>TCGGATTCCCT<br>CAGGAAGAGT<br>TTGGAAACCA<br>ATTCCAAAAA<br>GCAGAAACTA<br>TTCCTGTCTTG<br>CACGAAATGA<br>TCCAGCAAATA |

TABLE 11-continued

Interferon alpha 2b-AlbudAb sequences with and without myc-tag (as amino acid- and nucleotide sequence) The Interferon alpha 2b is N-terminal to the AlbudAb in the following fusions.

| aa + myc | nt + myc | aa no tag | nt no tag |
|---|---|---|---|
| ISSLQPEDFATYYC AQGLRHPKTFGQG TKVEIKR AAAEQKLISEEDL N* (SEQ ID NO: 388) | TTTGTTTTCTA CAAAGGACTC ATCAGCCGCTT GGGATGAAAC TCTGTTAGATA AATTCTACACT GAACTATATCA ACAACTGAAC GATCTAGAGGC TTGCGTTATTC AGGGTGTAGG AGTTACTGAAA CTCCCCTAATG AAAGAAGATT CAATTCTAGCC GTTAGAAAATA CTTTCAGCGTA TCACATTGTAT TTAAAGGAAA AGAAATACTCC CCATGTGCATG GGAGGTGGTTA GAGCAGAAAT TATGAGGTCCT TCTCTCTTTCT ACGAATTTGCA AGAATCTTTGA GATCTAAGGA AACCGTCGCTG CTCCATCTGAC ATCCAGATGAC CCAGTCTCCAT CCTCCCTGTCT GCATCTGTAGG AGACCGTGTCA CCATCACTTGC CGGGCAAGTC AGTGGATTGGG TCTCAGTTATC TTGGTACCAGC AGAAACCAGG GAAAGCCCCTA AGCTCCTGATC ATGTGGCGTTC CTCGTTGCAAA GTGGGGTCCCA TCACGTTTCAG TGGCAGTGGAT CTGGGACAGAT TTCACTCTCAC CATCAGCAGTC TGCAACCTGAA GATTTTGCTAC GTACTACTGTG CTCAGGGTTTG AGGCATCCTAA GACGTTCGGCC AAGGGACCAA GGTGGAAATC AAACGGGCGG CCGCAGAACA AAAACTCATC TCAGAAGAGG ATCTGAATTA A (SEQ ID NO: 389) | MTQSPSSLSA SVGDRVTITC RASQWIGSQL APKLLIMWR SSLQSGVPSR FSGSGSGTDF TLTISSLQPED FATYYCAQG LRHPKTFGQ GTKVEIKR (SEQ ID NO: 390) | TTCAATTTGTT TTCTACAAAGG ACTCATCAGCC GCTTGGGATGA AACTCTGTTAG ATAAATTCTAC ACTGAACTATA TCAACAACTGA ACGATCTAGA GGCTTGCGTTA TTCAGGGTGTA GGAGTTACTGA AACTCCCTAA TGAAAGAAGA TTCAATTCTAG CCGTTAGAAA ATACTTTCAGC GTATCACATTG TATTTAAAGGA AAAGAAATAC TCCCCATGTGC ATGGGAGGTG GTTAGAGCAG AAATTATGAG GTCCTTCTCTC TTTCTACGAAT TTGCAAGAATC TTTGAGATCTA AGGAAACCGT CGCTGCTCCAT CTGACATCCAG ATGACCCAGTC TCCATCCTCCC TGTCTGCATCT GTAGGAGACC GTGTCACCATC ACTTGCCGGGC AAGTCAGTGG ATTGGGTCTCA GTTATCTTGGT ACCAGCAGAA ACCAGGGAAA GCCCCTAAGCT CCTGATCATGT GGCGTTCCTCG TTGCAAAGTGG GTCCCATCAC GTTTCAGTGGC AGTGGATCTGG GACAGATTTCA CTCTCACCATC AGCAGTCTGCA ACCTGAAGATT TTGCTACGTAC TACTGTGCTCA GGGTTTGAGGC ATCCTAAGACG TTCGGCCAAGG GACCAAGGTG GAAATCAAAC GG (SEQ ID NO: 391) |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| | aa + myc | nt + myc | aa no tag | nt no tag |
|---|---|---|---|---|
| DMS7323 (IFNα2b-DOM7h-14-18) | CDLPQTHSLGSRRT LMLLAQMRRISLFS CLKDRHDFGFPQE EFGNQFQKAETIPV LHEMIQQIFNLFST KDSSAAWDETLLD KFYTELYQQLNDL EACVIQGVGVTETP LMKEDSILAVRKY FQRITLYLKEKKYS PCAWEVVRAEIMR SFSLSTNLQESLRS KETVAAPSDIQMT QSPSSLSASVGDRV TITCRASQWIGSQL SWYQQKPGKAPKL LIMWRSSLQSGVPS RFSGSGSGTDFTLT ISSLQPEDFATYYC AQGLMKPMTFGQ GTKVEIKRAAAEQ KLISEEDLN\* (SEQ ID NO: 392) | TGCGACTTGCC ACAGACACAT AGTTTGGGATC AAGAAGAACA TTGATGTTATT AGCACAAATG CGTAGAATTTC TTTGTTCTCTT GTCTAAAGGAC CGTCACGACTT CGGATTCCCTC AGGAAGAGTTT GGAAACCAATT CCAAAAAGCA GAAACTATTCC TGTCTTGCACG AAATGATCCAG CAAATATTCAA TTTGTTTTCTA CAAAGGACTC ATCAGCCGCTT GGGATGAAAC TCTGTTAGATA AATTCTACACT GAACTATATCA ACAACTGAAC GATCTAGAGGC TTGCGTTATTC AGGGTGTAGG AGTTACTGAAA CTCCCCTAATG AAAGAAGATT CAATTCTAGCC GTTAGAAAATA CTTTCAGCGTA TCACATTGTAT TTAAAGGAAA AGAAATACTCC CCATGTGCATG GGAGGTGGTTA GAGCAGAAAT TATGAGGTCCT TCTCTCTTTCT ACGAATTTGCA AGAATCTTTGA GATCTAAGGA AACCGTCGCTG CTCCATCTGAC ATCCAGATGAC CCAGTCTCCAT CCTCCCTGTCT GCATCTGTAGG AGACCGTGTCA CCATCACTTGC CGGGCAAGTC AGTGGATTGGG TCTCAGTTATC TTGGTACCAGC AGAAACCAGG GAAAGCCCCTA AGCTCCTGATC ATGTGGCGTTC CTCGTTGCAAA GTGGGTCCCA TCACGTTTCAG TGGCAGTGGAT CTGGGACAGAT TTCACTCTCAC CATCAGCAGTC TGCAACCTGAA GATTTTGCTAC GTACTACTGTG CTCAGGGTCTT | CDLPQTHSLG SRRTLMLLA QMRRISLFSC LKDRHDFGFP QEEFGNQFQ KAETIPVLHE MIQQIFNLFS TKDSSAAWD ETLLDKFYTE LYQQLNDLE ACVIQGVGV TETPLMKEDS ILAVRKYFQR ITLYLKEKKY SPCAWEVVR AEIMRSFSLS TNLQESLRSK ETVAAPSDIQ MTQSPSSLSA SVGDRVTITC RASQWIGSQL SWYQQKPGK APKLLIMWR SSLQSGVPSR FSGSGSGTDF TLTISSLQPED FATYYCAQG LMKPMTFGQ GTKVEIKR (SEQ ID NO: 394) | TGCGACTTGCC ACAGACACAT AGTTTGGGATC AAGAAGAACA TTGATGTTATT AGCACAAATG CGTAGAATTTC TTTGTTCTCTT GTCTAAAGGA CCGTCACGACT TCGGATTCCCT CAGGAAGAGT TTGGAAACCA ATTCCAAAAA GCAGAAACTA TTCCTGTCTTG CACGAAATGA TCCAGCAAATA TTCAATTTGTT TTCTACAAAGG ACTCATCAGCC GCTTGGGATGA AACTCTGTTAG ATAAATTCTAC ACTGAACTATA TCAACAACTGA ACGATCTAGA GGCTTGCGTTA TTCAGGGTGTA GGAGTTACTGA AACTCCCCTAA TGAAAGAAGA TTCAATTCTAG CCGTTAGAAA ATACTTTCAGC GTATCACATTG TATTTAAAGGA AAAGAAATAC TCCCCATGTGC ATGGGAGGTG GTTAGAGCAG AAATTATGAG GTCCTTCTCTC TTTCTACGAAT TTGCAAGAATC TTTGAGATCTA AGGAAACCGT CGCTGCTCCAT CTGACATCCAG ATGACCCAGTC TCCATCCTCCC TGTCTGCATCT GTAGGAGACC GTGTCACCATC ACTTGCCGGGC AAGTCAGTGG ATTGGGTCTCA GTTATCTTGGT ACCAGCAGAA ACCAGGGAAA GCCCCTAAGCT CCTGATCATGT GGCGTTCCTCG TTGCAAAGTGG GTCCCATCAC GTTTCAGTGGC AGTGGATCTGG GACAGATTCA CTCTCACCATC AGCAGTCTGCA ACCTGAAGATT TTGCTACGTAC TACTGTGCTCA |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| aa + myc | nt + myc | aa no tag | nt no tag |
|---|---|---|---|
| | ATGAAGCCTAT GACGTTCGGCC AAGGGACCAA GGTGGAAATC AAACGGGCGG CCGCAGAACA AAAACTCATC TCAGAAGAGG ATCTGAATTA A (SEQ ID NO: 393) | | GGGTCTTATGA AGCCTATGACG TTCGGCCAAGG GACCAAGGTG GAAATCAAAC GG (SEQ ID NO: 395) |
| DMS7324 (IFNα2b-DOM7h-14-19) CDLPQTHSLGSRRT LMLLAQMRRISLFS CLKDRHDFGFPQE EFGNQFQKAETIPV LHEMIQQIFNLFST KDSSAAWDETLLD KFYTELYQQLNDL EACVIQGVGVTETP LMKEDSILAVRKY FQRITLYLKEKKYS PCAWEVVRAEIMR SFSLSTNLQESLRS KETVAAPSDIQMT QSPSSLSASVGDRV TISCRASQWIGSQL SWYQQKPGEAPKL LIMWRSSLQSGVPS RFSGSGSGTDFTLT ISSLQPEDFATYYC AQGAALPRTFGQG TKVEIKR AAAEQKLISEEDL N* (SEQ ID NO: 396) | TGCGACTTGCC ACAGACACAT AGTTTGGGATC AAGAAGAACA TTGATGTTATT AGCACAAATG CGTAGAATTTC TTTGTTCTCTT GTCTAAAGGAC CGTCACGACTT CGGATTCCCTC AGGAAGAGTTT GGAAACCAATT CCAAAAAGCA GAAACTATTCC TGTCTTGCACG AAATGATCCAG CAAATATTCAA TTTGTTTTCTA CAAAGGACTC ATCAGCCGCTT GGGATGAAAC TCTGTTAGATA AATTCTACACT GAACTATATCA ACAACTGAAC GATCTAGAGGC TTGCGTTATTC AGGGTGTAGG AGTTACTGAAA CTCCCCTAATG AAAGAAGATT CAATTCTAGCC GTTAGAAAATA CTTTCAGCGTA TCACATTGTAT TTAAAGGAAA AGAAATACTCC CCATGTGCATG GGAGGTGGTTA GAGCAGAAAT TATGAGGTCCT TCTCTCTTTCT ACGAATTTGCA AGAATCTTTGA GATCTAAGGA AACCGTCGCTG CTCCATCTGAC ATCCAGATGAC CCAGTcTCCAT CCTCCCTGTCT GCATCTGTAGG AGACCGTGTCA CCATCTCTTGC CGGGCAAGTC AGTGGATTGGG TCTCAGTTATC TTGGTACCAGC AGAAACCAGG GGAAGCCCCTA AGCTCCTGATC | CDLPQTHSLG SRRTLMLLA QMRRISLFSC LKDRHDFGFP QEEFGNQFQ KAETIPVLHE MIQQIFNLFS TKDSSAAWD ETLLDKFYTE LYQQLNDLE ACVIQGVGV TETPLMKEDS ILAVRKYFQR ITLYLKEKKY SPCAWEVVR AEIMRSFSLS TNLQESLRSK ETVAAPSDIQ MTQSPSSLSA SVGDRVTISC RASQWIGSQL SWYQQKPGE APKLLIMWR SSLQSGVPSR FSGSGSGTDF TLTISSLQPED FATYYCAQG AALPRTFGQ GTKVEIKR (SEQ ID NO: 398) | TGCGACTTGCC ACAGACACAT AGTTTGGGATC AAGAAGAACA TTGATGTTATT AGCACAAATG CGTAGAATTTC TTTGTTCTCTT GTCTAAAGGA CCGTCACGACT TCGGATTCCCT CAGGAAGAGT TTGGAAACCA ATTCCAAAAA GCAGAAACTA TTCCTGTCTTG CACGAAATGA TCCAGCAAATA TTCAATTTGTT TTCTACAAAGG ACTCATCAGCC GCTTGGGATGA AACTCTGTTAG ATAAATTCTAC ACTGAACTATA TCAACAACTGA ACGATCTAGA GGCTTGCGTTA TTCAGGGTGTA GGAGTTACTGA AACTCCCCTAA TGAAAGAAGA TTCAATTCTAG CCGTTAGAAA ATACTTTCAGC GTATCACATTG TATTTAAAGGA AAAGAAATAC TCCCCATGTGC ATGGGAGGTG GTTAGAGCAG AAATTATGAG GTCCTTCTCTC TTTCTACGAAT TTGCAAGAATC TTTGAGATCTA AGGAAACCGT CGCTGCTCCAT CTGACATCCAG ATGACCCAGTc TCCATCCTCCC TGTCTGCATCT GTAGGAGACC GTGTCACCATC TCTTGCCGGGC AAGTCAGTGG ATTGGGTCTCA GTTATCTTGGT ACCAGCAGAA ACCAGGGGAA GCCCCTAAGCT |

TABLE 11-continued

Interferon alpha 2b-AlbudAb sequences with and without myc-tag (as amino acid- and nucleotide sequence) The Interferon alpha 2b is N-terminal to the AlbudAb in the following fusions.

| aa + myc | nt + myc | aa no tag | nt no tag |
|---|---|---|---|
|  | ATGTGGCGTTC CTCGTTGCAAA GTGGGGTCCCA TCACGTTTCAG TGGCAGTGGAT CTGGGACAGAT TTCACTCTCAC CATCAGCAGTC TGCAACCTGAA GATTTTGCTAC GTACTACTGTG CTCAGGGTGCG GCGTTGCCTAG GACGTTCGGCC AAGGGACCAA GGTGGAAATC AAACGGGCGG CCGCAGAACA AAAACTCATC TCAGAAGAGG ATCTGAATTA A (SEQ ID NO: 397) |  | CCTGATCATGT GGCGTTCCTCG TTGCAAAGTGG GGTCCCATCAC GTTTCAGTGGC AGTGGATCTGG GACAGATTTCA CTCTCACCATC AGCAGTCTGCA ACCTGAAGATT TTGCTACGTAC TACTGTGCTCA GGGTGCGGCG TTGCCTAGGAC GTTCGGCCAAG GGACCAAGGT GGAAATCAAA CGG (SEQ ID NO: 399) |
| DMS7325 (IFNα2b-DOM7h-11) | CDLPQTHSLGSRRT LMLLAQMRRISLFS CLKDRHDFGFPQE EFGNQFQKAETIPV LHEMIQQIFNLFST KDSSAAWDETLLD KFYTELYQQLNDL EACVIQGVGVTETP LMKEDSILAVRKY FQRITLYLKEKKYS PCAWEVVRAEIMR SFSLSTNLQESLRS KETVAAPSDIQMT QSPSSLSASVGDRV TITCRASRPIGTTLS WYQQKPGKAPKLL IWFGSRLQSGVPSR FSGSGSGTDFTLTIS SLQPEDFATYYCA QAGTHPTTFGQGT KVEIKR AAAEQKLISEEDL N* (SEQ ID NO: 400) | TGCGACTTGCC ACAGACACAT AGTTTGGGATC AAGAAGAACA TTGATGTTATT AGCACAAATG CGTAGAATTTC TTTGTTCTCTT GTCTAAAGGAC CGTCACGACTT CGGATTCCCTC AGGAAGAGTTT GGAAACCAATT CCAAAAAGCA GAAACTATTCC TGTCTTGCACG AAATGATCCAG CAAATATTCAA TTTGTTTTCTA ATGCAGTCGAC TTCAATTTGTT CAAAGGACTC ATCAGCCGCTT GGGATGAAAC TCTGTTAGATA AATTCTACACT GAACTATATCA ACAACTGAAC GATCTAGAGGC TTGCGTTATTC AGGGTGTAGG AGTTACTGAAA CTCCCCTAATG AAAGAAGATT CAATTCTAGCC GTTAGAAAATA CTTTCAGCGTA TCACATTGTAT TTAAAGGAAA AGAAATACTCC CCATGTGCATG GGAGGTGGTTA GAGCAGAAAT TATGAGGTCCT TCTCTCTTTCT ACGAATTTGCA AGAATCTTTGA GATCTAAGGA AACCGTCGCTG CTCCATCTGAC ATCCAGATGAC | CDLPQTHSLG SRRTLMLLA QMRRISLFSC LKDRHDFGFP QEEFGNQFQ KAETIPVLHE MIQQIFNLFS TKDSSAAWD ETLLDKFYTE LYQQLNDLE ACVIQGVGV TETPLMKEDS ILAVRKYFQR ITLYLKEKKY SPCAWEVVR AEIMRSFSLS TNLQESLRSK ETVAAPSDIQ MTQSPSSLSA SVGDRVTITC RASRPIGTTL SWYQQKPGK APKLLIWFGS RLQSGVPSRF SGSGSGTDFT LTISSLQPEDF ATYYCQAG THPTTFGQGT KVEIKR (SEQ ID NO: 402) | TGCGACTTGCC ACAGACACAT AGTTTGGGATC AAGAAGAACA TTGATGTTATT AGCACAAATG CGTAGAATTTC TTTGTTCTCTT GTCTAAAGGA CCGTCACGACT TCGGATTCCCT CAGGAAGAGT TTGGAAACCA ATTCCAAAAA GCAGAAACTA TTCCTGTCTTG CACGAAATGA TCCAGCAAATA TTCAATTTGTT TTCTACAAAGG ACTCATCAGCC GCTTGGGATGA AACTCTGTTAG ATAAATTCTAC ACTGAACTATA TCAACAACTGA ACGATCTAGA GGCTTGCGTTA TTCAGGGTGTA GGAGTTACTGA AACTCCCCTAA TGAAAGAAGA TTCAATTCTAG CCGTTAGAAA ATACTTTCAGC GTATCACATTG TATTTAAGGA AAAGAAATAC TCCCCATGTGC ATGGGAGGTG GTTAGAGCAG AAATTATGAG GTCCTTCTCTC TTTCTACGAAT TTGCAAGAATC TTTGAGATCTA AGGAAACCGT CGCTGCTCCAT CTGACATCCAG |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| aa + myc | nt + myc | aa no tag | nt no tag |
|---|---|---|---|
| | CCAGTCTCCAT | | ATGACCCAGTC |
| | CCTCCCTGTCT | | TCCATCCTCCC |
| | GCATCTGTAGG | | TGTCTGCATCT |
| | AGACCGTGTCA | | GTAGGAGACC |
| | CCATCACTTGC | | GTGTCACCATC |
| | CGGGCAAGTC | | ACTTGCCGGGC |
| | GTCCGATTGGG | | AAGTCGTCCGA |
| | ACGACGTTAAG | | TTGGGACGAC |
| | TTGGTACCAGC | | GTTAAGTTGGT |
| | AGAAACCAGG | | ACCAGCAGAA |
| | GAAAGCCCCTA | | ACCAGGGAAA |
| | AGCTCCTGATC | | GCCCCTAAGCT |
| | TGGTTTGGTTC | | CCTGATCTGGT |
| | CCGGTTGCAAA | | TTGGTTCCCGG |
| | GTGGGGTCCCA | | TTGCAAAGTGG |
| | TCACGTTTCAG | | GGTCCCATCAC |
| | TGGCAGTGGAT | | GTTTCAGTGGC |
| | CTGGGACAGAT | | AGTGGATCTGG |
| | TTCACTCTCAC | | GACAGATTTCA |
| | CATCAGCAGTC | | CTCTCACCATC |
| | TGCAACCTGAA | | AGCAGTCTGCA |
| | GATTTTGCTAC | | ACCTGAAGATT |
| | GTACTACTGTG | | TTGCTACGTAC |
| | CGCAGGCTGG | | TACTGTGCGCA |
| | GACGCATCCTA | | GGCTGGGACG |
| | CGACGTTCGGC | | CATCCTACGAC |
| | CAAGGGACCA | | GTTCGGCCAAG |
| | AGGTGGAAAT | | GGACCAAGGT |
| | CAAACGGGCG | | GGAAATCAAA |
| | GCCGCAGAAC | | CGG (SEQ ID |
| | AAAAACTCAT | | NO: 403) |
| | CTCAGAAGAG | | |
| | GATCTGAATT | | |
| | AA (SEQ ID | | |
| | NO: 401) | | |
| DMS7326 CDLPQTHSLGSRRT | TGCGACTTGCC | CDLPQTHSLG | TGCGACTTGCC |
| (IFNα2b- LMLLAQMRRISLFS | ACAGACACAT | SRRTLMLLA | ACAGACACAT |
| DOM7h- CLKDRHDFGFPQE | AGTTTGGGATC | QMRRISLFSC | AGTTTGGGATC |
| 11-12) EFGNQFQKAETIPV | AAGAAGAACA | LKDRHDFGFP | AAGAAGAACA |
| LHEMIQQIFNLFST | TTGATGTTATT | QEEFGNQFQ | TTGATGTTATT |
| KDSSAAWDETLLD | AGCACAAATG | KAETIPVLHE | AGCACAAATG |
| KFYTELYQQLNDL | CGTAGAATTTC | MIQQIFNLFS | CGTAGAATTTC |
| EACVIQGVGVTETP | TTTGTTCTCTT | TKDSSAAWD | TTTGTTCTCTT |
| LMKEDSILAVRKY | GTCTAAGGAC | ETLLDKFYTE | GTCTAAGGA |
| FQRITLYLKEKKYS | CGTCACGACTT | LYQQLNDLE | CCGTCACGACT |
| PCAWEVVRAEIMR | CGGATTCCCTC | ACVIQGVGV | TCGGATTCCCT |
| SFSLSTNLQESLRS | AGGAAGAGTTT | TETPLMKEDS | CAGGAAGAGT |
| KETVAAPSDIQMT | GGAAACCAATT | ILAVRKYFQR | TTGGAAACCA |
| QSPSSLSASVGDRV | CCAAAAAGCA | ITLYLKEKKY | ATTCCAAAAA |
| TITCRASRPIGTML | GAAACTATTCC | SPCAWEVVR | GCAGAAACTA |
| SWYQQKPGKAPKL | TGTCTTGCACG | AEIMRSFSLS | TTCCTGTCTTG |
| LILFGSRLQSGVPS | AAATGATCCAG | TNLQESLRSK | CACGAAATGA |
| RFSGSGSGTDFTLT | CAAATATTCAA | ETVAAPSDIQ | TCCAGCAAATA |
| ISSLQPEDFATYYC | TTTGTTTTCTA | MTQSPSSLSA | TTCAATTTGTT |
| AQAGTHPTTFGQG | CAAAGGACTC | SVGDRVTITC | TTCTCAAAGG |
| TKVEIKR | ATCAGCCGCTT | RASRPIGTML | ACTCATCAGCC |
| AAAEQKLISEEDL | GGGATGAAAC | SWYQQKPGK | GCTTGGGATGA |
| N* (SEQ ID NO: 404) | TCTGTTAGATA | APKLLILFGS | AACTCTGTTAG |
| | AATTCTACACT | RLQSGVPSRF | ATAAATTCTAC |
| | GAACTATATCA | SGSGSGTDFT | ACTGAACTATA |
| | ACAACTGAAC | LTISSLQPEDF | TCAACAACTGA |
| | GATCTAGAGGC | ATYYCAQAG | ACGATCTAGA |
| | TTGCGTTATTC | THPTTFGQGT | GGCTTGCGTTA |
| | AGGGTGTAGG | KVEIKR (SEQ | TTCAGGGTGTA |
| | AGTTACTGAAA | ID NO: 406) | GGAGTTACTGA |
| | CTCCCCTAATG | | AACTCCCTAA |
| | AAAGAAGATT | | TGAAAGAAGA |
| | CAATTCTAGCC | | TTCAATTCTAG |
| | GTTAGAAAATA | | CCGTTAGAAA |
| | CTTTCAGCGTA | | ATACTTTCAGC |
| | TCACATTGTAT | | GTATCACATTG |
| | TTAAAGGAAA | | TATTTAAAGGA |

TABLE 11-continued

Interferon alpha 2b-AlbudAb sequences with and without myc-tag (as amino acid- and nucleotide sequence) The Interferon alpha 2b is N-terminal to the AlbudAb in the following fusions.

| aa + myc | nt + myc | aa no tag | nt no tag |
|---|---|---|---|
| | AGAAATACTCC CCATGTGCATG GGAGGTGGTTA GAGCAGAAAT TATGAGGTCCT TCTCTCTTTCT ACGAATTTGCA AGAATCTTTGA GATCTAAGGA AACCGTCGCTG CTCCATCTGAC ATCCAGATGAC CCAGTCTCCAT CCTCCCTGTCT GCATCTGTAGG AGACCGTGTCA CCATCACTTGC CGGGCAAGTC GTCCGATTGGG ACGATGTTAAG TTGGTACCAGC AGAAACCAGG GAAAGCCCCTA AGCTCCTGATC TTGTTTGGTTC CCGGTTGCAAA GTGGGGTCCCA TCACGTTTCAG TGGCAGTGGAT CTGGGACAGAT TTCACTCTCAC CATCAGCAGTC TGCAACCTGAA GATTTTGCTAC GTACTACTGTG CGCAGGCTGG GACGCATCCTA CGACGTTCGGC CAAGGGACCA AGGTGGAAAT CAAACGGGCG GCCGCAGAAC AAAAACTCAT CTCAGAAGAG GATCTGAATT AA (SEQ ID NO: 405 | | AAAGAAATAC TCCCCATGTGC ATGGGAGGTG GTTAGAGCAG AAATTATGAG GTCCTTCTCTC TTTCTACGAAT TTGCAAGAATC TTTGAGATCTA AGGAAACCGT CGCTGCTCCAT CTGACATCCAG ATGACCCAGTC TCCATCCTCCC TGTCTGCATCT GTAGGAGACC GTGTCACCATC ACTTGCCGGGC AAGTCGTCCGA TTGGGACGATG TTAAGTTGGTA CCAGCAGAAA CCAGGGAAAG CCCCTAAGCTC CTGATCTTGTT TGGTTCCCGGT TGCAAAGTGG GGTCCCATCAC GTTTCAGTGGC AGTGGATCTGG GACAGATTTCA CTCTCACCATC AGCAGTCTGCA ACCTGAAGATT TTGCTACGTAC TACTGTGCGCA GGCTGGGACG CATCCTACGAC GTTCGGCCAAG GGACCAAGGT GGAAATCAAA CGG (SEQ ID NO: 407) |
| DMS7327 (IFNα2b-DOM7h-11-15) | CDLPQTHSLGSRRT LMLLAQMRRISLFS CLKDRHDFGFPQE EFGNQFQKAETIPV LHEMIQQIFNLFST KDSSAAWDETLLD KFYTELYQQLNDL EACVIQGVGVTETP LMKEDSILAVRKY FQRITLYLKEKKYS PCAWEVVRAEIMR SFSLSTNLQESLRS KETVAAPSDIQMT QSPSSLSASVGDRV TITCRASRPIGTML SWYQQKPGKAPKL LILAFSRLQSGVPS RFSGSGSGTDFTLT ISSLQPEDFATYYC AQAGTHPTTFGQG TKVEIKR AAAEQKLISEEDL N\* (SEQ ID NO: 408) | TGCGACTTGCC ACAGACACAT AGTTTGGGATC AAGAAGAACA TTGATGTTATT AGCACAAATG CGTAGAATTTC TTTGTTCTCTT GTCTAAAGGAC CGTCACGACTT CGGATTCCCTC AGGAAGAGTTT GGAAACCAATT CCAAAAAGCA GAAACTATTCC TGTCTTGCACG AAATGATCCAG CAAATATTCAA TTTGTTTTCTA CAAAGGACTC ATCAGCCGCTT GGGATGAAAC TCTGTTAGATA AATTCTACACT GAACTATATCA | CDLPQTHSLG SRRTLMLLA QMRRISLFSC LKDRHDFGFP QEEFGNQFQ KAETIPVLHE MIQQIFNLFS TKDSSAAWD ETLLDKFYTE LYQQLNDLE ACVIQGVGV TETPLMKEDS ILAVRKYFQR ITLYLKEKKY SPCAWEVVR AEIMRSFSLS TNLQESLRSK ETVAAPSDIQ MTQSPSSLSA SVGDRVTITC RASRPIGTML SWYQQKPGK APKLLILAFS RLQSGVPSRF SGSGSGTDFT | TGCGACTTGCC ACAGACACAT AGTTTGGGATC AAGAAGAACA TTGATGTTATT AGCACAAATG CGTAGAATTTC TTTGTTCTCTT GTCTAAAGGA CCGTCACGACT TCGGATTCCCT AGGAAGAGT TETPLMKEDS TTGGAAACCA ATTCCAAAAA GCAGAAACTA TTCCTGTCTTG CACGAAATGA TCCAGCAAATA TTCAATTTGTT TTCTACAAAGG ACTCATCAGCC GCTTGGGATGA AACTCTGTTAG ATAAATTCTAC ACTGAACTATA |

TABLE 11-continued

Interferon alpha 2b-AlbudAb sequences with and without myc-tag (as amino acid- and nucleotide sequence)
The Interferon alpha 2b is N-terminal to the AlbudAb in the following fusions.

| aa + myc | nt + myc | aa no tag | nt no tag |
|---|---|---|---|
| | ACAACTGAAC | LTISSLQPEDF | TCAACAACTGA |
| | GATCTAGAGGC | ATYYCAQAG | ACGATCTAGA |
| | TTGCGTTATTC | THPTTFGQGT | GGCTTGCGTTA |
| | AGGGTGTAGG | KVEIKR (SEQ | TTCAGGGTGTA |
| | AGTTACTGAAA | ID NO: 410) | GGAGTTACTGA |
| | CTCCCCTAATG | | AACTCCCTAA |
| | AAAGAAGATT | | TGAAAGAAGA |
| | CAATTCTAGCC | | TTCAATTCTAG |
| | GTTAGAAAATA | | CCGTTAGAAA |
| | CTTTCAGCGTA | | ATACTTTCAGC |
| | TCACATTGTAT | | GTATCACATTG |
| | TTAAAGGAAA | | TATTTAAAGGA |
| | AGAAATACTCC | | AAAGAAATAC |
| | CCATGTGCATG | | TCCCCATGTGC |
| | GGAGGTGGTTA | | ATGGGAGGTG |
| | GAGCAGAAAT | | GTTAGAGCAG |
| | TATGAGGTCCT | | AAATTATGAG |
| | TCTCTCTTTCT | | GTCCTTCTCTC |
| | ACGAATTTGCA | | TTTCTACGAAT |
| | AGAATCTTTGA | | TTGCAAGAATC |
| | GATCTAAGGA | | TTTGAGATCTA |
| | AACCGTCGCTG | | AGGAAACCGT |
| | CTCCATCTGAC | | CGCTGCTCCAT |
| | ATCCAGATGAC | | CTGACATCCAG |
| | CCAGTCTCCAT | | ATGACCCAGTC |
| | CCTCCCTGTCT | | TCCATCCTCCC |
| | GCATCTGTAGG | | TGTCTGCATCT |
| | AGACCGTGTCA | | GTAGGAGACC |
| | CCATCACTTGC | | GTGTCACCATC |
| | CGGGCAAGTC | | ACTTGCCGGGC |
| | GTCCGATTGGG | | AAGTCGTCCGA |
| | ACGATGTTAAG | | TTGGGACGATG |
| | TTGGTACCAGC | | TTAAGTTGGTA |
| | AGAAACCAGG | | CCAGCAGAAA |
| | GAAAGCCCCTA | | CCAGGGAAAG |
| | AGCTCCTGATC | | CCCCTAAGCTC |
| | CTTGCTTTTC | | CTGATCCTTGC |
| | CCGTTTGCAAA | | TTTTTCCCGTT |
| | GTGGGGTCCCA | | TGCAAAGTGG |
| | TCACGTTTCAG | | GGTCCCATCAC |
| | TGGCAGTGGAT | | GTTTCAGTGGC |
| | CTGGGACAGAT | | AGTGGATCTGG |
| | TTCACTCTCAC | | GACAGATTTCA |
| | CATCAGCAGTC | | CTCTCACCATC |
| | TGCAACCTGAA | | AGCAGTCTGCA |
| | GATTTTGCTAC | | ACCTGAAGATT |
| | GTACTACTGCG | | TTGCTACGTAC |
| | CGCAGGCTGG | | TACTGCGCGCA |
| | GACGCATCCTA | | GGCTGGGACG |
| | CGACGTTCGGC | | CATCCTACGAC |
| | CAAGGGACCA | | GTTCGGCCAAG |
| | AGGTGGAAAT | | GGACCAAGGT |
| | CAAACGGGCG | | GGAAATCAAA |
| | GCCGCAGAAC | | CGG (SEQ ID |
| | AAAAACTCAT | | NO: 411) |
| | CTCAGAAGAG | | |
| | GATCTGAATT | | |
| | AA (SEQ ID | | |
| | NO: 409) | | |

The amino acid and nucleotide sequences highlighted in bold represents the cloning site and MYC tag.
*represents the stop codon at the end of the gene.

Affinity Determination and Biophysical Characterisation:

To determine the binding affinity ($K_D$) of the AlbudAb-IFNα2b fusion proteins to each serum albumin; purified fusion proteins were analysed by BIAcore over albumin (immobilised by primary-amine coupling onto CM5 chips; BIAcore) using fusion protein concentrations from 5000 nM to 39 nM (5000 nM, 2500 nM, 1250 nM, 625 nM, 312 nM, 156 nM, 78 nM, 39 nM) in HBS-EP BIAcore buffer.

TABLE 12

Affinity to SA

| AlbudAb | Fusion | Affinity to SA (nM) | Kd | Ka |
|---|---|---|---|---|
| Rat | | | | |
| DOM7h-14 | IFNα2b | 350 | 4.500E-02 | 1.28E+05 |
| DOM7h-14-10 | IFNα2b | 16 | 4.970E-03 | 5.90E+05 |
| DOM 7h-14-18 | IFNα2b | 780 | 2.127E-01 | 5.80E+05 |
| DOM 7h-14-19 | IFNα2b | 1900 | 1.206E-01 | 7.96E+04 |
| DOM 7h-11 | IFNα2b | 6000 | 7.500E-01 | nd |
| DOM 7h-11-12 | IFNα2b | 1700 | 3.100E-01 | 1.30E+05 |
| DOM 7h-11-15 | IFNα2b | 200 | 1.660E-02 | 1.50E+05 |
| Cyno | | | | |
| DOM 7h-14 | IFNα2b | 60 | 1.32E-02 | 5.0E+05 |
| DOM 7h-14-10 | IFNα2b | 19 | 7.05E-03 | 4.50E+05 |
| DOM 7h-14-18 | IFNα2b | no binding | no binding | no binding |
| DOM 7h-14-19 | IFNα2b | 520 | 8.47E-02 | 2.73E+05 |
| DOM 7h-11 | IFNα2b | 3300 | 3.59E-01 | 1.20E+05 |
| DOM 7h-11-12 | IFNα2b | 630 | 3.45E-01 | 7.00E+05 |
| DOM 7h-11-15 | IFNα2b | 15 | 4.86E-03 | 3.60E+05 |
| Mouse | | | | |
| DOM 7h-14 | IFNα2b | 240 | 3.21E-02 | 1.50E+06 |
| DOM 7h-14-10 | IFNα2b | 60 | 3.45E-02 | 6.86E+05 |
| DOM 7h-14-18 | IFNα2b | 180 | 1.50E-01 | 9.84E+05 |
| DOM 7h-14-19 | IFNα2b | 490 | 4.03E-02 | 1.19E+05 |
| DOM 7h-11 | IFNα2b | 6000 | 1.55E-01 | nd |
| DOM 7h-11-12 | IFNα2b | 150 | 9.49E-02 | 6.30E+05 |
| DOM 7h-11-15 | IFNα2b | 28 | 6.69E-03 | 2.80E+05 |
| Human | | | | |
| DOM 7h-14 | IFNα2b | 244 | 2.21E-02 | 9.89E+04 |
| DOM 7h-14-10 | IFNα2b | 32 | 6.58E-03 | 3.48E+05 |
| DOM 7h-14-18 | IFNα2b | 470 | 2.75E-01 | 6.15E+05 |
| DOM 7h-14-19 | IFNα2b | 350 | 4.19E-02 | 1.55E+05 |
| DOM 7h-11 | IFNα2b | 670 | 2.02E-01 | 7.00E+05 |
| DOM 7h-11-12 | IFNα2b | 500 | 1.66E-01 | 3.90E+05 |
| DOM 7h-11-15 | IFNα2b | 10 | 1.87E-03 | 3.50E+05 |

When IFNα2b is linked to the AlbudAb variants, in all cases the affinity of AlbudAb binding to serum albumin is reduced. DOM7h-14-10 and DOM7-11-15 retain improved binding affinity to serum albumin across species compared to parent. DOM7h-11-12 also shows improved binding affinity to serum albumin across species compared to parent.

TABLE 13

Biophysical Characterisation
Biophysical Characterisation was carried out by SEC MALLS and DSC as described above for the single AlbudAbs.

| AlbudAb | Fusion | DMS number | SEC MALLS | DSC Tm (° C.) |
|---|---|---|---|---|
| | | | | Biophysical parameters |
| DOM 7h-14 | IFNα2b | DMS7321 | M/D | 58-65 |
| DOM 7h-14-10 | IFNα2b | DMS7322 | M/D | 55-65 |
| DOM 7h-14-18 | IFNα2b | DMS7323 | M/D | 55-65 |
| DOM 7h-14-19 | IFNα2b | DMS7324 | M/D | 59-66 |
| DOM 7h-11 | IFNα2b | DMS7325 | M/D | 65.8-66.2 |
| DOM 7h-11-12 | IFNα2b | DMS7326 | M/D | 67-67.3 |
| DOM 7h-11-15 | IFNα2b | DMS7327 | M/D | 56.3-66.2 |

M/D indicates a monomer/dimer equilibrium as detected by SEC MALLS

We observed expression for all clones in Table 13 in the range of 17.5 to 54 mg/L in HEK293.

For IFNα2b-DOM7h-14 and IFNα2b-DOM7h-11 variants, favorable biophysical parameters and expression levels were maintained during affinity maturation.

PK Determination for AlbudAb-IFNα2b Fusions

AlbudAbs IFNα2b fusions DMS7321 (IFNα2b-DOM7h-14) DMS7322 (IFNα2b-DOM7h-14-10) DMS7323 (IFNα2b-DOM7h-14-18), DMS7324 (IFNα2b-DOM7h-14-19), DMS7325 (IFNα2b-DOM7h-11), DMS7326 (IFNα2b-DOM7h-11-12), DMS7327 (IFNα2b-DOM7h-11-15) were expressed with the myc tag at 20-50 mg quantities in HEK293 cells and purified from culture supernatant using protein L affinity resin and eluted with 100 mM glycine pH2. The proteins were concentrated to greater than 1 mg/ml, buffer exchanged into Dulbecco's PBS and endotoxin depleted using Q spin columns (Vivascience).

For Rat PK, IFN-AlbudAbs were dosed as single i.v injections at 2.0 mg/kg using 3 rats per compound. Serum samples were taken at 0.16, 1, 4, 8, 24, 48, 72, 120, 168 hrs. Analysis of serum levels was by EASY ELISA according to manufacturers instructions (GE Healthcare, catalogue number RPN5960).

For Mouse PK, DMS7322 (IFN2b-DOM7h-14-10) DMS7325 (IFN2b-DOM7h-11), DMS7326 (IFN2b-DOM7h-11-12), DMS7327 (IFN2b-DOM7h-11-15) all with myc tags were dosed as single i.v injections at 2.0 mg/kg per dose group of 3 subjects and serum samples taken at 10 mins; 1 h; 8 h; 24 h; 48 h; 72 h; 96 h. Analysis of serum levels was by EASY ELISA according to manufacturers instructions (GE Healthcare, catalogue number RPN5960).

TABLE 14

| | | | | PK parameters | | | |
|---|---|---|---|---|---|---|---|
| Species | AlbudAb | Fusion | Albumin $K_D$ (nM) | AUC h × ug/ml | CL ml/h/kg | t½ h | Vz ml/kg |
| Rat | 7h-14 | IFNα2b | 350 | 832.1 | 2.4 | 27 | 94.5 |
| | 7h-14-10 | IFNα2b | 16 | 1380.7 | 1.5 | 35.8 | 75.2 |
| | 7h-14-18 | IFNα2b | 780 | 691.2 | 2.9 | 22.4 | 93.7 |
| | 7h-14-19 | IFNα2b | 1900 | 969.4 | 2.2 | 25 | 78.7 |
| | 7h-11 | IFNα2b | 6000 | 327.9 | 6.5 | 11 | 101.9 |
| | 7h-11-12 | IFNα2b | 1700 | 747.1 | 2.8 | 25.8 | 104.7 |
| | 7h-11-15 | IFNα2b | 200 | 1118.7 | 1.8 | 39.5 | 103.6 |
| mouse | 7h-14 | IFNα2b | 240 | 761.2 | 2.6 | 30.4 | 115.3 |
| | 7h-14-10 | IFNα2b | 60 | 750.5 | 2.7 | 30.9 | 118.6 |
| | 7h-11 | IFNα2b | 6000 | 493.9 | 4.0 | 8.8 | 51.2 |
| | 7h-11-12 | IFNα2b | 150 | 439.6 | 4.5 | 21.5 | 140.9 |
| | 7h-11-15 | IFNα2b | 28 | 971.8 | 2.1 | 33.6 | 99.6 |

Pharmacokinetic parameters derived from rat and mouse studies were fitted using a non-compartmental model. Key: AUC: Area under the curve from dosing time extrapolated to infinity; CL: clearance; t½: is the time during which the blood concentration is halved; Vz: volume of distribution based on the terminal phase.

IFNα2b—AlbudAbs were tested in rat and mouse. For all IFNα2b-DOM7h-11 variant fusion proteins in both rat and mouse, t½ is improved compared to parent. The improvement in t½ correlates with the improved in vitro $K_D$ to serum albumin. For IFNα2b-DOM7h-14-10 variants, the improvement in in vitro $K_D$ to serum albumin also correlated to an improvement in t½ in rat.

All IFNα2b-AlbudAb fusion proteins exhibit a 5 to 10-fold decrease in the binding to RSA compared to the single AlbudAb. This effect is more pronounced (i.e. 10-fold) for the DOM7h-14 series than the DOM7h-11 series (only 5-fold decrease).

Example 8

Further AlbudAb Fusions with Proteins, Peptides and NCEs

Various AlbudAbs fused to other chemical entities namely domain antibodies (dAbs), peptides and NCEs were tested. The results are shown in table 15.

TABLE 15

| | | | PK parameters | | | | |
|---|---|---|---|---|---|---|---|
| Species | AlbudAb | Fusion | Albumin $K_D$ (nM) | AUC h × ug/ml | CL ml/h/kg | t½ h | Vz ml/kg |
| Rat | DOM7h-14 | Exendin-4 | 2400 | 18 | 57.1 | 11 | 901.9 |
| | DOM7h-14-10 | Exendin-4 | 19 | 43.6 | 23.1 | 22.1 | 740.3 |
| | DOM7h-14-18 | Exendin-4 | 16000 | 16.9 | 75.7 | 9.4 | 1002.5 |
| | DOM7h-14-19 | Exendin-4 | 17000 | 31.4 | 32.5 | 11.9 | 556.7 |
| | DOM7h-11 | Exendin-4 | 24000 | 6.1 | 168 | 7.1 | 1684.1 |
| | DOM7h-11-12 | Exendin-4 | 1400 | 24.2 | 59.9 | 13 | 1068.7 |
| | DOM7h-11-15 | Exendin-4 | 130 | 36.3 | 27.6 | 19.3 | 765.7 |
| | DOM7h14-10 | NCE-GGGGSC | 62 | | | | |
| | DOM7h14-10 | NCE-TVAAPSC | 35 | | | | |
| Human | DOM7h-14 | NCE | 204 | | | | |
| mouse | DOM7h-11 | DOM1m-21-23 | | 234 | 10.7 | 4.7 | 72.5 |
| | DOM7h-11-12 | DOM1m-21-23 | | 755 | 3.3 | 18 | 86.2 |
| | DOM7h-11-15 | DOM1m-21-23 | | 1008 | 2.5 | 17.4 | 62.4 |

Key:
DOM1m-21-23 is an anti-TNFR1 dAb, Exendin-4 is a peptide (a GLP-1 agonist) of 39 amino acids length.
NCE, NCE-GGGGSC and NCE-TVAAPSC are described below.

Previously we have described the use of genetic fusions with an albumin-binding dAb (AlbudAb) to extend the PK half-life of anti-TNFR1 dAbs in vivo (see, eg, WO04003019, WO2006038027, WO2008149148). Reference is made to the protocols in these PCT applications. In the table above, DOM1m-21-23 is an anti-mouse TNFR1 dAb.

To produce genetic fusions of exendin-4 or with DOM7h-14 (or other AlbudAb) which binds serum albumin, the exendin-4-linker-AlbudAb sequence was cloned into the pTT-5 vector (obtainable from CNRC, Canada). In each case the exendin-4 was at the 5' end of the construct and the dAb at the 3' end. The linker was a $(G_4S)_3$ linker. Endotoxin-free DNA was prepared in E. coli using alkaline lysis (using the endotoxin-free plasmid Giga kit, obtainable from Qiagen CA) and used to transfect HEK293E cells (obtainable from CNRC, Canada). Transfection was into 250 ml/flask of HEK293E cells at $1.75 \times 10^6$ cells/ml using 333 ul of 293fectin (Invotrogen) and 250 ug of DNA per flask and expression was at 30° C. for 5 days. The supernatant was harvested by centrifugation and purification was by affinity purification on protein L. Protein was batch bound to the resin, packed on a column and washed with 10 column volumes of PBS. Protein was eluted with 50 ml of 0.1M glycine pH2 and neatralised with Tris pH8. Protein of the expected size was identified on an SDS-PAGE gel.

NCE Albudab Fusions:

A new chemical entity (NCE) AlbudAb fusion was tested. The NCE, a small molecule ADAMTS-4 inhibitor was synthesised with a PEG linker (PEG 4 linker (ie 4 PEG molecules before the maleimide) and a maleimide group for conjugation to the AlbudAb. Conjugation of the NCE to the AlbudAb is via an engineered cystine residue at amino acid position R108C, or following a 5 amino acid (GGGGSC (SEQ ID NO: 420)) or 6 amino acid (TVAAPSC (SEQ ID NO: 421)) spacer engineered at the end of the AlbudAb. Briefly, the AlbudAb was reduced with TCEP (Pierce, Catalogue Number 77720), desalted using a PD10 column (GE healthcare) into 25 mM Bis-Tris, 5 mM EDTA, 10% (v/v) glycerol pH6.5. A 5 fold molar excess of maleimide activated NCE was added in DMSO not to exceed 10% (V/V) final concentration. The reaction was incubated over night at room temperature and dialysed extensively into 20 mM Tris pH7.4

PEG Linker:

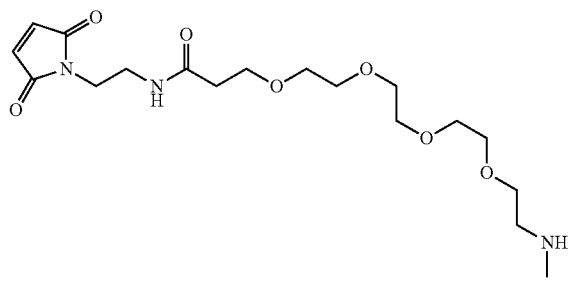 [SMILES: CNCCOCCOCCOCCOCCC(=O)NCCN1C(=O)C=CC1=O]

Sequences:
DOM7h-14-10 R108C:

(SEQ ID NO: 412)
DIQMTQSPSSLSASVGDRVTITCRASQWIGSQLSWYQQKPGKAPKLLIMW

RSSLQSGVPSRFSGSGSGTDFTLTISSLQPEDFATYYCAQGLRHPKTFGQ

GTKVEIKC

Nucleotide:

(SEQ ID NO: 413)
GACATCCAGATGACCCAGTCTCCATCCTCCCTGTCTGCATCTGTAGGAGA

CCGTGTCACCATCACTTGCCGGGCAAGTCAGTGGATTGGGTCTCAGTTAT

CTTGGTACCAGCAGAAACCAGGGAAAGCCCCTAAGCTCCTGATCATGTGG

CGTTCCTCGTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGTGCTCAGGGTTTGAGGCATCCTAAGACGTTCGGCCAA

GGGACCAAGGTGGAAATCAAATGC

See table 5 for the sequences of DOM7h-14-10/TVAAPSC (SEQ ID NO: 419) and DOM7h-14-10/GGGGSC(SEQ ID NO: 420) (ie, DOM7h-14-10/G4SC).

NCE-AlbudAbs DOM7h-14-10 GGGGSC (SEQ ID NO: 420) and DOM7h14-10 TVAAPSC(SEQ ID NO: 419), exhibit a 5 to 10 fold decrease in in vitro affinity ($K_D$) to RSA as determined by BIAcore when fused to the chemical entity. PK data are not available for these molecules yet.

dAb-Albudab fusion: the 2 DOM7h-11 AlbudAbs with the highest affinity to RSA experience a 2-fold decrease in affinity to RSA as on BIAcore when fused to a therapeutic domain antibody (DOM1m-21-23) compared to the unfused AlbudAb. The DOM7h-11 clone shows a micromolar $K_D$ when fused (2.8 uM) as well as when unfused (~5 uM).

Exendin 4-AlbudAb fusion: the effect of fusing the AlbudAbs to a peptide on the binding ability to RSA is about 10-fold, apart from DOM7h-14-10, which only shows a 4-fold decrease in binding. The effect, however, is more pronounced for the DOM7h-14 series (except DOM7h-14-10) than it appears to be for the DOM7h-11 series.

For all the above data, the T½ of the fusion increased with improved affinity to the species' SA.

We generally classify Albudab-therapeutics as being therapeutically amenable (for treatment and/or prophylaxis of diseases, conditions or indications) when the AlbudAb-drug fusions show an affinity range ($K_D$) of from 0.1 nM to 10 mM for serum albumin binding.

We define the therapeutic ranges of AlbudAbs and AlbudAb fusions (Protein-AlbudAbs for example IFNa2b-DOM7h-14-10; Peptide-AlbudAbs for example Exendin-4-DOM7h-14-10; dAb-AlbudAbs for example DOM1m21-23-DOM7h11-15; NCE-AlbudAb for example ADAMTS-4-DOM7h-14-10) as follows: Affinity ($K_D$) ranges that are useful for therapy of chronic or acute conditions, diseases or indictions are shown. Also shown are affinity ranges marked as "intermediate". AlbudAbs and fusions in this range have utility for chronic or acute diseases, conditions or indications. In this way, the affinity of the AlbudAb or fusion for serum albumin can be tailored or chosen according to the disease, condition or indication to be addressed. As described above, the invention provides AlbudAbs with affinities that allow for each AlbudAb to be categorised as "high affinity", "medium affinity" or "low affinity", thus enabling the skilled person to select the appropriate AlbudAb of the invention according to the therapy at hand. See FIG. 2.

Example 9

DOM7h-11-15$^{S12P}$ Sequences

Amino Acid Sequence of DOM7h-11-15$^{S12P}$ (SEQ ID NO: 414)
DIQMTQSPSSLPASVGDRVTITCRASRPIGTMLSWYQQKPGKAPKLLILA

FSRLQSGVPSRFSGSGSGTDFTLTISSLQPEDFATYYCAQAGTHPTTFGQ

GTKVEIKR

An aspect of the invention provides a nucleic acid comprising the nucleotide sequence of DOM7h-11-15$^{S12P}$ or a nucleotide sequence that is at least 80% identical to said selected sequence. DOM7h-11-15$^{S12P}$ was produced using the following nucleic acid sequence (the underlined C denotes the change (versus the nucleic acid encoding DOM7h-11-15) leading to a proline at position 12):—

(SEQ ID NO: 415)
GACATCCAGATGACCCAGTCTCCATCCTCCCTGCCTGCATCTGTAGGAGA

CCGTGTCACCATCACTTGCCGGGCAAGTCGTCCGATTGGGACGATGTTAA

GTTGGTACCAGCAGAAACCAGGGAAAGCCCCTAAGCTCCTGATCCTTGCT

TTTTCCCGTTTGCAAAGTGGGGTCCCATCACGTTTCAGTGGCAGTGGATC

TGGGACAGATTTCACTCTCACCATCAGCAGTCTGCAACCTGAAGATTTTG

CTACGTACTACTGCGCGCAGGCTGGGACGCATCCTACGACGTTCGGCCA

AGGGACCAAGGTGGAAATCAAACGG

DOM7h-11-15$^{S12P}$ was constructed by using DOM7h-11-15 as a template in a PCR where a primer was used to introduce the S12P mutation. The primer sequence is:—

(SEQ ID NO: 416)
GCAACAGCGTCGACGGACATCCAGATGACCCAGTCTCCATCCTCCCTGCC

TGCATCTGTAGG.

An alternative aspect of the invention provides a nucleic acid comprising the nucleotide sequence of SEQ ID NO: 415 or a nucleotide sequence that is at least 80% identical to said selected sequence. In one embodiment, DOM7h-11-15$^{S12P}$ is encoded by, and expressed from, a vector that contains a linker region and a C-terminal sequence encoding a protein or peptide drug or a single variable domain or other antibody fragment to make the in-line protein fusion product. The linker, in one embodiment, comprises the amino acid sequence TVA, eg, TVAAPS (SEQ ID NO: 421). Other aspects of the invention are a vector comprising the nucleic acid; and an isolated host cell comprising the vector. The invention also provides a method of treating or preventing a disease or disorder in a patient, comprising administering at least one dose of DOM7h-11-15$^{S12P}$ to said patient.

The invention claimed is:

1. An anti-serum albumin immunoglobulin single variable domain comprising an amino acid sequence selected from the group consisting of: SEQ ID NO: 412 (DOM7h-14-10 R108C).

2. A multispecific ligand comprising an anti-serum albumin immunoglobulin single variable domain of claim 1, and a binding moiety that specifically binds a target antigen other than serum albumin.

3. The anti-serum albumin immunoglobulin single variable domain of claim 1, wherein the variable domain is conjugated to an NCE drug.

4. A fusion protein comprising a polypeptide or peptide drug fused to an anti-serum albumin immunoglobulin single variable domain according to claim 1.

5. The fusion protein according to claim 4, wherein the fusion protein comprises a linker between the anti-serum albumin immunoglobulin single variable domain and the polypeptide or peptide drug.

6. The fusion protein according to claim 5, wherein the linker comprises the amino acid sequence TVA between the anti-serum albumin immunoglobulin single variable domain and the polypeptide or peptide drug.

7. The fusion protein according to claim 5, wherein the linker comprises the amino acid sequence TVAAPS (SEQ ID NO: 421) between the anti-serum albumin immunoglobulin single variable domain and the polypeptide or peptide drug.

8. A composition comprising the anti-serum albumin immunoglobulin single variable domain of claim 1, and a pharmaceutically acceptable diluent, carrier, excipient or vehicle.

9. A composition comprising the anti-serum albumin immunoglobulin single variable domain of claim 2, and a pharmaceutically acceptable diluent, carrier, excipient or vehicle.

10. A composition comprising the anti-serum albumin immunoglobulin single variable domain of claim 3, and a pharmaceutically acceptable diluent, carrier, excipient or vehicle.

11. A composition comprising the anti-serum albumin immunoglobulin single variable domain of claim 4, and a pharmaceutically acceptable diluent, carrier, excipient or vehicle.

12. A composition comprising the anti-serum albumin immunoglobulin single variable domain of claim 5, and a pharmaceutically acceptable diluent, carrier, excipient or vehicle.

13. A composition comprising the anti-serum albumin immunoglobulin single variable domain of claim 6, and a pharmaceutically acceptable diluent, carrier, excipient or vehicle.

14. A composition comprising the anti-serum albumin immunoglobulin single variable domain of claim 7, and a pharmaceutically acceptable diluent, carrier, excipient or vehicle.

15. An anti-serum albumin immunoglobulin single variable domain comprising comprising an amino acid sequence selected from the group consisting of: SEQ ID NO: 2 (DOM7h-14-18), SEQ ID NO: 3 (DOM7h-14-19), SEQ ID NO: 4 (DOM7h-14-28), and SEQ ID NO: 5 (DOM7h-14-36).

16. A multispecific ligand comprising an anti-serum albumin immunoglobulin single variable domain of claim 15, and a binding moiety that specifically binds a target antigen other than serum albumin.

17. The anti-serum albumin immunoglobulin single variable domain of claim 16, wherein the variable domain is conjugated to an NCE drug.

18. A fusion protein comprising a polypeptide or peptide drug fused to an anti-serum albumin immunoglobulin single variable domain according to claim 16.

19. The fusion protein according to claim 18, wherein the fusion protein comprises a linker between the anti-serum albumin immunoglobulin single variable domain and the polypeptide or peptide drug.

20. The fusion protein according to claim 19, wherein the linker comprises the amino acid sequence TVA between the anti-serum albumin immunoglobulin single variable domain and the polypeptide or peptide drug.

21. The fusion protein according to claim 19, wherein the linker comprises the amino acid sequence TVAAPS (SEQ ID NO: 421) between the anti-serum albumin immunoglobulin single variable domain and the polypeptide or peptide drug.

22. A composition comprising the anti-serum albumin immunoglobulin single variable domain of claim 15, and a pharmaceutically acceptable diluent, carrier, excipient or vehicle.

23. A composition comprising the anti-serum albumin immunoglobulin single variable domain of claim 16, and a pharmaceutically acceptable diluent, carrier, excipient or vehicle.

24. A composition comprising the anti-serum albumin immunoglobulin single variable domain of claim 17, and a pharmaceutically acceptable diluent, carrier, excipient or vehicle.

25. A composition comprising the anti-serum albumin immunoglobulin single variable domain of claim 18, and a pharmaceutically acceptable diluent, carrier, excipient or vehicle.

26. A composition comprising the anti-serum albumin immunoglobulin single variable domain of claim 19, and a pharmaceutically acceptable diluent, carrier, excipient or vehicle.

27. A composition comprising the anti-serum albumin immunoglobulin single variable domain of claim 20, and a pharmaceutically acceptable diluent, carrier, excipient or vehicle.

28. A composition comprising the anti-serum albumin immunoglobulin single variable domain of claim 21, and a pharmaceutically acceptable diluent, carrier, excipient or vehicle.

* * * * *